(12) United States Patent
Roeth et al.

(10) Patent No.: US 9,402,919 B2
(45) Date of Patent: Aug. 2, 2016

(54) VECTORS CONDITIONALLY EXPRESSING PROTEIN

(75) Inventors: Jeremiah F. Roeth, Blacksburg, VA (US); Charles C. Reed, Souderton, PA (US); Brandon Cuthbertson, Newland, NC (US); Sunil Chada, Missouri City, TX (US); William E. Fogler, Rockville, MD (US); Fayaz Khazi, Frederick, MD (US)

(73) Assignee: Intrexon Corporation, Blacksburg, VA (US)

( * ) Notice: Subject to any disclaimer, the term of this patent is extended or adjusted under 35 U.S.C. 154(b) by 0 days.

(21) Appl. No.: 14/001,943

(22) PCT Filed: Mar. 2, 2012

(86) PCT No.: PCT/US2012/027515
§ 371 (c)(1),
(2), (4) Date: Nov. 15, 2013

(87) PCT Pub. No.: WO2012/122025
PCT Pub. Date: Sep. 13, 2012

(65) Prior Publication Data
US 2014/0308247 A1    Oct. 16, 2014

Related U.S. Application Data

(60) Provisional application No. 61/449,536, filed on Mar. 4, 2011, provisional application No. 61/478,881, filed on Apr. 25, 2011, provisional application No. 61/490,535, filed on May 26, 2011, provisional application No. 61/562,342, filed on Nov. 21, 2011.

(51) Int. Cl.
| | | |
|---|---|---|
| *A61K 48/00* | (2006.01) | |
| *C12N 15/86* | (2006.01) | |
| *C07K 14/505* | (2006.01) | |
| *C07K 14/54* | (2006.01) | |
| *C07K 14/56* | (2006.01) | |
| *C07K 14/565* | (2006.01) | |
| *C07K 14/705* | (2006.01) | |
| *C07K 14/47* | (2006.01) | |
| *C12N 15/85* | (2006.01) | |

(52) U.S. Cl.
CPC ......... *A61K 48/0025* (2013.01); *A61K 48/0066* (2013.01); *A61K 48/0075* (2013.01); *C07K 14/4713* (2013.01); *C07K 14/505* (2013.01); *C07K 14/5428* (2013.01); *C07K 14/5434* (2013.01); *C07K 14/56* (2013.01); *C07K 14/565* (2013.01); *C07K 14/70567* (2013.01); *C12N 15/85* (2013.01); *C12N 15/86* (2013.01); *C07K 2319/70* (2013.01); *C07K 2319/715* (2013.01); *C07K 2319/81* (2013.01); *C12N 2710/10343* (2013.01); *C12N 2750/14143* (2013.01); *C12N 2830/002* (2013.01); *C12N 2830/75* (2013.01); *C12N 2830/85* (2013.01); *C12N 2840/203* (2013.01)

(58) Field of Classification Search
None
See application file for complete search history.

(56) References Cited

U.S. PATENT DOCUMENTS

| | | | |
|---|---|---|---|
| 6,258,603 B1 * | 7/2001 | Carlson et al. | 435/468 |
| 6,613,319 B2 * | 9/2003 | Leiden | 424/93.2 |
| 7,030,098 B2 | 4/2006 | Steinman et al. | |
| 2002/0049153 A1 | 4/2002 | Bridon et al. | |
| 2002/0107211 A1 | 8/2002 | Friedman et al. | |
| 2002/0137699 A1 | 9/2002 | Mueller et al. | |
| 2002/0168739 A1 | 11/2002 | Wu | |
| 2003/0054494 A1 | 3/2003 | DeSauvage et al. | |
| 2003/0082141 A1 | 5/2003 | O'Connor | |
| 2003/0091544 A1 | 5/2003 | Parker et al. | |
| 2003/0176328 A1 | 9/2003 | Rasmussen et al. | |
| 2003/0186386 A1 | 10/2003 | Hansen et al. | |
| 2004/0171794 A1 | 9/2004 | Ladner et al. | |
| 2005/0288218 A1 | 12/2005 | Davis et al. | |
| 2008/0020418 A1 | 1/2008 | Riordan et al. | |
| 2009/0136465 A1 | 5/2009 | Merenick et al. | |
| 2010/0160556 A1 | 6/2010 | Wallrapp et al. | |
| 2010/0234344 A1 | 9/2010 | Gibson et al. | |

OTHER PUBLICATIONS

Rivera, et al. (2005) "Long-term pharmacologically regulated expression of erythropoietin in primates following AAV-mediated gene transfer", Blood, 105(4): 1424-30.*
Goverdhana, et al. (2005) "Regulatable Gene Expression Systems for Gene Therapy Applications: Progress and Future Challenges", Molecular Therapy, 12(2): 189-211, downloaded as 45 page online PDF.*
https://en.wikipedia.org/wiki/Mammal, "Mammal" downloaded Aug. 4, 2015, authors unknown, no volume, no journal, no issue, 15 pages.*
International Search Report for International Application No. PCT/US2012/027515, United States Patent Office, Alexandria, Virginia, mailed on Sep. 7, 2012.
Examiner Report for Australian Patent Application No. 201225749, Australian Patent Office, Sydney, Australia, mailed on Nov. 8, 2013.
Examiner Report for Australian Patent Application No. 201225749, Australian Patent Office, Sydney, Australia, mailed on Oct. 31, 2014.

* cited by examiner

*Primary Examiner* — Robert M Kelly
(74) *Attorney, Agent, or Firm* — Sterne, Kessler, Goldstein & Fox P.L.L.C.

(57) ABSTRACT

This invention relates to the field of therapeutics. Disclosed are methods of conditionally expressing erythropoietin under the control of an ecdysone receptor-based gene expression modulation system in the presence of activating ligand and uses for therapeutic purposes in animals. The methods of the invention cause an in vivo increase in the expression of erythropoietin and an increase in the hematocrit or volume percentage of red blood cells in blood after administration of the ligand.

28 Claims, 14 Drawing Sheets

VECTORS CONDITIONALLY EXPRESSING PROTEIN

REFERENCE TO SEQUENCE LISTING SUBMITTED ELECTRONICALLY VIA EFS-WEB

The content of the electronically submitted sequence listing (Name: 2584_0960009SEQIDListing.acsii.txt, Size: 153,646 bytes, and Date of Creation: Aug. 22, 2013) submitted in this application is incorporated herein by reference in its entirety.

The content of the electronically submitted sequence listing (Name: SequenceListing.ascii.txt; Size: 153,629 bytes; Date Of Creation: Mar. 2, 2012) filed with this application is incorporated herein by reference in its entirety.

BACKGROUND OF THE INVENTION

Field of the Invention

Interleukin-12 (IL-12) is a member of the type I cytokine family involved in contributing to a number of biological processes including, but not limited to, protective immune response and suppression of tumorigenesis (Abdi et al., 2006; Adorini, 1999; Adorini, 2001; Adorini et al., 2002; Adorini et al., 1996; Akhtar et al., 2004; Akiyama et al., 2000; Al-Mohanna et al., 2002; Aliberti et al., 1996; Allavena et al., 1994; Alli and Khar, 2004; Alzona et al., 1996; Amemiya et al., 2006; Araujo et al., 2001; Arulanandam et al., 1999; Athie et al., 2000; Athie-Morales et al., 2004; Bertagnolli et al., 1992; Bhardwaj et al., 1996; Biedermann et al., 2006; Brunda and Gately, 1994; Buchanan et al., 1995; Romani et al., 1997; Rothe et al., 1996; Satoskar et al., 2000; Schopf et al., 1999; Thomas et al., 2000; Tsung et al., 1997; Wolf et al., 1994; Yuminamochi et al., 2007). A growing body of evidence suggests that IL-12 may be a promising target to control human diseases (e.g., cancer).

Despite the fact that IL-12 remains promising as a cancer therapeutic agent based on its potent supportive activity on Type-1 anti-tumor NK cells, CD4$^+$ T cells and CD8$^+$ T cells (Trinchieri, 2003), the reported toxicity of recombinant human IL-12 (rhIL-12) in patients (Atkins et al., 1997), together with limited sources of GMP-grade rhIL-12 for clinical application, have prevented successful IL-12-based therapeutic approaches. Thus it seems reasonable that gene therapy approaches may represent safer, more tenable treatment options. Indeed, phase I clinical trials implementing intra- or peri-tumoral delivery of recombinant viral- (Sangro et al., 2004; Triozzi et al., 2005) or plasmid-based IL-12 cDNA (Heinzerling et al., 2005), or IL-12 gene modified autologous fibroblasts (Kang et al., 2001) have been found safe and well-tolerated.

However, objective clinical responses in patients with melanoma or a diverse range of carcinomas receiving these gene therapies have been rare, variable, transient and largely focused at the site of treatment (Heinzerling et al., 2005; Kang et al., 2001; Sangro et al., 2004; Triozzi et al., 2005). In cases where disease resolution was partial or complete, increased frequencies of tumor-infiltrating lymphocytes (Heinzerling et al., 2005; Sangro et al., 2004) and elevated levels of circulating tumor-specific CD8$^+$ T cells (Heinzerling et al., 2005) have been noted, consistent with the improved cross-priming of antigen-specific T cells in these patients.

Since the cross-priming of specific T cells is best accomplished by dendritic cells (DC) that serve as a natural but regulated source of IL-12 (Berard et al., 2000), recent reports of the superior pre-clinical efficacy of DC-based IL-12 gene therapy have been of great interest (Satoh et al., 2002; Tatsumi et al., 2003; Yamanaka et al., 2002). For example, it was shown that intratumoral (i.t.) injection of DC engineered to produce IL-12p70 (via recombinant adenovirus infection) results in the dramatically improved cross-priming of a broadly-reactive, tumor-specific CD8$^+$ T cell repertoire in concert with tumor rejection in murine models (Tatsumi et al., 2003). Given the previous use of a recombinant adenovirus encoding mIL-12 under a CMV-based promoter (rAd.cIL12, (Tatsumi et al., 2003)), engineered DC production of IL-12 was constitutive, hence the immunologic impact of this cytokine early within the tumor lesion and later within tumor-draining lymph nodes could not be resolved with regards to therapeutic outcome. Thus, a need exists for DC engineered for conditional expression of IL-12 for the purpose of regulating both the level of transgene expression and the timing of the transgene activation. The invention provides a promising therapeutic outcome for the use of such cells.

In view of the problems associated with gene expression of genes through vector compositions containing the protein encoded by the nucleic acid sequence of interest in, there remains a need for an improved transfer vector compositions to be used for direct injection or for use in cell based therapies.

Erythropoietin (EPO) plays a central role in the regulation of red blood cell production by controlling the proliferation, differentiation and survival of erythroid progenitors in the bone marrow. Lack of EPO protein leads to anemia. Treatment with recombinant human EPO (huEPO) is efficient and safe in improving the management of the anemia associated with chronic disease. Despite the success of protein therapy various adverse effects have been reported. For example, patients can become EPO resistant and also hyporesponsive to the biologic. Furthermore, observations in clinical trials with patients that suffer from anemia due to chemotherapy indicated that rHuEPO protein increases lethality. Thus, there remains a need in the art for an EPO delivery approach for treating anemia that avoids the disadvantages of presently available delivery approaches.

Multiple sclerosis is an inflammatory disease in which the fatty myelin sheaths around the axons of the brain and spinal cord are damaged, leading to demyelination and scarring as well as a broad spectrum of signs and symptoms. Although much is known about the mechanisms involved in the disease process, the cause remains unknown. There is no known cure for multiple sclerosis. Treatments attempt to return function after an attack, prevent new attacks, and prevent disability. Multiple sclerosis medications can have adverse effects or be poorly tolerated, and many patients pursue alternative treatments, despite the lack of supporting scientific study.

Angioedema is the rapid swelling (edema) of the dermis, subcutaneous tissue, mucosa and submucosal tissues. Angioedema is classified as either acquired or hereditary. Acquired angioedema is usually caused by allergy and occurs together with other allergic symptoms and urticaria. It can also happen as a side-effect to certain medications, particularly ACE inhibitors. Hereditary angioedema (HAE) exists in three forms, all of which are caused by a genetic mutation that is inherited in an autosomal dominant form. They are distinguished by the underlying genetic abnormality. All forms of HAE lead to abnormal activation of the complement system, and all forms can cause swelling elsewhere in the body, such as the digestive tract. If HAE involves the larynx it can cause life-threatening asphyxiation Pulmonary hypertension is a disorder of the lung in which the pressure in the pulmonary artery (the blood vessel that leads from the heart to the lungs) rises above normal levels. Pulmonary arterial hypertension (PAH), is a disease characterized by increased pulmonary artery pressure and pulmonary vascular resistance. Harrison's Principles of Internal Medicine, 15th ed., pp. 1506-1507 (McGraw-Hill, 2001). Left untreated, PAH "usually has a dismal prognosis culminating in right ventricular failure and death." Ulrich, S., et al., Swiss Med. Wkly 137:73-82, 73 (2007).

Crohn's disease is a chronic inflammatory disorder of the gastrointestinal (GI) tract that is defined by relapsing and remitting episodes, with progression over time to complications of stricture, fistulas, or abscesses. In the U.S. Crohn's disease affects approximately one million individuals and the estimated annual disease-attributable direct costs of IBD (inflammatory bowel disease) have been estimated at $6.3 billion, with Crohn's disease estimated as contributing $3.6 billion of the costs in that figure. Azathioprine and 6-mercaptopurine are frequently prescribed for patients in whom first-line therapies fail—in particular, those who are dependent on or do not have a response to systemic corticosteroids. Approximately 40% of patients treated with azathioprine remain in remission at 1 year. Infliximab and other monoclonal antibodies targeting tumor necrosis factor (TNF) have shown efficacy in inducing and maintaining remission in patients with Crohn's disease, however in most guidelines and consensus articles, infliximab is considered the last medical resort before handing over the patient to the surgeon in the case of luminal disease. Hence, there continues to be a need for improved therapeutic methods for treating IBD and Crohn's disease.

IL-10 is a cytokine produced by activated Th2 cells, B cells, keratinocytes, monocytes, and macrophages. IL-10 inhibits the synthesis of a number of cytokines, including IFN-gamma, IL-2, IL-3, TNF and GM-CSF produced by activated macrophages and by helper T-cells. IL-10 is useful in promoting growth and differentiation of activated human B cells, inhibiting Th1 responses to prevent transplant rejection and T cell-mediated autoimmune diseases.

IL-10 (Interleukin-10) is an immunoregulatory cytokine that strongly downregulates the production of proinflammatory cytokines, and is involved in regulating intestinal inflammation. Clinical development of rhIL-10 (recombinant human IL-10) demonstrated a narrow therapeutic window and a pharmacokinetic profile leading to limited bioavailability for GI tissue. However, systemic adverse effects may not occur if IL-10 could be increased locally through in vivo cellular expression.

CF (Cystic Fibrosis) is an autosomal recessive disorder caused by defects in the gene for the CFTR (cystic fibrosis transmembrane conductance regulator) that result in abnormalities of chloride transport across epithelial cells on mucosal surfaces, because the CFTR protein functions as a chloride ion channel across the membrane of cells which produce mucus, sweat, saliva, tears, and digestive enzymes. The transport of chloride ions helps control the movement of water in tissues, which is necessary for the production of thin, freely flowing mucus (normal quantities of which are necessary for protecting the lining of the airways, digestive system, reproductive system, and other organs and tissues). The CFTR protein also regulates the function of other channels, such as those that transport positively charged particles called sodium ions across cell membranes. These channels are necessary for the normal function of organs such as the lungs and pancreas. Thus, CF affects exocrine gland function and causes a buildup of mucus in the lungs, pancreas, and other organs. This mucus obstruction can lead to infection and inflammation of the lungs, in addition to pancreatic enzyme insufficiency and problems with digestion.

Approximately 30,000 Americans have CF, making it one of the most common life-shortening inherited diseases in the United States, with a 37-year life expectancy of each CF patient. The most consistent aspect of therapy in CF has been maintaining quality of life and treating the lung damage caused by thick mucus and infection. More than 1,000 mutations in the CFTR gene have been identified in people with cystic fibrosis. Most of these mutations change a single amino acids in the CFTR protein or delete a small amount of DNA from the CFTR gene. The most common mutation, called delta F508, is a deletion of one amino acid at position 508 in the CFTR protein. The resulting abnormal channel breaks down shortly after it is made, so it never reaches the cell membrane to transport chloride ions. Disease-causing mutations in the CFTR gene alter the production, structure, or stability of the chloride channel. All of these changes prevent the channel from functioning properly, which impairs the transport of chloride ions and the movement of water into and out of cells. As a result, cells that line the passageways of the lungs, pancreas, and other organs produce mucus that is abnormally thick and sticky. The abnormal mucus obstructs the airways and glands, leading to the characteristic signs and symptoms of cystic fibrosis. Recently KALYDECO™ has been approved by the FDA as the first treatment targeting an underlying cause of CF (a G551D mutation in the CFTR gene). However, KALYDECO™ is not effective in treating patients having the most common CFTR mutation. Accordingly, there remains a need for improved treatment of CF.

Diabetes mellitus, often simply referred to as diabetes, is a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger). Metabolic syndrome is a combination of medical disorders that, when occurring together, increase the risk of developing cardiovascular disease and diabetes. It affects one in five people in the United States and prevalence increases with age. Some studies have shown the prevalence in the USA to be an estimated 25% of the population. Accordingly, there remains a need for improved treatment of diabetes mellitus.

Glucagon-like peptide-1 (GLP-1) is a potent antihyperglycemic hormone, inducing glucose-dependent stimulation of insulin secretion while suppressing glucagon secretion. GLP-1 appears to restore the glucose sensitivity of pancreatic β-cells, with the mechanism possibly involving the increased expression of GLUT2 and glucokinase. GLP-1 is also known to inhibit pancreatic β-cell apoptosis and stimulate the proliferation and differentiation of insulin-secreting β-cells. In addition, GLP-1 inhibits gastric secretion and motility. This delays and protracts carbohydrate absorption and contributes to a satiating effect.

Glucagon-like peptide-2 (GLP-2) is produced by the intestinal endocrine L cell and by various neurons in the central nervous system. Intestinal GLP-2 is co-secreted along with GLP-1 upon nutrient ingestion. When externally administered, GLP-2 produces a number of effects, including intestinal growth, enhancement of intestinal function, reduction in bone breakdown and neuroprotection.

Adiponectin is a protein hormone that modulates a number of metabolic processes, including glucose regulation and fatty acid catabolism. Adiponectin is exclusively secreted from adipose tissue (and also from the placenta in pregnancy) into the bloodstream and is very abundant in plasma relative to many hormones. Levels of the hormone are inversely correlated with body fat percentage in adults.

Human leptin is manufactured primarily in the adipocytes of white adipose tissue, and the level of circulating leptin is directly proportional to the total amount of fat in the body. Leptin acts on receptors in the hypothalamus of the brain where it inhibits appetite by (1) counteracting the effects of neuropeptide Y (a potent feeding stimulant secreted by cells in the gut and in the hypothalamus); (2) counteracting the effects of anandamide (another potent feeding stimulant that binds to the same receptors as THC), and (3) promoting the synthesis of α-MSH, an appetite suppressant.

SUMMARY OF THE INVENTION

The present invention provides a recombinant vector encoding protein(s) having the function(s) of one or more therapeutic proteins (e.g., immunomodulators), under the control of one or more promoters. In one embodiment, the one or more promoters are conditional. In another embodiment, the one or more promoters are constitutive. In another embodiment, the vector is an adenovirus vector encoding the protein(s) driven off a promoter that can be conditionally activated by provision of a soluble small molecule ligand such as diacylhydrazines (e.g., RG-115819, RG-115830 or RG-115932).

The present invention also provides a method of inducing, regulating, or enhancing erythropoietin (EPO) expression in a mammal, wherein the method comprises:

(a) administering intramuscularly to the mammal an adeno-associated virus wherein the virus comprises a polynucleotide encoding EPO; and (b) administering an activator ligand, wherein the adeno-associated virus further comprises a gene switch, wherein the gene switch comprises at least one transcription factor sequence operably linked to a promoter, wherein at least one transcription factor encoded by the at least one transcription factor sequence is a ligand-dependent transcription factor, wherein the adeno-associated virus further comprises a second promoter operably linked to the polynucleotide encoding EPO, and wherein the second promoter is activated by the at least one ligand-dependent transcription factor following administration of activator ligand.

The present invention also provides a vector comprising a polynucleotide encoding a gene switch, wherein the polynucleotide comprises (1) at least one transcription factor sequence which is operably linked to a promoter, wherein the at least one transcription factor sequence encodes a ligand-dependent transcription factor, and (2) a polynucleotide encoding one or more proteins operably linked to a promoter which is activated by the ligand-dependent transcription factor, wherein the one or more proteins is selected from the group consisting of a C1 esterase inhibitor, a kallikrein inhibitor, a bradykinin B2 receptor inhibitor, a prostaglandin synthase, a glucagon-like peptide-1 (GLP-1), a glucagon-like peptide-2 (GLP-2), adiponectin, leptin, and cystic fibrosis transmembrane conductance regulator (CFTR).

The present invention also provides a method of producing a population of cells expressing one or more proteins, wherein the method comprises modifying the cells with a recombinant vector conditionally expressing one or more proteins, wherein the vector comprises a polynucleotide encoding a gene switch, wherein the polynucleotide comprises (1) at least one transcription factor sequence operably linked to a promoter, wherein the at least one transcription factor sequence encodes a ligand-dependent transcription factor, and (2) a polynucleotide encoding one or more proteins linked to a promoter which is activated by the ligand-dependent transcription factor, wherein the one or more proteins are selected from the group consisting of a C1 esterase inhibitor, a kallikrein inhibitor, a bradykinin B2 receptor inhibitor, a prostaglandin synthase, a glucagon-like peptide-1 (GLP-1), a glucagon-like peptide-2 (GLP-2), adiponectin, leptin, and cystic fibrosis transmembrane conductance regulator (CFTR).

The present invention also provides a population of cells which have been modified with a recombinant vector conditionally expressing one or more proteins, wherein the vector comprises a polynucleotide encoding a gene switch, wherein the polynucleotide comprises (1) at least one transcription factor sequence operably linked to a promoter, wherein the at least one transcription factor sequence encodes a ligand-dependent transcription factor, and (2) a polynucleotide encoding one or more proteins selected from the group consisting of a C1 esterase inhibitor, a kallikrein inhibitor, a bradykinin B2 receptor inhibitor, a prostaglandin synthase, a glucagon-like peptide-1 (GLP-1), a glucagon-like peptide-2 (GLP-2), adiponectin, leptin, and cystic fibrosis transmembrane conductance regulator (CFTR).

The present invention also provides an in vitro engineered cell comprising a recombinant polynucleotide encoding a gene switch, wherein the polynucleotide encoding a gene switch comprises (1) at least one transcription factor sequence, wherein the at least one transcription factor sequence encodes a ligand-dependent transcription factor, operably linked to a promoter, and (2) a polynucleotide encoding one or more proteins linked to a promoter which is activated by the ligand-dependent transcription factor, wherein the one or more proteins is selected from the group consisting of a C1 esterase inhibitor, a kallikrein inhibitor, a bradykinin B2 receptor inhibitor, a prostaglandin synthase, a glucagon-like peptide-1 (GLP-1), a glucagon-like peptide-2 (GLP-2), adiponectin, leptin, and cystic fibrosis transmembrane conductance regulator (CFTR).

The present invention also provides a method for treating a disease in a mammal, comprising:

(a) administering a population of cells in vitro engineered to conditionally express one or more proteins; and (b) administering to the mammal a therapeutically effective amount of one or more activating ligands;

thereby inducing expression of the one or more proteins, wherein the one or more proteins is selected from the group consisting of a C1 esterase inhibitor, a kallikrein inhibitor, a bradykinin B2 receptor inhibitor, a prostaglandin synthase, a glucagon-like peptide-1 (GLP-1), a glucagon-like peptide-2 (GLP-2), adiponectin, leptin, and cystic fibrosis transmembrane conductance regulator (CFTR).

The present invention also provides a method for treating a disease in a mammal, comprising:

(a) administering to the mammal a vector for conditionally expressing one or more proteins, the vector comprising a polynucleotide encoding a gene switch, wherein the polynucleotide comprises (1) at least one transcription factor sequence which is operably linked to a promoter, wherein the at least one transcription factor sequence encodes a ligand-dependent transcription factor, and (2) a polynucleotide encoding one or more proteins operably linked to a promoter which is activated by the ligand-dependent transcription factor, wherein the vector is not contained within a cell; and (b) administering to the mammal a therapeutically effective amount of one or more activating ligands; thereby inducing expression of the one or more proteins and treating the disease, wherein the one or more proteins is selected from the group consisting of a C1 esterase inhibitor, a kallikrein inhibitor, a bradykinin B2 receptor inhibitor, a prostaglandin synthase, a glucagon-like peptide-1 (GLP-1), a glucagon-like peptide-2 (GLP-2), adiponectin, leptin, and cystic fibrosis transmembrane conductance regulator (CFTR).

The present invention also provides a method for treating multiple sclerosis in a mammal, comprising:

(a) administering to the mammal a vector for conditionally expressing one or more proteins, the vector comprising a polynucleotide encoding a gene switch, wherein the polynucleotide comprises (1) at least one transcription factor sequence which is operably linked to a promoter, wherein the at least one transcription factor sequence encodes a ligand-dependent transcription factor, and (2) a polynucleotide encoding one or more proteins operably linked to a promoter which is activated by the ligand-dependent transcription factor, wherein the vector is not contained within a cell; and (b) administering to the mammal a therapeutically effective amount of one or more activating ligands; thereby inducing expression of the one or more proteins and treating the disease, wherein the one or more proteins is selected from the group consisting of myelin basic protein (MBP) and interferon-beta (IFN-B).

A method for treating inflammatory bowel or Crohn's disease in a mammal, comprising:

(a) administering to the mammal a vector for conditionally expressing one or more proteins, the vector comprising a polynucleotide encoding a gene switch, wherein the polynucleotide comprises (1) at least one transcription factor sequence which is operably linked to a promoter, wherein the at least one transcription factor sequence encodes a ligand-dependent transcription factor, and (2) a polynucleotide encoding one or more proteins operably linked to a promoter which is activated by the ligand-dependent transcription factor, and (b) administering to the mammal a therapeutically effective amount of one or more activating ligands; thereby inducing expression of the one or more proteins and treating the disease, wherein one of the one or more proteins is interleukin-10 (IL-10).

DETAILED DESCRIPTION OF DRAWINGS

FIGS. 1A and 1B are line graphs that depict the potency of Ad-RTS-mIL12 with activator ligand in contralateral melanoma (B16F0) tumor in C57B16 mice. FIG. 1A depicts the volume of the treated tumor on the right flanks of the animals. FIG. 1B depicts the volume of the untreated tumor on the left flanks of the animals. Tumor sizes are shown as mean±SE.

DESCRIPTION OF SEQUENCE LISTING

Figure 1A:
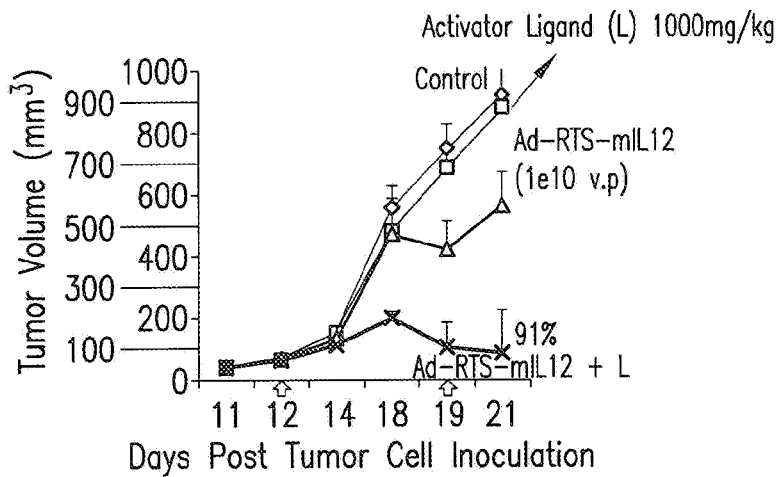

SEQ ID NO: 1 is an amino acid sequence of an ecdysone response element found in *Drosophila*.

SEQ ID NO: 2 is a nucleic acid sequence of an ecdysone response element found in *Drosophila melanogaster*.

SEQ ID NO: 3 is a nucleic acid sequence of an ecdysone response element found in *Drosophila melanogaster*.

SEQ ID NO: 4 is a DNA sequence of adenovirus vector comprising human IL-12 coding sequence: Ad-RTS-hIL-12 (SP1-RheoIL-12).

SEQ ID NO: 5 is a nucleic acid sequence for the vector (Ad-RTS-mIL-12).

SEQ ID NO: 6 is the amino acid sequence for human erythropoietin.

SEQ ID NO: 7 is the amino acid sequence for the *Choristoneura fumiferana* ecdysone receptor ligand binding domain.

SEQ ID NO: 8 is the nucleic acid sequence for the signal peptide sequence, human erythropoietin sequence, and stop codon.

SEQ ID NO: 9 is the nucleic acid sequence for human myelin basic protein.

SEQ ID NO: 10 is the amino acid sequence for human C1 esterase inhibitor.

SEQ ID NO: 11 is the amino acid sequence for ecallantide.

SEQ ID NO: 12 is the amino acid sequence for human prostaglandin synthetase 2.

SEQ ID NO: 13 is the amino acid sequence for human prostaglandin synthetase 1.

SEQ ID NO: 14 is the nucleic acid sequence for human prostaglandin synthetase 2.

SEQ ID NO: 15 is the nucleic acid sequence for human prostaglandin synthetase 1

SEQ ID NO: 16 is the amino acid sequence for human interferon-beta.

SEQ ID NO: 17 is the amino acid sequence for human GLP-1.

SEQ ID NO: 18 is the amino acid sequence for human GLP-2.

SEQ ID NO: 19 is the amino acid sequence for human adiponectin.

SEQ ID NO: 20 is the amino acid sequence for human leptin.

SEQ ID NO: 21 is the amino acid sequence for human CFTR.

SEQ ID NO: 22 is the amino acid sequence for human IL-10.

DETAILED DESCRIPTION OF INVENTION

Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference and understanding, and the inclusion of such definitions herein should not necessarily be construed to mean a substantial difference over what is generally understood in the art. Commonly understood definitions of molecular biology terms and/or methods and/or protocols can be found in Rieger et al., Glossary of Genetics: Classical and Molecular, 5th edition, Springer-Verlag: New York, 1991; Lewin, Genes V, Oxford University Press: New York, 1994; Sambrook et al., Molecular Cloning, A Laboratory Manual (3d ed. 2001) and Ausubel et al., Current Protocols in Molecular Biology (1994). As appropriate, procedures involving the use of commercially available kits and/or reagents are generally carried out in accordance with manufacturer's guidance and/or protocols and/or parameters unless otherwise noted.

The invention provides a recombinant vector encoding protein(s), under the control of one or more promoters. In one embodiment, the one or more promoters are conditional. In another embodiment, the one or more promoters are constitutive. In another embodiment, the vector is an adenovirus vector encoding the protein(s) driven off a promoter that can be conditionally activated by provision of a soluble small molecule ligand such as diacylhydrazines (e.g., RG-115819, RG-115830 or RG-115932). This vector allows for the control of expression of the protein(s) in cells.

In one embodiment, the polynucleotide coding for the one or more proteins having the functions of the immunomodulator is under control of the promoter of the gene switch and the polynucleotide coding for a protein having the function of IL-12 is under control of a constitutive promoter. In another embodiment, both the polynucleotide coding for protein(s) having the functions of the therapeutic proteins (e.g., immunomodulators) and the polynucleotide coding for a protein having the function of IL-12 are both under control of a multicistronic promoter of the gene switch. In another embodiment, the polynucleotide coding for a protein(s) having the function of the therapeutic proteins (e.g., immunomodulators) is under control of the promoter of the gene switch and the polynucleotide coding for a protein having the function of IL-12 is under control of a conditional promoter which is different than the gene switch promoter. In a further embodiment, the gene regulation system for the polynucleotide coding for the protein(s) having the function of the therapeutic proteins (e.g., immunomodulators) and the gene regulation system for the polynucleotide having the function of IL-12 are orthogonal. In a further embodiment, the gene regulation system for each polynucleotide coding for each protein is orthogonal.

In one embodiment, the invention also provides a treatment of cancer, such as, but not limited to, melanoma tumors, glioma tumors, renal cancer, and prostate cancers, as well as the cancers listed herein in Table 1. IL-12 gene therapy has demonstrated anti-tumor efficacy in animal model studies when applied as a recombinant cDNA vector (Faure et al., 1998; Sangro et al., 2005), but even more so, when applied in the context of gene-modified DC (Satoh et al., 2002; Svane et al., 1999; Tatsumi et al., 2003; Yamanaka et al., 2002). To date, however, human phase I trials of IL-12 gene therapy implementing plasmids or viral vectors have failed to achieve durable, objective clinical responses in the cancer setting (Heinzerling et al., 2005; Kang et al., 2001; Sangro et al., 2004; Triozzi et al., 2005) gene therapy as described herein provides a promising therapeutic modality.

In one embodiment, the invention provides a method for treating a tumor in a mammal, comprising the steps of:

(a) administering intratumorally to tumor microenvironments, in the area surrounding the tumor, or systemically a population of immune cells, TSCs or vectors of the invention (or a combination thereof), which are in vitro engineered to conditionally express one or more proteins having the function of a therapeutic protein (e.g., immunomodulator); and (b) administering to said mammal a therapeutically effective amount of an activating ligand;

thereby inducing expression of a protein having the function of the therapeutic protein (e.g., immunomodulator) and treating said tumor.

In another embodiment, the invention provides a method for treating a disease or disorder in a mammal, comprising the steps of:

(a) administering to said mammal a population of modified cells, which are modified to conditionally express one or more proteins having the function of an therapeutic protein (e.g., immunomodulator); and (b) administering to said mammal a therapeutically effective amount of an activating ligand;

thereby inducing expression of a protein having the function of the therapeutic protein (e.g., immunomodulator) and treating said disease or disorder.

In another embodiment, the invention provides a method for treating a disease or disorder in a mammal, comprising the steps of:

(a) administering to said mammal two or more populations of modified cells, which are modified to conditionally express one or more proteins having the function of a therapeutic protein (e.g., immunomodulator), wherein each population of modified cells expresses a different set of one or more therapeutic proteins (e.g., immunomodulators); and (b) administering to said mammal a therapeutically effective amount of one or more activating ligands;

thereby inducing expression of proteins having the function of the therapeutic proteins (e.g., immunomodulators) and treating said disease or disorder.

In another embodiment, the invention provides a method for treating a disease or disorder in a mammal, comprising the steps of:

(a) administering to said mammal a population of a modified cells, which are modified to conditionally express one or more proteins having the function of a therapeutic protein (e.g., immunomodulator) and a protein having the function of IL-12, wherein at least one of the proteins having the function of the therapeutic protein (e.g., immunomodulator) or IL-12 is under control of a conditional promoter that is activated by a ligand; and (b) administering to said mammal a therapeutically effective amount of the activating ligand;

thereby inducing expression of a protein having the function of the therapeutic protein (e.g., immunomodulator) and/or the protein having the function of IL-12 and treating said disease or disorder.

In another embodiment, the invention provides a method for treating a disease or disorder in a mammal, comprising the steps of:

(a) administering to said mammal two or more populations of modified cells, which are modified to conditionally express one or more proteins having the function of a therapeutic protein (e.g., immunomodulator) and a protein having the function of IL-12, wherein each population of modified cells expresses a different set of one or more proteins having the function of a therapeutic protein (e.g., immunomodulator), wherein at least one of the proteins having the function of the therapeutic protein (e.g., immunomodulator) or IL-12 is under control of a conditional promoter that is activated by a ligand; and (b) administering to said mammal a therapeutically effective amount of one or more activating ligands;

thereby inducing expression of a protein having the function of the therapeutic proteins (e.g., immunomodulators) and/or the protein having the function of IL-12 and treating said disease or disorder.

In one embodiment, the invention provides a vector for conditionally expressing protein(s) comprising a polynucleotide encoding a gene switch, wherein said polynucleotide encoding a gene switch comprises (1) at least one transcription factor sequence operably linked to a promoter, wherein said at least one transcription factor sequence encodes a ligand-dependent transcription factor, and (2) a polynucleotide encoding one or more proteins linked to a promoter which is activated by said ligand-dependent transcription factor.

In one embodiment, the vector of the invention conditionally expresses the protein. In another embodiment, the vector, e.g., adenoviral vector, conditionally expressing one or more proteins, further comprises a nucleic acid sequence encoding a signal peptide. The signal peptide can be codon-optimized. In other embodiments, the vector further comprises 5' untranslated region (UTR), 3' regulatory region, or both and improves protein expression and/or overall yield.

The invention further provides a method of producing a population of cells, expressing protein(s), by modifying (e.g., transfecting, electroporating, etc.) the cells with a recombinant vector conditionally expressing protein(s), wherein the vector comprises a polynucleotide encoding a gene switch, wherein said polynucleotide comprises (1) at least one transcription factor sequence operably linked to a promoter, wherein said at least one transcription factor sequence encodes a ligand-dependent transcription factor, and (2) a polynucleotide encoding one or more proteins linked to a promoter which is activated by said ligand-dependent transcription factor.

In some embodiments, the invention provides a method of increasing expression of a protein comprising generating the vector conditionally expressing one or more proteins and one or more regulatory sequence, wherein said one or more regulatory sequence improves expression of the protein.

The invention further provides a population of cells expressing protein(s), which has been modified (e.g., transfected, electroporated, etc.) with a recombinant vector conditionally the expressing protein(s), wherein the vector comprises a polynucleotide encoding a gene switch, wherein said polynucleotide comprises (1) at least one transcription factor sequence operably linked to a promoter, wherein said at least one transcription factor sequence encodes a ligand-dependent transcription factor, and (2) a polynucleotide encoding one or more proteins linked to the promoter which is activated by said ligand-dependent transcription factor.

In another embodiment, the invention provides a composition comprising two or more populations of cells of the present invention, wherein each population of cells in the composition expresses one or more proteins that are different from the one or more proteins expressed in the other population(s) of cells in the composition. In one embodiment, the composition contains two populations of cells. In another embodiment, the composition contains more than two populations of cells. In another embodiment, the composition contains three populations of cells. In another embodiment, the composition contains four populations of cells.

In another embodiment, the invention provides an in vitro engineered cell comprising a vector comprising a polynucleotide encoding a gene switch, wherein said polynucleotide comprises (1) at least one transcription factor sequence operably linked to a promoter, wherein said at least one transcription factor sequence encodes a ligand-dependent transcription factor, and (2) a polynucleotide encoding a protein linked to a promoter which is activated by said ligand-dependent transcription factor.

In another embodiment, the invention provides a composition comprising two or more populations of in vitro engineered cells, wherein each of the populations of in vitro engineered cells in the composition comprises a vector comprising a polynucleotide encoding a gene switch, wherein said polynucleotide comprises (1) at least one transcription factor sequence operably linked to a promoter, wherein said at least one transcription factor sequence encodes a ligand-dependent transcription factor, and (2) a polynucleotide encoding a protein linked to a promoter which is activated by said ligand-dependent transcription factor, and wherein each population of in vitro engineered cells in the composition expresses one or more proteins that are different from the one or more proteins expressed in the other population(s) of in vitro engineered cell in the composition.

In another embodiment, vectors and methods of the present invention are used to treat diabetes mellitus, metabolic disease, metabolic disorder and metabolic syndrome. In one embodiment, the vector comprises a polynucleotide sequence encoding GLP-1, GLP-2, adiponectin or leptin, or a fragment thereof of GLP-1, GLP-2, adiponectin or leptin. In another embodiment, the vector comprises a polynucleotide sequence encoding human GLP-1, GLP-2, adiponectin or leptin, or a fragment thereof of human GLP-1, GLP-2, adiponectin or leptin.

In another embodiment, vectors and methods of the present invention are used to treat inflammatory bowel disease (IBD) and/or Crohn's disease. In one embodiment, the vector comprises a polynucleotide sequence encoding IL-10, or a fragment thereof. In another embodiment, the vector comprises a polynucleotide sequence encoding human IL-10, or a fragment thereof.

In one embodiment, the present invention encompasses a vector or vectors comprising constitutive, inducible, or tissue-specific promoters which allow for in vivo production of the cystic fibrosis transmembrane conductance regulator (CFTR) to replace or supplement the deficient or mutant CFTR protein. Thus, in one embodiment, vectors and methods of the present invention are used to treat CF (Cystic Fibrosis). In one embodiment, the vector comprises a polynucleotide sequence encoding a normal (non-mutatant) CFTR, or a functional (bioactive/ion transport capable) fragment thereof. In another embodiment, the vector comprises a polynucleotide sequence encoding a normal human CFTR (non-mutatant CFTR), or a functional (bioactive/ion transport capable) fragment thereof.

The invention also provides a pharmaceutical composition comprising a population of cells, as described herein or a composition suitable for direct injection of the expression vectors absent a population of cells, i.e., directly injected.

The present invention also provides a vector for conditionally expressing a prostaglandin synthase, the vector comprising a polynucleotide encoding a gene switch, wherein the polynucleotide comprises (1) at least one transcription factor sequence which is operably linked to a promoter, wherein the at least one transcription factor sequence encodes a ligand-dependent transcription factor, and (2) a polynucleotide encoding a prostaglandin synthase. The present invention also provides a method for treating pulmonary hypertension comprising administering the vector.

IL-12 is a cytokine that can act as a growth factor for activated T and NK cells, enhance the lytic activity of NK/lymphokine-activated Killer cells, and stimulate the production of IFN-gamma by resting peripheral blood mononuclear cells (PBMC). The polynucleotide sequences of IL-12 are available from public databases as accession numbers NM_000882 (human IL12A); NM_02187 (human IL12B); NM_008351 (mouse IL12a); NM_008352 (mouse IL12b); NM_213588 (chicken IL12A); NM_4213571 (chicken IL12B); NM_053390 (rat IL12a); and NM_022611 (rat IL12b), sequences of which are incorporated by reference herein.

The amino acid sequences of interleukin 12 (IL-12) are available from public databases as accession numbers NP_000873 (human IL12A); NP_002178 (human IL12B); NP_032377 (mouse IL12a); NP_032378 (mouse IL12b); NP_998753 (chicken IL12A); NP_998736 (chicken IL12B); NP_445842 (rat IL12a); and NP_072133 (rat IL12b), sequences of which are incorporated by reference herein.

In one embodiment, the IL-12 gene is the wild type mouse IL-12 sequence. In another embodiment, the sequence is at least 85% identical to wild type mouse IL-12, e.g., at least 90%, 95%, or 99% identical to wild type mouse IL-12. In a further embodiment, the IL-12 gene sequence encodes the mouse IL-12 polypeptide. In another embodiment, the gene encodes a polypeptide that is at least 85% identical to wild type mouse IL-12, e.g., at least 90%, 95%, or 99% identical to wild type mouse IL-12.

Myelin basic protein (MBP) is a protein believed to be important in the process of myelination of nerves in the central nervous system. The protein encoded by the classic MBP gene is a major constituent of the myelin sheath of oligodendrocytes and Schwann cells in the nervous system. MBP-related transcripts are also present in the bone marrow and the immune system. Amino acid and polynucleotide sequences for MBP are available as accession numbers NM_001025081 and NP_001020252 (human) and NM_001025245 and NP_001020416 (mouse).

In one embodiment, the MBP is the wild type human MBP sequence. In another embodiment, the sequence is at least 85% identical to wild type human MBP, e.g., at least 90%, 95%, or 99% identical to wild type human MBP.

C1 esterase inhibitor (C1-inhibitor, C1-inh) is a protease inhibitor belonging to the serpin superfamily. Its main function is the inhibition of the complement system to prevent spontaneous activation. C1 esterase inhibitor is an acute-phase protein that circulates in blood at levels of around 0.25 g/L, and its level rises approximately 2-fold during inflammation. C1 esterase inhibitor irreversibly binds to and inactivates C1r and C1s proteases in the C1 complex of classical pathway of complement. MASP-1 and MASP-2 proteases in MBL complexes of the lectin pathway are also inactivated. C1 esterase inhibitor prevents the proteolytic cleavage of later complement components C4 and C2 by C1 and MBL. C1 esterase inhibitor also inhibits proteases of the fibrinolytic, clotting, and kinin pathways. C1 esterase inhibitor is an inhibitor of plasma kallikrein. The amino acid sequence for human C1 esterase inhibitor is found at GenBank ADU87625.1, Accession GU727623.1).

In one embodiment, the C1 esterase inhibitor is the wild type human C1 esterase inhibitor sequence. In another embodiment, the sequence is at least 85% identical to wild type human MBP, e.g., at least 90%, 95%, or 99% identical to wild type human C1 esterase inhibitor.

Ecallantide (trade name Kalbitor, investigational name DX-88) is an inhibitor of the protein kallikrein, and is useful in the treatment of hereditary angioedema (HAE) and in the prevention of blood loss in cardiothoracic surgery. The amino acid sequence for ecallantide is found in U.S. Patent Publication NO. 2007/0213275, which is incorporated by reference in its entirety.

In one embodiment, the ecallantide is the wild type human ecallantide sequence. In another embodiment, the sequence is at least 85% identical to wild type human MBP, e.g., at least 90%, 95%, or 99% identical to wild type human ecallantide.

In one embodiment, the GLP-1 is the wild type human GLP-1 sequence, in another embodiment, the sequence is at least 85% identical to wild type human GLP-1. e.g., at least 90%, 95%, or 99% identical to wild type human GLP-1.

In one embodiment, the GLP-2 is the wild type human GLP-2 sequence. In another embodiment, the sequence is at least 85% identical to wild type human GLP-2, e.g., at least 90%, 95%, or 99% identical to wild type human GLP-2.

In one embodiment, the adiponectin is the wild type human adiponectin sequence. In another embodiment, the sequence is at least 85% identical to wild type human adiponectin, e.g., at least 90%, 95%, or 99% identical to wild type human adiponectin.

In one embodiment, the leptin is the wild type human leptin sequence, in another embodiment, the sequence is at least 85% identical to wild type human leptin, e.g., at least 90%, 95%, or 99% identical to wild type human leptin.

In one embodiment, the IL-10 is the wild type human IL-10 sequence. In another embodiment, the sequence is at least 85% identical to wild type human. IL-10, e.g., at least 90%, 95%, or 99% identical to wild type human IL-10.

The term "isolated" for the purposes of the invention designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

The term "purified," as applied to biological materials does not require the material to be present in a form exhibiting absolute purity, exclusive of the presence of other compounds. It is rather a relative definition.

"Nucleic acid," "nucleic acid molecule," "oligonucleotide," "nucleotide," and "polynucleotide" are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes, but is not limited to, cDNA, genomic DNA, plasmid DNA, synthetic DNA, and semi-synthetic DNA.

The term "fragment," as applied to polynucleotide sequences, refers to a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000, 1500, 2000, 3000, 4000, 5000, or more consecutive nucleotides of a nucleic acid according to the invention.

As used herein, an "isolated nucleic acid fragment" refers to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to a polynucleotide comprising nucleotides that encode a functional molecule including functional molecules produced by transcription only (e.g., a bioactive RNA species) or by transcription and translation (e.g., a polypeptide). The term "gene" encompasses cDNA and genomic DNA nucleic acids. "Gene" also refers to a nucleic acid fragment that expresses a specific RNA, protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. For example, the interleukin-12 (IL-12) gene encodes the IL-12 protein. IL-12 is a heterodimer of a 35-kD subunit (p35) and a 40-kD subunit (p40) linked through a disulfide linkage to make fully functional IL-12p70. The IL-12 gene encodes both the p35 and p40 subunits.

"Heterologous DNA" refers to DNA not naturally located in the cell, or in a chromosomal site of the cell. The heterologous DNA may include a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook et al. in *Molecular Cloning: A Laboratory Manual*, Second Edition, Cold Spring Harbor Laboratory Press, Cold Spring Harbor (1989), particularly Chapter 11 and Table 11.1 therein). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the invention also includes isolated nucleic acid fragments that are complementary to the complete sequences as disclosed or used herein as well as those substantially similar nucleic acid sequences.

In one embodiment of the invention, polynucleotides are detected by employing hybridization conditions comprising a hybridization step at $T_m$ of 55° C., and utilizing conditions as set forth above. In other embodiments, the $T_m$ is 60° C., 63° C., or 65° C.

Post-hybridization washes also determine stringency conditions. One set of conditions uses a series of washes starting with 6×SSC, 0.5% SDS at room temperature for 15 minutes (min), then repeated with 2×SSC, 0.5% SDS at 45° C. for 30 min, and then repeated twice with 0.2×SSC, 0.5% SDS at 50° C. for 30 min. One set of stringent conditions uses higher temperatures in which the washes are identical to those above except for the temperature of the final two 30 min washes in 0.2×SSC, 0.5% SDS is increased to 60° C. Another set of highly stringent conditions uses two final washes in 0.1×SSC, 0.1% SDS at 65° C.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the invention are those nucleic acid fragments whose DNA sequences are at least about 70%, 80%, 90% or 95% identical to the DNA sequence of the nucleic acid fragments reported herein.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In one embodiment of the invention, polynucleotides are detected by employing hybridization conditions comprising a hybridization step in less than 500 mM salt and at least 37° C., and a washing step in 2×SSPE at a temperature of at least 63° C. In another embodiment, the hybridization conditions comprise less than 200 mM salt and at least 37° C. for the hybridization step. In a further embodiment, the hybridization conditions comprise 2×SSPE and 63° C. for both the hybridization and washing steps.

In another embodiment, the length for a hybridizable nucleic acid is at least about 10 nucleotides. Preferably a minimum length for a hybridizable nucleic acid is at least about 15 nucleotides; e.g., at least about 20 nucleotides; e.g., at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a short nucleic acid that is hybridizable to a genomic DNA molecule, a cDNA molecule, a plasmid DNA or an mRNA molecule. Oligonucleotides can be labeled, e.g., With $^{32}$P-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, for DNA sequencing, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" refers to an oligonucleotide that hybridizes to a target nucleic acid sequence to create a double stranded nucleic acid region that can serve as an initiation point for DNA synthesis under suitable conditions. Such primers may be used in a polymerase chain reaction or for DNA sequencing.

"Polymerase chain reaction" is abbreviated PCR and refers to an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and refers to an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" or "coding region" refers to a double-stranded DNA sequence that encodes a polypeptide and can be transcribed and translated into a polypeptide in a cell, ex vivo, in vitro or in vivo when placed under the control of suitable regulatory sequences. "Suitable regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in an eukaryotic cell, a polyadenylation signal and transcription termination sequence will usually be located 3' to the coding sequence.

"Open reading frame" is abbreviated ORF and refers to a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (← →) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other poly-nucleotide, whereby the direction of transcription of each polynucleotide proceeds toward the other polynucleotide. The term "tail-to-tail" may be abbreviated (3')-to-(3') and may also be indicated by the symbols (→ ←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→ →) or (5'→3'5'→3').

The term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to a reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" are used interchangeably and refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" includes both viral and nonviral vehicles for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. Another example of vectors that are useful in the invention is the UltraVector™ Production System (Intrexon Corp., Blacksburg, Va.) as described in WO 2007/038276 and US 2004/185556. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include, but are not limited to, retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" refers to a "replicon," which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector"). Cloning vectors may comprise one or more sequences that can be used for selection of cells comprising the vector and/or one or more multiple cloning sites for insertion of sequences of interest.

The term "expression vector" refers to a vector, plasmid or vehicle designed to enable the expression of an inserted nucleic acid sequence. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving expression of these genes can be used in an expression vector, including but not limited to, viral promoters, bacterial promoters, animal promoters, mammalian promoters, synthetic promoters, constitutive promoters, tissue specific promoters, pathogenesis or disease related promoters, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TP1, alkaline phosphatase promoters (useful for expression in *Saccharomyces*); AOX1 promoter (useful for expression in *Pichia*);

β-lactamase, lac, ara, tet, trp, $1P_L$, $1P_R$, T7, tac, and trc promoters (useful for expression in *Escherichia coli*); light regulated-, seed specific-, pollen specific-, ovary specific-, cauliflower mosaic virus 35S, CMV 35S minimal, cassava vein mosaic virus (CsVMV), chlorophyll a/b binding protein, ribulose 1,5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art including, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus 1E1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Vectors may be introduced into the desired host cells, by methods known in the art, e.g., transfection, electroporation, microinjection, transduction, cell fusion, DEAF dextran, calcium phosphate precipitation, lipofection (lysosome fusion), use of a gene gun, or a DNA vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311).

A vector of the invention may also be administered to a subject by any route of administration, including, but not limited to, intramuscular administration.

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Felgner et al., *Proc. Natl. Acad. Sci. USA.* 84:7413 (1987); Mackey et al., *Proc. Natl. Acad. Sci. USA* 85:8027 (1988); and Ulmer et al., *Science* 259:1745 (1993)). The use of cationic lipids may promote encapsulation of negatively charged nucleic acids, and also promote fusion with negatively charged cell membranes (Felgner et al., *Science* 337:387 (1989)). Particularly useful lipid compounds and compositions for transfer of nucleic acids are described in WO95/18863, WO96/17823 and U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey et al. 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., *Hum. Gene Ther.* 3:147 (1992 and Wu et al., *J. Biol. Chem.* 262:4429 (1987)).

The term "transfection" refers to the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

In addition, the recombinant vector comprising a polynucleotide according to the invention may include one or more origins for replication in the cellular hosts in which their amplification or their expression is sought, markers or selectable markers.

The term "selectable marker" refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include:

luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter" and "promoter sequence" are used interchangeably and refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths may have identical promoter activity.

In any of the vectors of the present invention, the vector optionally comprises a promoter disclosed herein. In one embodiment, the promoter is a promoter listed in Table 1 herein.

In any of the vectors of the present invention, the vector optionally comprises a tissue-specific promoter. In one embodiment, the tissue-specific promoter is a tissue specific promoter disclosed herein. In another embodiment, the tissue-specific promoter is a tissue specific promoter listed in Table 2 herein.

The promoter sequence is typically bounded at its 3' terminus by the transcription initiation site and extends upstream (5' direction) to include the minimum number of bases or elements necessary to initiate transcription at levels detectable above background. Within the promoter sequence is found a transcription initiation site (conveniently defined for example, by mapping with nuclease S1), as well as protein binding domains (consensus sequences) responsible for the binding of RNA polymerase.

"Therapeutic switch promoter" ("TSP") refers to a promoter that controls expression of a gene switch component. See, for example, US 2009/0098055, which is hereby incorporated by reference in its entirety. Gene switches and their various components are described in detail elsewhere herein. In certain embodiments a TSP is constitutive, i.e., continuously active. A constitutive TSP may be either constitutive-ubiquitous (i.e., generally functions, without the need for additional factors or regulators, in any tissue or cell) or constitutive-tissue or cell specific (i.e., generally functions, without the need for additional factors or regulators, in a specific tissue type or cell type). In certain embodiments a TSP of the invention is activated under conditions associated with a disease, disorder, or condition. In certain embodiments of the invention where two or more TSPs are involved the promoters may be a combination of constitutive and activatable promoters. As used herein, a "promoter activated under conditions associated with a disease, disorder, or condition" includes, without limitation, disease-specific promoters, promoters responsive to particular physiological, developmental, differentiation, or pathological conditions, promoters responsive to specific biological molecules, and promoters specific for a particular tissue or cell type associated with the disease, disorder, or condition, e.g. tumor tissue or malignant cells. TSPs can comprise the sequence of naturally occurring promoters, modified sequences derived from naturally occurring promoters, or synthetic sequences (e.g., insertion of a response element into a minimal promoter sequence to alter the responsiveness of the promoter).

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" refer to DNA regulatory sequences, such as promoters, enhancers, terminators, and the like, that provide for the expression of a coding sequence in a host cell. In eukaryotic cells, polyadenylation signals are control sequences.

The term "response element" refers to one or more cis-acting DNA elements which confer responsiveness on a promoter mediated through interaction with the DNA-binding domains of a transcription factor. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element is incorporated. The DNA binding domain of the transcription factor binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANTGAC/ACYY (SEQ ID NO: 1) (see Cherbas et. al., Genes Dev. 5:120 (1991)); AGGTCAN$_{(n)}$AGGTCA (SEQ ID NO: 2), where N$_{(n)}$ can be one or more spacer nucleotides (see D'Avino et al., Mol. Cell. Endocrinol. 113:1 (1995)); and GGGTTGAATGAATTT (SEQ ID NO: 3) (see Antoniewski et al., Mol. Cell Biol. 14:4465 (1994)).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein refers to the transcription and stable accumulation of sense (mRNA) or antisense RNA derived from a nucleic acid or polynucleotide. Expression may also refer to translation of mRNA into a protein or polypeptide.

The terms "cassette," "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and a ligand-dependent transcription factor-based system which, in the presence of one or more ligands, modulates the expression of a gene into which the response element and promoter are incorporated. The term "a polynucleotide encoding a gene switch" refers to the combination of a response element associated with a promoter, and a polynucleotide encoding a ligand-dependent transcription factor-based system which, in the presence of one or more ligands, modulates the expression of a gene into which the response element and promoter are incorporated.

The therapeutic switch promoters of the invention may be any promoter that is useful for treating, ameliorating, or preventing a specific disease, disorder, or condition. Examples include, without limitation, promoters of genes that exhibit increased expression only during a specific disease, disorder, or condition and promoters of genes that exhibit increased expression under specific cell conditions (e.g., proliferation, apoptosis, change in pH, oxidation state, oxygen level). In some embodiments where the gene switch comprises more than one transcription factor sequence, the specificity of the therapeutic methods can be increased by combining a disease- or condition-specific promoter with a tissue- or cell type-specific promoter to limit the tissues in which the therapeutic product is expressed. Thus, tissue- or cell type-specific promoters are encompassed within the definition of therapeutic switch promoter.

As an example of disease-specific promoters, useful promoters for treating cancer include the promoters of oncogenes, including promoters for treating anemia. Examples of classes of oncogenes include, but are not limited to, growth factors, growth factor receptors, protein kinases, programmed cell death regulators and transcription factors. Specific examples of oncogenes include, but are not limited to, sis, erb B, erb B-2, ras, abl, myc and bcl-2 and TERT. Examples of other cancer-related genes include tumor associated antigen genes and other genes that are overexpressed in neoplastic cells (e.g., MAGE-1, carcinoembryonic antigen, tyrosinase, prostate specific antigen, prostate specific membrane antigen, p53, MUC-1, MUC-2, MUC-4, HER-2/neu, T/Tn, MART-1, gp100, GM2, Tn, sTn, and Thompson-Friedenreich antigen (TF)).

Examples of promoter sequences and other regulatory elements (e.g., enhancers) that are known in the art and are useful as therapeutic switch promoters in the present invention are disclosed in the references listed in Tables 1 and 2, along with the disease/disorder (Table 1) or tissue specificity (Table 2) associated with each promoter. The promoter sequences disclosed in the U.S. patents and published U.S. applications cited in the Tables and the sequences disclosed therein are herein incorporated by reference in their entirety.

The polynucleotide encoding any of the proteins listed in Table 1 may also be expressed using a vector of the present invention with a promoter that is not a therapeutic promoter.

TABLE 1

| Promoter Sequence | Disease/Disorder | Patent/Published Application No. |
|---|---|---|
| Her-2/neu (ERBB2/c-erbB-2) | cancer | 5,518,885 |
| Osteocalcin | calcified tumors | 5,772,993 |
| stromelysin-1 | cancer | 5,824,794 |
| prostate specific antigen | prostate cancer | 5,919,652 |
| human sodium-iodide symporter | thyroid carcinoma | 6,015,376 |
| H19, IF-1, IGF-2 | cancer | 6,306,833 |
| thymosin β15 | breast, pancreatic, prostate cancer | 6,489,463 |
| T cell factor | cancer | 6,608,037 |
| cartilage-derived retinoic acid-sensitive protein | chondrosarcoma, mammary tumor | 6,610,509 |
| Insulin | pancreatic cancer | 6,716,824 |
| PEG-3 | cancer | 6,737,523 |
| telomerase reverse transcriptase | cancer | 6,777,203 |
| melanoma differentiation associated gene-7 | cancer | 6,841,362 |
| Prostasin | cancer | 6,864,093 |
| telomerase catalytic subunit; cyclin-A | cancer | 6,936,595 |
| midkine; c-erbB-2 | cancer | 7,030,099 |
| prostate-specific membrane antigen | prostate cancer | 7,037,647 |
| p51 | cancer | 7,038,028 |
| telomerase RNA | cancer | 7,084,267 |
| prostatic acid phosphatase | prostate cancer | 7,094,533 |
| PCA3$_{dd3}$ | prostate cancer | 7,138,235 |
| DF3/MUC1 | cancer | 7,247,297 |
| hex II | cancer | 2001/0011128 |
| cyclooxygenase-2 | cancer | 2002/0107219 |
| super PSA | prostate cancer | 2003/0078224 |
| skp2 | cancer | 2003/0109481 |
| PRL-3 | metastatic colon cancer | 2004/0126785 |
| CA125/M17S2 | ovarian cancer | 2004/0126824 |
| IAI.3B | ovarian cancer | 2005/0031591 |
| CRG-L2 | liver cancer | 2005/0124068 |
| TRPM4 | prostate cancer | 2006/0188990 |
| RTVP | glioma | 2006/0216731 |
| TARP | prostate cancer, breast cancer | 2007/0032439 |
| telomere reverse transcriptase | cancer | 2007/0059287 |
| A4 amyloid protein | Alzheimer's disease | 5,151,508 |
| amyloid β-protein precursor | Alzheimer's disease | 5,643,726 |
| precursor of the Alzheimer's Disease A4 amyloid protein | Alzheimer's disease | 5,853,985 |
| neuropeptide FF | CNS disorders | 6,320,038 |
| endoplasmic reticulum stress elements | stress | 7,049,132 |
| urocortin II | psychopathologies | 7,087,385 |
| tyrosine hydroxylase | neurological disorders | 7,195,910 |
| complement factor 3; serum amyloid A3 | inflammation | 5,851,822 |
| tissue inhibitor of metalloproteinase-3 (TIMP-3) | rheumatism, cancer, autoimmune disease, inflammation | 5,854,019 |
| p75 tumor necrosis factor receptor | autoimmune disease | 5,959,094 |
| tumor necrosis factor-α | inflammation | 6,537,784 |
| peroxisome proliferator activated receptor/IIA-1 nonpancreatic secreted phospholipase A2 | inflammation | 6,870,044 |
| SOCS-3 | growth disorders, autoimmune disease, inflammation | 2002/0174448 |
| SR-BI | lipid disorders | 5,965,790 |
| Ob | obesity | 5,698,389 |
| site-1 protease | obesity, diabetes | 7,045,294 |
| TIGR | glaucoma | 7,138,511 |
| VL30 | anoxia | 5,681,706 |
| excitatory amino acid | nervous system | 2004/0171108 |

TABLE 1-continued

| Promoter Sequence | Disease/Disorder | Patent/Published Application No. |
|---|---|---|
| transporter-2 | ischemia | |
| MDTS9 | renal failure | 2006/0014931 |
| LIM, pyrroline 5-carboxylate eductase, SIM2 | prostate disorders | 2006/0134688 |
| Bax | apoptosis | 5,744,310 |
| Fas | apoptosis | 5,888,764 |
| bbc3 | apoptosis | 7,202,024 |
| PINK-1 | PI-3 kinase/Akt pathway disorders | 2006/0228776 |

TABLE 2

| Promoter Sequence | Tissue Specificity | Patent/Published Application No. |
|---|---|---|
| troponin T | skeletal muscle | 5,266,488 |
| myoD | muscle | 5,352,595 |
| Actin | muscle | 5,374,544 |
| smooth muscle 22α | arterial smooth muscle | 5,837,534 |
| Utrophin | muscle | 5,972,609 |
| Myostatin | muscle | 6,284,882 |
| smooth muscle myosin heavy chain | smooth muscle | 6,780,610 |
| cardiac ankyrin repeat protein | cardiac muscle | 7,193,075 |
| MLP | muscle | 2002/0042057 |
| Smoothelin | smooth muscle | 2003/0157494 |
| MYBPC3 | cardiomyocytes | 2004/0175699 |
| Tα1 α-tubulin | neurons | 5,661,032 |
| intercellular adhesion molecule-4 (ICAM-4) | neurons | 5,753,502 |
| γ-aminobutyric acid type A receptor β1 subunit | hippocampus | 6,066,726 |
| neuronal nicotinic acetylcholine receptor β2-subunit | neurons | 6,177,242 |
| presenilin-1 | neurons | 6,255,473 |
| calcium-calmodulin-dependent kinase IIα | forebrain | 6,509,190 |
| CRF$_{2\alpha}$ receptor | brain | 7,071,323 |
| nerve growth factor | neurons | 2003/159159 |
| GLP-2 receptor | gut, brain | 2002/0045173 |
| type I transglutaminase | keratinocytes | 5,643,746 |
| K14 | keratinocytes | 6,596,515 |
| stearoyl-CoA desaturase | skin | 2002/0151018 |
| Megsin | renal cells | 6,790,617 |
| Prolactin | pituitary | 5,082,779 |
| GDF-9 | ovary, testes, hypothalamus, pituitary, placenta | 7,227,013 |
| PSP94 | prostate | 2003/0110522 |
| NRL; NGAL | mammary gland | 5,773,290 |
| long whey acidic protein | mammary gland | 5,831,141 |
| mammary associated amyloid A | mammary ductal epithelial cells | 2005/0107315 |
| endothelin-1 | endothelial cells | 5,288,846 |
| Serglycin | hematopoietic cells | 5,340,739 |
| platelet-endothelial cell adhesion molecule-1 (PECAM-1) | platelets, leukocytes, endothelial cells | 5,668,012 |
| Tie receptor tyrosine kinase | endothelial cells, bone marrow | 5,877,020 |
| KDR/flk-1 | endothelial cells | 5,888,765 |
| Endoglin | endothelial cells | 6,103,527 |
| CCR5 | myeloid and lymphoid cells | 6,383,746 |
| CD11d | myeloid cells | 6,881,834 |
| platelet glycoprotein IIb | hematopoietic cells | 6,884,616 |
| preproendothelin-1 | endothelial cells | 7,067,649 |
| interleukin-18 binding protein | mononuclear cells | 2006/0239984 |
| CD34 | hematopoietic stem cells | 5,556,954 |
| Tec tyrosine kinase | hematopoietic stem cells, liver | 6,225,459 |

Other genes that exhibit changes in expression levels during specific diseases or disorders and therefore may provide promoters that are useful in the present invention include, without limitation, the genes (along with the associated disease/disorder) listed in Table 3.

TABLE 3

| Gene | Disease/Disorder | Patent/Published Application No. |
|---|---|---|
| MLH1, MSH2, MSH6, PMS1, APC | Colorectal cancer | 7,148,016 |
| LEF-1 | Colon cancer | 2002/0169300 |
| F$_2$ receptor | Colon cancer | 2002/0187502 |
| TGF-β type II receptor | Colon cancer | 2004/0038284 |
| EYA4 | Colon cancer | 2005/0003463 |
| PCA3 | Prostate cancer | 7,138,235 |
| K2 | Prostate cancer | 6,303,361 |
| PROST 03 | Prostate cancer metastases | 2002/0009455 |
| PCAM -1 | Prostate cancer | 2002/0042062 |
| PC-ADM-1 | Prostate cancer | 2003/0100033 |
| PCA3$_{dd3}$ | Prostate cancer | 2003/0165850 |
| PCAV | Prostate cancer | 2006/0275747 |
| PAcP | Androgen-insensitive prostate cancer | 2006/0294615 |
| SEQ ID NO: 1 of the U.S. Pat. No. 5,866,329, incorporated by reference herein | Liver cancer | 5,866,329 |
| SEQ ID NOS: 1, 3 of the U.S. patent application publication 2002/0115094, incorporated by reference herein | Hepatocellular cancer | 2002/6115094 |
| SEQ ID NO: 1 of the patent U.S. application publication 2005/0037372, incorporated by reference herein | Hepatocellular carcinoma | 2005/0037372 |
| ATB$_0$ | Hepatocellular carcinoma | 2006/0280725 |
| SEQ ID NOS: 1, 3 of the U.S. patent application publication 2007/0042420 | Liver cancer | 2007/0042420 |
| CSA-1 | Chondrosarcoma | 2001/0016649 |
| SEQ ID NOS: 1-15 of the U.S. patent application publication 2001/0016651, incorporated by reference herein | Pancreatic cancer | 2001/0016651 |
| SEQ ID NOS: 1-15 of the U.S. patent application publication 2003/0212264, incorporated by reference herein | Pancreatic cancer | 2003/0212264 |
| SYG972 | Breast cancer | 2002/0055107 |
| Urb-ctf | Breast cancer | 2003/0143546 |
| BCU399 | Breast cancer | 2003/0180728 |
| TBX2 | Breast cancer | 2004/0029185 |
| Cyr61 | Breast cancer | 2004/0086504 |
| DIAPH3 | Breast cancer | 2005/0054826 |
| SEQ ID NOS: 1-24 of the U.S. patent application publication 2007/0134669, incorporated by reference herein | Breast cancer | 2007/0134669 |
| Human aspartyl (asparaginyl) beta-hydroxylase | CNS cancer | 2002/0102263 |
| BEHAB | CNS cancer | 2003/0068661 |
| IL-8 | Kaposi's Sarcoma | 2003/0096781 |
| SEQ ID NOS: 1-278 of the U.S. patent application | Hematological cancers | 2002/0198362 |

TABLE 3-continued

| Gene | Disease/Disorder | Patent/Published Application No. |
|---|---|---|
| publication 2002/0198362, incorporated by reference herein | | |
| BLSA | B-cell cancer | 2003/0147887 |
| BP1 | Leukemia | 2003/0171273 |
| DAP-kinase, HOXA9 | Non-small cell lung cancer | 2003/0224509 |
| ARP | Clear cell renal carcinoma, inflammatory disorders | 2004/0010119 |
| Nbk | Renal cancer | 2005/0053931 |
| CD43 | Ovarian cancer | 2006/0216231 |
| SEQ ID NOS: 1-84 of the U.S. patent application publication 2007/0054268, incorporated by reference herein | Ovarian cancer | 2007/0054268 |
| β7-hcG, β6-hCG, β6e-hCG, β5-hCG, β8-hcG, β3-hCG | Uterine tumors | 2006/0292567 |
| MTA1s | Hormone insensitive cancer | 2006/0204957 |
| Old-35, Old-64 | Tumor proliferation | 2003/0099660 |
| LAGE-1 | Cancer | 6,794,131 |
| CIF150/hTAFH$_{II}$150 | Cancer | 6,174,679 |
| P65 oncofetal protein | Cancer | 5,773,215 |
| Telomerase | Cancer | 2002/0025518 |
| CYP1B1 | Cancer | 2002/0052013 |
| 14-3-3σ | Cancer | 2002/0102245 |
| NES1 | Cancer | 2002/0106367 |
| CAR-1 | Cancer | 2002/0119541 |
| HMGI, MAG | Cancer | 2002/0120120 |
| ELL2 | Cancer | 2002/0132329 |
| Ephrin B2 | Cancer | 2002/0136726 |
| WAF1 | Cancer | 2002/0142442 |
| CIF130 | Cancer | 2002/0143154 |
| C35 | Cancer | 2002/0155447 |
| BMP2 | Cancer | 2002/0159986 |
| BUB3 | Cancer | 2002/0160403 |
| Polymerase kappa | Cancer | 2003/0017573 |
| EAG1, EAG2 | Cancer | 2003/0040476 |
| SEQ ID NOS: 18, 20, 22 of the U.S patent application publication 2003/00 44813, incorporated by reference herein | Cancer | 2003/0044813 |
| HMG I | Cancer | 2003/0051260 |
| HLTF | Cancer | 2003/0082526 |
| Barx2 | Cancer | 2003/0087243 |
| SEQ ID NOS: 18, 20, 22, 32, 34, 36 of the U.S. patent application publication 2003/0108920, incorporated by reference herein | Cancer | 2003/0108920 |
| Cables | Cancer | 2003/0109443 |
| Pp 32r1 | Cancer | 2003/0129631 |
| BMP4 | Cancer | 2003/0134790 |
| TS10q23.3 | Cancer | 2003/0139324 |
| Nuclear spindle-associating protein | Cancer | 2003/0157072 |
| PFTAIRE | Cancer | 2003/0166217 |
| SEMA3B | Cancer | 2003/0166557 |
| MOGp | Cancer, multiple sclerosis, inflammatory disease | 2003/0166898 |
| Fortilin | Cancer | 2003/0172388 |
| SEQ ID NO: 1 of the U.S. patent application publication 2003/0215833, incorporated by reference herein | Cancer | 2003/0215833 |
| IGFBP-3 | Cancer | 2004/0005294 |
| Polyhomeotic 2 | Cancer | 2004/0006210 |
| PNQALRE | Cancer | 2004/0077009 |
| SEQ ID NOS: 1, 3 of the U.S. patent application publication 2004/0086916, incorporated by reference herein | Cancer | 2004/0086916 |
| SCN5A | Cancer | 2004/0146877 |
| miR15, miR16 | Cancer | 2004/0152112 |
| Headpin | Cancer | 2004/0180371 |
| PAOh1/SMO | Cancer | 2004/0229241 |
| Hippo, Mst2 | Cancer | 2005/0053592 |
| PSMA-like | Cancer, neurological disorders | 2005/0064504 |
| rJAB1 | Cancer | 2005/0069918 |
| NF-AT | Cancer | 2005/0079496 |
| P28ING5 | Cancer | 2005/0097626 |
| MTG16 | Cancer | 2005/0107313 |
| ErbB-2 | Cancer | 2005/0123538 |
| HDAC9 | Cancer | 2005/0130146 |
| GPBP | Cancer | 2005/0130227 |
| MG20 | Cancer | 2005/0153352 |
| KLF6 | Cancer | 2005/0181374 |
| ARTS1 | Cancer | 2005/0266443 |
| Dock 3 | Cancer | 2006/0041111 |
| Annexin 8 | Cancer | 2006/0052320 |
| MH15 | Cancer | 2006/0068411 |
| DELTA-N p73 | Cancer | 2006/0088825 |
| RapR6 | Cancer | 2006/099676 |
| StarD10 | Cancer | 2006/0148032 |
| Ciz1 | Cancer | 2006/0155113 |
| HLJ1 | Cancer | 2006/0194235 |
| RapR7 | Cancer | 2006/0240021 |
| A34 | Cancer | 2006/0292154 |
| Sef | Cancer | 2006/0293240 |
| Killin | Cancer | 2007/0072218 |
| SGA-1M | Cancer | 2007/0128593 |
| TGFβ Type II receptor | Cancer | 2002/0064786 |
| GCA-associated genes | Giant cell arteritis | 6,743,903 |
| PRV-1 | Polycythemia vera | 6,686,153 |
| SEQ ID NOS: 2, 4 of the U.S. Pat. No. 5,948,637, incorporated by reference herein | Ischemia | 5,948,637 |
| Vezf1 | Vascular disorders | 2002/0023277 |
| MLP | Dilatative cardiomyopathy | 2002/0042057 |
| VEGI | Pathological angiogenesis | 2002/0111325 |
| PRO256 | Cardiovascular disorders | 2002/0123091 |
| AOP2 | Atherosclerosis | 2002/0142417 |
| Remodelin | Arterial restenosis, fibrosis | 2002/0161211 |
| Phosphodiesterase 4D | Stroke | 2003/0054531 |
| Prostaglandin receptor subtype EP3 | Peripheral arterial occlusive disease | 2003/0157599 |
| CARP | Heart disorders | 2004/0014706 |
| HOP | Congenital heart disease | 2004/0029158 |
| SEQ ID NOS: 1-4 of the U.S. patent application publication 2004/0087784, incorporated by reference herein | Apoplexy | 2004/0087784 |
| PLTP | Atherosclerosis, vascular disease, hypercholesterolemia, Tangier's disease, familial HDL deficiency disease | 2006/0252787 |
| SEQ ID NOS: 1, 3-8, 15, 16 of the U.S. patent application publication 2007/0160996, incorporated by reference herein | Thrombosis | 2007/0160996 |
| UCP-2 | Stroke | 2002/0172958 |
| FLJ11011 | Fanconi's Anemia | 2006/0070134 |
| Codanin-1 | Anemia | 2006/0154331 |
| SEQ ID NOS: 1, 6, 8 of the U.S. Pat. No. 5,763,591, incorporated by reference herein | Insulin-dependent diabetes mellitus | 5,763,591 |
| Resistin | Type II diabetes | 2002/0161210 |
| Archipelin | Diabetes | 2003/0202976 |
| SEQ ID NOS: 2, 7, 16, 27 of the U.S. patent application publication 2004/0053397, | Diabetes, hyperlipidernia | 2004/0053397 |

TABLE 3-continued

| Gene | Disease/Disorder | Patent/Published Application No. |
|---|---|---|
| incorporated by reference herein | | |
| Neuronatin | Metabolic disorders | 2004/0259777 |
| Neb5or | Diabetes | 2005/0031605 |
| 7B2 | Endocrine disorders | 2005/0086709 |
| PTHrp, PEX | Metabolic bone diseases | 2005/0113303 |
| KChIPI | Type II diabetes | 2005/0196784 |
| SLIT-3 | Type II diabetes | 2006/0141462 |
| CX3CR1 | Type II diabetes | 2006/0160076 |
| SMAP-2 | Diabetes | 2006/0210974 |
| SEQ ID NOS: 2, 8, 12, 16, 22, 26, 28, 32 of the U.S. patent application publication 2006/0228706, incorporated by reference herein | Type II diabetes | 2006/0228706 |
| IC-RFX | Diabetes | 2006/0264611 |
| E2IG4 | Diabetes, insulin resistance, obesity | 2007/0036787 |
| SEQ ID NOS: 2, 8, 10, 14, 18, 24, 26, 30, 34, 38, 44, 50, 54, 60, 62, 68, 74, 80, 86, 92, 98, 104, 110 of the U.S. patent application publication 2007/0122802, incorporated by reference herein | Diabetes | 2007/0122802 |
| UCP2 | Body weight disorders | 2002/0127600 |
| Ob receptor | Body weight disorders | 2002/0182676 |
| Ob | Bodyweight disorders | 2004/0214214 |
| Dp1 | Neurodegenerative disorders | 2001/0021771 |
| NRG-1 | Schizophrenia | 2002/0045577 |
| Synapsin III | Schizophrenia | 2002/0064811 |
| NRG1AG1 | Schizophrenia | 2002/0094954 |
| AL-2 | Neuronal disorders | 2002/0142444 |
| Proline dehydrogenase | Bipolar disorder, major depressive disorder, schizophrenia, obsessive compulsive disorder | 2002/0193581 |
| MNR2 | Chronic neurodegenerative disease | 2002/0197678 |
| ATM | Ataxia-telangiectasia | 2004/0029198 |
| Ho-1 | Dementing diseases | 2004/0033563 |
| CON202 | Schizophrenia | 2004/0091928 |
| Ataxin-1 | Neurodegenerative disorders | 2004/0177388 |
| NR3B | Motor neuron disorders | 2005/0153287 |
| NIPA-1 | Hereditary spastic paraplegia | 2005/0164228 |
| DEPP, adrenomedullin, csdA | Schizophrenia | 2005/0227233 |
| Inf-20 | Neurodegenerative diseases | 2006/0079675 |
| EOPA | Brain development and degeneration disorders | 2007/0031830 |
| SERT | Autism | 2007/0037194 |
| FRP-1 | Glaucoma | 2002/0049177 |
| Serum amyloid A | Glaucoma | 2005/0153927 |
| BMP2 | Osteoporosis | 2002/0072066 |
| BMPR1A | Juvenile polyposis | 2003/0072758 |
| ACLP | Gastroschisis | 2003/0084464 |
| Resistin-like molecule β | Familial adenomatous polyposis, diabetes, insulin resistance, colon cancer, inflammatory bowel disorder | 2003/0138826 |
| Dlg5 | Inflammatory bowel disease | 2006/0100132 |
| SEQ ID NOS: 1-82 of the U.S. patent application publication 2002/0119452, incorporated by reference herein | Osteoarthritis | 2002/0119452 |
| TRANCE | Immune system disorders | 2003/0185820 |
| Matrilin-3 | Osteoarthritis | 2003/0203380 |
| Synoviolin | Rheumatoid arthritis | 2004/0152871 |
| SEQ ID NOS: 9, 35 of the U.S. patent application publication 2007/0028314, incorporated by reference herein | Osteoarthritis | 2007/0028314 |
| HIV LTR | HIV infection | 5,627,023 |
| SHIVA | HIV infection | 2004/0197770 |
| EBI 1, EBI 2, EBI 3 | Epstein Barr virus infection | 2002/0040133 |
| NM23 family | Skin/intestinal disorders | 2002/0034741 |
| SEQ ID NO: 1 of the U.S. patent application publication 2002/0169127, incorporated by reference herein | Psoriasis | 2002/0169127 |
| Eps8 | Skin disorders, wound healing | 2003/0180302 |
| Beta-10 | Thyroid gland pathology | 2002/0015981 |
| SEQ ID NO: 2 of the U.S. patent application publication 2003/0207403, incorporated by reference herein | Thyroid conditions | 2003/0207403 |
| SEQ ID NO: 3 of the U.S. patent application publication 2007/0020275, incorporated by reference herein | Thyroid disorders | 2007/0020275 |
| Hair follicle growth factor | Alopecia | 2003/0036174 |
| Corneodesmosin | Alopecia | 2003/0211065 |
| GCR9 | Asthma, lymphoma, leukemia | 2003/0166150 |
| SEQ ID NO: 1-71 of the U.S. patent application publication 2004/0002084, incorporated by reference herein | Asthma | 2004/0002084 |
| Bg | Chediak-Higashi | 2002/0115144 |
| SEQ ID NOS: 1-16 of the U.S. patent application publication 2002/0127555, incorporated by reference herein | Endometriosis | 2002/0127555 |
| FGF23 | Hypophosphatemic disorders | 2005/0156014 |
| BBSR | Bardet-Biedl syndrome | 2003/0152963 |
| MIC-1 | Fetal abnormalities, cancer, inflammatory disorders, miscarriage, premature birth | 2004/0053325 |
| MIA-2 | Liver damage | 2004/0076965 |
| IL-17B | Cartilage degenerative disorders | 2004/0171109 |
| Formylglycine generating enzyme | Multiple sulfatase deficiency | 2004/0229250 |
| LPLA2 | Pulmonary alveolar proteinosis | 2006/0008455 |
| CXCL10 | Respiratory illnesses | 2006/0040329 |
| SEQ ID NOS: 1, 2 of the U.S. patent application publication 2006/0140945, incorporated by reference herein | Nephropathy | 2006/0140945 |
| HFE2A | Iron metabolism disease | 2007/0166711 |

Once a gene with an expression pattern that is modulated during a disease, disorder, or condition is identified, the promoter of the gene may be used in the gene switch of the invention. The sequence of many genes, including the promoter region, is known in the art and available in public databases, e.g., GenBank. Thus, once an appropriate gene is identified, the promoter sequence can be readily identified and obtained. Another aspect of the present invention is directed towards identifying suitable genes whose promoter can be isolated and placed into a gene switch. The identity of the gene, therefore, may not be critical to specific embodiments of the present invention, provided the promoter can be isolated and used in subsequent settings or environments. The current invention thus includes the use of promoters from genes that are yet to be identified. Once suitable genes are identified, it is a matter of routine skill or experimentation to determine the genetic sequences needed for promoter function. Indeed, several commercial protocols exist to aid in the determination of the promoter region of genes of interest. By way of example, Ding et al. recently elucidated the promoter sequence of the novel Sprouty4 gene (*Am. J. Physiol. Lung Cell. Mol. Physiol.* 287: L52 (2004), which is incorporated by reference) by progressively deleting the flanking sequence of the human Sprouty4 gene. Briefly, once the transcription initiation site was determined, PCR fragments were generated using common PCR primers to clone segments of the 5'-flanking segment in a unidirectional manner. The generated segments were cloned into a luciferase reporter vector and luciferase activity was measured to determine the promoter region of the human Sprouty4 gene.

Another example of a protocol for acquiring and validating gene promoters includes the following steps: (1) acquire diseased and non-diseased cell/tissue samples of similar/same tissue type; (2) isolate total RNA or mRNA from the samples; (3) perform differential microarray analysis of diseased and non-diseased RNA; (4) identify candidate disease-specific transcripts; (5) identify genomic sequences associated with the disease-specific transcripts; (6) acquire or synthesize DNA sequence upstream and downstream of the predicted transcription start site of the disease-specific transcript; (7) design and produce promoter reporter vectors using different lengths of DNA from step 6; and (8) test promoter reporter vectors in diseased and non-diseased cells/tissues, as well as in unrelated cells/tissues.

The source of the promoter that is inserted into the gene switch can be natural or synthetic, and the source of the promoter should not limit the scope of the invention described herein. In other words, the promoter may be directly cloned from cells, or the promoter may have been previously cloned from a different source, or the promoter may have been synthesized.

In another embodiment, a polynucleotide encoding any of gene products referred to in Tables 1-3 may be used in the vector and methods of the present invention, for therapeutic uses and for diagnostic purposes.

Gene Switch Systems

The gene switch may be any gene switch that regulates gene expression by addition or removal of a specific ligand. In one embodiment, the gene switch is one in which the level of gene expression is dependent on the level of ligand that is present, Examples of ligand-dependent transcription factor complexes that may be used in the gene switches of the invention include, without limitation, members of the nuclear receptor superfamily activated by their respective ligands (e.g., glucocorticoid, estrogen, progestin, retinoid, ecdysone, and analogs and mimetics thereof) and rTTA activated by tetracycline. In one aspect of the invention, the gene switch is an EcR-based gene switch. Examples of such systems include, without limitation, the systems described in U.S. Pat. Nos. 6,258,603, 7,045,315, U.S. Published Patent Application Nos. 2006/0014711, 2007/0161086, and international Published Application No. WO 01/70816, Examples of chimeric ecdysone receptor systems are described in U.S. Pat. No. 7,091,038, U.S. Published Patent Application Nos. 2002/0110861, 2004/0033600, 2004/0096942, 2005/0266457, and 2006/0100416, and International Published Application Nos. WO 01/70816, WO 02/066612, WO 02/066613, WO 02/066614, WO 02/066615, WO 02/29075, and WO 2005/108617, each of which is incorporated by reference in its entirety. An example of a non-steroidal ecdysone agonist-regulated system is the RheoSwitch® Mammalian Inducible Expression System (New England Biolabs, Ipswich, Mass.), In another aspect of the invention, the gene switch is based on heterodimerization of FK506 binding protein (FKBP) with FKBP rapamycin associated protein (FRAP) and is regulated through rapamycin or its non-immunosuppressive analogs. Examples of such systems, include, without limitation, the ARGENT™ Transcriptional Technology (ARIAD Pharmaceuticals, Cambridge, Mass.) and the systems described in U.S. Pat. Nos. 6,015,709, 6,117,681, 6,479,653, 6,187,757, and 6,649,595.

In one embodiment, the gene switch comprises a single transcription factor sequence encoding a ligand-dependent transcription factor complex under the control of a therapeutic switch promoter. The transcription factor sequence may encode a ligand-dependent transcription factor complex that is a naturally occurring or an artificial ligand-dependent transcription factor complex. An artificial transcription factor is one in which the natural sequence of the transcription factor has been altered, e.g., by mutation of the sequence or by the combining of domains from different transcription factors. In one embodiment, the transcription factor comprises a Group H nuclear receptor ligand binding domain. In one embodiment, the Group H nuclear receptor ligand binding domain is from an ecdysone receptor, a ubiquitous receptor (UR), an orphan receptor 1 (OR-1), a steroid hormone nuclear receptor 1 (NER-1), a retinoid X receptor interacting protein-15 (RIP-15), a liver X receptor β (LXRβ), a steroid hormone receptor like protein (RLD-1), a liver X receptor (LXR), a liver X receptor α (LXRα), a farnesoid X receptor (FXR), a receptor interacting protein 14 (RIP-14), or a farnesol receptor (HRR-1). In another embodiment, the Group H nuclear receptor LBD is from an ecdysone receptor.

A. Ecdysone-Based Gene Switch

The EcR and the other Group H nuclear receptors are members of the nuclear receptor superfamily wherein all members are generally characterized by the presence of an amino-terminal transactivation domain (AD, also referred to interchangeably as "TA" or "TD"), optionally fused to a heterodimerization partner (HP) to form a coactivation protein (CAP), a DNA binding domain (DBD), and a LBD fused to the DBD via a hinge region to form a ligand-dependent transcription factor (LTF). As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, *Science* 240:889 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The following polypeptide sequence was reported as a polypeptide sequence of Ecdysone receptor (Ecdysteroid receptor) (20-hydroxy-ecdysone receptor) (20E receptor) (EcRH) (Nuclear receptor subfamily 1 group H member 1) and has the accession number P34021 in Genbank.

Ecdysone receptor (878aa) from *Drosophila melanogaster* (Fruit fly)

(SEQ ID NO: 5)

```
  1  mkrrwsnngg fmrlpeesss evtsssnglv lpsgvnmsps
     sldshdycdq dlwlcgnesg 61  sfggsnghgl sqqqsvitl amhgcsstlp aqttiiping
     nangnggstn gqyvpgatnl 121  galanymlng gfngmqqqiq nghglinstt pstpttplhlq
     qnlggaggg giggmgilhh 181  angtpnglig vvgggggvgl gvggggvggl gmqhtprsds
     vnsissgzdd lspssslngy 241  sanescdakk skkgpaprvq eelclvcgdr asgyhynalt
     cegckgffrr svtksavycc 301  kfgracemdm ymrrkcqecr lkkclavgmr pecvvpenqc
     amkrrekkaq kekdkmttsp 361  ssqhggngsl asgggqdfvk keildlmtce ppqhatipll
     pdeilakcqa rnipsltynq 421  laviykliwy qdgyeqpsee dlrrimsqpd enesqtdvsf
     rhiteitilt vqlivefakg 481  lpaftkipqe dqitllkacs sevmmlrmar rydhssdsif
     fannrsytrd sykmagmadn 541  iedllhfcrq mfsmkvdnve yalltaivif sdrpglekaq
     lveaiqsyyi dtlriyilnr 601  hcgdsmslvf yakllsilte lrtlgnqnae mcfslklknr
     klpkfleeiw dvhaippsvq 661  shlqitqeen erleraermr asvggaitag idcdsastsa
     aaaaaqhqpq pqpqpqpssl 721  tqndsqhqtq pqlqpqlppq lqgqlqpqlq pqlqtqlqpq
     iqpqpqllpv sapvpasvta 781  pgslsaysts seymggsaai gpitpattss itaavtasst
     tsavpmgngv gvgvgvggnv 841  smyanaqtam almgvalhsh qeqliggvav ksehstta
```

In one embodiment, the ecdysone receptor ligand binding domain is selected from the group consisting of an invertebrate ecdysone receptor ligand binding domain, an Arthropod ecdysone receptor ligand binding domain, a Lepidopteran ecdysone receptor ligand binding domain, a Dipteran ecdysone receptor ligand binding domain, an Orthopteran ecdysone receptor ligand binding domain, a Homopteran ecdysone receptor ligand binding domain, a Hemipteran ecdysone receptor ligand binding domain, a spruce budworm *Choristoneura fumiferana* EcR ecdysone receptor ligand binding domain, a beetle *Tenebrio molitor* ecdysone receptor ligand binding domain, a *Manduca sexta* ecdysone receptor ligand binding domain, a *Heliothies virescens* ecdysone receptor ligand binding domain, a midge *Chironomus tentans* ecdysone receptor ligand binding domain, a silk moth *Bombyx mori* ecdysone receptor ligand binding domain, a squinting bush brown *Bicyclus anynana* ecdysone receptor ligand binding domain, a buckeye *Junonia coenia* ecdysone receptor ligand binding domain, a fruit fly *Drosophila melanogaster* ecdysone receptor ligand binding domain, a mosquito *Aedes aegypti* ecdysone receptor ligand binding domain, a blowfly *Lucilia capitata* ecdysone receptor ligand binding domain, a blowfly *Lucilia cuprina* ecdysone receptor ligand binding domain, a blowfly *Calliphora vicinia* ecdysone receptor ligand binding domain, a Mediterranean fruit fly *Ceratitis capitata* ecdysone receptor ligand binding domain, a locust *Locusta migratoria* ecdysone receptor ligand binding domain, an aphid *Myzus persicae* ecdysone receptor ligand binding domain, a fiddler crab *Celuca pugilator* ecdysone receptor ligand binding domain, an ixodid tick *Amblyomma americanum* ecdysone receptor ligand binding domain, a whitefly *Bamecia argentifoli* ecdysone receptor ligand binding domain and a leafhopper *Nephotetix cincticeps* ecdysone receptor ligand binding domain.

Figure 2:
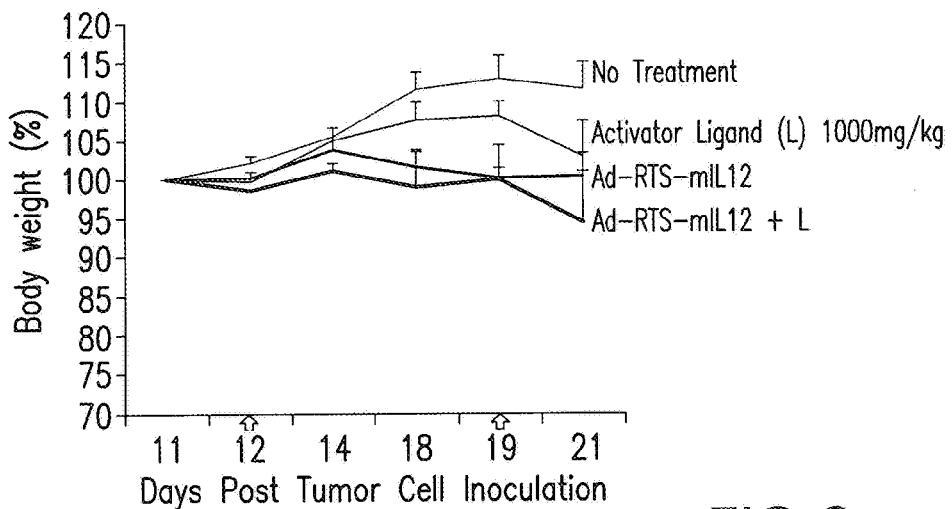
FIG. 2 is a line graph that depicts changes in body weight of mice bearing melanoma tumors on both flanks, in response to Ad-RTS-mIL 12 and activator ligand.

In another embodiment, the ecdysone receptor ligand binding domain is the *Christoneura fumiferana* ecdysone receptor ligand binding domain, for which the amino acid sequence is set forth in SEQ ID NO: 1.

In another embodiment, the ecdysone receptor ligand binding domain is an analog of the *Christoneura fumiferana* ecdysone receptor ligand binding domain that retains at least 80%, 85%, 90%, 95%, 96%, 97%, 98% 99% or 100% of the in vitro *Christoneura fumiferana* ecdysone receptor ligand binding activity of the *Christoneura fumiferana* ecdysone receptor ligand binding domain. In vitro ecdysone receptor ligand binding assays are well know to those of ordinary skill in the art. For example, see WO 02/066612.

In another embodiment, the ecdysone receptor ligand binding domain analog is an ecdysone receptor ligand binding domain disclosed in WO 02/066612, US 2006/0100416, WO 05/108617 and 2005/0266457. In another embodiment, the ecdysone receptor ligand binding domain analog is the V107I/Y127E substitution mutant of SEQ ID NO: 7.

The DBD is characterized by the presence of two cysteine zinc fingers between which are two amino acid motifs, the P-box and the D-box, which confer specificity for response elements. These domains may be either native, modified, or chimeras of different domains of heterologous receptor proteins. The EcR, like a subset of the nuclear receptor family, also possesses less well-defined regions responsible for heterodimerization properties. Because the domains of nuclear receptors are modular in nature, the LBD, DBD, and AD may be interchanged.

In another embodiment, the transcription factor comprises a AD, a DBD that recognizes a response element associated with the therapeutic protein or therapeutic polynucleotide whose expression is to be modulated; and a Group H nuclear receptor LBD. In certain embodiments, the Group H nuclear receptor LBD comprises a substitution mutation.

The DNA binding domain can be any DNA binding domain (DBD) with a known response element, including synthetic and chimeric DNA binding domains, or analogs, combinations, or modifications thereof. In one embodiment, the DNA binding domain is selected from the group consisting of a GAL4 DBD, a LexA DBD, a transcription factor DBD, a Group H nuclear receptor member DBD, a steroid/thyroid hormone nuclear receptor superfamily member DBD, a bacterial LacZ DBD, an EcR DBD, a GAL4 DBD and a LexA DBD.

The transactivation domain (abbreviated "AD" or "TA") may be any Group H nuclear receptor member AD, steroid/thyroid hormone nuclear receptor AD, synthetic or chimeric AD, polyglutamine AD, basic or acidic amino acid AD, a VP16 AD, a GAL4 AD, an NF-κB AD, a BP64 AD, a B42 acidic activation domain (B42AD), a p65 transactivation domain (p65AD), or an analog, combination, or modification thereof.

In another embodiment, the gene switch comprises a first transcription factor sequence, e.g., a CAP, under the control of a first therapeutic switch promoter (TSP-1) and a second transcription factor sequence, e.g., a LTF, under the control of a second therapeutic switch promoter (TSP-2), wherein the proteins encoded by said first transcription factor sequence and said second transcription factor sequence interact to form a protein complex (LDTFC), i.e., a "dual switch"- or "two-hybrid"-based gene switch. The first and second TSPs may be the same or different. In this embodiment, the presence of two different TSPs in the gene switch that are required for therapeutic molecule expression enhances the specificity of the therapeutic method (see FIG. 2 of WO 2011/1/9773). FIG. 2 of WO 2011/119773 also demonstrates the ability to modify the therapeutic gene switch to treat any disease, disorder, or condition simply by inserting the appropriate TSPs.

In a further embodiment, both the first and the second transcription factor sequence, e.g., a CAP or a LTF, are under the control of a single therapeutic switch promoter (e.g. TSP-1 in FIG. 1 of WO 2011/119773). Activation of this promoter will generate both CAP and LTF with a single open reading frame. This can be achieved with the use of a transcriptional linker such as an IRES (internal ribosomal entry site). In this embodiment, both portions of the ligand-dependent transcription factor complex are synthesized upon activation of TSP-1. TSP-1 can be a constitutive promoter or only activated under conditions associated with the disease, disorder, or condition.

Figures 4A, 4B:
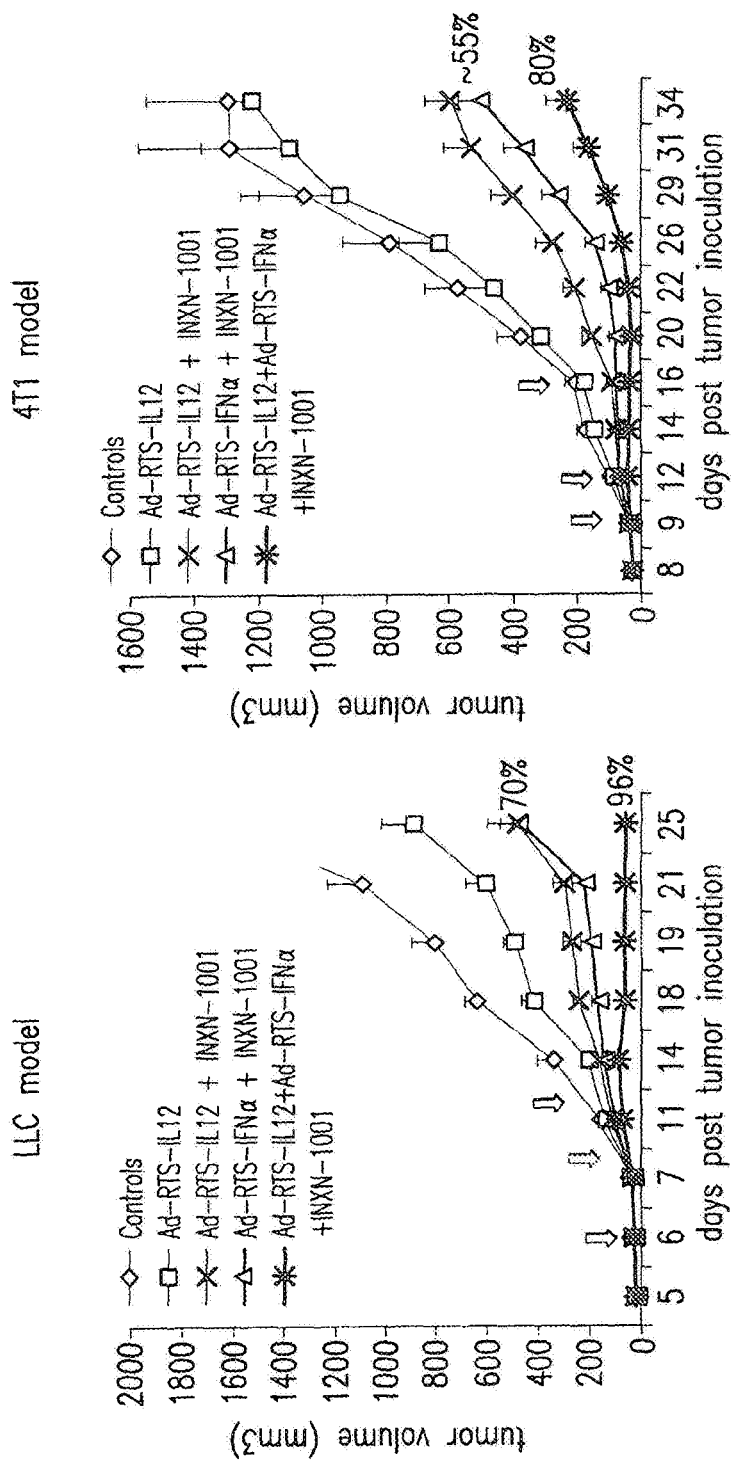
FIGS. 4A and 4B are line graphs that depict the effect of mIL12 and mIFNα in the LLC and 4T1 cell lines.

In a further embodiment, one transcription factor sequence, e.g. a LTF, is under the control of a therapeutic switch promoter only activated under conditions associated with the disease, disorder, or condition (e.g., TSP-2 or TSP-3 in FIG. 4 in WO 2011/119773) and the other transcription factor sequence, e.g., CAP, is under the control of a constitutive therapeutic switch promoter (e.g., TSP-1 in FIG. 4 in WO 2011/119773). In this embodiment, one portion of the ligand-dependent transcription factor complex is constitutively present while the second portion will only be synthesized under conditions associated with the disease, disorder, or condition.

Figure 3:
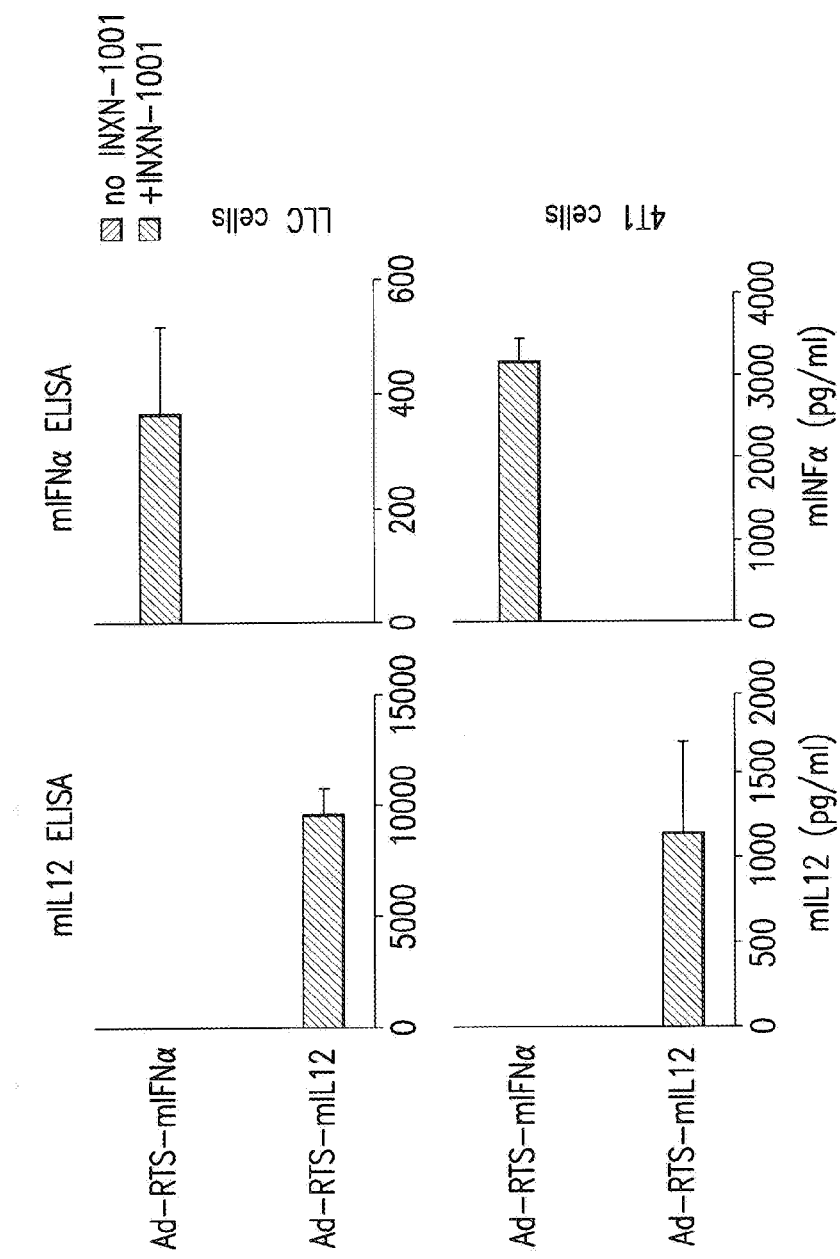
FIG. 3 is a bar graph that depicts the in vitro regulated expression of mIL12 and mIfNα in the LLC and 4T1 cell lines.

In another embodiment, one transcription factor sequence, e.g., CAP, is under the control of a first TSP (e.g., TSP-1 in FIG. 3 in WO 2011/119773) and two or more different second transcription factor sequences, e.g., LTF-1 and LTF-2 are under the control of different TSPs (e.g., TSP-2 and TSP-3 in FIG. 3 in WO 2011/119773). In this embodiment, each of the LTFs may have a different DBD that recognizes a different factor-regulated promoter sequence (e.g., DBD-A binds to a response element associated with factor-regulated promoter-1 (FRP-1) and DBD-B binds to a response element associated with factor-regulated promoter-2 (FRP-2). Each of the factor-regulated promoters may be operably linked to a different therapeutic gene. In this manner, multiple treatments may be provided simultaneously.

In one embodiment, the first transcription factor sequence encodes a polypeptide comprising a AD, a DBD that recognizes a response element associated with the therapeutic product sequence whose expression is to be modulated; and a Group H nuclear receptor LBD, and the second transcription factor sequence encodes a transcription factor comprising a nuclear receptor LBD selected from a vertebrate retinoid X receptor (RXR), an invertebrate RXR, an ultraspiracle protein (USP), or a chimeric nuclear receptor comprising at least two different nuclear receptor ligand binding domain polypeptide fragments selected from a vertebrate RXR, an invertebrate RXR, and a USP (see WO 01/70816 A2 and US 2004/0096942 A1). The "partner" nuclear receptor ligand binding domain may further comprise a truncation mutation, a deletion mutation, a substitution mutation, or another modification.

In another embodiment, the gene switch comprises a first transcription factor sequence encoding a first polypeptide comprising a nuclear receptor LBD and a DBD that recognizes a response element associated with the therapeutic product sequence whose expression is to be modulated, and a second transcription factor sequence encoding a second polypeptide comprising an AD and a nuclear receptor LBD, wherein one of the nuclear receptor LBDs is a Group H nuclear receptor LBD. In one embodiment, the first polypeptide is substantially free of an AD and the second polypeptide is substantially free of a DBD. For purposes of the invention, "substantially free" means that the protein in question does not contain a sufficient sequence of the domain in question to provide activation or binding activity.

In another aspect of the invention, the first transcription factor sequence encodes a protein comprising a heterodimerization partner and an AD (a "CAP") and the second transcription factor sequence encodes a protein comprising a DBD and a LBD (a "LTF").

When only one nuclear receptor LBD is a Group H LBD, the other nuclear receptor LBD may be from any other nuclear receptor that forms a dimer with the Group H LBD. For example, when the Group H nuclear receptor LBD is an EcR LBD, the other nuclear receptor LBD "partner" may be from an EcR, a vertebrate RXR, an invertebrate RXR, an ultraspiracle protein (USP), or a chimeric nuclear receptor comprising at least two different nuclear receptor LBD polypeptide fragments selected from a vertebrate RXR, an invertebrate RXR, or a USP (see WO 01/70816 A2, International Patent Application No. PCT/US02/05235, US 2004/0096942 A1 and U.S. Pat. No. 7,531,326, incorporated herein by reference in their entirety). The "partner" nuclear receptor ligand binding domain may further comprise a truncation mutation, a deletion mutation, a substitution mutation, or another modification.

In one embodiment, the vertebrate RXR LBD is from a human *Homo sapiens*, mouse *Mus musculus*, rat *Rattus norvegicus*, chicken *Gallus gallus*, pig *Sus scrofa domestica*, frog *Xenopus laevis*, zebrafish *Danio rerio*, tunicate *Polyandrocarpa misakiensis*, or jellyfish *Tripedalia cysophora* RXR.

In one embodiment, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), an ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellijera* RXR homolog ("AmRXR"), an aphid *Myzus persicae* RXR homolog ("MpRXR"), or a non-Dipteran/non-Lepidopteran RXR homolog.

In one embodiment, the chimeric RXR, LBD comprises at least two polypeptide fragments selected from a vertebrate species RXR polypeptide fragment, an invertebrate species RXR polypeptide fragment, or a non-Dipteran/non-Lepidopteran invertebrate species RXR homolog polypeptide fragment. A chimeric RXR ligand binding domain for use in the present invention may comprise at least two different species RXR polypeptide fragments, or when the species is the same, the two or more polypeptide fragments may be from two or more different isoforms of the species RXR polypeptide fragment. Such chimeric RXR LBDs are disclosed, for example, in WO 2002/066614.

In one embodiment, the chimeric RXR ligand binding domain comprises at least one vertebrate species RXR polypeptide fragment and one invertebrate species RXR polypeptide fragment.

In another embodiment, the chimeric RXR ligand binding domain comprises at least one vertebrate species RXR polypeptide fragment and one non-Dipteran/non-Lepidopteran invertebrate species RXR homolog polypeptide fragment.

The ligand, when combined with the LBD of the nuclear receptor(s), which in turn are bound to the response element of a FRP associated with a therapeutic product sequence, provides external temporal regulation of expression of the therapeutic product sequence. The binding mechanism or the order in which the various components of this invention bind to each other, that is, for example, ligand to LBD, DBD to response element, AD to promoter, etc., is not critical.

In a specific example, binding of the ligand to the LBD of a Group H nuclear receptor and its nuclear receptor LBD partner enables expression of the therapeutic product sequence. This mechanism does not exclude the potential for ligand binding to the Group H nuclear receptor (GHNR) or its partner, and the resulting formation of active homodimer complexes (e.g. GHNR+GHNR or partner+partner). Preferably, one or more of the receptor domains is varied producing a hybrid gene switch. Typically, one or more of the three domains, DBD, LBD, and AD, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988)) or LexA protein from *Escherichia coli* (see Brent et al., *Cell* 43:729 (1985)), or synthetic response elements specific for targeted interactions with proteins designed, modified, and selected for such specific interactions (see, for example, Kim et al., *Proc. Natl. Acad. Sci. USA,* 94:3616 (1997)) to accommodate hybrid receptors. Another advantage of two-hybrid systems is that they allow choice of a promoter used to drive the gene expression according to a desired end result. Such double control may be particularly important in areas of gene therapy, especially when cytotoxic proteins are produced, because both the timing of expression as well as the cells wherein expression occurs may be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism.

The DNA binding domain of the first hybrid protein binds, in the presence or absence of a ligand, to the DNA sequence of a response element to initiate or suppress transcription of downstream gene(s) under the regulation of this response element.

The functional LDTFC, e.g., an EcR complex, may also include additional protein(s) such as immunophilins. Additional members of the nuclear receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/ NCoA-2, ACTR/AIB1/RAC3/pCIP as well as the promiscuous coactivator C response element B binding protein, CBP/ p300 (for review see Glass et al., *Curr. Opin. Cell Biol.* 9:222 (1997)). Also, protein cofactors generally known as corepressors (also known as repressors, silencers, or silencing mediators) may be required to effectively inhibit transcriptional activation in the absence of ligand. These corepressors may interact with the unliganded EcR to silence the activity at the response element, Current evidence suggests that the binding of ligand changes the conformation of the receptor, which results in release of the corepressor and recruitment of the above described coactivators, thereby abolishing their silencing activity. Examples of corepressors include N-CoR and SMRT (for review, see Horwitz et al., *Mol Endocrinol.* 10:1167 (1996)). These cofactors may either be endogenous within the cell or organism, or may be added exogenously as transgenes to be expressed in either a regulated or unregulated fashion.

B. Rapamycin Based Gene Switch

The present invention further provides a gene switch system which utilizes FK506 binding protein as the ligand-dependent transcription factor complex and rapamycin as the ligand. In one embodiment, the construct encoding the gene switch comprises (a) a first polynucleotide encoding a first chimeric protein which binds to rapamycin or an analog thereof and which comprises at least one FK506-binding protein (FKBP) domain and at least one protein domain heterologous thereto, wherein the FKBP domain comprises a peptide sequence selected from:
  (1) a naturally occurring FKBP
  (2) a variant of a naturally occurring FKBP in which up to 10 amino acid residues have been deleted, inserted, or replaced with substitute amino acids, and
  (3) an FKBP encoded by a DNA sequence which selectively hybridizes to a DNA sequence encoding an FKBP of (1) or (2);

(b) a second polynucleotide encoding a second chimeric protein which forms a complex with both (a) rapamycin or a rapamycin analog and (b) the first chimeric protein, and which comprises at least one FKBP:rapamycin binding (FRB) domain and at least one protein domain heterologous thereto, wherein the FRB domain comprises a peptide sequence selected from:
  (4) a naturally occurring FRB domain,
  (5) a variant of a naturally occurring FRB domain in which up to 10 amino acid residues have been deleted, inserted, or replaced with substitute amino acids, and
  (6) an FRB domain encoded by a DNA sequence which selectively hybridizes to a DNA sequence encoding an FRB of (4) or (5).

In this gene switch system, each of the first polynucleotide and the second polynucleotide are under the control of one or more therapeutic switch promoters as described elsewhere herein. Furthermore, in certain embodiments, at least one protein domain heterologous to the FKBP and/or FRB domains in the first and second chimeric protein may be one or more "action" or "effector" domains. Effector domains may be selected from a wide variety of protein domains including DNA binding domains, transcription activation domains, cellular localization domains and signaling domains (i.e., domains which are capable upon clustering or multimerization, of triggering cell growth, proliferation, differentiation, apoptosis, gene transcription, etc.).

In certain embodiments, one fusion protein contains at least one DNA binding domain (e.g., a GAL4 or ZFHD1 DNA-binding domain) and another fusion protein contains at least one transcription activation domain (e.g., a VP16 or p65 transcription activation domain). Ligand-mediated association of the fusion proteins represents the formation of a transcription factor complex and leads to initiation of transcription of a target gene linked to a DNA sequence recognized by (i.e., capable of binding with) the DNA-binding domain on one of the fusion proteins. Information regarding the gene expression system as well as the ligand is disclosed in U.S. Pat. Nos. 6,187,757 B1, 6,649,595 B1, 6,509,152 B1, 6,479,653 B1, and 6,117,680 B1.

In other embodiments, the present invention provides a gene switch system which comprises polynucleotides encoding two fusion proteins which self-aggregate in the absence of a ligand, wherein (a) the first fusion protein comprises a conditional aggregation domain which binds to a selected ligand and a transcription activation domain, and (b) the second fusion protein comprising a conditional aggregation domain which binds to a selected ligand and a DNA binding domain, and (c) in the absence of ligand, the cells express a gene operably linked to regulatory DNA to which said DNA binding domain binds. Modified cells comprising the gene switch system are expanded in the presence of the ligand in an amount sufficient for repression of the gene. Ligand removal induces expression of the encoded protein that causes cell death. The nucleic acids encoding the two fusion proteins are under the control of at least one conditional promoter. The gene expression system utilizing conditional aggregation domains is disclosed in U.S. Publication No. 2002/0048792.

C. Procaryotic Repressor/Operator Based Gene Switch System

In one embodiment, the present invention provides gene switch system comprising (a) a first polynucleotide coding for a transactivator fusion protein comprising a prokaryotic tetracycline ("tet") repressor and a eucaryotic transcriptional activator protein domain; and (b) a second polynucleotide coding for a therapeutic protein or therapeutic polypeptide, wherein said second polynucleotide is operably linked to a minimal promoter and at least one tet operator sequence. The first polynucleotide coding for a transactivator fusion protein may comprise therapeutic switch promoter as described elsewhere herein. The expression of the lethal protein is up-regulated in the absence of tetracycline. (see, e.g., Gossen et al. (1992) Proc. Natl. Acad. Sci. 89: 5547-5551; Gossen et al. (1993) TIBS 18: 471-475; Furth et al. (1994) Proc. Natl. Acad. Sci. 91: 9302-9306; and Shockett et al. (1995) Proc. Natl. Acad. Sci. 92: 6522-6526). The TetO expression system is disclosed in U.S. Pat. No. 5,464,758 B1.

In another embodiment, the gene switch system comprises the lactose ("Lac") repressor-operator systems from the bacterium *Escherichia coli*. The gene switch system of the present invention may also comprise (a) a first polynucleotide coding for a transactivator fusion protein comprising a prokaryotic lac I repressor and a eucaryotic transcriptional activator protein domain; and (b) a second polynucleotide coding for a therapeutic protein or therapeutic polypeptide, wherein said second polynucleotide is operably linked to a therapeutic switch promoter. In the Lac system, a lac operon is inactivated in the absence of lactose, or synthetic analogs such as isopropyl-b-D-thiogalactoside.

Additional gene switch systems include those described in the following; U.S. Pat. No. 7,091,038; WO2004078924; EP1266015; US20010044151; US20020110861; US20020119521; US20040033600; US20040197861; US20040235097; US20060020146; US20040049437; US20040096942; US20050228016; US20050266457; US20060100416; WO2001/70816; WO2002/29075; WO2002/066612; WO2002/066613; WO2002/066614; WO2002/066615; WO2005/108617; U.S. Pat. No. 6,258,603; US20050209283; US20050228016; US20060020146; EP0965644; U.S. Pat. No. 7,304,162; U.S. Pat. No. 7,304,161; MX234742; KR10-0563143; AU765306; AU2002-248500; and AU2002-306550.

D. Combination of the Gene Switch Systems

The present invention provides nucleic acid compositions, modified cells, and bioreactors comprising two or more gene switch systems comprising different ligand-dependent transcription factor complexes which are activated by an effective amount of one or more ligands, wherein the two or more gene switch systems comprise a first gene switch and a second gene switch, both of which selectively induce expression of one or more therapeutic polypeptides or therapeutic polynucleotides, upon binding to one or more ligands. Within the scope of the present invention are any numbers of and/or combinations of gene switch systems.

In one embodiment, the present invention provides a nucleic acid composition comprising:

a. a first gene switch system which comprises:
i. a first gene expression cassette comprising a polynucleotide encoding a first hybrid polypeptide which comprises:
    1. a transactivation domain, which activates a factor-regulated promoter operably associated with a polynucleotide encoding a therapeutic polypeptide or therapeutic polynucleotide; and
    2. a heterodimer partner domain,
ii. a second gene expression cassette comprising a polynucleotide encoding a second hybrid polypeptide which comprises:
    1. a DNA-binding domain, which recognizes a factor-regulated promoter operably associated with a polynucleotide encoding a therapeutic polypeptide or therapeutic polynucleotide; and
    2. a ligand binding domain; and
iii. a third gene expression cassette comprising a polynucleotide encoding a therapeutic polypeptide or therapeutic polynucleotide comprising:
    1. a factor-regulated promoter, which is activated by the transactivation domain of the second hybrid polypeptide; and,
    2. a polynucleotide encoding a therapeutic polypeptide or therapeutic polynucleotide, and b. a second gene expression system which comprises:
i. a first gene expression cassette comprising a polynucleotide encoding a first hybrid polypeptide which comprises:
    1. a transactivation domain, which activates a factor-regulated promoter operably associated with a polynucleotide encoding a therapeutic polypeptide or therapeutic polynucleotide; and
    2. a heterodimer partner domain,
ii. a second gene expression cassette comprising a polynucleotide encoding a second hybrid polypeptide which comprises:
    1. a DNA-binding domain, which recognizes a factor-regulated promoter operably associated with a polynucleotide encoding a therapeutic polypeptide or therapeutic polynucleotide; and
    2. a ligand binding domain; and
iii. a third gene expression cassette comprising a polynucleotide encoding a therapeutic polypeptide or therapeutic polynucleotide comprising:
    1. a factor-regulated promoter, which is activated by the transactivation domain of the second hybrid polypeptide; and,
    2. a polynucleotide encoding a therapeutic polypeptide or therapeutic polynucleotide.

The multiple inducible gene expression systems provide for expression of a given therapeutic polynucleotide or therapeutic polypeptide under conditions associated with different diseases, disorders or conditions, or expression of multiple therapeutic polypeptides or therapeutic polynucleotides either under the same conditions associated with the same disease disorder or condition, or under different conditions associated with different diseases, disorders, or conditions.

In certain embodiments, the combination of two or more gene switch systems may be (1) a dual-switch ecdysone receptor based gene expression system and (2) a single-switch ecdysone receptor based gene switch. In other embodiments, the combination may be (1) an single- or dual-switch ecdysone receptor based gene switch and (2) a rapamycin based gene switch. Alternatively, the combination of gene switch systems may be two identical rapamycin based gene switch systems disclosed above. Any possible combinations of the gene switch systems are within the scope of the invention. Examples of dual-switch ecdysone systems can be found, for example, in WO 2002/29075 and US 2002/0110861.

Ligands

As used herein, the term "ligand," as applied to LDTFC-based gene switches e.g., EcD complex based gene switches, describes small and soluble molecules having the capability of activating a gene switch to stimulate expression of a polypeptide encoded therein. The ligand for a ligand-dependent transcription factor complex of the invention binds to the protein complex comprising one or more of the ligand binding domain, the heterodimer partner domain, the DNA binding domain, and the transactivation domain. The choice of ligand to activate the ligand-dependent transcription factor complex depends on the type of the gene switch utilized.

Examples of ligands include, without limitation, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; amidoketones such as those described in U.S. Published Application No. 2004/0049037; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, famesol, bile acids, 1,1-biphosphonate esters, juvenile hormone III, and the like. Examples of diacylhydrazine ligands useful in the present invention include RG-115819 (3,5-Dimethyl-benzoic acid N-(1-ethyl-2,2-dimethyl-propyl)-N'-(2-methyl-3-methoxy-benzoyl)-hydrazide), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N-(2-ethyl-3-methoxy-benzoyl)-hydrazide). See, e.g., U.S. patent application Ser. No. 12/155,111, published as US 2009/0163592, and PCT Appl. No. PCT/US2008/006757, both of which are incorporated herein by reference in their entireties.

For example, a ligand for the edysone receptor based gene switch may be selected from any suitable ligands. Both naturally occurring ecdysone or ecdyson analogs (e.g., 20-hydroxyecdysone, muristerone A, ponasterone A, ponasterone B, ponasterone C, 26-iodoponasterone A, inokosterone or 26-mesylinokosterone) and non-steroid inducers may be used as a ligand for gene switch of the present invention. U.S. Pat. No. 6,379,945 B1, describes an insect steroid receptor isolated from Heliothis virescens ("HEcR") which is capable of acting as a gene switch responsive to both steroid and certain non-steroidal inducers. Non-steroidal inducers have a distinct advantage over steroids, in this and many other systems which are responsive to both steroids and non-steroid inducers, for a number of reasons including, for example: lower manufacturing cost, metabolic stability, absence from insects, plants, or mammals, and environmental acceptability. U.S. Pat. No. 6,379,945 B1 describes the utility of two dibenzoylhydrazines, 1,2-dibenzoyl-1-tert-butyl-hydrazine and tebufenozide (N-(4-ethylbenzoyl)-N'-(3,5-dimethylbenzoyl)-N'-tert-butyl-hydrazine) as ligands for an ecdysone-based gene switch. Also included in the present invention as a ligand are other dibenzoylhydrazines, such as those disclosed in U.S. Pat. No. 5,117,057 B1. Use of tebufenozide as a chemical ligand for the ecdysone receptor from Drosophila melanogaster is also disclosed in U.S. Pat. No. 6,147,282. Additional, non-limiting examples of ecdysone ligands are 3,5-di-tert-butyl-4-hydroxy-N-isobutyl-benzamide, 8-O-acetylharpagide, a 1,2-diacyl hydrazine, an N'-substituted-N,N'-disubstituted hydrazine, a dibenzoylalkyl cyanohydrazine, an N-substituted-N-alkyl-N,N-diaroyl hydrazine, an N-substituted-N-acyl-N-alkyl, carbonyl hydrazine or an N-aroyl-N-alkyl-N'-aroyl hydrazine. (See U.S. Pat. No. 6,723,531).

In one embodiment, the ligand for an ecdysone based gene switch system is a diacylhydrazine ligand or chiral diacylhydrazine ligand. The ligand used in the gene switch system may be compounds of Formula I

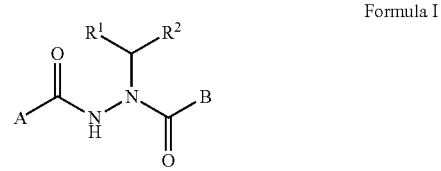

Formula I wherein

A is alkoxy, arylalkyloxy or aryloxy;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

or pharmaceutically acceptable salts, hydrates, crystalline forms or amorphous forms thereof.

In another embodiment, the ligand may be enantiomerically enriched compounds of Formula II

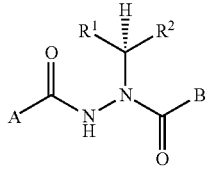

Formula II wherein
A is alkoxy, arylalkyloxy, aryloxy, arylalkyl, optionally substituted aryl or optionally substituted heteroaryl;
B is optionally substituted aryl or optionally substituted heteroaryl; and
$R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;
with the proviso that $R^1$ does not equal $R^2$;
wherein the absolute configuration at the asymmetric carbon atom bearing $R^1$ and $R^2$ is predominantly S;
or pharmaceutically acceptable salts, hydrates, crystalline forms or amorphous forms thereof.

In certain embodiments, the ligand may be enantiomerically enriched compounds of Formula III

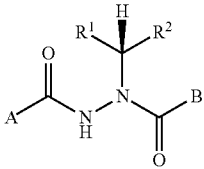

Formula III wherein
A is alkoxy, arylalkyloxy, aryloxy, arylalkyl, optionally substituted aryl or optionally substituted heteroaryl;
B is optionally substituted aryl or optionally substituted heteroaryl; and
$R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;
with the proviso that $R^1$ does not equal $R^2$;
wherein the absolute configuration at the asymmetric carbon atom bearing $R^1$ and $R^2$ is predominantly R;
or pharmaceutically acceptable salts, hydrates, crystalline forms or amorphous forms thereof.

In one embodiment, a ligand may be (R)-3,5-dimethylbenzoic acid N-(1-tert-butyl-butyl)-N'-(2-ethyl-3-methoxybenzoyl-hydrazide having an enantiomeric excess of at least 95% or a pharmaceutically acceptable salt, hydrate, crystalline form or amorphous form thereof.

The diacylhydrazine ligands of Formula I and chiral diacylhydrazine ligands of Formula II or III, when used with an ecdysone-based gene switch system, provide the means for external temporal regulation of expression of a therapeutic polypeptide or therapeutic polynucleotide of the present invention. See U.S. application Ser. No. 12/155,111, published as US 2009/0163592, filed May 29, 2008, which is fully incorporated by reference herein.

The ligands used in the present invention may form salts. The term "salt(s)" as used herein denotes acidic and/or basic salts formed with inorganic and/or organic acids and bases. In addition, when a compound of Formula I, II or III contains both a basic moiety and an acidic moiety, zwitterions ("inner salts") may be formed and are included within the term "salt (s)" as used herein. Pharmaceutically acceptable (i.e., non-toxic, physiologically acceptable) salts are used, although other salts are also useful, e.g., in isolation or purification steps which may be employed during preparation. Salts of the compounds of Formula I, II or III may be formed, for example, by reacting a compound with an amount of acid or base, such as an equivalent amount, in a medium such as one in which the salt precipitates or in an aqueous medium followed by lyophilization.

The ligands which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The ligands which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis (dehydroabietyl)ethylenediamine), N-methyl-D-glucamines, N-methyl-D-glucamides, t-butyl amines, and salts with amino acids such as arginine, lysine and the like.

Non-limiting examples of the ligands for the inducible gene expression system utilizing the FK506 binding domain are FK506, Cyclosporin A, or Rapamycin. FK506, rapamycin, and their analogs are disclosed in U.S. Pat. Nos. 6,649,595 B2 and 6,187,757. See also U.S. Pat. Nos. 7,276,498 and 7,273,874.

The ligands described herein may be administered alone or as part of a pharmaceutical composition comprising a pharmaceutically acceptable carrier. In one embodiment, the pharmaceutical composition are in the form of solutions, suspensions, tablets, capsules, ointments, elixirs, or injectable compositions.

In one embodiment, the polynucleotide encoding an antibody encodes a monoclonal antibody.

In another embodiment, the vector and methods of the present invention can be used to express nucleic acid as a vaccine. The present invention also provides a vaccine composition comprising a vector or expression system of the present invention. In another embodiment, the vaccine composition comprises an adjuvant.

An "erythropoietin or agonist thereof" is an erythropoietin polypeptide, a polypeptide having at least about 85%, 90%, 95%, 96%, 97%, 98% or 99% sequence identity with an erythropoietin, or a fragment of an erythropoietin that retains at least about 80%, 85%, 90%, 95%, 96%, 97%, 98%, 99% or 100% of the in vitro erythropoietin receptor binding activity of erythropoietin.

Any erythropoietin polynucleotide sequence can be used in the method of the present invention. In one embodiment, the erythropoietin polynucleotide sequence encodes human erythropoietin, for which the amino acid sequence is set forth in Accession No. AAF23134 (SEQ ID NO: 6). The amino acid sequences coding for erythropoietin are also available from public databases as accession numbers AAH93628 (human); AA119266 (mouse); and BAA01593 (rat), sequences of which are incorporated by reference herein. The polynucleotide sequences coding for erythropoietin are available from public databases as accession numbers BC093628 (human); BC119265 (mouse); and D10763 (rat), sequences of which are incorporated by reference herein.

In another embodiment, the erythropoietin polynucleotide sequence encodes is analog of human erythropoietin that retains at least 80%, 85%, 90%, 95%, 96%, 97%, 98% 99% or 100% of the in vitro erythropoietin receptor binding activity of human erythropoietin. In vitro erythropoietin receptor binding assays are well know to those of ordinary skill in the art. For example, see Harris, K. W. et al., *J. Biol. Chem.* 25: 15205-9 (1992); Wrighton, N. C. et al., *Science* 273: 458-463 (1996); and Jarsch, M. et al., *Pharmacology* 81: 63-69 (2008).

Non-limiting examples of erthropoietins include darbepoietin alfa, epoetin alfa, epoetin alfa, epoetin beta, and epoetin kappa.

Non-limiting examples of ertythropoietin agonists include those agonists disclosed in U.S. Pat. Nos. 7,767,643; 7,786,163; 7,674,913; 7,553,861; 7,410,941; 7,345,019; 7,309,687; 6,531,121; 5,858,670; 5,650,489; and 5,510,240. Other non-limiting examples of ertythropoietin agonists include those agonists disclosed in in U.S. patent publication nos. 2011/0027890, 2010/0305002, 2010/297117, 2010/0297106, 2010/0190692, 2010/0145006, 2010/136015, 2010/0120661, 2010/093608, 2010/0028331, 2010/016218, 2010/0009961, 2009/0233844, 2009/0022734, 2009/0004202, 2008/0213277, 2008/0014193, 2007/0298031, 2007/0293421, 2007/0060547, 2006/027071, 2006/0009518, 2003/0134798, 2003/0104988 and 2002/008616. Other non-limiting examples of ertythropoietin agonists include those agonists disclosed in MacDougal, I. C. et al., *N. Engl. J. Med.* 361: 1848-55 (2009); Pankratova, S. et al., *Brain* 133(Pt. 8): 2281-94 (2010); and Zarychanski, R. et al., *Canadian Medical Association Journal* 177: 725-34 (2007).

The term "ecdysone receptor-based," with respect to a gene switch, refers to a gene switch comprising at least a functional part of a naturally occurring or synthetic ecdysone receptor ligand binding domain and which regulates gene expression in response to a ligand that binds to the ecdysone receptor ligand binding domain. Examples of ecdysone-responsive systems are described in U.S. Pat. Nos. 7,091,038 and 6,258,603. In one embodiment, the system is the RheoSwitch® Therapeutic System (RTS), which contains two fusion proteins, the DEF domains of a mutagenized ecdysone receptor (EcR) fused with a Gal4 DNA binding domain and the EF domains of a chimeric RXR fused with a VP16 transcription activation domain, expressed under a constitutive promoter as illustrated in FIG. 1.

The terms "modulate" and "modulates" mean to induce, reduce or inhibit nucleic acid or gene expression, resulting in the respective induction, reduction or inhibition of protein or polypeptide production.

The polynucleotides or vectors according to the invention may further comprise at least one promoter suitable for driving expression of a gene in a host cell.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i.e., terminator or polyadenylation sequences, may also be derived from various genes native to the preferred hosts. Optionally, a termination site may be unnecessary, however, it is most preferred if included. In one embodiment of the invention, the termination control region may be comprised or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3 end of the mRNA precursor.

"Regulatory region" refers to a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" refers to a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

"Polypeptide," "peptide" and "protein" are used interchangeably and refer to a polymeric compound comprised of covalently linked amino acid residues.

An "isolated polypeptide," "isolated peptide" or "isolated protein" refer to a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be, for example, due to incomplete purification, addition of stabilizers, or compounding into a pharmaceutically acceptable preparation.

A "substitution mutant polypeptide" or a "substitution mutant" will be understood to mean a mutant polypeptide comprising a substitution of at least one wild-type or naturally occurring amino acid with a different amino acid relative to the wild-type or naturally occurring polypeptide. A substitution mutant polypeptide may comprise only one wild-type or naturally occurring amino acid substitution and may be referred to as a "point mutant" or a "single point mutant" polypeptide. Alternatively, a substitution mutant polypeptide may comprise a substitution of two or more wild-type or naturally occurring amino acids with two or more amino acids relative to the wild-type or naturally occurring polypeptide. According to the invention, a Group H nuclear receptor ligand binding domain polypeptide comprising a substitution mutation comprises a substitution of at least one wild-type or naturally occurring amino acid with a different amino acid relative to the wild-type or naturally occurring Group H nuclear receptor ligand binding domain polypeptide. Non-limiting examples of substitution mutant Group H nuclear receptor ligand binding domain polypeptides are found in WO 2002/066612 and US 2006/0100416.

When the substitution mutant polypeptide comprises a substitution of two or more wild-type or naturally occurring amino acids, this substitution may comprise either an equivalent number of wild-type or naturally occurring amino acids deleted for the substitution, i.e., 2 wild-type or naturally occurring amino acids replaced with 2 non-wild-type or non-naturally occurring amino acids, or a non-equivalent number of wild-type amino acids deleted for the substitution, i.e., 2 wild-type amino acids replaced with 1 non-wild-type amino acid (a substitution+deletion mutation), or 2 wild-type amino acids replaced with 3 non-wild-type amino acids (a substitution+insertion mutation).

Substitution mutants may be described using an abbreviated nomenclature system to indicate the amino acid residue and number replaced within the reference polypeptide sequence and the new substituted amino acid residue. For example, a substitution mutant in which the twentieth ($20^{th}$) amino acid residue of a polypeptide is substituted may be abbreviated as "x20z", wherein "x" is the amino acid to be replaced, "20" is the amino acid residue position or number within the polypeptide, and "z" is the new substituted amino acid. Therefore a substitution mutant abbreviated interchangeably as "E20A" or "Glu20Ala" indicates that the mutant comprises an alanine residue (commonly abbreviated in the art as "A" or "Ala") in place of the glutamic acid (commonly abbreviated in the art as "E" or "Glu") at position 20 of the polypeptide.

A substitution mutation may be made by any technique for mutagenesis known in the art, including but not limited to, in vitro site-directed mutagenesis (Hutchinson et al., *J. Biol. Chem.* 253:6551 (1978); Zoller et al., DNA 3:479 (1984); Oliphant et al., *Gene* 44:177 (1986); Hutchinson et al., *Proc. Natl. Acad. Sci. USA* 83:710 (1986)), use of TAB® linkers (Pharmacia), restriction endonuclease digestion/fragment deletion and substitution, PCR-mediated/oligonucleotide-directed mutagenesis, and the like. PCR-based techniques are preferred for site-directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

The term "fragment," as applied to a polypeptide, refers to a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 or more amino acids.

A "variant" of a polypeptide or protein refers to any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. In one embodiment, a variant polypeptide comprises at least about 14 amino acids.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., *Cell* 50:667 (1987)). Such proteins (and their encoding genes) have sequence homology, as reflected by their high degree of sequence similarity. However, in common usage and in the application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., Cell 50:667 (1987)). In one embodiment, two DNA sequences are "substantially homologous" or "substantially similar" when at least about 50% (e.g., at least about 75%, 90%, or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art (see e.g., Sambrook et al., 1989, supra).

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul et al., J. Mol. Biol. 215:403 (1993)); available at ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using sequence analysis software such as the Megalign program of the LASERGENE bioinformatics computing suite (DNASTAR Inc., Madison, Wis.). Multiple alignment of the sequences may be performed using the Clustal method of alignment (Higgins et al., CABIOS. 5:151 (1989)) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independent); developed. Typical sequence analysis software includes, but is not limited to, the GCG suite of programs (Wisconsin Package Version 9.0, Genetics Computer Group (GCG), Madison, Wis.), BLASTP, BLASTN, BLASTX (Altschul et al., J. Mol. Biol. 215:403 (1990)), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, two or more individually operable gene regulation systems are said to be "orthogonal" when; a) modulation of each of the given systems by its respective ligand, at a chosen concentration, results in a measurable change in the magnitude of expression of the gene of that system, and b) the change is statistically significantly different than the change in expression of all other systems simultaneously operable in the cell, tissue, or organism, regardless of the simultaneity or sequentiality of the actual modulation. Preferably, modulation of each individually operable gene regulation system effects a change in gene expression at least 2-fold greater than all other operable systems in the cell, tissue, or organism, e.g., at least 5-fold, 10-fold, 100-fold, or 500-fold greater. Ideally, modulation of each of the given systems by its respective ligand at a chosen concentration results in a measurable change in the magnitude of expression of the gene of that system and no measurable change in expression of all other systems operable in the cell, tissue, or organism. In such cases the multiple inducible gene regulation system is said to be "fully orthogonal." Useful orthogonal ligands and orthogonal receptor-based gene expression systems are described in US 2002/0110861 A1.

The term "exogenous gene" means a gene foreign to the subject, that is, a gene which is introduced into the subject through a transformation process, an unmutated version of an endogenous mutated gene or a mutated version of an endogenous unmutated gene. The method of transformation is not critical to this invention and may be any method suitable for the subject known to those in the art. Exogenous genes can be either natural or synthetic genes which are introduced into the subject in the form of DNA or RNA which may function through a DNA intermediate such as by reverse transcriptase. Such genes can be introduced into target cells, directly introduced into the subject, or indirectly introduced by the transfer of transformed cells into the subject.

The term "therapeutic product" refers to a therapeutic polypeptide or therapeutic polynucleotide which imparts a beneficial function to the host cell in which such product is expressed. Therapeutic polypeptides may include, without limitation, peptides as small as three amino acids in length, single- or multiple-chain proteins, and fusion proteins. Therapeutic polynucleotides may include, without limitation, antisense oligonucleotides, small interfering RNAs, ribozymes, and RNA external guide sequences. The therapeutic product may comprise a naturally occurring sequence, a synthetic sequence or a combination of natural and synthetic sequences.

The term "ligand-dependent transcription factor complex" or "LDTFC" refers to a transcription factor comprising one or more protein subunits, which complex can regulate gene expression driven by a "factor-regulated promoter" as defined herein. A model LDTFC is an "ecdysone receptor complex" generally refers to a heterodimeric protein complex having at least two members of the nuclear receptor family, ecdysone receptor ("EcR") and ultraspiracle ("USP") proteins (see Yao et al., Nature 366:476 (1993)); Yao et al., Cell 71:63 (1992)). A functional LDTFC such as an EcR complex may also include additional protein(s) such as immunophilins. Additional members of the nuclear receptor family of proteins, known as transcriptional factors (such as DHR38, betaFTZ-1 or other insect homologs), may also be ligand dependent or independent partners for EcR and/or USP. A LDTFC such as an EcR complex can also be a heterodimer of EcR protein and the vertebrate homolog of ultraspiracle protein, retinoic acid-X-receptor ("RXR") protein or a chimera of USP and RXR.

The terms "LDTFC" and "EcR complex" also encompass homodimer complexes of the EcR protein or USP, as well as single polypeptides or trimers, tetramer, and other multimers serving the same function.

A LDTFC such as an EcR complex can be activated by an active ecdysteroid or non-steroidal ligand bound to one of the proteins of the complex, inclusive of EcR, but not excluding other proteins of the complex. A LDTFC such as an EcR complex includes proteins which are members of the nuclear receptor superfamily wherein all members are characterized by the presence of one or more polypeptide subunits comprising an amino-terminal transactivation domain ("AD," "TD," or "TA," used interchangeably herein), a DNA binding domain ("DBD"), and a ligand binding domain ("LBD"). The AD may be present as a fusion with a "heterodimerization partner" or "HP." A fusion protein comprising an AD and HP of the invention is referred to herein as a "coactivation protein" or "CAP." The DBD and LBD may be expressed as a fusion protein, referred to herein as a "ligand-inducible transcription factor ("LTF"). The fusion partners may be separated by a linker, e.g., a hinge region. Some members of the LTF family may also have another transactivation domain on the carboxy-terminal side of the LBD. The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins.

The DNA sequences making up the exogenous gene, the response element, and the LDTFC, e.g., EcR complex, may be incorporated into archaebacteria, procaryotic cells such as *Escherichia coli, Bacillus subtilis*, or other enterobacteria, or eucaryotic cells such as plant or animal cells. However, because many of the proteins expressed by the gene are processed incorrectly in bacteria, eucaryotic cells are preferred. The cells may be in the form of single cells or multicellular organisms. The nucleotide sequences for the exogenous gene, the response element, and the receptor complex can also be incorporated as RNA molecules, preferably in the form of functional viral RNAs such as tobacco mosaic virus. Of the eucaryotic cells, vertebrate cells are preferred because they naturally lack the molecules which confer responses to the ligands of this invention for the EcR. As a result, they are "substantially insensitive" to the ligands of this invention. Thus, the ligands useful in this invention will have negligible physiological or other effects on transformed cells, or the whole organism. Therefore, cells can grow and express the desired product, substantially unaffected by the presence of the ligand itself.

The term "ecdysone receptor complex" generally refers to a heterodimeric protein complex having at least two members of the nuclear receptor family, ecdysone receptor ("EcR") and ultraspiracle ("USP") proteins (see Yao et al., Nature 366:476 (1993)); Yao et al., Cell 71:63 (1992)). The functional EcR complex may also include additional protein(s) such as immunophilins. Additional members of the nuclear receptor family of proteins, known as transcriptional factors (such as DHR38, betaFTZ-1 or other insect homologs), may also be ligand dependent or independent partners for EcR and/or USP. The EcR complex can also be a heterodimer of EcR protein and the vertebrate homolog of ultraspiracle protein, retinoic acid-X-receptor ("RXR") protein or a chimera of USP and RXR. The term EcR complex also encompasses homodimer complexes of the EcR protein or USP.

An EcR complex can be activated by an active ecdysteroid or non-steroidal ligand bound to one of the proteins of the complex, inclusive of EcR, but not excluding other proteins of the complex. As used herein, the term "ligand," as applied to EcR-based gene switches, describes small and soluble molecules having the capability of activating a gene switch to stimulate expression of a polypeptide encoded therein. Examples of ligands include, without limitation, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N-aroylhydrazines such as those described in U.S. Pat. No. 4,985,461; amidoketones such as those described in U.S. Published Application No. 2004/0049037; and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, famesol, bile acids, 1,1-biphosphonate esters, juvenile hormone III, and the like. Examples of diacylhydrazine ligands useful in the invention include RG-115819 (3,5-Dimethyl-benzoic acid N-(1-ethyl-2,2-dimethyl-propyl)-N'-(2-methyl-3-methoxy-benzoyl)-hydrazide), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See U.S. application Ser. No. 12/155,111, filed May 29, 2008, and PCT/US2008/006757 filed May 29, 2008, for additional diacylhydrazines that are useful in the practice of the invention.

The EcR complex includes proteins which are members of the nuclear receptor superfamily wherein all members are characterized by the presence of an amino-terminal transactivation domain ("TA"), a DNA binding domain ("DBD"), and a ligand binding domain ("LBD") separated by a hinge region. Some members of the family may also have another transactivation domain on the carboxy-terminal side of the LBD. The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins.

The DNA sequences making up the exogenous gene, the response element, and the EcR complex may be incorporated into archaebacteria, procaryotic cells such as *Escherichia coli, Bacillus subtilis*, or other enterobacteria, or eucaryotic cells such as plant or animal cells. However, because many of the proteins expressed by the gene are processed incorrectly in bacteria, eucaryotic cells are preferred. The cells may be in the form of single cells or multicellular organisms. The nucleotide sequences for the exogenous gene, the response element, and the receptor complex can also be incorporated as RNA molecules, preferably in the form of functional viral RNAs such as tobacco mosaic virus. Of the eucaryotic cells, vertebrate cells are preferred because they naturally lack the molecules which confer responses to the ligands of this invention for the EcR. As a result, they are "substantially insensitive" to the ligands of this invention. Thus, the ligands useful in this invention will have negligible physiological or other effects on transformed cells, or the whole organism. Therefore, cells can grow and express the desired product, substantially unaffected by the presence of the ligand itself.

EcR ligands, when used with the EcR complex which in turn is bound to the response element linked to an exogenous gene provide the means for external temporal regulation of expression of the exogenous gene. The order in which the various components bind to each other, that is, ligand to receptor complex and receptor complex to response element, is not critical. Typically, modulation of expression of the exogenous gene is in response to the binding of the EcR complex to a specific control, or regulatory, DNA element. The EcR protein, like other members of the nuclear receptor family, possesses at least three domains, a transactivation domain, a DNA binding domain, and a ligand binding domain. This receptor, like a subset of the nuclear receptor family, also possesses less well-defined regions responsible for heterodimerization properties. Binding of the ligand to the ligand binding domain of EcR protein, after heterodimerization with USP or RXR protein, enables the DNA binding domains of the heterodimeric proteins to bind to the response element in an activated form, thus resulting in expression or suppression of the exogenous gene. This mechanism does not exclude the potential for ligand binding to either EcR or USP, and the resulting formation of active homodimer complexes (e.g., EcR+EcR or USP+USP). In one embodiment, one or more of the receptor domains can be varied producing a chimeric gene switch. Typically, one or more of the three domains may be chosen from a source different than the source of the other domains so that the chimeric receptor is optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988) or LexA protein from *E. coli* (see Brent et al., *Cell* 43:729 (1985)) to accommodate chimeric EcR complexes. Another advantage of chimeric systems is that they allow choice of a promoter used to drive the exogenous gene according to a desired end result. Such double control can be particularly important in areas of gene therapy, especially when cytotoxic proteins are produced, because both the timing of expression as well as the cells wherein expression occurs can be controlled. When exogenous genes, operatively linked to a suitable promoter, are introduced into the cells of the subject, expression of the exogenous genes is controlled by the presence of the ligand of this invention. Promoters may be constitutively or inducibly regulated or may be tissue-specific (that is, expressed only in a particular type of cell) or specific to certain developmental stages of the organism.

In certain embodiments, the therapeutic switch promoter described in the methods is constitutive. In certain embodiments, the therapeutic switch promoter is activated under conditions associated with a disease, disorder, or condition, e.g., the promoter is activated in response to a disease, in response to a particular physiological, developmental, differentiation, or pathological condition, and/or in response to one or more specific biological molecules; and/or the promoter is activated in particular tissue or cell types. In certain embodiments, the disease, disorder, or condition is responsive to the therapeutic polypeptide or polynucleotide. For example in certain non-limiting embodiments the therapeutic polynucleotide or polypeptide is useful to treat, prevent, ameliorate, reduce symptoms, prevent progression, or cure the disease, disorder or condition, but need not accomplish any one or all of these things. In certain embodiments, the first and second polynucleotides are introduced so as to permit expression of the ligand-dependent transcription factor complex under conditions associated with a disease, disorder or condition. In one embodiment, the therapeutic methods are carried out such that the therapeutic polypeptide or therapeutic polynucleotide is expressed and disseminated through the subject at a level sufficient to treat, ameliorate, or prevent said disease, disorder, or condition. As used herein, "disseminated" means that the polypeptide is expressed and released from the modified cell sufficiently to have an effect or activity in the subject. Dissemination may be systemic, local or anything in between. For example, the therapeutic polypeptide or therapeutic polynucleotide might be systemically disseminated through the bloodstream or lymph system. Alternatively, the therapeutic polypeptide or therapeutic polynucleotide might be disseminated locally in a tissue or organ to be treated.

Numerous genomic and cDNA nucleic acid sequences coding for a variety of polypeptides, such as transcription factors and reporter proteins, are well known in the art. Those skilled in the art have access to nucleic acid sequence information for virtually all known genes and can either obtain the nucleic acid molecule directly from a public depository, the institution that published the sequence, or employ routine methods to prepare the molecule. See for example the description of the sequence accession numbers, infra.

The gene switch may be any gene switch system that regulates gene expression by addition or removal of a specific ligand. In one embodiment, the gene switch is one in which the level of gene expression is dependent on the level of ligand that is present. Examples of ligand-dependent transcription factors that may be used in the gene switches of the invention include, without limitation, members of the nuclear receptor superfamily activated by their respective ligands (e.g., glucocorticoid, estrogen, progestin, retinoid, ecdysone, and analogs and mimetics thereof) and rTTA activated by tetracycline. In one aspect of the invention, the gene switch is an EcR-based gene switch. Examples of such systems include, without limitation, the systems described in U.S. Pat. Nos. 6,258,603, 7,045,315, U.S. Published Patent Application Nos. 2006/0014711, 2007/0161086, and International Published Application No. WO 01/70816. Examples of chimeric ecdysone receptor systems are described in U.S. Pat. No. 7,091,038, U.S. Published Patent Application Nos. 2002/0110861, 2004/0033600, 2004/0096942, 2005/0266457, and 2006/0100416, and International Published Application Nos. WO 01/70816, WO 02/066612, WO 02/066613, WO 02/066614, WO 02/066615, WO 02/29075, and WO 2005/108617. An example of a non-steroidal ecdysone agonist-regulated system is the RheoSwitch® Mammalian Inducible Expression System (New England Biolabs, Ipswich, Mass.).

In one embodiment, a polynucleotide encoding the gene switch comprises a single transcription factor sequence encoding a ligand-dependent transcription factor under the control of a promoter. The transcription factor sequence may encode a ligand-dependent transcription factor that is a naturally occurring or an artificial transcription factor. An artificial transcription factor is one in which the natural sequence of the transcription factor has been altered, e.g., by mutation of the sequence or by the combining of domains from different transcription factors. In one embodiment, the transcription factor comprises a Group H nuclear receptor ligand binding domain (LBD). In one embodiment, the Group H nuclear receptor LBD is from an EcR, a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, or a farnesol receptor. In another embodiment, the Group H nuclear receptor LBD is from an ecdysone receptor.

In one embodiment, a polynucleotide encoding the gene switch comprises a single transcription factor sequence encoding a ligand-dependent transcription factor under the control of a promoter. The transcription factor sequence may encode a ligand-dependent transcription factor that is a naturally occurring or an artificial transcription factor. An artificial transcription factor is one in which the natural sequence of the transcription factor has been altered, e.g., by mutation of the sequence or by the combining of domains from different transcription factors. In one embodiment, the transcription factor comprises a Group H nuclear receptor ligand binding domain (LBD). In one embodiment, the Group H nuclear receptor LBD is from an EcR, a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, or a farnesol receptor. In another embodiment, the Group H nuclear receptor LBD is from an ecdysone receptor.

The EcR and the other Group H nuclear receptors are members of the nuclear receptor superfamily wherein all members are generally characterized by the presence of an amino-terminal transactivation domain (TD), a DNA binding domain (DBD), and a LBD separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, B, and in some members F (see U.S. Pat. No. 4,981,784 and Evans, *Science* 240:889 (1988)). The "A/B" domain corresponds to the transactivation domain, "C" corresponds to the DNA binding domain, "D" corresponds to the hinge region, and "E," corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for response elements. These domains may be either native, modified, or chimeras of different domains of heterologous receptor proteins. The EcR, like a subset of the nuclear receptor family, also possesses less well-defined regions responsible for heterodimerization properties. Because the domains of nuclear receptors are modular in nature, the LBD, DBD, and TD may be interchanged.

In another embodiment, the transcription factor comprises a TD, a DBD that recognizes a response element associated with the exogenous gene whose expression is to be modulated; and a Group H nuclear receptor LBD. In certain embodiments, the Group H nuclear receptor LBD comprises a substitution mutation.

In another embodiment, a polynucleotide encoding the gene switch comprises a first transcription factor sequence under the control of a first promoter and a second transcription factor sequence under the control of a second promoter, wherein the proteins encoded by said first transcription factor sequence and said second transcription factor sequence interact to form a protein complex which functions as a ligand-dependent transcription factor, i.e., a "dual switch"- or "two-hybrid"-based gene switch. The first and second promoters may be the same or different.

In certain embodiments, the polynucleotide encoding a gene switch comprises a first transcription factor sequence and a second transcription factor sequence under the control of a promoter, wherein the proteins encoded by said first transcription factor sequence and said second transcription factor sequence interact to form a protein complex which functions as a ligand-dependent transcription factor, i.e., a "single gene switch". The first transcription factor sequence and a second transcription factor sequence may be connected by an internal ribosomal entry site (IRES). The IRES may be an EMCV IRES.

In one embodiment, the first transcription factor sequence encodes a polypeptide comprising a TD, a DBD that recognizes a response element associated with the exogenous gene whose expression is to be modulated; and a Group H nuclear receptor LBD, and the second transcription factor sequence encodes a transcription factor comprising a nuclear receptor LBD selected from a vertebrate RXR LBD, an invertebrate RXR LBD, an ultraspiracle protein LBD, and a chimeric LBD comprising two polypeptide fragments, wherein the first polypeptide fragment is from a vertebrate RXR LBD, an invertebrate RXR LBD, or an ultraspiracle protein LBD, and the second polypeptide fragment is from a different vertebrate RXR LBD, invertebrate RXR LBD, or ultraspiracle protein LBD.

In another embodiment, the gene switch comprises a first transcription factor sequence encoding a first polypeptide comprising a nuclear receptor LBD and a DBD that recognizes a response element associated with the exogenous gene whose expression is to be modulated, and a second transcription factor sequence encoding a second polypeptide comprising a TD and a nuclear receptor LBD, wherein one of the nuclear receptor LBDs is a Group H nuclear receptor LBD. In one embodiment, the first polypeptide is substantially free of a TD and the second polypeptide is substantially free of a DBD. For purposes of the invention, "substantially free" means that the protein in question does not contain a sufficient sequence of the domain in question to provide activation or binding activity.

In another aspect of the invention, the first transcription factor sequence encodes a protein comprising a heterodimer partner and a TD and the second transcription factor sequence encodes a protein comprising a DBD and a LBD.

When only one nuclear receptor LBD is a Group H LBD, the other nuclear receptor LBD may be from any other nuclear receptor that forms a dimer with the Group H LBD. For example, when the Group H nuclear receptor LBD is an EcR LBD, the other nuclear receptor LBD "partner" may be from an EcR, a vertebrate RXR, an invertebrate RXR, an ultraspiracle protein (USP), or a chimeric nuclear receptor comprising at least two different nuclear receptor LBD polypeptide fragments selected from a vertebrate RXR, an invertebrate RXR, and a USP (see WO 01/70816 A2, International Patent Application No. PCT/US02/05235 and US 2004/0096942 A1). The "partner" nuclear receptor ligand binding domain may further comprise a truncation mutation, a deletion mutation, a substitution mutation, or another modification.

In one embodiment, the vertebrate RXR LBD is from a human *Homo sapiens*, mouse *Mus musculus*, rat *Rattus norvegicus*, chicken *Gallus gallus*, pig *Sus scrofa domestica*, frog *Xenopus laevis*, zebrafish *Danio rerio*, tunicate *Polyandrocarpa misakiensis*, or jellyfish *Tripedalia cysophora* RXR.

In one embodiment, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), an ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

In one embodiment, the chimeric RXR LBD comprises at least two polypeptide fragments selected from a vertebrate species RXR polypeptide fragment, an invertebrate species RXR polypeptide fragment, and a non-Dipteran/non-Lepidopteran invertebrate species RXR homolog polypeptide fragment. A chimeric RXR ligand binding domain for use in the invention may comprise at least two different species RXR polypeptide fragments, or when the species is the same, the two or more polypeptide fragments may be from two or more different isoforms of the species RXR polypeptide fragment.

In one embodiment, the chimeric RXR ligand binding domain comprises at least one vertebrate species RXR polypeptide fragment and one invertebrate species RXR polypeptide fragment.

In another embodiment, the chimeric RXR ligand binding domain comprises at least one vertebrate species RXR polypeptide fragment and one non-Dipteran/non Lepidopteran invertebrate species RXR homolog polypeptide fragment.

The ligand, when combined with the LBD of the nuclear receptor(s), which in turn are bound to the response element linked to the exogenous gene, provides external temporal regulation of expression of the exogenous gene. The binding mechanism or the order in which the various components of this invention bind to each other, that is, for example, ligand to LBD, DBD to response element, TD to promoter, etc., is not critical.

In a specific example, binding of the ligand to the LBD of a Group H nuclear receptor and its nuclear receptor LBD partner enables expression of the exogenous gene. This mechanism does not exclude the potential for ligand binding to the Group H nuclear receptor (GHNR) or its partner, and the resulting formation of active homodimer complexes (e.g., GHNR+GHNR or partner+partner). Preferably, one or more of the receptor domains is varied producing a hybrid gene switch. Typically, one or more of the three domains, DBD, LBD, and TD, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988)) or LexA protein from *Escherichia coli* (see Brent et al., *Cell* 43:729 (1985)), or synthetic response elements specific for targeted interactions with proteins designed, modified, and selected for such specific interactions (see, for example, Kim et al., *Proc. Natl. Acad. Sci. USA,* 94:3616 (1997)) to accommodate hybrid receptors.

The functional EcR complex may also include additional protein(s) such as immunophilins. Additional members of the nuclear receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al., Curr. Opin. Cell Biol. 9:222 (1997)). Also, protein cofactors generally known as corepressors (also known as repressors, silencers, or silencing mediators) may be required to effectively inhibit transcriptional activation in the absence of ligand. These corepressors may interact with the unliganded EcR to silence the activity at the response element. Current evidence suggests that the binding of ligand changes the conformation of the receptor, which results in release of the corepressor and recruitment of the above described coactivators, thereby abolishing their silencing activity. Examples of corepressors include N-CoR and SMRT (for review, see Horwitz et al., Mol Endocrinol. 10:1167 (1996)). These cofactors may either be endogenous within the cell or organism, or may be added exogenously as transgenes to be expressed in either a regulated or unregulated fashion.

The exogenous gene is operably linked to a promoter comprising at least one response element that is recognized by the DBD of the ligand-dependent transcription factor encoded by the gene switch. In one embodiment, the promoter comprises 1, 2, 3, 4, 5, 6, 7, 8, 9, 10, or more copies of the response element. Promoters comprising the desired response elements may be naturally occurring promoters or artificial promoters created using techniques that are well known in the art, e.g., one or more response elements operably linked to a minimal promoter.

A gene encoding a protein can also be codon-optimized. In one embodiment, a coding region of a protein is codon-optimized for expression in human. As appreciated by one of ordinary skill in the art, various nucleic acid coding regions will encode the same polypeptide due to the redundancy of the genetic code. Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 4. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the polypeptides encoded by the DNA.

TABLE 4

The Standard Genetic Code

|   | T | C | A | G |
|---|---|---|---|---|
| T | TTT Phe (F) | TCT Ser (S) | TAT Tyr (Y) | TGT Cys (C) |
|   | TTC " | TCC " | TAC " | TGC " |
|   | TTA Leu (L) | TCA " | TAA Ter | TGA Ter |
|   | TTG " | TCG " | TAG Ter | TGG Trp (W) |
| C | CTT Leu (L) | CCT Pro (P) | CAT His (H) | CGT Arg (R) |
|   | CTC " | CCC " | CAC " | CGC " |
|   | CTA " | CCA " | CAA Gln (Q) | CGA " |
|   | CTG " | CCG " | CAG " | CGG " |
| A | ATT Ile (I) | ACT Thr (T) | AAT Asn (N) | AGT Ser (S) |
|   | ATC " | ACC " | AAC " | AGC " |
|   | ATA " | ACA " | AAA Lys (K) | AGA Arg (R) |
|   | ATG Met (M) | ACG " | AAG " | AGG " |
| G | GTT Val (V) | GCT Ala (A) | GAT Asp (D) | GCT Gly (G) |
|   | GTC " | GCC " | GAC " | GCG " |
|   | GTA " | GCA " | GAA Glu (E) | GGA " |
|   | GTG " | GCG " | GAG " | GGG " |

It is to be appreciated that any polynucleotide that encodes a polypeptide in accordance with the invention falls within the scope of this invention, regardless of the codons used.

Many organisms display a bias for use of particular codons to code for insertion of a particular amino acid in a growing polypeptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

The polynucleotides are prepared by incorporating codons preferred for use in the genes of a given species into the DNA sequence.

Given the large number of gene sequences available for a wide variety of animal, plant and microbial species, it is possible to calculate the relative frequencies of codon usage. Codon usage tables are readily available, for example, at the "Codon Usage Database" available at http://www.kazusa.or.jp/codon/ (visited May 30, 2006), and these tables can be adapted in a number of ways. See Nakamura, Y., et al., "Codon usage tabulated from the international DNA sequence databases: status for the year 2000" Nucl. Acids Res. 28:292 (2000). Codon usage tables for humans calculated from GenBank Release 151.0, are reproduced below as Table 5 (from http://www.kazusa.or.jp/codon/ supra). These tables use mRNA nomenclature, and so instead of thymine (T) which is found in DNA, the tables use uracil (U) which is found in RNA. The tables have been adapted so that frequencies are calculated for each amino acid, rather than for all 64 codons.

TABLE 5

Codon Usage Table for Human Genes (*Homo sapiens*)

| Amino Acid | Codon | Frequency of Usage |
|---|---|---|
| Phe | UUU | 0.4525 |
|  | UUC | 0.5475 |
| Leu | UUA | 0.0728 |
|  | UUG | 0.1266 |

TABLE 5-continued

Codon Usage Table for Human Genes (*Homo sapiens*)

| Amino Acid | Codon | Frequency of Usage |
|---|---|---|
| | CUU | 0.1287 |
| | CUC | 0.1956 |
| | CUA | 0.0700 |
| | CUG | 0.4062 |
| Ile | AUU | 0.3554 |
| | AUC | 0.4850 |
| | AUA | 0.1596 |
| Met | AUG | 1.0000 |
| Val | GUU | 0.1773 |
| | GUC | 0.2380 |
| | GUA | 0.1137 |
| | GUG | 0.4710 |
| Ser | UCU | 0.1840 |
| | UCC | 0.2191 |
| | UCA | 0.1472 |
| | UCG | 0.0565 |
| | AGU | 0.1499 |
| | AGC | 0.2433 |
| Pro | ECU | 0.2834 |
| | CCC | 0.3281 |
| | CCA | 0.2736 |
| | CCG | 0.1149 |
| Thr | ACU | 0.2419 |
| | ACC | 0.3624 |
| | ACA | 0.2787 |
| | ACG | 0.1171 |
| Ala | GCU | 0.2637 |
| | GCC | 0.4037 |
| | GCA | 0.2255 |
| | GCG | 0.1071 |
| Tyr | UAU | 0.4347 |
| | UAC | 0.5653 |
| His | CAU | 0.4113 |
| | CAC | 0.5887 |
| Gln | CAA | 0.2541 |
| | CAG | 0.7459 |
| Asn | AAU | 0.4614 |
| | AAC | 0.5386 |
| Lys | AAA | 0.4212 |
| | AAG | 0.5788 |
| Asp | GAU | 0.4613 |
| | GAC | 0.5387 |
| Glu | GAA | 0.4161 |
| | GAG | 0.5839 |
| Cys | UGU | 0.4468 |
| | UGC | 0.5532 |
| Trp | UGG | 1.0000 |
| Arg | CGU | 0.0830 |
| | CGC | 0.1927 |
| | CGA | 0.1120 |
| | CGG | 0.2092 |
| | AGA | 0.2021 |
| | AGG | 0.2011 |
| Gly | GGU | 0.1632 |
| | GGC | 0.3438 |
| | GGA | 0.2459 |
| | GGG | 0.2471 |

By utilizing these or similar tables, one of ordinary skill in the art can apply the frequencies to any given polypeptide sequence, and produce a nucleic acid fragment of a codon-optimized coding region which encodes the polypeptide, but which uses codons optimal for a given species.

A number of options are available for synthesizing codon-optimized coding regions designed by any of the methods described above, using standard and routine molecular biological manipulations well known to those of ordinary skill in the art.

In one embodiment, the coding region encoding the protein in the vector of the invention is codon-optimized. In another embodiment, the coding region is codon-optimized for expression in human. In a particular embodiment, the sequence is a codon-optimized nucleic acid sequence.

To introduce the polynucleotides into the cells in vivo or ex vivo, a vector can be used. The vector may be, for example, a plasmid vector or a single- or double-stranded RNA or DNA viral vector. Such vectors may be introduced into cells of a subject in need thereof, e.g., mammal, by well-known techniques for introducing DNA and RNA into cells. Viral vectors may be replication competent or replication defective. In the latter case, viral propagation generally will occur only in complementing host cells. As used herein, the term "host cell" or "host" is used to mean a cell of the invention that is harboring one or more polynucleotides of the invention.

Thus, at a minimum, the vectors must include the polynucleotides of the invention. Other components of the vector may include, but are not limited to, selectable markers, chromatin modification domains, additional promoters driving expression of other polypeptides that may also be present on the vector (e.g., a lethal polypeptide), gnomic integration sites, recombination sites, and molecular insertion pivots. The vectors may comprise any number of these additional elements, either within or not within the polynucleotides, such that the vector can be tailored to the specific goals of the therapeutic methods desired.

In one embodiment of the invention, the vectors that are introduced into the cells further comprise a "selectable marker gene" which, when expressed, indicates that the gene switch construct of the invention has been integrated into the genome of the host cell. In this manner, the selector gene can be a positive marker for the genome integration. While not critical to the methods of the invention, the presence of a selectable marker gene allows the practitioner to select for a population of live cells where the vector construct has been integrated into the genome of the cells. Thus, certain embodiments of the invention comprise selecting cells where the vector has successfully been integrated. As used herein, the term "select" or variations thereof, when used in conjunction with cells, is intended to mean standard, well-known methods for choosing cells with a specific genetic make-up or phenotype. Typical methods include, but are not limited to, culturing cells in the presence of antibiotics, such as G418, neomycin and ampicillin. Other examples of selectable marker genes include, but are not limited to, genes that confer resistance to dihydrofolate reductase, hygromycin, or mycophenolic acid. Other methods of selection include, but are not limited to, a selectable marker gene that allows for the use of thymidine kinase, hypoxanthine-guanine phosphoribosyltransferase or adenine phosphoribosyltransferase as selection agents. Cells comprising a vector construct comprising an antibiotic resistance gene or genes would then be capable of tolerating the antibiotic in culture. Likewise, cells not comprising a vector construct comprising an antibiotic resistance gene or genes would not be capable of tolerating the antibiotic in culture.

As used herein, a "chromatin modification domain" (CMD) refers to nucleotide sequences that interact with a variety of proteins associated with maintaining and/or altering chromatin structure, such as, but not limited to, DNA insulators. See Ciavatta et al., *Proc. Nat'l Acad. Sci. U.S.A.*, 103:9958 (2006). Examples of CMDs include, but are not limited to, the chicken β-globulin insulator and the chicken hypersensitive site 4 (cHS4). The use of different CMD sequences between one or more gene programs (i.e., a promoter, coding sequence, and 3' regulatory region), for example, can facilitate the use of the differential CMD DNA sequences as "mini homology arms" in combination with various microorganism or in vitro recombineering technologies to "swap" gene programs between existing multigenic and monogenic shuttle vectors. Other examples of chromatin modification domains are known in the art or can be readily identified.

Polynucleotide and nucleic acid coding regions in the vector of the invention can be associated with additional coding regions which encode secretory or signal peptides, which direct the secretion of a protein. According to the signal hypothesis, proteins secreted by mammalian cells have a signal peptide or secretory leader sequence which is cleaved from the mature protein once export of the growing protein chain across the rough endoplasmic reticulum has been initiated. Polypeptides secreted by vertebrate cells generally have a signal peptide fused to the N-terminus of the polypeptide, which is cleaved from the complete or "full length" polypeptide to produce a secreted or "mature" form of the polypeptide.

In one embodiment, a vector of the invention comprises a polynucleotide encoding a gene switch, wherein said polynucleotide comprises (1) at least one transcription factor sequence which is operably linked to a promoter, wherein said at least one transcription factor sequence encodes a ligand-dependent transcription factor, and (2) a polynucleotide encoding one or more proteins operably linked to a promoter which is activated by said ligand-dependent transcription factor, wherein said polynucleotide encoding one or more proteins further comprises a nucleic acid sequence encoding a signal peptide. In another embodiment, the signal peptide increases secretion of the protein encoded by the vector, compared to a vector comprising the protein's native signal peptide gene. In particular, the signal peptide used in the invention can be codon-optimized.

The vector of the invention can comprise various regulatory regions, for example, 5' untranslated region (5' UTR), 3' UTR, or both. The present invention is also directed to using various regulatory regions to induce improved secretion, protein translation, post-translation, mRNA transcription, or post-transcription process. As used herein, the "5' untranslated region" or "5'UTR" of a gene is to be understood as that part of a gene which is transcribed into a primary RNA transcript (pre-mRNA) and which part is located upstream of the coding sequence. The primary transcript is the initial RNA product, containing introns and exons, produced by transcription of DNA. Many primary transcripts must undergo RNA processing to form the physiologically active RNA species. The processing into a mature mRNA may comprise trimming of the ends, removal of introns, capping and/or cutting out of individual rRNA molecules from their precursor RNAs. The 5'UTR of an mRNA is thus that part of the mRNA which is not translated into protein and which is located upstream of the coding sequence. In a genomic sequence, the 5'UTR is typically defined as the region between the transcription initiation site and the start codon. The 5' untranslated regions (5' UTRs) of vertebrate mRNAs may be a few tens of bases to several hundred bases in length (Crowe et al., 2006 *BMC Genomics* 7:16). The 5'UTR used herein may occur naturally or be modified to contain one or more nucleic acid sequences not contiguous in nature (chimeric sequences), and/or may encompass substitutions, insertions, and deletions and combinations thereof. In one embodiment, the 5'UTR sequence is derived from the wild-type TNF-alpha sequence or 5U2 sequence. In another embodiment, the 5'UTR sequence is 5'UTR of 5U2. In some embodiments, the 5'UTR induces improved protein expression, e.g, mRNA transcription, pre-transcription, or post-transcription.

The 3' untranslated region (UTR) used in the invention refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor. Any suitable polyadenylation sequence can be used, including a synthetic optimized sequence, as well as the polyadenylation sequence of BGH (Bovine Growth Hormone), polyoma virus, TK (Thymidine Kinase), EBV (Epstein Barr Virus), and the papillomaviruses, including human papillomaviruses and BPV (Bovine Papilloma Virus). In a particular embodiment, a 3' regulatory region is the SV40e (human Sarcoma Virus-40) polyadenylation sequence. In another particular embodiment, a 3' regulatory region is the polyadenylation sequence of human growth hormone.

In certain embodiments, the signal peptide and/or the regulatory region alone or in combination can improve the protein secretion, transcription, or translation at least two fold, three fold, four fold, five fold, six fold, seven fold, eight fold, nine fold, 10 fold, 50 fold, 100 fold, 200 fold, 300 fold, 400 fold, or 500 fold compared to a control, which does not contain the signal peptide and/or the regulatory region. The secretion level of a protein, e.g., TNF-alpha, can be normalized to the protein expression encoded by a vector having a wild-type gene. In another specific embodiment of the present invention, the signal peptide and/or the regulatory region alone or in combination increase productivity of the protein about 5% to about 10%, about 11% to about 20%, about 21% to about 30%, about 31% to about 40%, about 41% to about 50%, about 51% to about 60%, about 61% to about 70%, about 71% to about 80%, about 81% to about 90%, about 91% to about 100%, about to about 149%, about 150% to about 199%, about 200% to about 299%, about 300% to about 499%, or about 500% to about 1000%. In a specific embodiment, the present invention comprises a vector conditionally expressing a protein wherein said vector comprises 5' UTR of 5U2, a codon-optimized nucleic acid sequence encoding IL-2 signal peptide, a codon-optimized coding region encoding a protein and a polyadenylation signal of SV40e or human growth hormone.

Particular vectors for use with the invention are expression vectors that code for proteins or polynucleotides. Generally, such vectors comprise cis-acting control regions effective for expression in a host operatively linked to the polynucleotide to be expressed. Appropriate trans-acting factors are supplied by the host, supplied by a complementing vector or supplied by the vector itself upon introduction into the host.

A great variety of expression vectors can be used to express proteins or polynucleotides. Such vectors include chromosomal, episomal and virus-derived vectors, e.g., vectors derived from bacterial plasmids, from bacteriophage, from yeast episomes, from yeast chromosomal elements, from viruses such as adeno-associated viruses, lentiviruses, baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. All may be used for expression in accordance with this aspect of the invention. Generally, any vector suitable to maintain, propagate or express polynucleotides or proteins in a host may be used for expression in this regard.

Suitable viral vectors used in the invention include, but not limited to, adenovirus based vectors, retroviral vectors, herpes simplex virus (HSV)-based vectors, parvovirus-based vectors, e.g., adeno-associated virus (AAV)-based vectors, and AAV-adenoviral chimeric vectors. These viral vectors can be prepared using standard recombinant DNA techniques described in, for example, Sambrook et al., Molecular Cloning, a Laboratory Manual, 2d edition, Cold Spring Harbor Press, Cold Spring Harbor, N.Y. (1989), and Ausubel et al., Current Protocols in Molecular Biology, Greene Publishing Associates and John Wiley & Sons, New York, N.Y. (1994).

In one embodiment, a viral vector of the invention is an adenoviral vector. Adenovirus (Ad) is a 36 kb double-stranded DNA virus that efficiently transfers DNA in vivo to a variety of different target cell types. The adenoviral vector can be produced in high titers and can efficiently transfer DNA to replicating and non-replicating cells. The adenoviral vector genome can be generated using any species, strain, subtype, mixture of species, strains, or subtypes, or chimeric adenovirus as the source of vector DNA. Adenoviral stocks that can be employed as a source of adenovirus can be amplified from the adenoviral serotypes 1 through 51, which are currently available from the American Type Culture Collection (ATCC, Manassas, Va.), or from any other serotype of adenovirus available from any other source. For instance, an adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 9, 10, 13, 15, 17, 19, 20, 22-30, 32, 33, 36-39, and 42-47), subgroup F (serotype 4), subgroup F (serotypes 40 and 41); or any other adenoviral serotype. Given that the human adenovirus serotype 5 (Ad5) genome has been completely sequenced, the adenoviral vector of the invention is described herein with respect to the Ad5 serotype. The adenoviral vector can be any adenoviral vector capable of growth in a cell, which is in some significant part (although not necessarily substantially) derived from or based upon the genome of an adenovirus. The adenoviral vector can be based on the genome of any suitable wild-type adenovirus. In certain embodiments, the adenoviral vector is derived from the genome of a wild-type adenovirus of group C, especially of serotype 2 or 5. Adenoviral vectors are well known in the art and are described in, for example, U.S. Pat. Nos. 5,559,099, 5,712,136, 5,731,190, 5,837,511, 5,846,782, 5,851,806, 5,962,311, 5,965,541, 5,981,225, 5,994,106, 6,020,191, and 6,113,913, International Patent Applications WO 95/34671, WO 97/21826, and WO 00/00628, and Thomas Shenk, "Adenoviridae and their Replication," and M. S. Horwitz; "Adenoviruses," Chapters 67 and 68, respectively, in *Virology*, B. N. Fields et al., eds., 3d ed., Raven Press, Ltd., New York (1996).

In other embodiments, the adenoviral vector is replication-deficient. The term "replication-deficient" used herein means that the adenoviral vector comprises a genome that lacks at least one replication-essential gene function. A deficiency in a gene, gene function, or gene or genomic region, as used herein, is defined as a deletion of sufficient genetic material of the viral genome to impair or obliterate the function of the gene whose nucleic acid sequence was deleted in whole or in part. Replication-essential gene functions are those gene functions that are required for replication (i.e., propagation) of a replication-deficient adenoviral vector. Replication-essential gene functions are encoded by, for example, the adenoviral early regions (e.g., the E1, E2, and E4 regions), late regions (e.g., the L1-L5 regions), genes involved in viral packaging (e.g., the IVa2 gene), and virus-associated RNAs (e.g., VA-RNA I and/or VA-RNA II). In still other embodiments, the replication-deficient adenoviral vector comprises an adenoviral genome deficient in at least one replication-essential gene function of one or more regions of an adenoviral genome (e.g., two or more regions of an adenoviral genome so as to result in a multiply replication-deficient adenoviral vector). The one or more regions of the adenoviral genome are selected from the group consisting of the E1, E2, and E4 regions. The replication-deficient adenoviral vector can comprise a deficiency in at least one replication-essential gene function of the E1 region (denoted an E1-deficient adenoviral vector), particularly a deficiency in a replication-essential gene function of each of the adenoviral E1A region and the adenoviral E1B region. In addition to such a deficiency in the E1 region, the recombinant adenovirus also can have a mutation in the major late promoter (MLP), as discussed in International Patent Application WO 00/00628. In a particular embodiment, the vector is deficient in at least one replication-essential gene function of the E1 region and at least part of the nonessential E3 region (e.g., an Xba I deletion of the E3 region) (denoted an E1/E3-deficient adenoviral vector).

In certain embodiments, the adenoviral vector is "multiply deficient," meaning that the adenoviral vector is deficient in one or more gene functions required for viral replication in each of two or more regions of the adenoviral genome. For example, the aforementioned E1-deficient or E1/E3-deficient adenoviral vector can be further deficient in at least one replication-essential gene function of the E4 region (denoted an E1/E4-deficient adenoviral vector). An adenoviral vector deleted of the entire E4 region can elicit a lower host immune response.

Alternatively, the adenoviral vector lacks replication-essential gene functions in all or part of the E1 region and all or part of the E2 region (denoted an E1/E2-deficient adenoviral vector). Adenoviral vectors lacking replication-essential gene functions in all or part of the E1 region, all or part of the E2 region, and all or part of the E3 region also are contemplated herein. If the adenoviral vector of the invention is deficient in a replication-essential gene function of the E2A region, the vector does not comprise a complete deletion of the E2A region, which is less than about 230 base pairs in length. Generally, the E2A region of the adenovirus codes for a DBP (DNA binding protein), a polypeptide required for DNA replication. DBP is composed of 473 to 529 amino acids depending on the viral serotype. It is believed that DBP is an asymmetric protein that exists as a prolate ellipsoid consisting of a globular Ct with an extended Nt domain. Studies indicate that the Ct domain is responsible for DBP's ability to bind to nucleic acids, bind to zinc, and function in DNA synthesis at the level of DNA chain elongation. However, the Nt domain is believed to function in late gene expression at both transcriptional and post-transcriptional levels, is responsible for efficient nuclear localization of the protein, and also may be involved in enhancement of its own expression. Deletions in the Nt domain between amino acids 2 to 38 have indicated that this region is important for DBP function (Brough et al., *Virology*, 196, 269-281 (1993)). While deletions in the E2A region coding for the Ct region of the DBP have no effect on viral replication, deletions in the E2A region which code for amino acids 2 to 38 of the Nt domain of the DBP impair viral replication. In one embodiment, the multiply replication-deficient adenoviral vector contains this portion of the E2A region of the adenoviral genome. In particular, for example, the desired portion of the E2A region to be retained is that portion of the E2A region of the adenoviral genome which is defined by the 5' end of the E2A region, specifically positions Ad5(23816) to Ad5(24032) of the E2A region of the adenoviral genome of serotype Ad5.

The adenoviral vector can be deficient in replication-essential gene functions of only the early regions of the adenoviral genome, only the late regions of the adenoviral genome, and both the early and late regions of the adenoviral genome. The adenoviral vector also can have essentially the entire adenoviral genome removed, in which case at least either the viral inverted terminal repeats (ITRs) and one or more promoters or the viral ITRs and a packaging signal are left intact (i.e., an adenoviral amplicon). The larger the region of the adenoviral genome that is removed, the larger the piece of exogenous nucleic acid sequence that can be inserted into the genome. For example, given that the adenoviral genome is 36 kb, by leaving the viral ITRs and one or more promoters intact, the exogenous insert capacity of the adenovirus is approximately 35 kb. Alternatively, a multiply deficient adenoviral vector that contains only an ITR and a packaging signal effectively allows insertion of an exogenous nucleic acid sequence of approximately 37-38 kb. Of course, the inclusion of a spacer element in any or all of the deficient adenoviral regions will decrease the capacity of the adenoviral vector for large inserts. Suitable replication-deficient adenoviral vectors, including multiply deficient adenoviral vectors, are disclosed in U.S. Pat. Nos. 5,851,806 and 5,994,106 and International Patent Applications WO 95/34671 and WO 97/21826. In one embodiment, the vector for use in the present inventive method is that described in International Patent Application PCT/US01/20536.

It should be appreciated that the deletion of different regions of the adenoviral vector can alter the immune response of the mammal. In particular, the deletion of different regions can reduce the inflammatory response generated by the adenoviral vector. Furthermore, the adenoviral vector's coat protein can be modified so as to decrease the adenoviral vector's ability or inability to be recognized by a neutralizing antibody directed against the wild-type coat protein, as described in International Patent Application WO 98/40509.

The adenoviral vector, when multiply replication-deficient, especially in replication-essential gene functions of the E1 and E4 regions, can include a spacer element to provide viral growth in a complementing cell line similar to that achieved by singly replication deficient adenoviral vectors, particularly an adeno viral vector comprising a deficiency in the E1 region. The spacer element can contain any sequence or sequences which are of the desired length. The spacer element sequence can be coding or non-coding and native or non-native with respect to the adenoviral genome, but does not restore the replication-essential function to the deficient region. In the absence of a spacer, production of fiber protein and/or viral growth of the multiply replication-deficient adenoviral vector is reduced by comparison to that of a singly replication-deficient adenoviral vector. However, inclusion of the spacer in at least one of the deficient adenoviral regions, preferably the E4 region, can counteract this decrease in fiber protein production and viral growth. The use of a spacer in an adenoviral vector is described in U.S. Pat. No. 5,851,806.

Construction of adenoviral vectors is well understood in the art. Adenoviral vectors can be constructed and/or purified using the methods set forth, for example, in U.S. Pat. No. 5,965,358 and International Patent Applications WO 98/56937, WO 99/15686, and WO 99/54441. The production of adenoviral gene transfer vectors is well known in the art, and involves using standard molecular biological techniques such as those described in, for example, Sambrook et al., supra, Watson et al., supra, Ausubel et al., supra, and in several of the other references mentioned herein.

Replication-deficient adenoviral vectors are typically produced in complementing cell lines that provide gene functions not present in the replication-deficient adenoviral vectors, but required for viral propagation, at appropriate levels in order to generate high titers of viral vector stock. In one embodiment, a cell line complements for at least one and/or all replication-essential gene functions not present in a replication-deficient adenovirus. The complementing cell line can complement for a deficiency in at least one replication-essential gene function encoded by the early regions, late regions, viral packaging regions, virus-associated RNA regions, or combinations thereof, including all adenoviral functions (e.g., to enable propagation of adenoviral amplicons, which comprise minimal adenoviral sequences, such as only inverted terminal repeats (ITRs) and the packaging signal or only ITRs and an adenoviral promoter). In another embodiment, the complementing cell line complements for a deficiency in at least one replication-essential gene function (e.g., two or more replication-essential gene functions) of the E1 region of the adenoviral genome, particularly a deficiency in a replication-essential gene function of each of the E1A and E1B regions. In addition, the complementing cell line can complement for a deficiency in at least one replication-essential gene function of the E2 (particularly as concerns the adenoviral DNA polymerase and terminal protein) and/or E4 regions of the adenoviral genome. Desirably, a cell that complements for a deficiency in the E4 region comprises the E4-ORF6 gene sequence and produces the E4-ORF6 protein. Such a cell desirably comprises at least ORF6 and no other ORF of the E4 region of the adenoviral genome. The cell line preferably is further characterized in that it contains the complementing genes in a non-overlapping fashion with the adenoviral vector, which minimizes, and practically eliminates, the possibility of the vector genome recombining with the cellular DNA. Accordingly, the presence of replication competent adenoviruses (RCA) is minimized if not avoided in the vector stock, which, therefore, is suitable for certain therapeutic purposes, especially gene therapy purposes. The lack of RCA in the vector stock avoids the replication of the adenoviral vector in non-complementing cells. The construction of complementing cell lines involves standard molecular biology and cell culture techniques, such as those described by Sambrook et al., supra, and Ausubel et al., supra. Complementing cell lines for producing the gene transfer vector (e.g., adenoviral vector) include, but are not limited to, 293 cells (described in, e.g., Graham et al., J. Gen. Virol., 36, 59-72 (1977)), PER.C6 cells (described in, e.g., International Patent Application WO 97/00326, and U.S. Pat. Nos. 5,994,128 and 6,033,908), and 293-ORF6 cells (described in, e.g., International Patent Application WO 95/34671 and Brough et al., J. Virol., 71, 9206-9213 (1997)). The insertion of a nucleic acid sequence into the adenoviral genome (e.g., the E1 region of the adenoviral genome) can be facilitated by known methods, for example, by the introduction of a unique restriction site at a given position of the adenoviral genome.

Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. As such, long-term expression of a therapeutic factor(s) is achievable when using retrovirus. Retroviruses contemplated for use in gene therapy are relatively non-pathogenic, although pathogenic retroviruses exist. When employing pathogenic retroviruses, e.g., human immunodeficiency virus (HIV) or human T-cell lymphotrophic viruses (HTLV), care must be taken in altering the viral genome to eliminate toxicity to the host. A retroviral vector additionally can be manipulated to render the virus replication-deficient. As such, retroviral vectors are considered particularly useful for stable gene transfer in vivo. Lentiviral vectors, such as HIV-based vectors, are exemplary of retroviral vectors used for gene delivery. Unlike other retroviruses, HIV-based vectors are known to incorporate their passenger genes into non-dividing cells and, therefore, can be of use in treating persistent forms of disease.

An HSV-based viral vector is suitable for use as a gene transfer vector to introduce a nucleic acid into numerous cell types. The mature HSV virion consists of an enveloped icosahedral capsid with a viral genome consisting of a linear double-stranded: DNA molecule that is 152 kb. Most replication-deficient HSV vectors contain a deletion to remove one or more intermediate-early genes to prevent replication. Advantages of the HSV vector are its ability to enter a latent stage that can result in long-term DNA expression and its large viral DNA genome that can accommodate exogenous DNA inserts of up to 25 kb. Of course, the ability of HSV to promote long-term production of exogenous protein is potentially disadvantageous in terms of short-term treatment regimens. However, one of ordinary skill in the art has the requisite understanding to determine the appropriate vector for a particular situation. HSV-based vectors are described in, for example, U.S. Pat. Nos. 5,837,532, 5,846,782, 5,849,572, and 5,804,413, and International Patent Applications WO 91/02788, WO 96/04394, WO 98/15637, and WO 99/06583.

AAV vectors are viral vectors of particular interest for use in gene therapy protocols. AAV is a DNA virus, which is not known to cause human disease. The AAV genome is comprised of two genes, rep and cap, flanked by inverted terminal repeats (ITRs), which contain recognition signals for DNA replication and packaging of the virus. AAV requires co-infection with a helper virus an adenovirus or a herpes simplex virus), or expression of helper genes, for efficient replication. AAV can be propagated in a wide array of host cells including human, simian, and rodent cells, depending on the helper virus employed. An AAV vector used for administration of a nucleic acid sequence typically has approximately 96% of the parental genome deleted, such that only the ITRs remain. This eliminates immunologic or toxic side effects due to expression of viral genes. If desired, the AAV rep protein can be co-administered with the AAV vector to enable integration of the AAV vector into the host cell genome. Host cells comprising an integrated AAV genome show no change in cell growth or morphology (see, e.g., U.S. Pat. No. 4,797, 368). As such, prolonged expression of therapeutic factors from AAV vectors can be useful in treating persistent and chronic diseases.

The polynucleotide sequence in the expression vector is operatively linked to appropriate expression control sequence(s) including, for instance, a promoter to direct mRNA transcription. Representatives of additional promoters include, but are not limited to, constitutive promoters and tissue specific or inducible promoters. Examples of constitutive eukaryotic promoters include, but are not limited to, the promoter of the mouse metallothionein I gene (Hamer et al., J. Mol. Appl. Gen. 1:273 (1982)); the TK promoter of Herpes virus (McKnight, Cell 31:355 (1.982)); the SV40 early promoter (Benoist et al., Nature 290:304 (1981)); and the vaccinia virus promoter. Additional examples of the promoters that could be used to drive expression of a protein or polynucleotide include, but are not limited to, tissue-specific promoters and other endogenous promoters for specific proteins, such as the albumin promoter (hepatocytes), a proinsulin promoter (pancreatic beta cells) and the like. In general, expression constructs will contain sites for transcription, initiation and termination and, in the transcribed region, a ribosome binding site for translation. The coding portion of the mature transcripts expressed by the constructs may include a translation initiating AUG at the beginning and a termination codon (UAA, UGA or UAG) appropriately positioned at the end of the polypeptide to be translated.

In addition, the constructs may contain control regions that regulate, as well as engender expression. Generally, such regions will operate by controlling transcription, such as repressor binding sites and enhancers, among others.

Examples of eukaryotic vectors include, but are not limited to, pW-LNEO, pSV2CAT, pOG44, pXT1 and pSG available from Stratagene; pSVK3, pBPV, pMSG and pSVL available from Amersham Pharmacia Biotech; and pCMVDsRed2-express, pIRES2-DsRed2, pDsRed2-Mito, and pCMV-EGFP available from Clontech. Many other vectors are well-known and commercially available.

Particularly useful vectors, which comprise molecular insertion pivots for rapid insertion and removal of elements of gene programs, are, described in United States Published Patent Application No. 2004/0185556, U.S. patent application Ser. No. 11/233,246 and International Published Application Nos. WO 2005/040336 and WO 2005/116231. An example of such vectors is the UltraVector™ Production System (Intrexon Corp., Blacksburg, Va.), as described in WO 2007/038276. As used herein, a "gene program" is a combination of genetic elements comprising a promoter (P), an expression sequence (E) and a 3' regulatory sequence (3), such that "PE3" is a gene program. The elements within the gene program can be easily swapped between molecular pivots that flank each of the elements of the gene program. A molecular pivot, as used herein, is defined as a polynucleotide comprising at least two non-variable rare or uncommon restriction sites arranged in a linear fashion. In one embodiment, the molecular pivot comprises at least three non-variable rare or uncommon restriction sites arranged in a linear fashion. Typically any one molecular pivot would not include a rare or uncommon restriction site of any other molecular pivot within the same gene program. Cognate sequences of greater than 6 nucleotides upon which a given restriction enzyme acts are referred to as "rare" restriction sites. There are, however, restriction sites of 6 bp that occur more infrequently than would be statistically predicted, and these sites and the endonucleases that cleave them are referred to as "uncommon" restriction sites. Examples of either rare or uncommon restriction enzymes include, but are not limited to, AsiS I, Pac I, Sbf I, Fse I, Asc I, Mlu I, SnaB I, Not I, Sal I, Swa I, Rsr II, BSiW I, Sfo I, SgrAI, AflIII, Pvu I, Ngo MIV, Ase I, Flp I, Pme I, Sda I, Sgf I, Srf I, Nru I, Acl I, Cla I, Csp45 I, Age I, Bst1107 I, BstB I, Hpa I, Aat II, EcoR V, Nhe I, Spe I, Avi II, Avr II, Mfe I, Afe I, Fsp I, Kpn I, Sca I, BspE I, Nde I, Bfr I, Xho I, Pml I, ApaL I, Kas I, Xma I, BsrB I, Nsi I, Sac II, Sac I, Blp I, PspoM I, Pci I, Stu I, Sph I, BamH I, Bsu36 I, Xba I, BbvC I, Bgl II, Nco I, Hind III, EcoR I, BsrG I and Sse8781 I.

The vector may also comprise restriction sites for a second class of restriction enzymes called homing endonuclease (HE) enzymes. HE enzymes have large, asymmetric restriction sites (12-40 base pairs), and their restriction sites are infrequent in nature. For example, the HE known as I-SceI has an 18 bp restriction site (5'TAGGGATAACAGGGTAAT3'), predicted to occur only once in every $7 \times 10^{10}$ base pairs of random sequence. This rate of occurrence is equivalent to only one site in a genome that is 20 times the size of a mammalian genome. The rare nature of HE sites greatly increases the likelihood that a genetic engineer can cut a gene program without disrupting the integrity of the gene program if HE sites are included in appropriate locations in a cloning vector plasmid.

Selection of appropriate vectors and promoters for expression in a host cell is a well-known procedure, and the requisite techniques for vector construction and introduction into the host, as well as its expression in the host are routine skills in the art.

The introduction of the polynucleotides into the cells can be a transient transfection, stable transfection, or can be a locus-specific insertion of the vector. Transient and stable transfection of the vectors into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods in Molecular Biology (1986); Keown et al., 1990, Methods Enzymol. 185: 527-37; Sambrook et al., 2001, Molecular Cloning, A Laboratory Manual, Third Edition, Cold Spring Harbor Laboratory Press, N.Y. These stable transfection methods result in random insertion of the vector into the genome of the cell. Further, the copy number and orientation of the vectors are also, generally speaking, random.

In one embodiment of the invention, the vector is inserted into a bio-neutral site in the genome. A bio-neutral site is a site in the genome where insertion of the polynucleotides interferes very little, if any, with the normal function of the cell. Bio-neutral sites may be analyzed using available bioinformatics. Many bio-neutral sites are known in the art, e.g., the ROSA-equivalent locus. Other bio-neutral sites may be identified using routine techniques well known in the art. Characterization of the genomic insertion site(s) is performed using methods known in the art. To control the location, copy number and/or orientation of the polynucleotides when introducing the vector into the cells, methods of locus-specific insertion may be used. Methods of locus-specific insertion are well-known in the art and include, but are not limited to, homologous recombination and recombinase-mediated genome insertion. Of course, if locus-specific insertion methods are to be used in the methods of the invention, the vectors may comprise elements that aid in this locus-specific insertion, such as, but not limited to, homologous recombination. For example, the vectors may comprise one, two, three, four or more genomic integration sites (GISs). As used herein, a "genomic integration site" is defined as a portion of the vector sequence which nucleotide sequence is identical or nearly identical to portions of the genome within the cells that allows for insertion of the vector in the genome. In particular, the vector may comprise two genomic insertion sites that flank at least the polynucleotides. Of course, the GISs may flank additional elements or even all elements present on the vector.

In another embodiment, locus-specific insertion may be carried out by recombinase-site specific gene insertion. Briefly, bacterial recombinase enzymes, such as, but not limited to, PhiC31 integrase can act on "pseudo" recombination sites within the human genome. These pseudo recombination sites can be targets for locus-specific insertion using the recombinases. Recombinase-site specific gene insertion is described in Thyagarajan et al., *Mol. Cell. Biol.* 21:3926 (2001). Other examples of recombinases and their respective sites that may be used for recombinase-site specific gene insertion include, but are not limited to, serine recombinases such as R4 and TP901-1 and recombinases described in WO 2006/083253.

In a further embodiment, the vector may comprise a chemo-resistance gene, e.g., the multidrug resistance gene mdr1, dihydrofolate reductase, or $O^6$-alkylguanine-DNA alkyltransferase. The chemo-resistance gene may be under the control of a constitutive (e.g., CMV) or inducible (e.g., RheoSwitch®) promoter. In this embodiment, if it is desired to treat a disease in a subject while maintaining the modified cells within the subject, a clinician may apply a chemotherapeutic agent to destroy diseased cells while the modified cells would be protected from the agent due to expression of a suitable chemo-resistance gene and may continue to be used for treatment, amelioration, or prevention of a disease or disorder. By placing the chemo-resistance gene under an inducible promoter, the unnecessary expression of the chemo-resistance gene can be avoided, yet it will still be available in case continued treatment is needed. If the modified cells themselves become diseased, they could still be destroyed by inducing expression of a lethal polypeptide as described below.

The methods of the invention are carried out by introducing the polynucleotides encoding the gene switch and the exogenous gene into cells of a subject. Any method known for introducing a polynucleotide into a cell known in the art, such as those described above, can be used.

When the polynucleotides are to be introduced into cells ex vivo, the cells may be obtained from a subject by any technique known in the art, including, but not limited to, biopsies, scrapings, and surgical tissue removal. The isolated cells may be cultured for a sufficient amount of time to allow the polynucleotides to be introduced into the cells, e.g., 2, 4, 6, 8, 10, 12, 18, 24, 36, 48, hours or more. Methods for culturing primary cells for short periods of time are well known in the art. For example, cells may be cultured in plates (e.g., in microwell plates) either attached or in suspension.

For ex vivo therapeutic methods, cells are isolated from a subject and cultured under conditions suitable for introducing the polynucleotides into the cells. Once the polynucleotides have been introduced into the cells, the cells are incubated for a sufficient period of time to allow the ligand-dependent transcription factor to be expressed, e.g., 0.5, 1, 2, 3, 4, 5, 6, 7, 8, 9, 10, 12, 18, or 24 hours or more. At some point after the introduction of the polynucleotides into the cells (either before or after significant levels of the ligand-dependent transcription factor is expressed), the cells are introduced back into the subject. Reintroduction may be carried out by any method known in the art, e.g., intravenous infusion or direct injection into a tissue or cavity. In one embodiment, the presence of the polynucleotides in the cells is determined prior to introducing the cells back into the subject. In another embodiment, cells containing the polynucleotides are selected (e.g., based on the presence of a selectable marker in the polynucleotides) and only those cells containing the polynucleotides are reintroduced into the subject. After the cells are reintroduced to the subject, ligand is administered to the subject to induce expression of the therapeutic polypeptide or therapeutic polynucleotide. In an alternative embodiment, the ligand may be added to the cells even before the cells are reintroduced to the subject such that the therapeutic polypeptide or therapeutic polynucleotide is expressed prior to reintroduction of the cells. The ligand may be administered by any suitable method, either systemically (e.g., orally, intravenously) or locally (e.g., intraperitoneally, intrathecally, intraventricularly, direct injection into the tissue or organ where the cells are reintroduced). The optimal timing of ligand administration can be determined for each type of cell and disease or disorder using only routine techniques.

The in vivo therapeutic methods of the invention involve direct in vivo introduction of the polynucleotides, e.g., adenoviral vector, into the cells of the subject. The polynucleotides may be introduced into the subject systemically or locally (e.g., at the site of the disease or disorder). Once the polynucleotides have been introduced to the subject, the ligand may be administered to induce expression of the therapeutic polypeptide or therapeutic polynucleotide. The ligand may be administered by any suitable method, either systemically (e.g., orally, intravenously) or locally (e.g., intraperitoneally, intrathecally, intraventricularly, direct injection into the tissue or organ where the disease or disorder is occurring). The optimal timing of ligand administration can be determined for each type of cell and disease or disorder using only routine techniques.

For in vivo use, the ligands described herein may be taken up in pharmaceutically acceptable carriers, such as, for example, solutions, suspensions, tablets, capsules, ointments, elixirs, and injectable compositions. Pharmaceutical compositions may contain from 0.01% to 99% by weight of the ligand. Compositions may be either in single or multiple dose forms. The amount of ligand in any particular pharmaceutical composition will depend upon the effective dose, that is, the dose required to elicit the desired gene expression or suppression.

As used herein, the term "rAD.RheoIL12" refers to an adenoviral polynucleotide vector harboring the IL-12 gene under the control of a gene switch of the RheoSwitch® Therapeutic System (RTS), which is capable of producing IL-12 protein in the presence of activating ligand. As used herein, the term "rAd.cIL12" refers to an adenoviral polynucleotide control vector containing the IL-12 gene under the control of a constitutive promoter.

As used herein, the term "IL-12p70" refers to IL-12 protein, which naturally has two subunits commonly referred to as p40 and p35. The term IL-12p70 encompasses fusion proteins comprising the two subunits of IL-12 (p40 and p35), wherein the fusion protein may include linker amino acids between subunits.

Suitable routes of administering the pharmaceutical preparations include oral, rectal, topical (including dermal, buccal and sublingual), vaginal, parenteral (including subcutaneous, intramuscular, intravenous, intratumoral, intradermal, intrathecal and epidural) and by naso-gastric tube. It will be understood by those skilled in the art that the route of administration will depend upon the condition being treated and may vary with factors such as the condition of the recipient.

As used herein, the terms "activating" or "activate" refer to any measurable increase in cellular activity of a gene switch, resulting in expression of a gene of interest.

As used herein, the terms "treating" or "treatment" of a disease refer to executing a protocol, which may include administering one or more drugs or in vitro engineered cells to a mammal (human or non-human), in an effort to alleviate signs or symptoms of the disease. Thus, "treating" or "treatment" should not necessarily be construed to require complete alleviation of signs or symptoms, does not require a cure, and specifically includes protocols that have only marginal effect on the subject.

As used herein, the terms "in vitro engineered cells" or "in vitro engineered population of cells" or "a population of engineered cells" or "cells expressing a protein" refer to cells conditionally expressing a protein under the control of a gene switch, which can be activated by an activating ligand.

As used herein, the term "modified cell" refers to cells which have been altered by a process including, but not limited to, transfection, electroporation, microinjection, transduction, cell fusion, DEAE dextran, calcium phosphate precipitation and lipofection (lysosome fusion).

As used herein, the terms "MOI" or "Multiplicity of Infection" refer to the average number of adenovirus particles that infect a single cell in a specific experiment (e.g., recombinant adenovirus or control adenovirus)

In another embodiment, the vector and methods of the present invention can be used to treat disease.

In another embodiment, the vector and methods of the present invention can be used to treat a kidney disease. In one embodiment, the kidney disease is a renal failure. In another embodiment, the kidney disease is chronic renal failure.

In another embodiment, the vector and methods of the present invention can be used to treat anemia. In one embodiment, the anemia is anemia associated with kidney disease, for example, renal failure or chronic renal failure. In another embodiment, the anemia is associated with cancer therapy with, for example, one or more chemotherapeutic agents. In another embodiment, the anemia is associated with advanced age. In another embodiment, the anemia is associated with impaired lung function. In another embodiment, the anemia is associated with myelodisplasia. In another embodiment, the anemia is associated with radiation therapy. In another embodiment, the anemia is associated with a critical illness.

In one embodiment, the anemia is not associated with cardiac disease. In another embodiment, the disease, disorder or condition that is responsive to treatment with erythropoietin is not a cardiac disease. Nonlimiting types of "cardiac disease" are congestive heart failure, hypoxia, ischemic heart disease, hypertensive heart disease, coronary artery disease, peripheral vascular disease and ischemic cardiac events, e.g., myocardial infarction, heart attack, heart failure, arrhythmia, myocardial rupture, pericarditis, cardiogenic shock, thrombosis, embolism, atherosclerosis, and arterial stenosis.

In another embodiment, the polynucleotide comprising a polynucleotide encoding an erythropoietin or agonist thereof does not also encode with etanercept, which is a TNF receptor-Fc fusion. In another embodiment, the polynucleotide comprising a polynucleotide encoding an erythropoietin or agonist thereof is not administered to a subject to whom is also administered a polynucleotide comprising a polynucleotide encoding etanercept.

In one embodiment, the vector and methods of the present invention are used to treat multiple sclerosis. In one embodiment, the vector comprises a polynucleotide sequence encoding an interferon, or a fragment thereof. In another embodiment, the vector comprises a polynucleotide sequence encoding an interferon-beta, or a fragment thereof. In another embodiment, the vector comprises a polynucleotide sequence encoding myelin basic protein (MBP), or a fragment thereof. In one embodiment, the vector comprises a polynucleotide sequence encoding an interferon, e.g., an interferon-beta, or a fragment thereof, and myelin basic protein, or a fragment thereof.

In another embodiment, the vector and methods of the present invention are used to treat angioedema. In another embodiment, the angioedema is hereditary angioedema. In one embodiment, the vector comprises a polynucleotide sequence encoding molecule selected from the group consisting of a C1 esterase inhibitor (for example, a human C1 esterase inhibitor), a kallikrein inhibitor, and a bradykinin B2 receptor antagonist.

In another embodiment, the vector and methods of the present invention are used to treat a disease, condition or disorder, Wherein inhibition of C1 esterase provides a therapeutically beneficial effect. In this embodiment, the vector comprises a polynucleotide sequence encoding a C1 esterase inhibitor to treat, for example, a disease, condition or disorder selected from the group consisting of sepsis, hypercoagulability, pulmonary dysfunction, hypoxemia, hemorrhagic pancreatitis, myocardial infarction, lung transplantation, trauma, thermal injury and vascular leak.

In another embodiment, the vector and methods of the present invention are used to treat a disease, condition or disorder wherein inhibition of kallikrein provides a therapeutically beneficial effect. Examples of such diseases, conditions or disorders include, but are not limited to, disease, conditions or disorders of the contact system. See e.g., Shariat-Madar et al., *Innate Immunity*, vol. 10, no. 1, 3-13 (2004) and Frick, et al., *EMBO J.*, (2006) 25, 5569-5578 (2006). In this embodiment, the vector comprises a polynucleotide sequence encoding a kallirein inhibitor to treat, for example, a disease, condition or disorder selected from the group consisting of atherothrombosis, coronary artery disease, Alzheimer's Disease, inflammatory bowel disease (for example, Crohn's Disease), vascular leak, acute respiratory distress syndrome and bradykinin-mediated inflammation. In one embodiment, the vector comprises a polynucleotide sequence encoding a kallikrein inhibitor. Examples of kallikrein inhibitors include, but are not limited to, ecallantide and those kallikrein inhibits set forth U.S. Patent Publication Nos. 2010/0034805, 2009/0264350, 2009/0234009, 2008/0221031, 2007/0213275, 2006/0264603 and 2005/0089515, each of which are incorporated by reference in their entireties.

In another embodiment, the vector and methods of the present invention are used to treat pulmonary hypertension. In one embodiment, the pulmonary hypertension is pulmonary arterial hypertension. In another embodiment, the pulmonary arterial hypertension is idiopathic pulmonary arterial hypertension. In another embodiment, the pulmonary arterial hypertension is familial pulmonary arterial hypertension. In another embodiment, the pulmonary arterial hypertension is pulmonary arterial hypertension associated with other diseases or conditions. In another embodiment, the pulmonary arterial hypertension is pulmonary arterial hypertension secondary to other conditions. In another embodiment, the pulmonary arterial hypertension is secondary pulmonary arterial hypertension. In another embodiment, the pulmonary arterial hypertension is associated with significant venous or capillary involvement, for example, pulmonary veno-occlusive disease and pulmonary capillary hemangiomatosis. In another embodiment, the pulmonary arterial hypertension is persistent pulmonary hypertension of the newborn. In one embodiment, the vector is administered intramuscularly.

In one embodiment, the term "prostaglandin synthase" is a polypeptide selected from the group consisting of prostaglandin synthase, prostaglandin synthetase, prostaglandin synthetase 1, prostaglandin synthetase 2, prostaglandin endoperoxide synthetase, prostaglandin E synthetase, prostaglandin H2 synthetase, prostaglandin G/H synthetase 1, prostaglandin G/H synthetase 2, PG synthetase, cyclooxygenase (COX), COX-1, COX-2 and COX-3.

The accession number for the human Prosteglandin G/H Synthase 1 nucleotide sequence is NC_000009, and the accession number for the human Prostoglandin G/H Synthase 1 amino acid sequence is Accession No.: NP_000953. See, e.g., Lander et al., *Nature* 429: 369-374 (2004).

The accession number for the human Prosteglandin G/H Synthase 2 nucleotide sequence is NC_000001, and the accession number for the human Prostoglandin G/H Synthase 2 amino acid sequence is Accession No.; NP_000954.1. See, e.g., Lander et al., *Nature* 431: 931-945 (2004).

The accession number for the human interferon-beta is NP_002167.1

The accession number for the human GLP-1 is RP_12738.
The accession number for the human GLP-2 is RP_10769.
The accession number for the human adiponectin is ABZ10942.1.
The accession number for the human leptin is AAH69323.1.
The accession number for the human CFTR is ABD72213.1

The accession number for the human IL-10 NP_000563.

In another embodiment, the vector and methods of the present invention are used to treat a disease, condition or disorder wherein inhibition of bradykinin B2 receptor provides a therapeutically beneficial effect. In this embodiment, the vector comprises a polynucleotide sequence encoding a bradykinin B2 receptor inhibitor to treat, for example, a disease, condition or disorder selected from the group consisting of glomerulosclerosis, Alzheimer's Disease, cerebral edema, vascular leak, acute respiratory distress syndrome, pain, inflammation, trauma, burns, shock, allergy, and cardiovascular disease. Examples of bradykinin B2 receptor inhibitors include, but are not limited to, helokinestatin and anti-bradykinin B2 receptor antibodies. The amino acid sequence of helokinestatin is Gly-Pro-Pro-Tyr-Gln-Pro-Leu-Val-Pro-Arg (Kwok, H. F. et al., *Peptides* 29I 65-72 (2008), which is incorporated by reference in its entirety). Nonlimiting examples of anti-bradykinin B2 receptor antibodies are set forthin Alla, S. A. et al., *J. Biol. Chem.* 271: 1748-1755 (1996).

In one embodiment, the vector administered to the mammal afflicted with one or more of the disclosed diseases is an adenoviral vector. In one embodiment, the vector comprises a polynucleotide encoding a gene switch. En one aspect, the gene switch is an EcR-based gene switch. In another embodiment, the polynucleotide encoding a gene switch comprises a first transcription factor sequence under the control of a first promoter and a second transcription factor sequence under the control of a second promoter, wherein the proteins encoded by said first transcription factor sequence and said second transcription factor sequence interact to form a protein complex which functions as a ligand-dependent transcription factor. In one aspect, the ligand is a diacylhydrazine. In another aspect the ligand is selected from RG-115819, RG-115932, and RG-115830. In yet another aspect, the ligand is an amidoketone or an oxadiazoline.

In one embodiment, a nucleic acid adenoviral vector is provided containing a gene switch, wherein the coding sequences for VP16-RXR and Gal4-EcR are separated by the EMCV internal ribosome entry site (IRES) sequence are inserted into the adenoviral shuttle vector under the control of the human ubiquitin C promoter. For example, the coding sequences for the p40 and p35 subunits of IL12 separated by an IRES sequence, and placed under the control of a synthetic inducible promoter, are inserted upstream of the ubiquitin C promoter. In another example, the coding sequence of TNF-alpha, which is placed under the control of a synthetic inducible promoter, is inserted upstream of the ubiquitin C promoter.

Purification of the vector to enhance the concentration can be accomplished by any suitable method, such as by density gradient purification (e.g., cesium chloride (CsCl)) or by chromatography techniques (e.g., column or batch chromatography). For example, the vector of the invention can be subjected to two or three CsCl density gradient purification steps. The vector, e.g., a replication-deficient adenoviral vector, is desirably purified from cells infected with the replication-deficient adenoviral vector using a method that comprises lysing cells infected with adenovirus, applying the lysate to a chromatography resin, eluting the adenovirus from the chromatography resin, and collecting a fraction containing adenovirus.

In a particular embodiment, the resulting primary viral stock is amplified by re-infection of HEK 293 cells or CHO cells and is purified by CsCl density-gradient centrifugation.

Protein-based tags reduce or eliminate the need for highly specific post-translational modifications for effective targeting. Useful protein-based tags include, but are not limited to, IGF2R targeting (10F2 (GILT)/IGF2 engineering), transferrin receptor targeting (transferrin, TfR-targeting peptides), and Tat protein (in which cell surface heparin sulfate proteoglycans (HSPGs) mediate internalization of Tat).

Other proteins that target to the lysosome than can be used as tag include, but are not limited to, Vitamin D binding protein, folate binding protein, lactotransferrin, sex hormone binding globulin, transthyretin, pro saposin, retinol binding protein, Apo lipoprotein B, Apo lipoprotein E, prolactin, receptor associated protein (in one embodiment, without the HNEL sequence), native transferrin, and mutant transferring (e.g., the K225E/R651A mutant or the K225E/K553A mutant).

In one aspect, the invention provides a pharmaceutical composition suitable for administration to a human or a non-human comprising a population of in vitro engineered cells or a vector, e.g., an adenoviral vector, expressing a protein, wherein the formulation is suitable for administration by intratumoral administration. In another embodiment, a composition, e.g., pharmaceutical composition, comprises a vector conditionally expressing a protein. In some embodiments, the composition comprises about $1 \times 10^5$ or more particle units (pu) of the gene transfer vector, A "particle unit" is a single vector particle. In certain embodiments, the composition comprises about $1 \times 10^6$ particle units of the gene transfer vector (e.g., about $1 \times 10^7$ or more particle units, about $1 \times 10^8$ or more particle units, or about $1 \times 10^9$ or more particle units). In other embodiments, the composition comprises about $1 \times 10^{10}$ or more pu, $1 \times 10^{15}$ or more pu, $1 \times 10^{12}$ or more $1 \times 10^{13}$ or more pu, $1 \times 10^{14}$ or more pu, or $1 \times 10^{15}$ or more pu of the gene transfer vector, especially of a viral vector, such as a replication-deficient adenoviral vector. The number of particle units of the gene transfer vector in the composition can be determined using any suitable method known, such as by comparing the absorbance of the composition with the absorbance of a standard solution of gene transfer vector (i.e., a solution of known gene transfer vector concentration) as described further herein.

In one embodiment, the activating ligand is selected from the group consisting of RG-115819, RG-115830 and RG-115932.

The invention further provides a pharmaceutical composition comprising an activating ligand, such as RG-115819, RG-115830 or RG-115932, wherein the composition is suitable for administration by intraperitoneal, oral, or subcutaneous administration.

In one embodiment, the activating ligand is administered orally. In another embodiment, the activating ligand is administered parenterally. In another embodiment, the activating ligand is administered, intraperitoneally, subcutaneously, or intramuscularly.

A composition of the invention can further comprise a pharmaceutically acceptable carrier. The carrier can be any suitable carrier for the an engineered dendritic cells, gene transfer vector, or activating ligand. Suitable carriers for the composition are described in U.S. Pat. No. 6,225,289. The carrier typically will be liquid, but also can be solid, or a combination of liquid and solid components. The carrier desirably is a pharmaceutically acceptable (e.g., a physiologically or pharmacologically acceptable) carrier (e.g., excipient or diluent). Pharmaceutically acceptable carriers are well known and are readily available. The choice of carrier will be determined, at least in part, by the particular components in the composition and the particular method used to administer the composition. The composition can further comprise any other suitable components, especially for enhancing the stability of the composition and/or its end-use. Accordingly, there is a wide variety of suitable formulations of the composition of the invention.

Formulations suitable for oral administration include (a) liquid solutions, such as an effective amount of the active ingredient dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base (such as gelatin and glycerin, or sucrose and acacia), and emulsions, gels, and the like containing, in addition to the active ingredient, such excipients as are known in the art.

Formulations suitable for administration via inhalation include aerosol formulations. The aerosol formulations can be placed into pressurized acceptable propellants, such as dichlorodifluoromethane, propane, nitrogen, and the like. They also can be formulated as non-pressurized preparations, for delivery from a nebulizer or an atomizer.

Formulations suitable for parenteral administration include aqueous and nonaqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described.

Formulations suitable for anal administration can be prepared as suppositories by mixing the active ingredient with a variety of bases such as emulsifying bases or water soluble bases. Formulations suitable for vaginal administration can be presented as pessaries, tampons, creams, gels pastes, foams, or spray formulas containing, in addition to the active ingredient, such carriers as are known in the art to be appropriate.

In addition, the composition can comprise additional therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the gene transfer vector and physiological distress. Immune system suppressors can be administered with the composition method to reduce any immune response to the gene transfer vector itself or associated with a disorder. Alternatively, immune enhancers can be included in the composition to upregulate the body's natural defenses against disease. Moreover cytokines can be administered with the composition to attract immune effector cells to the tumor site.

In the particular embodiment described herein, the invention provides a method for treating a tumor, comprising the steps in order of:

a. administering intratumorally in a mammal a population of an in vitro engineered immune cells or TSC; and b. administering to said mammal a therapeutically effective amount of an activating ligand.

In one embodiment, the activating ligand is administered at substantially the same time as the composition comprising the in vitro engineered cells or the vector, e.g., adenoviral vector, e.g., within one hour before or after administration of the cells or the vector compositions. In another embodiment, the activating ligand is administered at or less than about 24 hours after administration of the in vitro cells or the vector. In still another embodiment, the activating ligand is administered at or less than about 48 hours after the in vitro engineered cells or the vector. In another embodiment, the ligand is RG-115932. In another embodiment, the ligand is administered at a dose of about 1 to 50 mg/kg/day. In another embodiment, the ligand is administered at a dose of about 30 mg/kg/day. In another embodiment, the ligand is administered daily for a period of 7 to 28 days. In another embodiment, the ligand is administered daily for a period of 14 days. In another embodiment, about $1 \times 10^6$ to $1 \times 10^8$ cells are administered. In another embodiment, about $1 \times 10^7$ cells are administered.

The term "subject" means a mammal. Mammals include humans, rodents, monkeys, and other animals, with humans or mice being more preferred. Other mammals include veterinary animals such as dogs, cats, horses, cattle, sheep, goats, pigs and the like.

As used herein, the term "protein expression" includes without limitation transcription, post-transcription, translation, and/or post-translation.

Also included in the invention is a method of increasing mRNA or protein expression of a protein, comprising generating a vector conditionally expressing the protein, wherein said vector further comprises one or more regulatory sequences connected to the polynucleotide sequence encoding said protein, and adding an activating ligand, thereby inducing expression of the protein, wherein said one or more regulatory sequences and/or signal peptides improves expression of said protein. Various regulatory regions for the invention including, but not limited to, 5' untranslated region (5' UTR), 3' UTR, or both have been described. In one embodiment, the 5' UTR is 5U2. 5U2 is a fusion canine SERCA2 intron 2 with a mutated putative consensus poly-A site, with exon 2 splice donor flanking on the 5' end and exon 3 splice acceptor flanking on the 3' end followed by a portion of the portion of bovine casein 5'UTR. In another embodiment, the 3' regulatory region is a polyadenylation signal of SV40 or hGH.

The invention further supports the therapeutic applications of in vitro engineered cells with conditionally expressed genes of interest as innovative approaches for the effective and efficient treatment of human diseases.

In this embodiment, the vector is administered to the subject without being packaged in a cell.

In one embodiment, cells are not administered intratumorally with the vector.

In another embodiment, a vector of the invention that is not contained within a cell is administered simulataneously with, before, or after cells, are administered.

In one embodiment, the dosage is at least about $1.0 \times 10^9$ viral particles per cycle of vector administration. In another embodiment, the dosage is at least about $1.0 \times 10^{10}$ viral particles per cycle of vector administration. In another embodiment, the dosage is about $1.0 \times 10^9$ to about $1.0 \times 10^{13}$ viral particles per cycle of vector administration. In another embodiment, the dosage is about $1.0 \times 10^{10}$ to about $1.0 \times 10^{13}$ viral particles per cycle of vector administration. In another embodiment, the dosage is about $1.0 \times 10^{10}$, about $1.0 \times 10^{11}$, about $1.0 \times 10^{12}$ about $1.0 \times 10^{13}$ viral particles per cycle of vector administration.

The activating ligand dosage is about 5-100 mg/day, e.g., about 5, 10, 15, 20, 25, 30, 35, 40, 45, 50, 55, 60, 65, 70, 75, 80, 85, 90, 95 or 100 mg/day. In one embodiment, the activating ligand is administered at least once a day. In another embodiment, the activating ligand is administered once a day for about 14 days.

In one embodiment, at least two dosages of the vector (e.g., about $1 \times 10^{11}$ and $1 \times 10^{12}$) are used in combination with at least three different dosage levels of the activating ligand (e.g., about 5 mg/day to about 100 mg/day).

One of ordinary skill in the art will be able to optimize dosages in order to provide range of effective plasma levels of the vector, for various degrees of activating ligand activation.

In one embodiment, the dosage of activating ligand administered to the subject is changed over the period of administration of the activating ligand within the cycle of intratumoral vector administration. In another embodiment, the dosage of activating ligand administered to the subject is decreased over the period of administration of the activating ligand within the cycle of intratumoral vector administration. In another embodiment, the dosage of activating ligand administered to the subject is increased (escalated) over the period of administration of the activating ligand within the cycle of intratumoral vector administration.

In one embodiment, the subject is treated with 2, 3, 4, 5, 6, 7, 8, 9 or 10 cycles of vector administration. In another embodiment, the subject is treated with 3-7 cycles of vector administration. In another embodiment, the subject is treated with 4-6 cycles of vector administration. In another embodiment, the subject is treated with 5 or 6 cycles of vector administration. In another embodiment, the subject is treated with 6 cycles of vector administration.

In one embodiment, each cycle of vector administration is performed 1, 2, 3, 4, 5, 6, 7, 8, 9 or 10 weeks apart. In another embodiment, each cycle of vector administration is performed 4 weeks apart.

In one embodiment, the dosage of the vector is changed in each subsequent cycle of vector administration. In another embodiment, the dosage of the vector is decreased in each subsequent cycle of vector administration. In another embodiment, the dosage of the vector is increased in each subsequent cycle of vector administration.

In one embodiment, the invention also provides a pharmaceutical composition comprising pharmaceutically acceptable carrier and a vector of the invention that is not contained within a cell. Suitable carriers include, but are not limited to, saline, distilled water, sodium chloride solutions, the mixtures of sodium chloride and inorganic salts or their similar mixtures, the solutions of materials such as mannitol, lactose, dextran, and glucose, amino acid solutions such as glycine and arginine, the mixtures of organic acid solutions or salt solutions and glucose solutions, aqueous and nonaqueous, isotonic sterile injection solutions, which can contain antioxidants, chelating agents, buffers, bacteriostats, and solutes that render the formulation isotonic, and aqueous and nonaqueous sterile suspensions that can include suspending agents, solubilizers, thickening agents, stabilizers, and preservatives. The formulations can be presented in unit dose or multidose sealed containers, such as ampules and vials, and can be stored in a freeze-dried (lyophilized) condition requiring only the addition of the sterile liquid carrier, for example, water, for injections, immediately prior to use.

In one embodiment, the polynucleotide of the invention is contained in a host cell. In one embodiment, the host cell is selected from the group consisting of a mammalian cell, a prokaryotic cell, a bacterial cell, a fungal cell, a nematode cell, an insect cell, a fish cell, a plant cell, an avian cell, a eukaryotic cell, an animal cell, a mammalian cell, an invertebrate host cell, a vertebrate host cell, a yeast cell, a zebrafish cell, a chicken cell, a hamster cell, a mouse cell, a rat cell, a rabbit cell, a cat cell, a dog cell, a bovine cell, a goat cell, a cow cell, a pig cell, a horse cell, a sheep cell, a simian cell, a monkey cell, a chimpanzee cell, or a human cell.

In one embodiment, the host cell is not a cardiac cell or a myocyte.

Host cell transformation is well known in the art and may be achieved by a variety of methods including but not limited to electroporation, viral infection, plasmid/vector transfection, non-viral vector mediated transfection, *Agrobacterium*-mediated transformation, particle bombardment, and the like. Expression of desired gene products involves culturing the transformed host cells under suitable conditions and inducing expression of the transformed gene. Culture conditions and gene expression protocols in prokaryotic and eukaryotic cells are well known in the art. Cells may be harvested and the gene products isolated according to protocols specific for the gene product.

In the event of conflict between any teaching or suggestion of any reference cited herein and the specification, the latter shall prevail, for purposes of the invention.

All patents, patent applications and publications cited herein are fully incorporated by reference in their entireties.

It is to be understood that the foregoing described embodiments and exemplifications are not intended to be limiting in any respect to the scope of the invention, and that the claims presented herein are intended to encompass all embodiments and exemplifications whether or not explicitly presented herein.

U.S. application Ser. No. 12/247,738, entitled "Engineered Dendritic Cells And Uses For Treatment Of Cancer," filed Oct. 8, 2008, is hereby incorporated by reference in its entirety. U.S. application Ser. No. 12/241,018, entitled "Therapeutic Gene-Switch Constructs And Bioreactors For The Expression Of Biotherapeutic Molecules, And Uses Thereof," filed Sep. 29, 2008, is also hereby incorporated by reference in its entirety.

Embodiments of the invention also include the following (where "E" indicates "Embodiment"):

E1. A method of inducing, regulating, or enhancing erythropoietin (EPO) expression in a mammal, wherein the method comprises (a) administering an adeno-associated virus to the mammal wherein the virus comprises a polynucleotide encoding EPO; and (b) administering an activator ligand which induces EPO expression from the virus polynucleotide encoding EPO, wherein the adeno-associated virus is administered intramuscularly, wherein the adeno-associated virus further comprises a gene switch, wherein the gene switch comprises at least one transcription factor sequence operably linked to a promoter, wherein at least one transcription factor encoded by the at least one transcription factor sequence is a ligand-dependent transcription factor, wherein the adeno-associated virus further comprises a second promoter operably linked to the polynucleotide encoding EPO, wherein the second promoter is activated by the at least one ligand-dependent transcription factor following administration of activator ligand.

E2. The method of embodiment E1, wherein the manual is human.

E3. The method of embodiments E1 or E2, wherein expression of EPO is induced, regulated or enhanced by controlling the administered dose or doses of activator ligand.

E4. The method of any one of embodiments E1 to E3, wherein activator ligand is adminstered in a dose or doses sufficient to induce or maintain EPO expression levels within a normal physiologic range.

E5. The method of any one of embodiments E1 to E4, wherein the polynucleotide encoding EPO comprises an amino acid sequence at least 80%, 85%, 90%, 95%, 96%, 97%, 98%, 99%, or 100% identical to SEQ ID NO: 6 or SEQ ID NO: 8 (human EPO).

E6. The method of any one of embodiments E1 to E5, wherein the hematocrit or volume percentage of red blood cells in blood is increased in the mammal.

E7. A vector comprising a polynucleotide encoding a gene switch, wherein the polynucleotide comprises (1) at least one transcription factor sequence which is operably linked to a promoter, wherein the at least one transcription factor sequence encodes a ligand-dependent transcription factor, and (2) a polynucleotide encoding one or more proteins operably linked to a promoter which is activated by the ligand-dependent transcription factor, wherein the one or more proteins is selected from the group consisting of a C1 esterase inhibitor, a kallikrein inhibitor, a bradykinin B2 receptor inhibitor, a prostaglandin synthase, a glucagon-like peptide-1 (GLP-1), a glucagon-like peptide-2 (GLP-2), adiponectin, leptin, and cystic fibrosis transmembrane conductance regulator (CFTR).

E8. The vector of embodiment E7, wherein one or more of the proteins is a human protein.

E9. The vector of embodiments E7 or E8, wherein the vector is a viral vector.

E10. The vector of embodiment E9, wherein the viral vector is selected from the group consisting of an adenovirus, an adeno-associated virus, a retrovirus, a pox virus, a baculovirus, a vaccinia virus, a herpes simplex virus, an Epstein-Barr virus, a geminivirus, a pseudorabies virus, a parvovirus, and a caulimovirus virus vector.

E11. The vector of any one of embodiments E7 to E10, wherein the gene switch is an ecdysone receptor (EcR)-based gene switch.

E12. The vector of any one of embodiments E7 to E11, wherein the polynucleotide encoding a gene switch comprises a first transcription factor sequence under the control of a first promoter and a second transcription factor sequence under the control of a second promoter, wherein a first transcription factor encoded by the first transcription factor sequence and a second transcription factor encoded by the second transcription factor sequence interact to form a complex which functions as a ligand-dependent transcription factor.

E13. The vector of any one of embodiments E7 to E11, wherein the polynucleotide encoding a gene switch comprises a first transcription factor sequence and a second transcription factor sequence under the control of a promoter, wherein a first transcription factor encoded by the first transcription factor sequence and a second transcription factor encoded by the second transcription factor sequence interact to form a complex which functions as a ligand-dependent transcription factor.

E14. The vector of any one of embodiments E7 to E13, wherein the first transcription factor sequence and the second transcription factor sequence are connected by an EMCV internal ribosomal entry site (IRES).

E15. The vector of any one of embodiments E7 to E14, wherein one of the one or more proteins comprises an amino acid sequence at least 80%, 85%, 90%, 95%, 96%, 97%, 98%, 99%, or 100% identical to the amino acid encoded by SEQ ID NO: 9 (human myelin basic protein).

E16. The vector of any one of embodiments E7 to E15, wherein one of the one or more proteins comprises an amino acid sequence at least 80%, 85%, 90%, 95%, 96%, 97%, 98%, 99%, or 100% identical to SEQ ID NO: 10 (human C1 esterase inhibitor.).

E17. The vector of any one of embodiments E7 to E16, wherein one of the one or more proteins comprises an amino acid sequence at least 80%, 85%, 90%, 95%, 96%, 97%, 98%, 99%, or 100% identical to SEQ ID NO: 11 (ecallantide).

E18. The vector of any one of embodiments E7 to E17, wherein one of the one or more proteins comprises an amino acid sequence at least 80%, 85%, 90%, 95%, 96%, 97%, 98%, 99%, or 100% identical to SEQ ID NO: 12, SEQ ID NO: 13, SEQ ID NO: 14, or SEQ ID NO: 15 (prostaglandin synthase).

E19. The vector of any one of embodiments E7 to E17, wherein one of the one or more proteins comprises an amino acid sequence at least 80%, 85%, 90%, 95%, 96%, 97%, 98%, 99%, or 100% identical to SEQ ID NO: 17 (GLP-1) or SEQ ID NO: 18 (GLP-2).

E20. The vector of any one of embodiments E7 to E17, wherein one of the one or more proteins comprises an amino acid sequence at least 80%, 85%, 90%, 95%, 96%, 97%, 98%, 99%, or 100% identical to SEQ ID NO: 19 (Adiponectin).

E21. The vector of any one of embodiments E7 to E17, wherein one of the one or more proteins comprises an amino acid sequence at least 80%, 85%, 90%, 95%, 96%, 97%, 98%, 99%, or 100% identical to SEQ ID NO: 20 (Leptin).

E22. The vector of any one of embodiments E7 to E17, wherein one of the one or more proteins comprises an amino acid sequence at least 80%, 85%, 90%, 95%, 96%, 97%, 98%, 99%, or 100% identical to SEQ ID NO: 21 (CFTR).

E23. A method of producing a population of cells expressing one or more proteins, wherein the method comprises modifying the cells with a recombinant vector conditionally expressing one or more proteins, wherein the vector comprises a polynucleotide encoding a gene switch, wherein the polynucleotide comprises (1) at least one transcription factor sequence operably linked to a promoter, wherein the at least one transcription factor sequence encodes a ligand-dependent transcription factor, and (2) a polynucleotide encoding one or more proteins linked to a promoter which is activated by the ligand-dependent transcription factor, wherein the one or more proteins are selected from the group consisting of a C1 esterase inhibitor, a kallikrein inhibitor, a bradykinin B2 receptor inhibitor, a prostaglandin synthase, a glucagon-like peptide-1 (GLP-1), a glucagon-like peptide-2 (GLP-2), adiponectin, leptin, and cystic fibrosis transmembrane conductance regulator (CFTR).

E24. The method of embodiment E23, wherein one or more of the proteins is a human protein.

E25. The method of embodiments E23 or E24, wherein the vector is a viral vector.

E26. The method of embodiment E25, wherein the viral vector is selected from the group consisting of an adenovirus, an adeno-associated virus, a retrovirus, a pox virus, a baculovirus, a vaccinia virus, a herpes simplex virus, an Epstein-Barr virus, a geminivirus, a pseudorabies virus, a parvovirus, and a caulimovirus virus vector.

E27. The method of any one of embodiments E23 to E26, wherein the gene switch is an ecdysone receptor (EcR)-based gene switch.

E28. The method of any one of embodiments E23 to E27, wherein the polynucleotide encoding a gene switch comprises a first transcription factor sequence under the control of a first promoter and a second transcription factor sequence under the control of a second promoter, wherein a first transcription factor encoded by the first transcription factor sequence and a second transcription factor encoded by the second transcription factor sequence interact to form a complex which functions as a ligand-dependent transcription factor.

E29. The method of any one of embodiments E23 to E27, wherein the polynucleotide encoding a gene switch comprises a first transcription factor sequence and a second transcription factor sequence under the control of a promoter, wherein a first transcription factor encoded by the first transcription factor sequence and a second transcription factor encoded by the second transcription factor sequence interact to form a complex which functions as a ligand-dependent transcription factor.

E30. The method of embodiments E29. Wherein the first transcription factor sequence and the second transcription factor sequence are connected by an EMCV internal ribosomal entry site (IRES).

E31. A population of cells which have been modified with a recombinant vector conditionally expressing one or more proteins, wherein the vector comprises a polynucleotide encoding a gene switch, Wherein the polynucleotide comprises (1) at least one transcription factor sequence operably linked to a promoter, wherein the at least one transcription factor sequence encodes a ligand-dependent transcription factor, and (2) a polynucleotide encoding one or more proteins selected from the group consisting of a C1 esterase inhibitor, a kallikrein inhibitor, a bradykinin B2 receptor inhibitor, a prostaglandin synthase, a glucagon-like peptide-1 (GLP-1), a glucagon-like peptide-2 (GLP-2), adiponectin, leptin, and cystic fibrosis transmembrane conductance regulator (CFTR).

E32. The population of cells of embodiment E31, wherein one or more of the proteins is a human protein.

E33. The population of cells of embodiments E31 or E32, wherein the vector is a viral vector.

E34. The population of cells of embodiment E33, wherein the viral vector is selected from the group consisting of an adenovirus, an adeno-associated virus, a retrovirus, a pox virus, a baculovirus, a vaccinia virus, a herpes simplex virus, an Epstein-Barr virus, a geminivirus, a pseudorabies virus, a parvovirus, and a caulimovirus virus vector.

E35. The population of cells of any one of embodiments E31 to E34, wherein the gene switch is an ecdysone receptor (EcR)-based gene switch.

E36. The population of cells of any one of embodiments E31 to E35, wherein the polynucleotide encoding a gene switch comprises a first transcription factor sequence under the control of a first promoter and a second transcription factor sequence under the control of a second promoter, wherein a first transcription factor encoded by the first transcription factor sequence and a second transcription factor encoded by the second transcription factor sequence interact to form a complex which functions as a ligand-dependent transcription factor.

E37. The population of cells of any one of embodiments E31 to E35, wherein the polynucleotide encoding a gene switch comprises a first transcription factor sequence and a second transcription factor sequence under the control of a promoter, wherein a first transcription factor encoded by the first transcription factor sequence and a second transcription factor encoded by the second transcription factor sequence interact to form a complex which functions as a ligand-dependent transcription factor.

E38. The population of embodiments E37, wherein the first transcription factor sequence and the second transcription factor sequence are connected by an EMCV internal ribosomal entry site (IRES).

E39. A method for treating a disease in a mammal, comprising:
(a) administering a population of cells which conditionally express one or more proteins; and
(b) administering to the mammal a therapeutically effective amount of one or more activating ligands;
thereby inducing expression of the one or more proteins, wherein the one or more proteins is selected from the group consisting of a C1 esterase inhibitor, a kallikrein inhibitor, a bradykinin B2 receptor inhibitor, a prostaglandin synthase, a glucagon-like peptide-1 (GLP-1), a glucagon-like peptide-2 (GLP-2), adiponectin, leptin, and cystic fibrosis transmembrane conductance regulator (CFTR).

E40. A method for treating a disease in a mammal, comprising:
(a) administering to the mammal a vector for conditionally expressing one or more proteins, the vector comprising a polynucleotide encoding a gene switch, wherein the polynucleotide comprises
(1) at least one transcription factor sequence which is operably linked to a promoter, wherein the at least one transcription factor sequence encodes a ligand-dependent transcription factor, and
(2) a polynucleotide encoding one or more proteins operably linked to a promoter which is activated by the ligand-dependent transcription factor, and
(b) administering to the mammal a therapeutically effective amount of one or more activating ligands; thereby inducing expression of the one or more proteins and treating the disease,
wherein the one or more proteins is selected from the group consisting of a C1 esterase inhibitor, a kallikrein inhibitor, a bradykinin B2 receptor inhibitor, a prostaglandin synthase, a glucagon-like peptide-1 (GLP-1), a glucagon-like peptide-2 (GLP-2), adiponectin, leptin, and cystic fibrosis transmembrane conductance regulator (CFTR).

E41. The method of embodiments E39 or E40, wherein at least one of the proteins is a C1 esterase inhibitor and the disease is selected from the group consisting of angioedema, hereditary angioedema, sepsis, hypercoagulability, pulmonary dysfunction, hypoxemia, hemorrhagic pancreatitis, myocardial infarction, lung transplantation, trauma, thermal injury, or vascular leak.

E42. The method of embodiments E39 or E40, wherein at least one of the proteins is a kallikrein inhibitor and the disease is selected from the group consisting of angioedema, hereditary angioedema, atherothrombosis, coronary artery disease, Alzheimer's Disease, inflammatory bowel disease, Crohn's Disease, vascular leak, acute respiratory distress syndrome, bradykinin-mediated inflammation and a disease, condition or disorders of the contact system.

E43. The method of embodiments E39 or E40, wherein at least one of the proteins is a bradykinin B2 receptor inhibitor and the disease is selected from the group consisting of angioedema, hereditary angioedema, bradykinin-mediated inflammation, glomerulosclerosis, Alzheimer's Disease, cerebral edema, vascular leak, acute respiratory distress syndrome, pain, inflammation, trauma, burns, shock, allergy, and cardiovascular disease.

E44. The method of embodiments E39 or E40, wherein at least one of the proteins is a prostaglandin synthase and the disease is selected from the group consisting of pulmonary hypertension, pulmonary arterial hypertension (PAH), idiopathic pulmonary arterial hypertension, familial pulmonary arterial hypertension, secondary pulmonary arterial hypertension, pulmonary veno-occlusive disease, pulmonary capillary hemangiomatosis, persistent pulmonary hypertension of the newborn.

E45. The method of embodiments E39 or E40, wherein at least one of the proteins is a glucagon-like peptide-1 (GLP-1) and the disease is diabetes or other metabolic disease or disorder.

E46. The method of embodiments E39 or E40, wherein at least one of the proteins is a glucagon-like peptide-2 (GLP-2) and the disease is diabetes or other metabolic disease or disorder.

E47. The method of embodiments E39 or E40, wherein at least one of the proteins is adiponectin and the disease is diabetes or other metabolic disease or disorder.

E48. The method of embodiments E39 or E40, wherein at least one of the proteins is leptin and the disease is diabetes or other metabolic disease or disorder.

E49. The method of embodiments E39 or E40, wherein at least one of the proteins is cystic fibrosis transmembrane conductance regulator (CFTR) and the disease is cystic fibrosis.

E50. A method for treating multiple sclerosis in a mammal, comprising:
(a) administering to the mammal a vector for conditionally expressing one or more proteins, the vector comprising a polynucleotide encoding a gene switch, wherein the polynucleotide comprises
(1) at least one transcription factor sequence which is operably linked to a promoter, wherein the at least one transcription factor sequence encodes a ligand-dependent transcription factor, and
(2) a polynucleotide encoding one or more proteins operably linked to a promoter which is activated by the ligand-dependent transcription factor, and
(b) administering to the mammal a therapeutically effective amount of one or more activating ligands; thereby inducing expression of the one or more proteins and treating the disease,
wherein the one or more proteins is selected from the group consisting of myelin basic protein (MBP) and interferon-beta (IFN-B).

E51. The method of embodiment E50, wherein one of the one or more proteins comprises an amino acid sequence at least 80%, 85%, 90%, 95%, 96%, 97%, 98%, 99%, or 100% identical to SEQ ID NO: 9 (human myelin basic protein).

E52. The method of embodiment E50, wherein one of the one or more proteins comprises an amino acid sequence at least 80%, 85%, 90%, 95%, 96%, 97%, 98%, 99%, or 100% identical to to SEQ ID NO: 17 (interferon-beta).

E53. The method of embodiment E50, wherein the one or more proteins comprise both myelin basic protein (MBP) and interferon-beta (IFN-B).

E54. The method of any one of embodiments E50 to E53, wherein one or more of the proteins is a human protein.

E55. The method of any one of embodiments E50 to E54, wherein the vector is a viral vector.

E56. The method of embodiments E55, wherein the viral vector is selected from the group consisting of an adenovirus, an adeno-associated virus, a retrovirus, a pox virus, a baculovirus, a vaccinia virus, a herpes simplex virus, an Epstein-Barr virus, a geminivirus, a pseudorabies virus, a parvovirus, and a caulimovirus virus vector.

E57. The method of any one of embodiments E50 to E56, wherein the gene switch is an ecdysone receptor (EcR)-based gene switch.

E58. The method of any one of embodiments E50 to E57, wherein the polynucleotide encoding a gene switch comprises a first transcription factor sequence under the control of a first promoter and a second transcription factor sequence under the control of a second promoter, wherein a first transcription factor encoded by the first transcription factor sequence and a second transcription factor encoded by the second transcription factor sequence interact to form a complex which functions as a ligand-dependent transcription factor.

E59. The method of any one of embodiments E50 to E57, wherein the polynucleotide encoding a gene switch comprises a first transcription factor sequence and a second transcription factor sequence under the control of a promoter, wherein a first transcription factor encoded by the first transcription factor sequence and a second transcription factor encoded by the second transcription factor sequence interact to form a complex which functions as a ligand-dependent transcription factor.

E60. The method of embodiment E59, wherein the first transcription factor sequence and the second transcription factor sequence are connected by an EMCV internal ribosomal entry site (IRES).

E61. A method for treating inflammatory bowel or Crohn's disease in a mammal, comprising:

(a) administering to the mammal a vector for conditionally expressing one or more proteins, the vector comprising a polynucleotide encoding a gene switch, wherein the polynucleotide comprises (1) at least one transcription factor sequence which is operably linked to a promoter, wherein the at least one transcription factor sequence encodes a ligand-dependent transcription factor, and (2) a polynucleotide encoding one or more proteins operably linked to a promoter which is activated by the ligand-dependent transcription factor, and (b) administering to the mammal a therapeutically effective amount of one or more activating ligands; thereby inducing expression of the one or more proteins and treating the disease, wherein one of the one or more proteins is interleukin-10 (IL-10).

E62. The method of embodiment E61, wherein one of the one or more proteins comprises an amino acid sequence at least 80%, 85%, 90%, 95%, 96%, 97%, 98%, 99%, or 100% identical to SEQ ID NO: 22 (interleukin-10).

E63. The method of embodiments E61 or E62, wherein the interleukin-10 is a human IL-10 protein.

E64. The method of any one of embodiments E61 to E63, wherein the vector is a viral vector.

E65. The method of embodiment E64, wherein the viral vector is selected from the group consisting of an adenovirus, an adeno-associated virus, a retrovirus, a pox virus, a baculovirus, a vaccinia virus, a herpes simplex virus, an Epstein-Barr virus, a geminivirus, a pseudorabies virus, a parvovirus, and a caulimovirus virus vector.

E66. The method of any one of embodiments E61 to E65, wherein the gene switch is an ecdysone receptor (EcR)-based gene switch.

E67. The method of any one of embodiments E61 to E66, wherein the polynucleotide encoding a gene switch comprises a first transcription factor sequence under the control of a first promoter and a second transcription factor sequence under the control of a second promoter, wherein a first transcription factor encoded by the first transcription factor sequence and a second transcription factor encoded by the second transcription factor sequence interact to form a complex which functions as a ligand-dependent transcription factor.

E68. The method of any one of embodiments E61 to E66, wherein the polynucleotide encoding a gene switch comprises a first transcription factor sequence and a second transcription factor sequence under the control of a promoter, wherein a first transcription factor encoded by the first transcription factor sequence and a second transcription factor encoded by the second transcription factor sequence interact to form a complex which functions as a ligand-dependent transcription factor.

E69. The method of embodiment E68, wherein the first transcription factor sequence and the second transcription factor sequence are connected by an EMCV internal ribosomal entry site (IRES).

E70. A composition comprising the vector of any one of embodiments E7 to E22, or the population of cells of any one of E31 to E38, and a pharmaceutically acceptable carrier.

E71. The composition of embodiments E70, which is administered systemically, intravenously, intratumorally, orally, intraperitoneally, intramuscularly, intravertebrally, intracerebrally, intrathecally, intradermally, or subcutaneously.

E72. A medicament comprising the vector of any one of embodiments E7 to E22, or the population of cells of any one of E31 to E38, and a pharmaceutically acceptable carrier.

E73. The medicament of embodiment E72, which is administered systemically, intravenously, intratumorally, orally, intraperitoneally, intramuscularly, intravertebrally, intracerebrally, intrathecally, intradermally, or subcutaneously.

E74. A kit comprising the vector of any one of embodiments E7 to E22 or the population of cells of any one of embodiments E31 to E38.

E75. The vector of any one of embodiments E7 to E22, or the population of cells of any one of embodiments E31 to E38, and a ligand which activates the gene switch.

E76. The vector or population of cells and ligand of embodiments E75, wherein the ligand is a diacylhydrazine.

E77. The vector or population of cells and diacylhydrazine ligand of embodiments E76, wherein the diacylhydrazine is RG-115819, RG-115830 or RG-115932.

E78. The vector or population of cells and ligand of embodiments E75, wherein the ligand is an amidoketone or oxadiazoline.

E79. The vector of any one of embodiments E7 to E22, the method of any one of embodiments E23 to E30 and embodiments E39 to E69, the population of cells of any one of embodiments E31 to E38, wherein the ligand which activates ligand-dependent transcription is a diacylhydrazine.

E80. The vector, method, or population of cells of embodiments E79, wherein the diacylhydrazine is RG-115819, RG-115830 or RG-115932.

E81. The vector of any one of embodiments E7 to E22, the method of any one of embodiments E23 to E30 and E39 to E69, the population of any one of embodiments E31 to E38, wherein the ligand which activates ligand-dependent transcription is an amidoketone or oxadiazoline.

E82. A kit comprising the vector of any one of embodiments E7 to E22, or the population of cells of any one of embodiments E31 to E38, and a ligand.

E83. The kit of embodiment E82, wherein the ligand is a diacylhydrazine.

E84. The kit of embodiment E83, wherein the diacylhydrazine is RG-115819, RG-115830 or RG-115932.

E85. The kit and ligand of embodiment E82, wherein the ligand is an amidoketone or oxadiazoline.

EXAMPLE 1

Effect of Local Injection of Ad-RTS-mIL 1.2 Against Local and Contralateral Tumors in the B16F0 Melanoma Model We investigated if the treatment of a local tumor with Ad-RTS-mIL12 (resulting in local tumor growth regression) would also lead to anti-tumor activity in the distant tumor. Toward this goal, we developed melanoma tumors on both flank regions of immunocompetent mice (C57BL/6) and treated the tumor on the right flank with Ad-RTS-mIL12 in the presence of activator ligand.

Six- to eight-week-old female C57B1/6 mice were purchased from Harlan (USA). Animal care and experimental procedures were performed according to Intrexon's Institutional Animal Care and Use Committee guidelines.

The murine melanoma (B16F0) cells were purchased from ATCC (Manassas, Va.). B16F0 cells were grown in Dulbecco's modified Eagle's medium (ATCC, Manassas, Va.), The DMEM was supplemented with heat-inactivated fetal calf serum (FCS) 10% v/v, 2-mM L-glutamine (Atlanta Biologicals, Inc, Lawrenceville, Ga.), 100 IU/ml penicillin C, and 100 µg/ml streptomycin. The cells were grown at 37° C. in 5% CO2. All cell lines were routinely tested and found to be free of mycoplasma.

A total of 45 C57BL/6 animals were inoculated subcutaneously with murine melanoma, B16F0 (ATCC), 1e5 cells/50 µl, on the right and left hind flanks. Twelve days later, when macroscopic tumor was visible, the animals were randomized into four groups of ten animals, as shown in the Table below: No treatment (Group 1), Activator alone (Group 2), Ad-RTS-mIL12 alone ($1\times10^{10}$ vp dose, Group 3), and Ad-RTS-mIL12 ($1\times10^{10}$ vp dose) with activator ligand present in the chow (1000 mg/kg chow, Groups 4).

Cohorts receiving activator ligand were fed rodent chow blended with the activator ligand RG-115932 ad libitum until the end of the study. Cohorts not receiving activator continued to receive a regular diet.

Vector was administered intratumorally on Day 12 and Day 19 post tumor cell inoculation. Tumor size and body weight of each mouse were monitored three times a week until the end of the study. The animals were sacrificed when their cumulative tumor size exceeded 1000 mm³ or displayed body weight loss >15% for greater than 3 days. Upon completion of the study, all remaining animals were euthanized.

The tumor volumes were calculated using the formula, $L \times W^2/2$. Tumor sizes are shown as mean±SE. Statistical analysis was performed using a two-tailed t test. Differences between groups were considered significant when $p<0.05$.

| Groups | N | Chow | Treatment (1e10 vp) | Treatment Days post cell inoculation | Tumor size, body weight |
|---|---|---|---|---|---|
| 1 | 10 | Normal Custom | | | Mon, Wed and Fri |
| 2 | 10 | (1000 mg/kg) | | | Mon, Wed and Fri |
| 3 | 10 | Normal Custom | Ad-RTS-mIL-12 | Day 12, 19 | Mon, Wed and Fri |
| 4 | 10 | (1000 mg/kg) | Ad-RTS-mIL-12 | Day 12, 19 | Mon, Wed and Fri |

When the tumor on the right flank reached an average volume of 44 mm³, treatment was initiated. For localized delivery, two intratumoral injections were given into right tumors with 1e10 vp of Ad-RTS-mIL12 7 days apart. These animals received activator ligand chow (1000 mg/kg). The control animals received either no treatment or activator ligand (1000 mg/kg) alone or Ad-RTS-mIL12 without activator. Twenty four hours prior to vector administration, the indicated cohorts received activator ligand (1000 mg/kg). These animals thrice weekly for any signs of tumor progression or regression. As shown in FIG. 1A the control animals treated with either activator ligand or no treatment had average tumor volumes of 924±80 mm³ and 884±142 mm³, respectively on day 21 post cell inoculation.

In contrast, the tumors treated with Ad-RTS-mIL12+activator ligand had tumor volumes of 86±138 mm³ thereby indicating a statistically significant ($p<0.0001$) ~91% tumor growth inhibition compared to animals with no treatment. Ad-RTS-mIL12 without activator ligand had tumor volume 565±305 mm³ and was not significant ($p<0.07$) relative to control animals. These data demonstrated that Ad-RTS-mIL12 without activator ligand had little impact on tumor growth while Ad-RTS-mIL12 in the presence of activator ligand had marked anti-tumor activity.

Figure 1B:
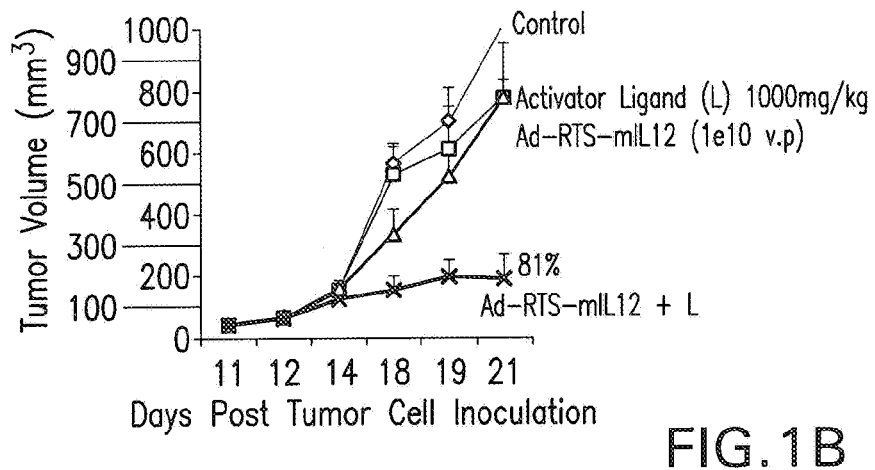

Importantly, the animals that received Ad-RTS-mIL12 plus ligand into the right flank tumor, displayed a statistically significant ($p<0.005$) tumor growth inhibition of 81% of the uninjected left flank tumor (189±231 mm³) as compared to the uninjected contralateral tumors (1019±233 mm³) in the control group with no treatment (FIG. 1B). However, for Ad-RTS-mIL12 without ligand-treated tumors, there was no significant reduction in the contralateral untreated tumors. The tumors in the control group treated with either Ad-RTS-mIL12 alone or activator ligand alone, as well as the contralateral uninjected tumors, continued to grow much more rapidly after 21 days post-tumor implantation. These data suggest that the systemic immune response against tumor cells that developed following treatment with Ad-RTS-mIL12 plus ligand in the primary tumor may be responsible for the anti-tumor effect observed in the distant untreated tumor.

Body weight was measured as a function of toxicity in this study. Animals were weighed three times a week until completion of the study. The mice were observed frequently for overt signs of any adverse and treatment related side effects. Acceptable toxicity was defined as a mean body-weight loss of less than 15% during the study. All treatments in this study were well tolerated. Maximum mean body weight losses were within acceptable limits (<15%) (FIG. 2) and no treatment related deaths were found. However, we found sporadic death in all the groups.

It has been well established that the immune system is capable of recognizing tumor-specific antigens and of eradicating malignant cells (Brunda, M. J. et al., *J. Exp. Med.* 178: 1223-1230 (1993); Brunda, M. J. et al., *Cancer Chemother.*

Pharmacol. 38 (Suppl): S16-S21 (1996); and Golab J. et al., Int. J. Mol. Med. 3(5):537-44 (1999)). However, the ability to harness the immune system for therapeutic purposes in cancer treatment remains elusive. This strategy involves the use of intratumoral injection of replication defective virus vectors with regulated IL-12 expression, Ad-RTS-mIL12, to reduce the tumor growth without inducing systemic toxicity (Kornita, H. et al, *Cancer Gene Ther.* 16: 883-91 (2009)) and to activate the immune system to kill distal and metastatic cancers.

In this study, intratumoral injection of established tumors with Ad-RTS-mIL12 in the presence of activator ligand inhibited, tumor growth in B16F0 model. Here, using a bilateral established subcutaneous B16F0 tumor model, in C57BL/6 mice, it was demonstrated that unilateral intratumoral injection with Ad-RTS-mIL12 caused a significant reduction in the growth of both the injected and contralateral uninjected tumors. This antitumor effect was significant compared to animals treated with activator ligand alone or Ad-RTS-mIL12 without activator ligand. These results suggests that direct delivery of Ad-RTS-mIL12 into the tumor microenvironment provides a therapeutic benefit and generates protective anti-tumor immunity against metastatic cancer cells.

EXAMPLE 2

IL-12 and IFNalpha Combination Therapy

Current cancer immunotherapies have provided limited success in the clinic and innovative strategies are required to further enhance the effectiveness of an anti-tumor immune response. This study assessed anti-tumor activity utilizing intratumoral (i.t.) administration of adenovirus (Ad) with the novel Rheoswitch Therapeutic System® (RTS®), an inducible promoter system, for regulated expression of murine IL-12 or IFNa. Oral administration of a small molecule activator ligand (AL), INXN-1001, regulates the expression of IL-12 in Ad-RTS-mIL-12 and IFNa in Ad-RTS-mIFNa. The regulated expression and therapeutic benefit of IL-12 and IFNa from i.t. administered Ad-RTS-mIL-12 and Ad-RTS-mIFNa, either alone or in combination, was examined in syngeneic Lewis lung carcinoma (LLC) and syngeneic mammary carcinoma (4T1) models.

In the LLC model, daily treatment with oral AL alone (administered in feed at 1000 ppm, representing a daily dose of ~225 mg/kg/day) or i.t. cytokine gene therapy in the absence of AL did not result in significant inhibition of tumor growth compared to control, untreated tumors. In contrast, i.t. injection with $10^{10}$ vp Ad-RTS-mIL-12 or Ad-RTS-mIFNa and daily oral AL led to significant tumor growth inhibition by day 25 (72 and 71%, respectively; $p<0.05$). Notably; combined treatment of the LLC tumors with Ad-RTS-mIL-12 and Ad-RTS-mIFNa with oral AL resulted in significant anti-tumor effect compared to either treatment alone (97% growth inhibition; $p<0.05$) without overt toxicity as assessed by no change in body weight. In the 4T1 model, i.t. treatment with $10^{10}$ vp of Ad-RTS-mIL-12 plus AL or Ad-RTS-mIFNa plus AL led to 58 and 53% inhibition of tumor growth compared to control untreated tumors by day 34 ($p<0.05$). Notably, concomitant treatment with both Ad-RTS-mIL-12 plus AL and Ad-RTS-mIFNa plus AL resulted in enhanced anti-tumor activity with 80% growth inhibition. These data indicate that the combined treatment strategy using RTS-regulated IL-12 and IFNa in Ad vectors concomitant with AL induces effective therapeutic activity against aggressive murine tumors.

Future studies will investigate the mechanism by which both IL-12 and IFNα exert their anti-tumor effect in the above tumor models.

Interleukin-12 (IL-12) is a potent pleiotropic cytokine used for treatment of several infectious and malignant diseases. IL-12 antitumor activity is mediated by direct tumor cell cytotoxicity, anti-angiogenic properties and enhancement of immunoregulatory activities including activation of natural killer cells, $CD4^+$ T cells and $CD8^+$ T cells. Despite these anti-tumor effects, systemic infusion of recombinant IL-12 in humans results in severe systemic toxicity which severely limits its use clinically.

Interferon alpha (IFNa) is a cytokine with potent antiviral and antitumor effects. Administration of IFNa stimulates T cells and natural killer cells proliferation leading to tumor cell cytotoxicity, anti-angiogensis, and increased expression of major histocompatibility complex (MHC), tumor antigens as well as adhesion molecules. Similarly to IL-12, high levels of IFNa also displays severe side effects including influenza-like syndrome, severe nausea, fatigue, and depression.

Therefore, there is a clear need to control the expression levels of these cytokines. The RTS™ (Rheoswitch Therapeutic System) represents a novel regulation system that allows control of gene expression using INXN-1001, the activator ligand which is an orally bioavailable small molecule drug. Utilizing the RTS technology to control cytokine expression, we have previously demonstrated tumor growth reduction in several preclinical animal models using either Ad-RTS-IL-12 transduced dendritic cells and more recently, the direct intratumoral (IT) injection of Ad-RTS-IL-12. This has led to the initiation of a Phase 1 clinical trial of direct Ad-RTS-IL-12 into tumor lesions of patients with Stage III/IV malignant melanoma.

Combinatorial therapies are showing promising potential in preclinical models as well as in the clinic. Therefore, in this study, we address the synergistic effect of Ad-RTS-IL-12 and Ad-RTS-IFNa co-administered IT in two different syngeneic tumor models, Lewis Lung carcinoma (LLC) and 4T1 breast cancer.

The RheoSwitch Therapeutic System (RTS) contains three basic components: (1) an inducible promoter; (2) a ligand-inducible transcription factor and a co-activation partner; (3) RheoSwitch activator ligand (AL).

In the absence of ligand, the switch protein complex provides an "off" signal. In contrast, in the presence of ligand, the complex changes conformation and provides a dose-dependent "on" signal for target gene expression. In vivo, the orally administered AL turns on gene expression within 24 hours, and upon withdrawal of the AL, gene expression returns to baseline levels within about 24 hours.

LLC and 4T1 cells were transiently transduced with Ad-RTS-murine IL12 or Ad-RTS-murine IFNa at a MOI of 100. To induce gene expression, activator ligand INXN-1001 was added to the culture medium at a concentration of 75 nM or treated with 0.1% DMSO as a control. Supernatants were collected at 48 h and cytokine levels assessed by ELISA. n=3, mean±s.d. The results are shown in FIG. 3.

LLC and 4T1 cells were transiently transduced with Ad-RTS-murine IL12 or Ad-RTS-murine IFNa at a MOI of 100. To induce gene expression, activator ligand INXN-1001 was added to the culture medium at a concentration of 75 nM or treated with 0.1% DMSO as a control. Supernatants were collected at 48 h and cytokine levels assessed by ELISA. n=3, mean±s.d. The results are shown in Figure. Intratumor administration of adenovirus on specific days are indicated by arrows in FIG. 4. Controls included PBS and Ad-RTS-Luc injected mice treated with or without activator ligand (INXN- 1001), which were grouped since no effects on tumors size occurred. Percentage of tumor inhibition is reported in the graph and are significantly lower than controls and single cytokine therapy groups (p<0.01). n=5, mean±s.e.m.

Figure 5:
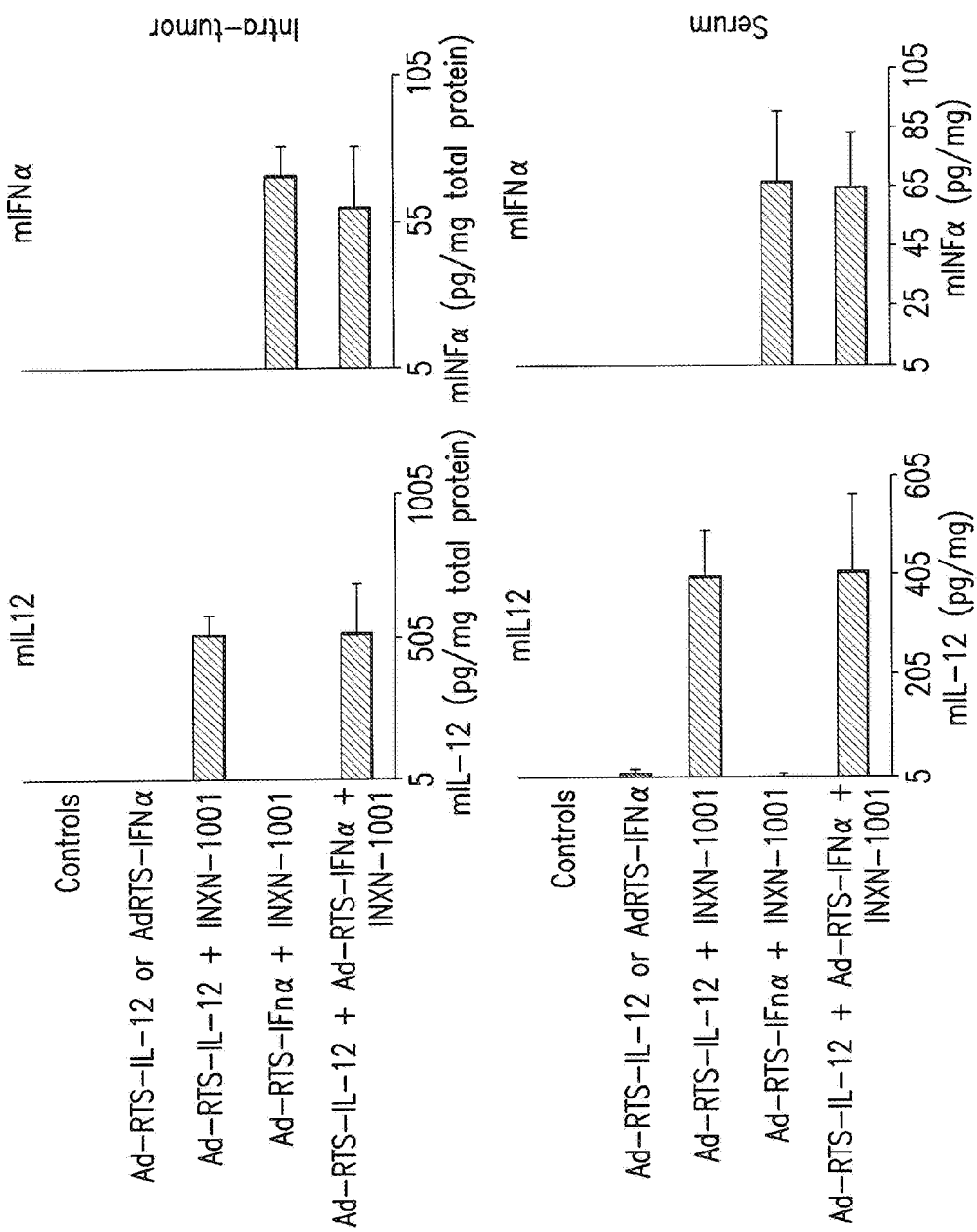
FIG. 5 is a bar graph that depicts the systemic and intratumoral effects of IL12 and IFNα in mice.

In a separate study, we injected mice with $1 \times 10^5$ 4T1 cancer cells via s.c. route. When tumors reached palpable size, mice were randomized into treatment groups with Ad-RTS-IL-12 and/or Ad-RTS-IFNa ($10^{10}$ vp/mouse/vector) alone or in combination administered intratumorally. Sera and tumors were collected at 48 hours after intratumor injection. Controls includes PBS and Ad-RTS-Luc injected mice with or without INXN-1001 activator ligand which were grouped since no effects on tumor size occurred. INXN-1001 was formulated in Labrasol and delivered by oral gavage on a daily basis. Cytokines levels in circulation and intra-tumor were assessed using sera and tumor homogenates and detected by ELISAs. n=4, mean±s.e.m. The results are shown in FIG. 5.

Figure 6:
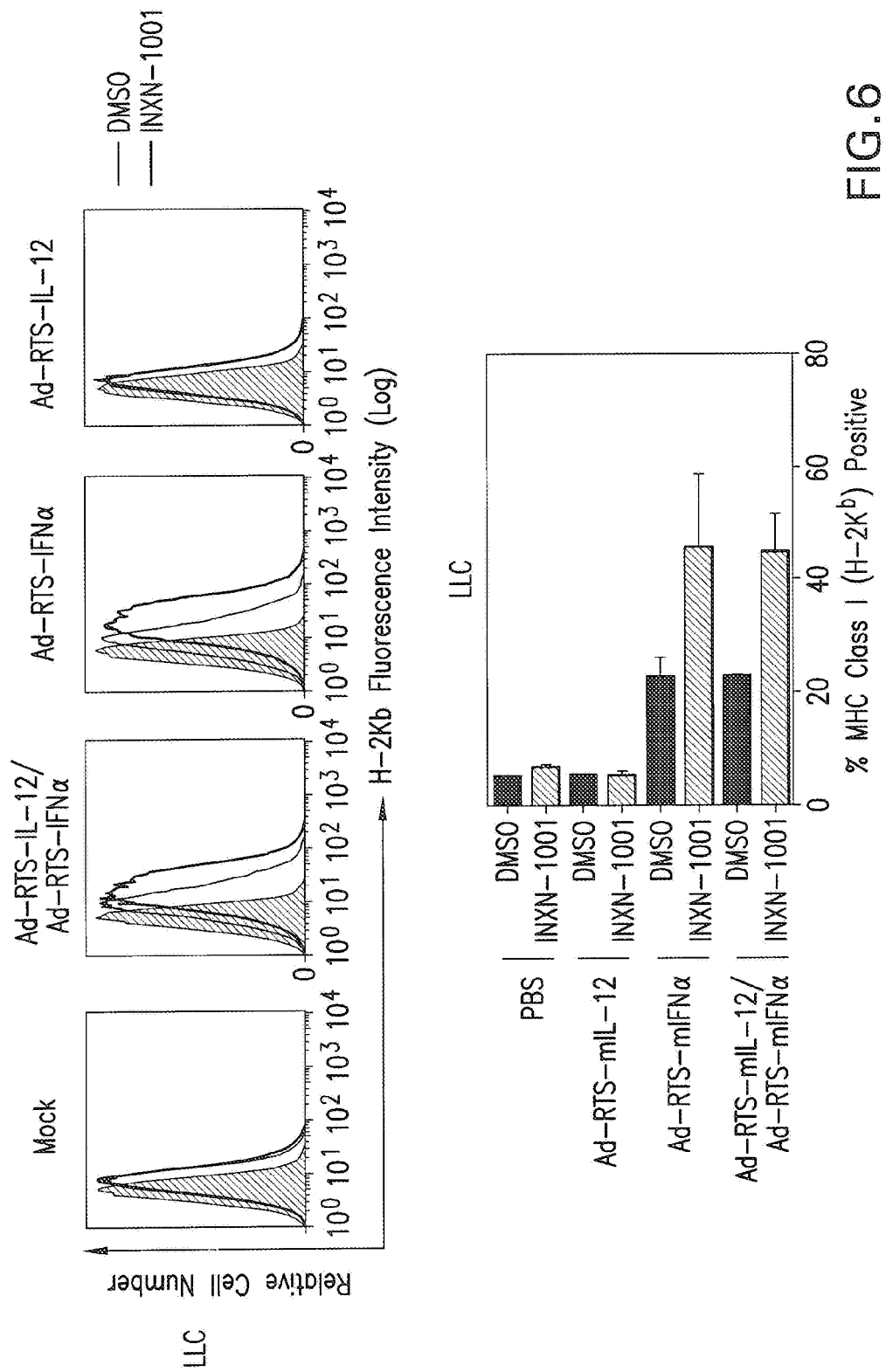
FIG. 6 is a combined line and bar graph that depicts that the co-expression of IL12 and IFNα enhances MHC Class I expression in 4T1 and LLC cancer cells.

LLC and 4T1 (results later this week) cells were transduced with Ad-RTS-IL-12 and Ad-RTS-IFNa alone or in combinations at concentration of 500 MOI for each vector. Transduced cells were cultured in the presence of 75 nm INXN-1001 or 0.1% DMSO for 48 h. Cell culture supernatants were collected for cytokine analysis. Cells were also harvested for flow cytometric analysis of MHC Class I expression. n=2-3, mean±s.d. The results are shown in FIG. 6.

The data demonstrate a synergistic effect of IL12 and IFNa cytokines to inhibit tumor growth. While IL-12 was previously shown to reduce tumor growth, the combination with Ad-RTS-IFNa significantly enhanced efficacy, as measured by tumor growth reduction in the LLC and 4T1 models. Notably, no toxicity was observed after cytokines expression, demonstrating the regulated expression of IL12 and IFNa with the Rheoswitch system. Mechanistically, IFNa triggers MHC-I expression on tumor cells, thus leading to an augmented cell death. Additional MOA studies are currently underway.

Overall, cytokines combination delivered in a safe, controlled and inducible fashion represent a novel strategy to treat aggressive tumors that commonly affect human population.

EXAMPLE 3

Methods

The experiments in the following Examples 4-8 were performed as follows.

Animals

Female C3H/H and Balb/c mice, 6-8 weeks old, were purchased from Harlan Laboratories. Animals were maintained and treated in accordance with the Institutional Animal Care and Use Committee of Intrexon Corporation. Animals were fed water and alfalfa free chow with 18% protein purchased from Harlan.

All procedures were performed on anaesthetized animals. Area surrounding the quadriceps muscle was pre-injected with 50 U (in 50 µl final volume) of Hylanex (rHuPH20, Halozyme) 1 hr prior to DNA injection. A small incision was made to expose the quadriceps muscle and 250 ug of preclinical grade RTS-hEPO plasmid was injected in a final volume of 100 ul using a tuberculin syringe fitted with a 29 gauge needle. The incision was quickly sutured. The DNA was electroporated with the help of a 2-needle electrode (5 mm) inserted into the muscle, with each needle on either side of the DNA injection site. 8 pulses at 50V/cm (20 ms, 1 Hz) were delivered to enhance gene transfer.

Ligand

RG-115932 ligand was formulated into animal diet and was given at a concentration of 1000 mg/kg. For OG ligand was formulated in Labrasol at 10 mg/ml.

Intramuscular Administration of AAV-HuEPO (0034A, 0034B)

Animals were anesthetized, their quadriceps were visualized and the injection site sterilized. The mice were injected with vector using a 0.5 ml insulin syringe and a 29.5 gauge needle. Each animal was injected with total of $10^{11}$ virus genomes in a 100 µl volume. After the procedure, the animals were placed in their cage and observed for normal ambulation.

Protein Analyses

Plasma samples were assayed for the presence of human erythropoietin using Enzyme Linked Immunosorbent Assay (ELISA) (StemCell Technologies, #01630).

Hematocrit Measurement

Mice were bled via retro-orbital sinus and samples were measured by Heska CBC hematology analyzer.

EXAMPLE 4

Evaluation of Human Erythropoietin Efficacy in Mice Following Single Intramuscular Administration of AAV-RTS-HuEpo "AAV-RTS-HuEPO" refers to the adeno-associated viral vector-RheoSwitch® Therapeutic System-Human EPO. The nucleic acid sequence of the signal peptide sequence, human erythropoietin sequence, and stop codon are set forth in SEQ ID NO: 8.

Figure 7A:
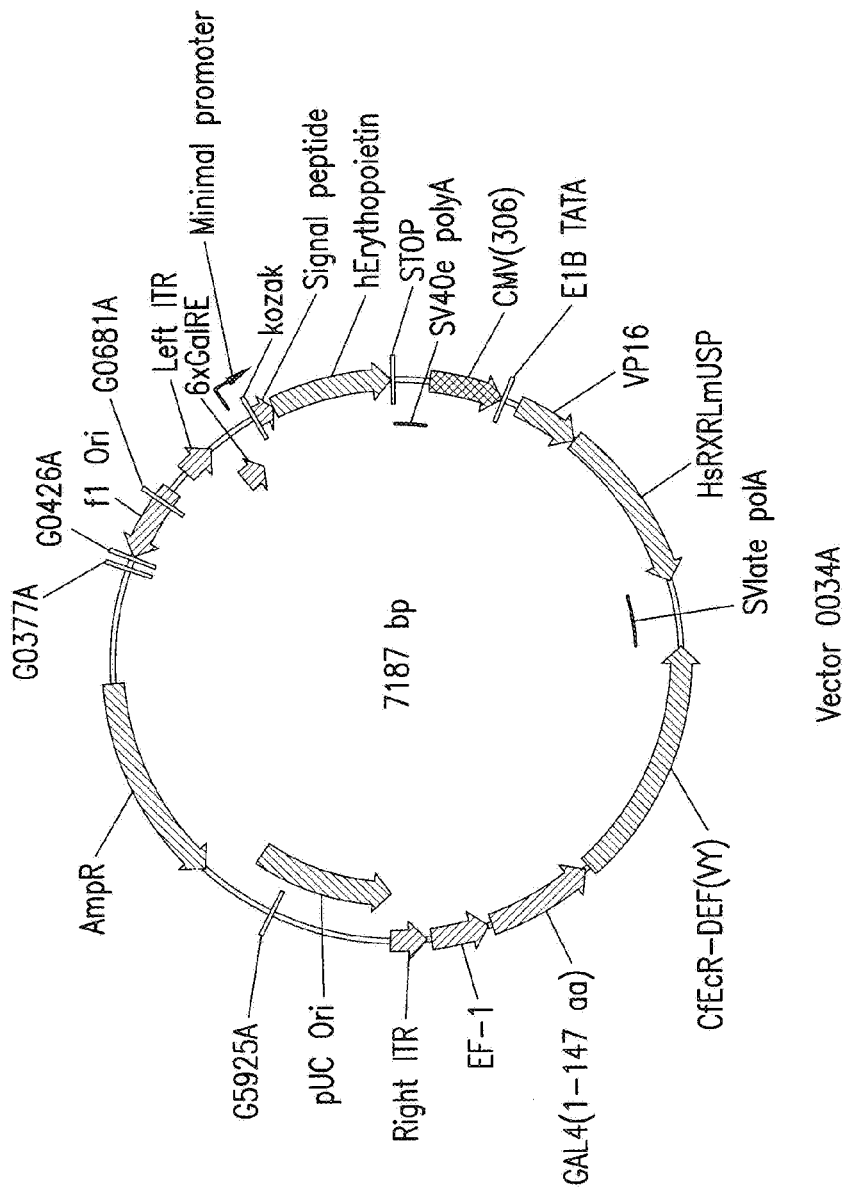
FIGS. 7A, 7B, 7C and 7D depict vector maps for vectors 0034A, 0034B, 0034CB and 0034D, respectively. 0034A carries standard switch system elements. 0034B carries a modified regulated promoter.
Figure 7B:
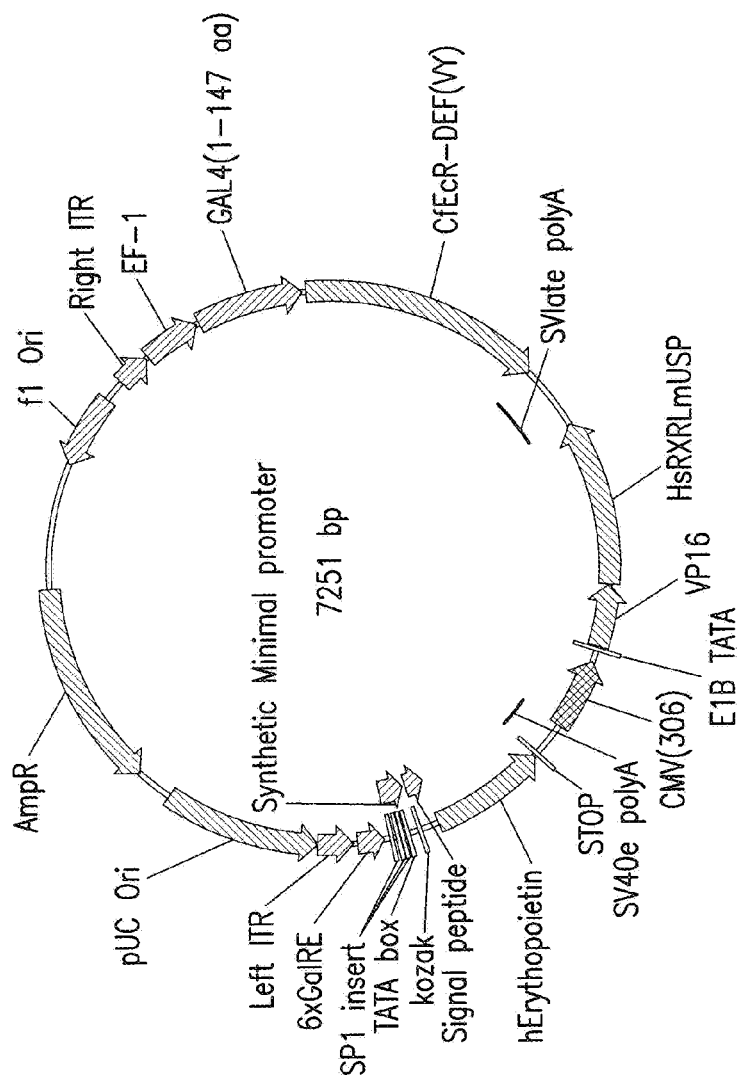
Figure 7C:
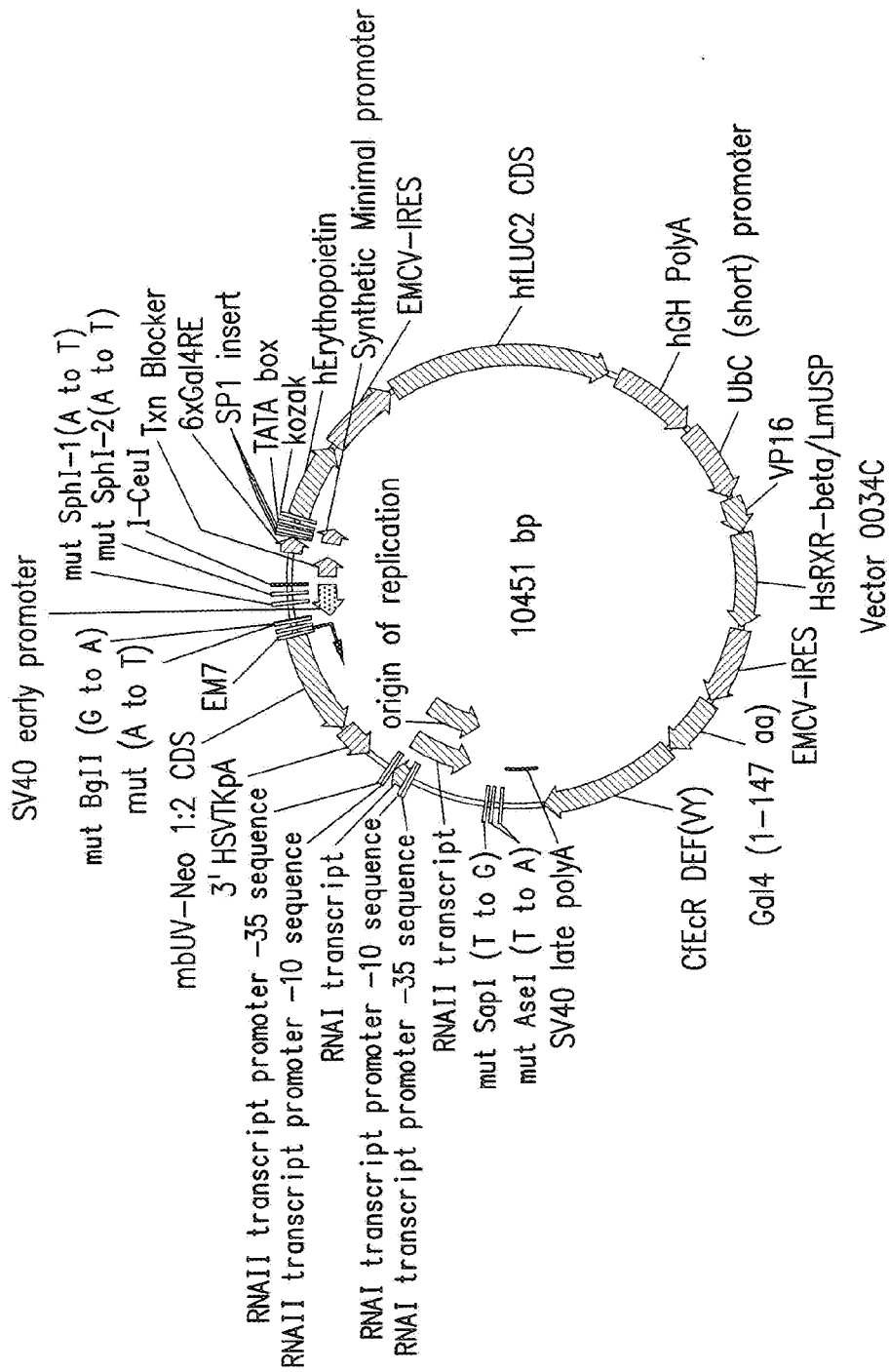
Figure 7D:
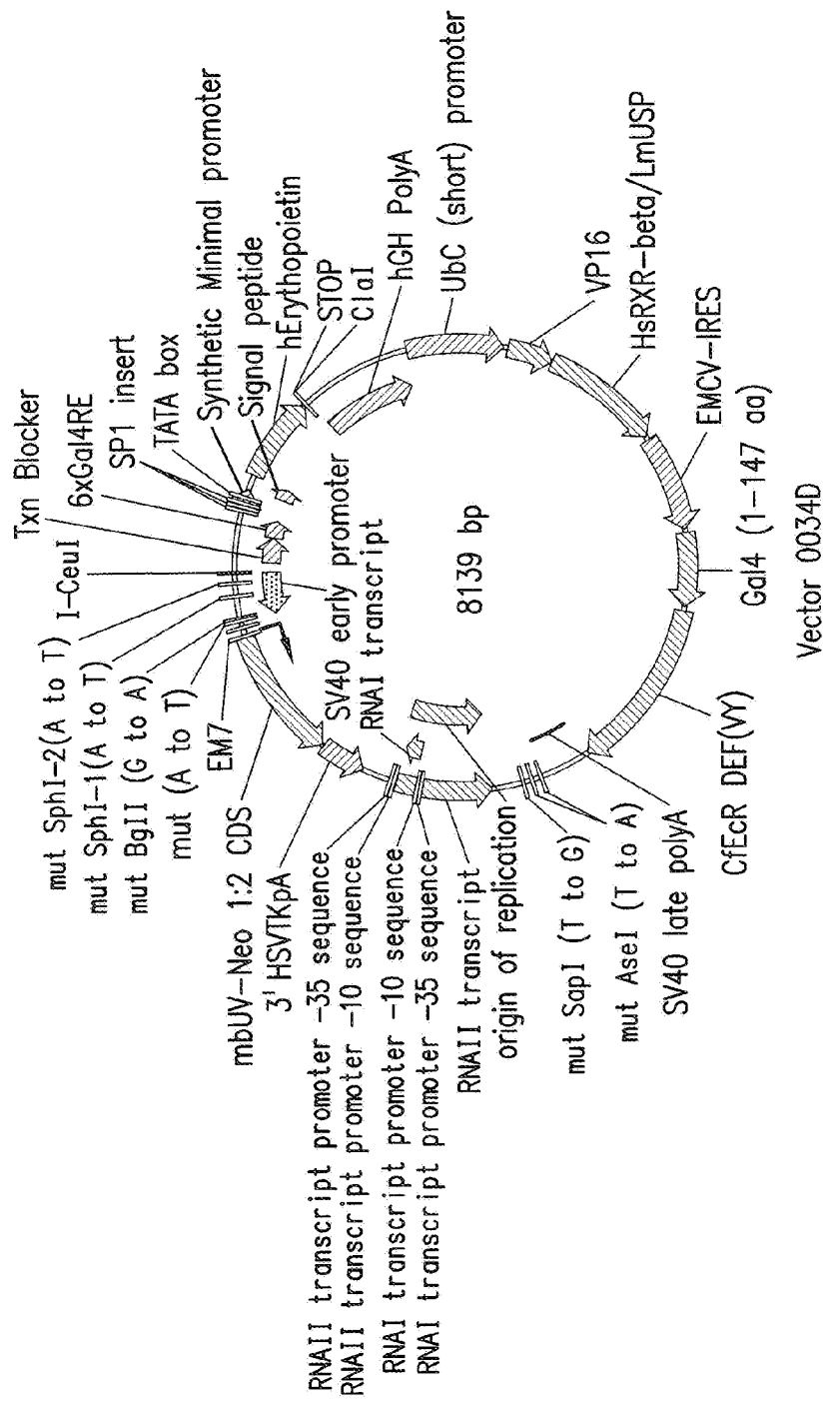

The goal of this study was to determine if AAV-mediated, intramuscular (IM) delivery of the HuEPO transgene to mice would result in measurable huEPO expression and a concurrent increase in hematocrit (HCT). Two AAV-huEPO vectors, 0034A and 0034B (FIGS. 7A and 7B), were tested using two mouse strains, C3H/H and BALB/c. The huEPO expression cassettes in both AAV vectors are under the control of the inducible promoter. HuEpo levels in the plasma and HCT were measured weekly.

On the start of the study, mice were bled for baseline hematocrit levels, followed by IM administration of $10^{11}$ AAV-HuEPO viral genomes per animal. Animals received activator ligand-containing chow (18-1000) starting on the day of AAV administration. Control animals received either vector administration and normal chow (no activator ligand), or they received vehicle-alone IM administration (saline) with or without activator ligand. HCTs were measured in all groups every 7 days. Both groups that received the HuEPO vectors in the presence of activator ligand displayed elevated hematocrits.

Figure 8:
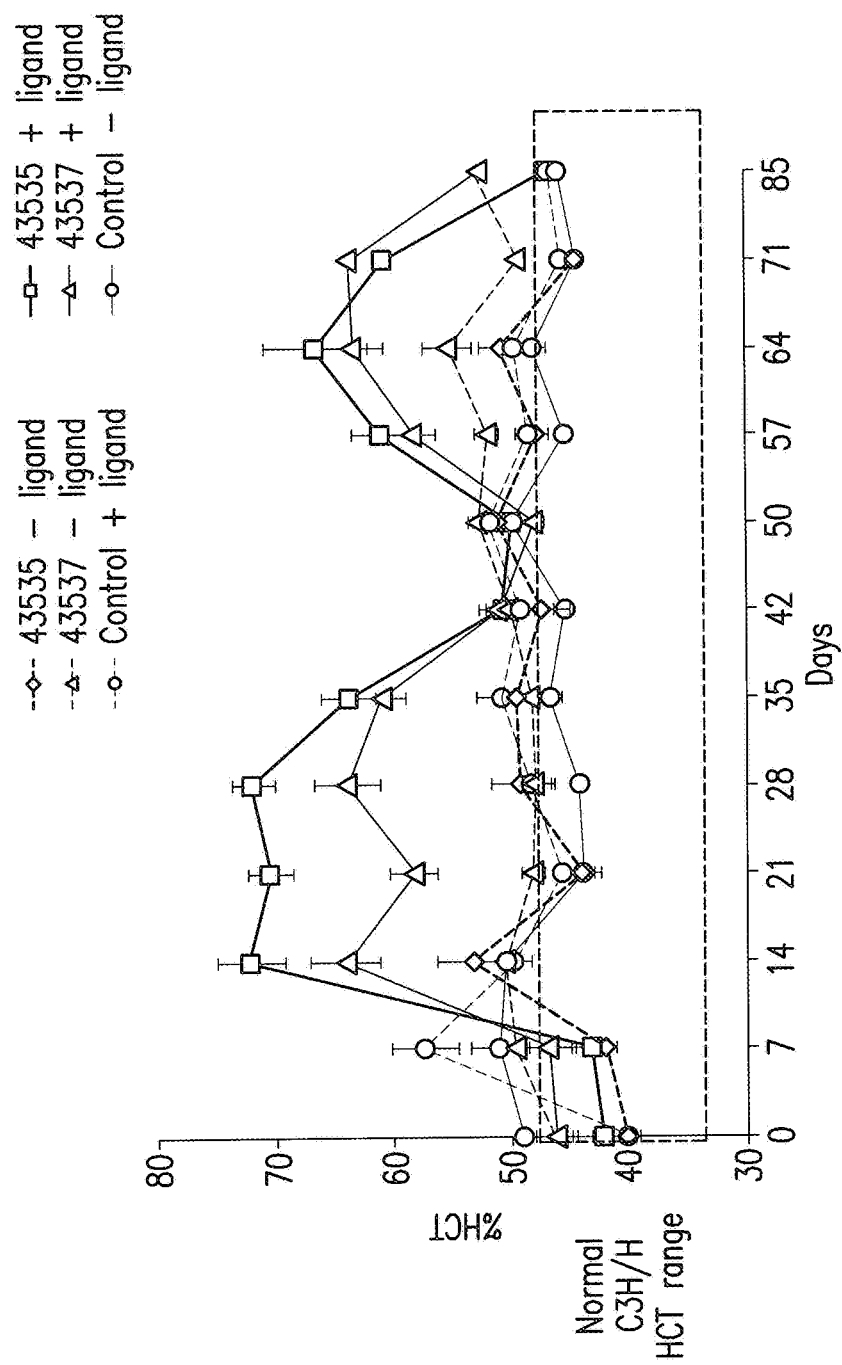
FIG. 8 is a line graph that depicts the physiological response of C3H/H mice following intramuscular (IM) administration of AAV-HuEPO.

As shown in FIG. 8, 0034A displayed a 40% HCT increase and 0034B, displayed a 25% HCT increase, compared to the controls. On study day 29, ligand inducer was removed and all groups received normal chow. Importantly, hematocrit levels decreased into the normal range by two weeks after removal of the activator ligand. Ligand-containing chow was reintroduced on day 50, again resulting in an increased HCT and removed again on day 64, resulting in a decrease in HCT.

These data demonstrate regulated HuEPO expression following a single IM administration of the AAV-huEPO vector that mediated physiological changes. In the presence of activator ligand, high levels of HuEPO were expressed with resulted in an increase in HCT. When activator ligand was removed, HCT fell within the normal range. HuEPO expression and subsequent HCT increases could be induced at least twice by introduction of the activator ligand.

EXAMPLE 5

Regulated Expression of HuEPO in C3H/H and Balb/c Mice

Figure 9:
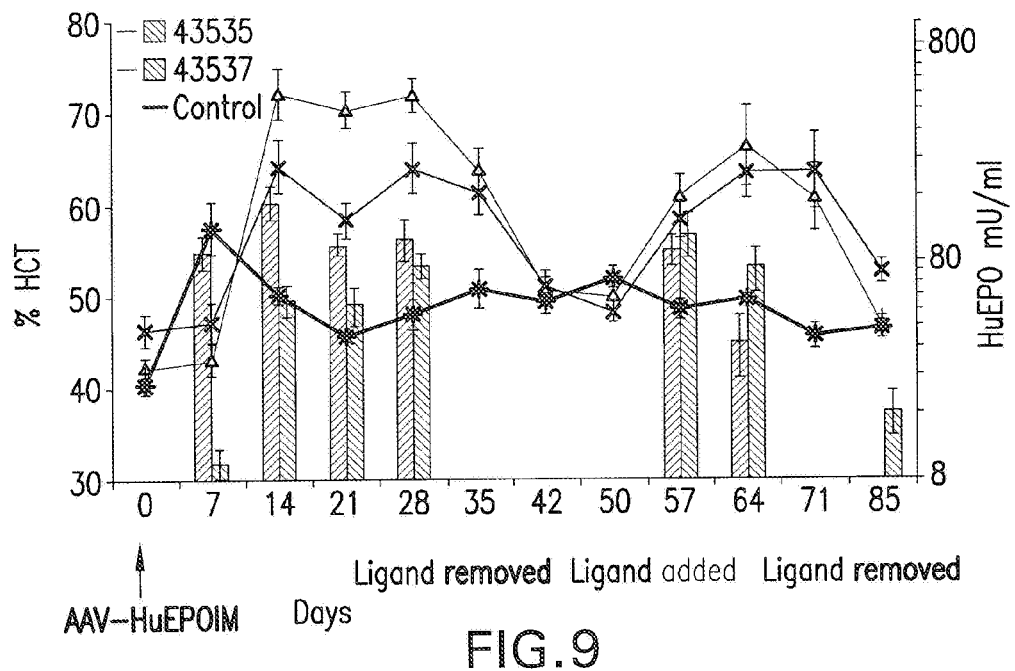
FIG. 9 is a combined line graph and bar graph that shows the effect of regulated expression of HuEPO on hematocrit in C3H/H mice.

The presence of HuEPO in the plasma of treated C3H/H mice was assessed by ELISA, HuEPO expression was detected with both AAV-huEPO vectors. As shown in FIG. 9, HuEPO expression levels were four times higher than the normal human physiological levels (normal human EPO levels are 4 to 24 mU/ml). Plasma HuEPO levels were ten times higher in animals treated with 0034A compared with animals that received the 0034B vector. No HuEPO expression was detected in the control animals. HuEPO expression levels peaked between day 7 and 14 and remained steady from day 14 to 28.

Importantly, HuEPO expression paralleled HCT increases and displayed an expected lag time between the induction of huEPO expression and measurable HCT changes (time necessary for the red blood cells to proliferate in response to EPO). Ligand was removed on day 29. No HuEPO was detected in the plasma at days 35, 42, and 50 (vector-treated and control). At Day 50, the relevant animals were put back on chow containing activator ligand. HuEPO expression again was detectable at levels similar to what was observed in the first induction cycle. Ligand was removed on day 64. HuEPO expression was not detectable on day 71, and was not detectable with the 0034A vector at day 85. Low levels of HuEPO expression were detected with the 0034B vector at day 85.

Figure 10:
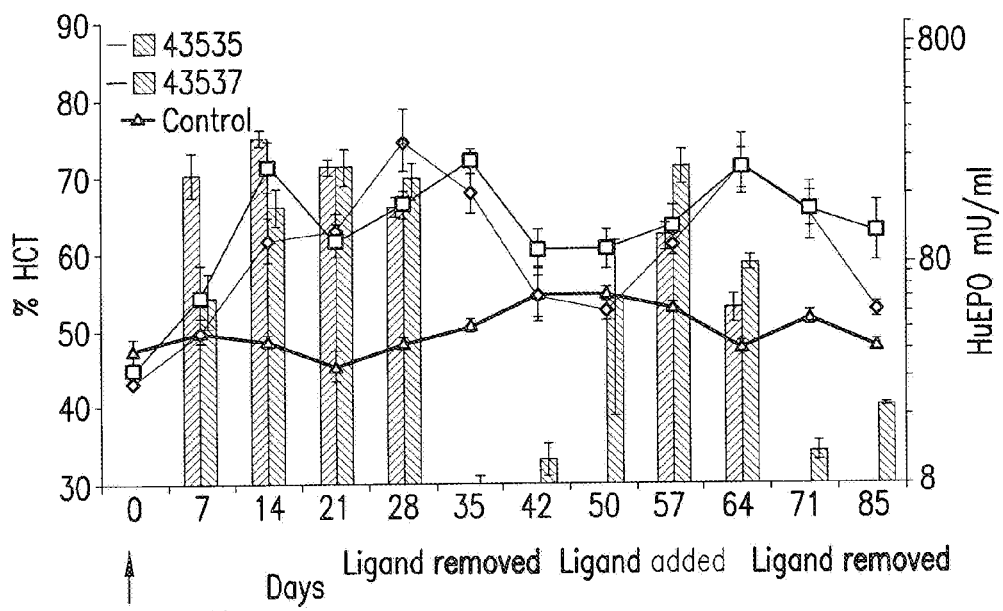
FIG. 10 is a combined line graph and bar graph that shows the effect of regulated expression of HuEPO on hematocrit in Balb/c mice.

An identical study to that displayed in FIG. 9 was performed in parallel using normal Balb/c mice (FIG. 10).

EXAMPLE 6

Regulated Expression of HuEPO Following a Single IM Injection of AAV-HuEPO

Figure 11:
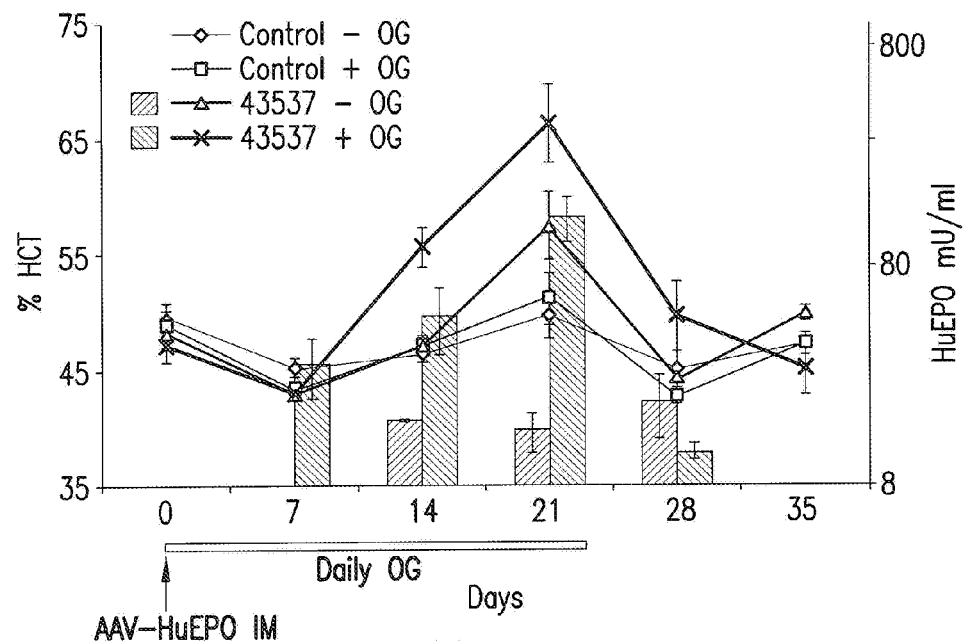
FIG. 11 is a combined line graph and bar graph that shows the effect of regulated expression of HuEPO on hematocrit following a single IM injection of AAV-HuEPO.

Animals were dosed via IM injection of $10^{11}$ vp of AAV-HuEPO (0034B) on day 0. Ligand was delivered on a daily basis during the first 21 days of the study via oral gavage (OG). The presence of HuEPO in the plasma of the treated mice was assessed by ELISA and HuEPO expression paralleled HCT changes. As shown in FIG. 11, HCT levels and HuEPO expression peaked on day 21. Ligand delivery was stopped on day 21 and huEPO expression and HCT displayed a sharp decrease when activator ligand was not present. HuEPO ELISA data for the day 35 samples were not yet available when FIG. 11 was prepared.

Figures 12A, 12B:
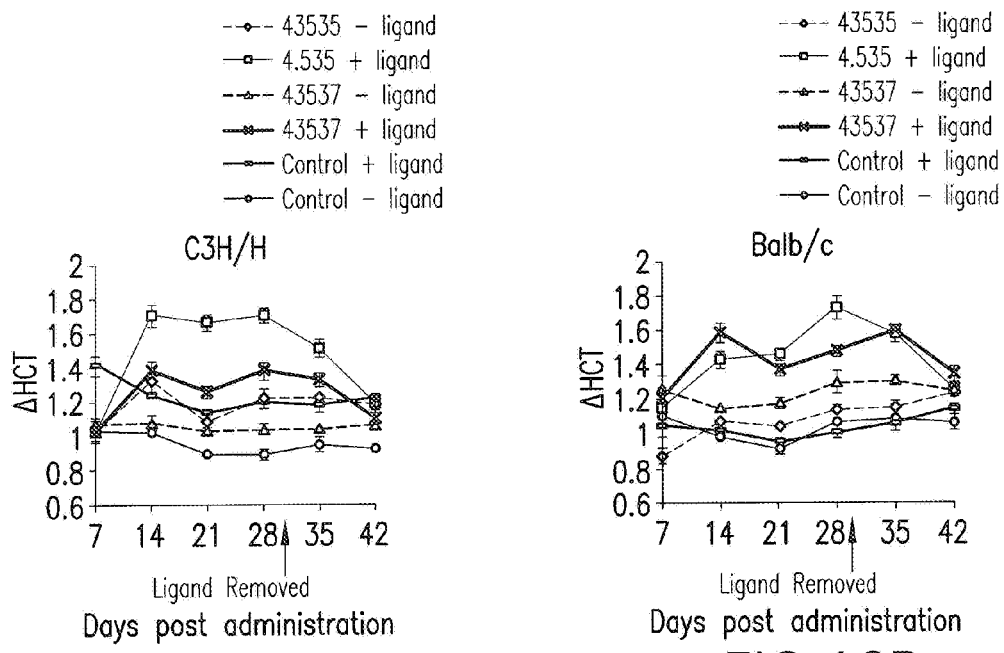
FIGS. 12A and 12B are line graphs that show the absolute changes in hematocrit following IM delivery of AAV-HuEPO.

HCTs were compared to the baseline (time 0, pre-bleed) for each animal and group averaged for each time point. As shown in FIGS. 12A and 12B, an up to 1.7 time increase in HCT at 14 days with 0034A in C3H/H mice and 28 days in Balb/c mice. HCT levels increased up to 1.4 times following administration with 0034B in C3H/H and up to 1.6 times in Balb/c mice. HCT decreased to within the normal range following ligand inducer removal.

EXAMPLE 7

Regulated Expression of HuEPO by Activator Ligand Dose

Animals were bled for baseline HCT levels, followed by IM administration of $10^{11}$ AAV-HuEPO viral genomes per animal (0034A). Animals received activator ligand-containing chow, with activator ligand concentrations 1000 mg/kg (18-1000), 250 mg/kg (18-250), 100 mg/kg (18-100), 50 mg/kg (18-50), or 0 mg/kg (18-0) starting on the day of AAV administration. Control animals received either vector administration and normal chow (no activator ligand, 18-0), or they received vehicle-alone IM administration (saline) with (18-1000) or without (18-0) activator ligand. HCT and HuEPO expression levels were measured in all groups every 7 days.

Figure 13:
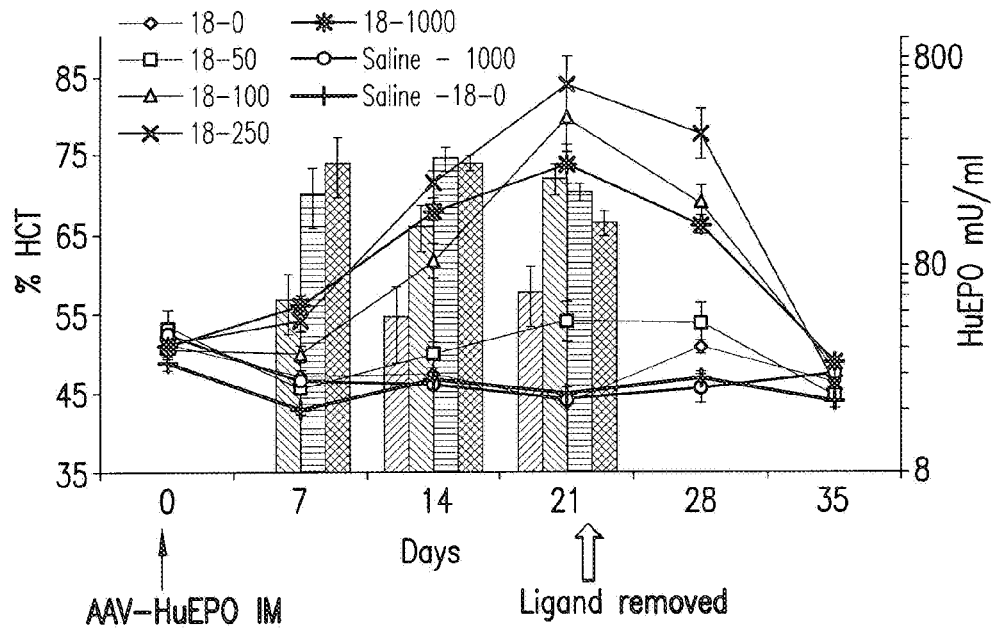
FIG. 13 is a combined line graph and bar graph that shows the effect of regulated expression of HuEPO on hematocrit as a function of activator ligand dose.

As shown in FIG. 13, no HuEPO was detected in the baseline, prebleed samples. HuEPO expression was detected on day 7 to 21. At the lowest concentration of activator ligand (18-50) HuEPO expression was not detected above the limit of sensitivity of the assay (8 mU/ml) at 7 days, but was detectable at 14 and 21 days, albeit at lower levels than animals that received the higher activator ligand doses. HuEPO reached a similar peak expression level in cohorts that received the two highest concentrations of activator ligand (18-1000 and 18-250). HuEPO levels in the plasma of animals that were on the intermediate concentration of activator ligand (18-100) displayed lower HuEPO expression at 7 days which reached to similar levels as the 18-1000 and 18-250 animals at days 14 and 21. HCT changes paralleled HuEPO expression levels. Following ligand removal on day 21 HCT levels decreased to with the normal range.

These data demonstrate regulated HuEPO expression following a single intramuscular administration of AAV vector. Importantly, HuEPO expression levels were regulated by activator ligand dose. These data suggest that HuEPO expression may be maintained within the normal physiological range by titration of the activator ligand concentration, and has clinical application.

EXAMPLE 8

Regulated Expression of HuEPO Following a Single IM Injection of AAV-HuEPO

A total of 25¾-nephrectornized C3H/H mice were obtained from Taconic. Animals were bled for baseline HuEPO levels and HCT. The indicated cohorts received RG-115932 activator ligand in the chow (18-1000, 1000 mg/kg chow) for the duration of the study. On day 0, RTS-HuEPO plasmid DNA (0034D) was administered through open muscle IM injection with electroporation (EP) one hour following pretreatment with Hyase (50 U rHUPH20 from Halozyme). The animal cohorts included 1) HuEPO DNA+EP+Hyase+ligand, 2) HuEPO DNA+EP+Hyase without ligand, 3) HuEPO DNA+EP, no Hyase, +ligand, 4) Saline+EP+Hyase, +ligand, and 5) animals treated with IP injections of recombinant human EPO protein twice per week.

Figure 14:
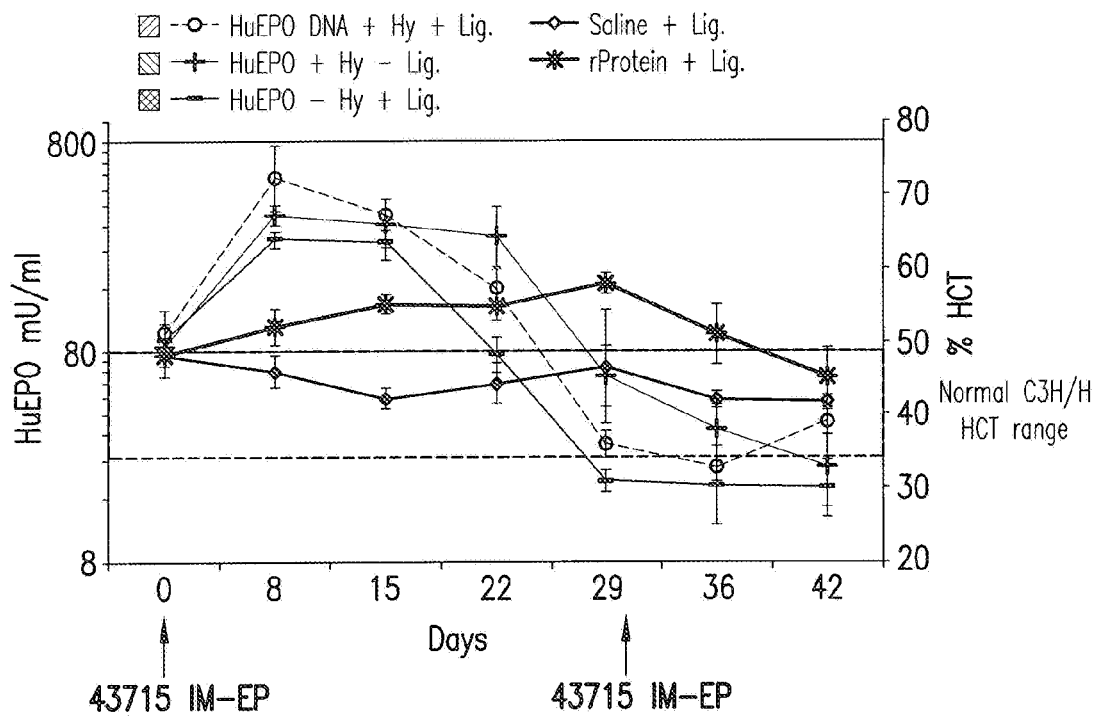
FIG. 14 is a combined line graph and bar graph that shows the effect of the expression of HuEPO in ¾ nephrectomized C3H/H mice results on hematocrit.

As shown in FIG. 14, high HuEPO expression was detected in the plasma on day 8 and decreased to a lower normal range on day 22. HCT changes paralleled HuEPO levels in the plasma. HCT changes were not detected in the plasma following re-administration of the vector on day 30.

HuEPO plasmid DNA (0034C, RTS-hEpo-IRES-fLuc) was delivered to Balb/c mice (quadriceps, 200 ug of DNA per animal), followed by electroporation. Animals were also treated one hour prior to DNA delivery and electroporation with hyaluronidase (50 U rHUPH20 from Halozyme), or saline alone. All animals received activator ligand via chow for the duration of this study.

Figure 15:
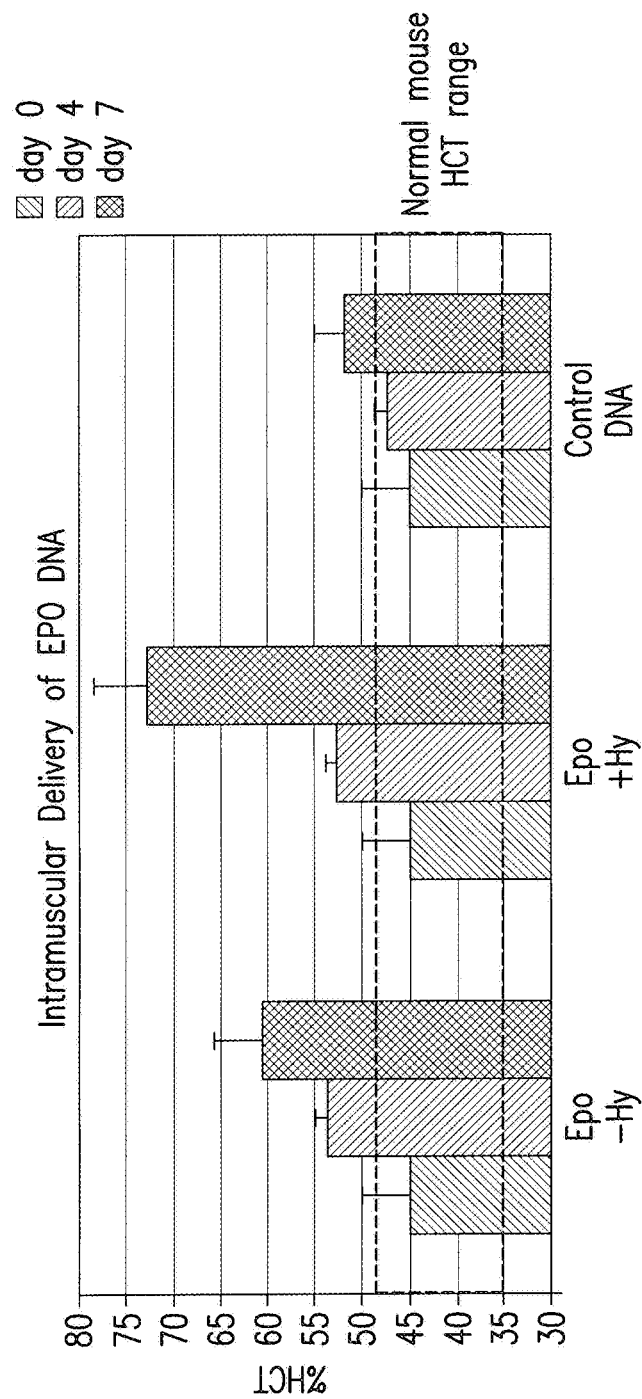
FIG. 15 is a bar graph that shows the effect of the expression of IM delivery of RTS-HuEPO to Balb/c mice on hematocrit.

HCTs were measured in mice prior to DNA delivery and at Day 4 and Day 7 after delivery. As shown in FIG. 15, a 40% increase in HCT at 7 days was detected in animals that received the huEPO plasmid plus hyaluronidase pretreatment, while animals that received huEPO without hyaluronidase pretreatment displayed a 25% increase in HCT at 7 days.

It is to be understood that the foregoing described embodiments and exemplifications are not intended to be limiting in any respect to the scope of the invention, and that the claims presented herein are intended to encompass all embodiments and exemplifications whether or not explicitly presented herein.

LITERATURE

Abdalla, 2007.

What is claimed is:

1. A method of inducing, regulating, or enhancing erythropoietin (EPO) expression in a mammal, wherein the method comprises
   (a) administering an adeno-associated virus to the mammal, wherein the virus comprises a polynucleotide encoding EPO; and
   (b) administering an activator ligand which induces EPO expression from the virus polynucleotide encoding EPO,
   wherein the adeno-associated virus is administered intramuscularly,
   wherein the adeno-associated virus further comprises an ecdysone receptor (EcR)-based gene switch, wherein the gene switch comprises at least one transcription factor sequence operably linked to a first promoter, wherein at least one transcription factor encoded by the at least one transcription factor sequence is a ligand-dependent transcription factor,
   wherein the adeno-associated virus further comprises a second promoter operably linked to the polynucleotide encoding EPO, wherein the second promoter is activated by the at least one ligand-dependent transcription factor following administration of activator ligand,
   wherein EPO expression is increased in the mammal, and
   wherein the hematocrit or volume percentage of red blood cells in blood is increased in the mammal by at least 25%, compared with the hematocrit or volume percentage of red blood cells prior to administration of ligand.

2. The method of claim 1, wherein the mammal is human.

3. The method of claim 1, wherein activator ligand is administered in a dose or doses sufficient to induce or maintain EPO expression levels within a normal physiologic range.

4. The method of claim 1, wherein the polynucleotide encoding EPO comprises an amino acid sequence at least 90% identical to SEQ ID NO: 6.

5. The method of claim 1, wherein the polynucleotide encoding EPO comprises an amino acid sequence at least 95% identical to SEQ ID NO 6.

6. The method of claim 1, wherein the polynucleotide encoding EPO comprises an amino acid sequence at least 90% identical to SEQ ID NO: 8.

7. The method of claim 1, wherein the polynucleotide encoding EPO comprises an amino acid sequence at least 95% identical to SEQ ID NO: 8.

8. The method of claim 1, wherein the hematocrit or volume percentage of red blood cells in blood is increased in the mammal by at least 40%, compared with the hematocrit or volume percentage of red blood cells prior to administration of ligand.

9. The method of claim 1, wherein the second promoter is a constitutive promoter.

10. The method of claim 1, wherein the second promoter is a cytomegalovirus (CMV) promoter.

11. The method of claim 1, wherein the second promoter is an elongation factor 1 alpha (EF1) promoter.

12. The method of claim 1, wherein the gene switch is the RheoSwitch® gene switch.

13. The method of claim 1, wherein the ligand is a diacylhydrazine ligand.

14. The method of claim 1, wherein the ligand is selected from the group consisting of RG-115819, RG-115932 and RG-115830.

15. The method of claim 1, wherein the ligand is RG-11593.

16. The method of claim 1, wherein the ligand is administered at a dose of about 1 to about 50 mg/kg/day.

17. The method of claim 16, wherein the ligand is administered at a dose of about 30 mg/kg/day.

18. The method of claim 1, wherein about $1.0 \times 10^9$ to about $1 \times 10^{13}$ viral particles are administered to the mammal per cycle of vector administration.

19. The method of claim 18, wherein about $1.0 \times 10^{11}$ viral particles are administered to the mammal per cycle of vector administration.

20. The method of claim 1, wherein the adeno-associated virus is administered following a pre-administration of hyaluronidase.

21. The method of claim 1, wherein the polynucleotide encoding a gene switch comprises a first transcription factor sequence under the control of a first therapeutic switch promoter and a second transcription factor sequence under the control of a second therapeutic switch promoter, wherein the proteins encoded by the first transcription factor sequence and the second transcription factor sequence interact to form a protein complex which functions as a ligand-dependent transcription factor.

22. The method of claim 21, wherein the first transcription factor sequence comprises a nucleic acid encoding for a VP-16 transactivation domain and a retinoic X receptor (RXR) protein.

23. The method of claim 22, wherein the second transcription factor sequence comprises a nucleic acid encoding for a GAL-4 DNA binding domain and Ecdysone receptor (EcR) protein.

24. The method of claim 21, wherein the first transcription factor sequence comprises a nucleic acid encoding for a fusion protein comprising the transcription activation domain of HSV-VP 16 and a chimeric RXR derived from human sequence and a locust migration ultraspiracle polypeptide (Lm USP).

25. The method of claim 24, wherein the second transcription factor sequence comprises a nucleic acid encoding for a fusion protein comprising the DNA binding domain of yeast Gal4 and the DEF domains of the mutagenized ecdysone receptor from the insect *Choristoneura fumiferana*.

26. The method of claim 21, wherein the both the first therapeutic switch promoter and the second therapeutic switch promoter are constitutive promoters.

27. The method of claim 21, wherein the first therapeutic switch promoter is a CMV promoter.

28. The method of claim 21, wherein the second therapeutic switch promoter is an EF1 promoter.

* * * * *

```
                              SEQUENCE LISTING

<160> NUMBER OF SEQ ID NOS: 22

<210> SEQ ID NO 1
  <211> LENGTH: 17
  <212> TYPE: PRT
  <213> ORGANISM: Drosophila melanogaster

<400> SEQUENCE: 1

Arg Arg Gly Gly Thr Thr Cys Ala Asn Thr Gly Ala Cys Ala Cys Tyr
  1               5                   10                  15

Tyr

<210> SEQ ID NO 2
  <211> LENGTH: 13
  <212> TYPE: DNA
  <213> ORGANISM: Drosophila melanogaster
  <220> FEATURE:
  <221> NAME/KEY: misc_feature
  <222> LOCATION: (7)..(7)
  <223> OTHER INFORMATION: n is a, c, g, or t

<400> SEQUENCE: 2
aggtcanagg tca                                                          13

<210> SEQ ID NO 3
  <211> LENGTH: 15
  <212> TYPE: DNA
  <213> ORGANISM: Drosophila melanogaster

<400> SEQUENCE: 3
gggttgaatg aattt                                                        15

<210> SEQ ID NO 4
  <211> LENGTH: 37323
  <212> TYPE: DNA
  <213> ORGANISM: Artificial Sequence
  <220> FEATURE:
  <223> OTHER INFORMATION: Synthetic Ad-RTS-hIL-12 (SP1-RheoIL-12)

<400> SEQUENCE: 4
catcatcaat aatatacctt attttggatt gaagccaata tgataatgag ggggtggagt        60
ttgtgacgtg gcgcggggcg tgggaacggg gcgggtgacg tagtagtgtg gcggaagtgt       120
gatgttgcaa gtgtggcgga acacatgtaa gcgacggatg tggcaaaagt gacgttttg        180 gtgtgcgccg gtgtacacag gaagtgacaa ttttcgcgcg gttttaggcg gatgttgtag       240
taaatttggg cgtaaccgag taagatttgg ccattttcgc gggaaaactg aataagagga       300
agtgaaatct gaataatttt gtgttactca tagcgcgtaa tatttgtcta gggagatccg       360
gtaccggcgc gcgcgccgtt tggccgcctc gagtctagag atccggtgag tattaggcgc       420
gcaccaggtg ccgcaataaa atatctttat tttcattaca tctgtgtgtt ggttttttgt       480
gtgaatcgat agtactaaca tacgctctcc atcaaaacaa aacgaaacaa aacaaactag       540
caaaataggc tgtccccagt gcaagtgcag gtgccagaac atttctctat cgataatgca       600
```

-continued

```
ggtcggagta ctgtcctccg agcggagtac tgtcctccga gcggagtact gtcctccgag      660
cggagtactg tcctccgagc ggagtactgt cctccgagcg gagtactgtc ctccgagcgg      720
agactcttcg aaggaagagg ggcggggtcg atcgaccccg cccctcttcc ttcgaaggaa      780
gaggggcggg gtcgaagacc tagagggtat ataatgggtg ccttagctgg tgtgtgagct      840
catcttcctg tagatcacgc gtgccaccat gggtcaccag cagttggtca tctcttggtt      900
ttccctggtt tttctggcat ctcccctcgt ggccatatgg gaactgaaga aagatgttta      960
tgtcgtagaa ttggattggt atccggatgc ccctggagaa atggtggtcc tcacctgtga     1020
cacccctgaa gaagatggta tcacctggac cttggaccag agcagtgagg tcttaggctc     1080
tggcaaaacc ctgaccatcc aagtcaaaga gtttggagat gctggccagt acacctgtca     1140
caaaggaggc gaggttctaa gccattcgct cctgctgctt cacaaaaagg aagatggaat     1200
ttggtccact gatattttaa aggaccagaa agaacccaaa aataagacct ttctaagatg     1260
cgaggccaag aattattctg gacgtttcac ctgctggtgg ctgacgacaa tcagtactga     1320
tttgacattc agtgtcaaaa gcagcagagg ctcttctgac ccccaagggg tgacgtgcgg     1380
agctgctaca ctctctgcag agagtcag aggggacaac aaggagtatg agtactcagt      1440
ggagtgccag gaggacagtg cctgcccagc tgctgaggag agtctgccca ttgaggtcat     1500
ggtggatgcc gttcacaagc tcaagtatga aaactacacc agcagcttct tcatcaggga     1560
catcatcaaa cctgacccac ccaagaactt gcagctgaag ccattaaaga attctcggca     1620
ggtggaggtc agctgggagt accctgacac ctggagtact ccacattcct acttctccct     1680
gacattctgc gttcaggtcc agggcaagag caagagagaa aagaaagata gagtcttcac     1740
ggacaagacc tcagccacgg tcatctgccg caaaaatgcc agcattagcg tgcgggccca     1800
ggaccgctac tatagctcat cttggagcga atgggcatct gtgccctgca gttaggttgg     1860
gcgagctcga attcattgat cccccgggct gcaggaattc gatatcaagc tcgggatccg     1920
aattccgccc ccccccccccc cccccccta acgttactgg ccgaagccgc ttggaataag     1980
gccggtgtgc gtttgtctat atgttatttt ccaccatatt gccgtctttt ggcaatgtga     2040
gggcccggaa acctggccct gtcttcttga cgagcattcc taggggtctt tcccctctcg     2100
ccaaaggaat gcaaggtctg ttgaatgtcg tgaaggaagc agttcctctg gaagcttctt     2160
gaagacaaac aacgtctgta gcgaccctt gcaggcagcg gaacccccca cctggcgaca     2220
ggtgcctctg cggccaaaag ccacgtgtat aagatacacc tgcaaaggcg gcacaacccc     2280
agtgccacgt tgtgagttgg atagttgtgg aaagagtcaa atggctctcc tcaagcgtat     2340
tcaacaaggg gctgaaggat gcccagaagg taccccattg tatgggatct gatctggggc     2400
ctcggtgcac atgctttaca tgtgtttagt cgaggttaaa aaaacgtcta ggccccccga     2460
accacgggga cgtggttttc ctttgaaaaa cacgatgata atatggccac aaccatgggt     2520
ccagcgcgca gcctcctcct tgtggctacc ctggtcctcc tggaccacct cagtttggcc     2580
agaaacctcc ccgtggccac tccagaccca ggaatgttcc catgccttca ccactcccaa     2640
aacctgctga gggccgtcag caacatgctc cagaaggcca gacaaactct agaattttac     2700
ccttgcactt ctgaagagat tgatcatgaa gatatcacaa aagataaaac cagcacagtg     2760
gaggcctgtt taccattgga attaaccaag aatgagagtt gcctaaattc cagagagacc     2820
tctttcataa ctaatgggag ttgcctggcc tccagaaaga cctcttttat gatggcctg     2880 tgccttagta gtatttatga agacttgaag atgtaccagg tggagttcaa gaccatgaat     2940
gcaaagcttc tgatggatcc taagaggcag atctttctag atcaaaacat gctggcagtt     3000
```

-continued

```
attgatgagc tgatgcaggc cctgaatttc aacagtgaga ctgtgccaca aaaatcctcc    3060
cttgaagaac cggattttta taaaactaaa atcaagctct gcatacttct tcatgctttc    3120
agaattcggg cagtgactat tgatagagtg atgagctatc tgaatgcttc ctaacgtacg    3180
tcgacatcga gaacttgttt attgcagctt ataatggtta caaataaagc aatagcatca    3240
caaatttcac aaataaagca ttttttttcac tgcattctag ttgtggtttg tccaaactca    3300
tcaatgtatc ttatcatgtc tgggcgcgcc ggcctccgcg ccgggttttg gcgcctcccg    3360
cgggcgcccc cctcctcacg gcgagcgctg ccacgtcaga cgaagggcgc agcgagcgtc    3420
ctgatccttc cgcccggacg ctcaggacag cggcccgctg ctcataagac tcggccttag    3480
aaccccagta tcagcagaag gacattttag gacgggactt gggtgactct agggcactgg    3540
ttttctttcc agagagcgga acaggcgagg aaaagtagtc ccttctcggc gattctgcgg    3600
agggatctcc gtggggcggt gaacgccgat gattatataa ggacgcgccg ggtgtggcac    3660
agctagttcc gtcgcagccg ggatttgggt cgcggttctt gtttgtggat cgctgtgatc    3720
gtcacttggt gagtagcggg ctgctgggct gggtacgtgc gctcggggtt ggcgagtgtg    3780
ttttgtgaag ttttttaggc accttttgaa atgtaatcat ttgggtcaat atgtaatttt    3840
cagtgttaga ctagtaaatt gtccgctaaa ttctggccgt ttttggcttt tttgttagac    3900
gagctagcgc cgccaccatg ggccctaaaa agaagcgtaa agtcgccccc cgaccgatg    3960
tcagcctggg ggacgagctc cacttagacg gcgaggacgt ggcgatggcg catgccgacg    4020
cgctagacga tttcgatctg gacatgttgg gggacgggga ttccccgggt ccgggattta    4080
ccccccacga ctccgccccc tacggcgctc tggatatggc cgacttcgag tttgagcaga    4140
tgtttaccga tgcccttgga attgacgagt acggtgggga attcgagatg cctgtggaca    4200
ggatcctgga ggcagagctt gctgtggaac agaagagtga ccagggcgtt gagggtcctg    4260
ggggaaccgg gggtagcggc agcagcccaa atgaccctgt gactaacatc tgtcaggcag    4320
ctgacaaaca gctattcacg cttgttgagt gggcgaagag gatcccacac ttttcctcct    4380
tgcctctgga tgatcaggtc atattgctgc gggcaggctg gaatgaactc ctcattgcct    4440
cctttttcaca ccgatccatt gatgttcgag atggcatcct ccttgccaca ggtcttcacg    4500
tgcaccgcaa ctcagcccat tcagcaggag taggagccat cttttgatcgg gtgctgacag    4560
agctagtgtc caaaatgcgt gacatgagga tggacaagac agagcttggc tgcctgaggg    4620
caatcattct gtttaatcca gaggtgaggg gtttgaaatc cgcccaggaa gttgaacttc    4680
tacgtgaaaa agtatatgcc gctttggaag aatatactag aacaacacat cccgatgaac    4740
caggaagatt tgcaaaactt ttgcttcgtc tgccttcttt acgttccata ggccttaagt    4800
gtttggagca tttgttttttc tttcgcctta ttggagatgt tccaattgat acgttcctga    4860
tggagatgct tgaatcacct tctgattcat aatctagcct agcccccctc tcctcccccc    4920
cccctaacg ttactggccg aagccgcttg gaataaggcc ggtgtgcgtt tgtctatatg    4980
ttattttcca ccatattgcc gtcttttggc aatgtgaggg cccggaaacc tggccctgtc    5040
ttcttgacga gcattcctag gggtctttcc cctctcgcca aggaatgca aggtctgttg    5100
aatgtcgtga aggaagcagt tcctctggaa gcttcttgaa gacaaacaac gtctgtagcg    5160
acccttttgca ggcagcggaa ccccccacct ggcgacaggt gcctctgcgg ccaaaagcca    5220
cgtgtataag atacacctgc aaaggcggca acccccagt gccacgttgt gagttggata    5280
gttgtggaaa gagtcaaatg gctctcctca agcgtattca acaaggggct gaaggatgcc    5340
```

| | |
|---|---|
| cagaaggtac cccattgtat gggatctgat ctggggcctc ggtgcacatg ctttacatgt | 5400 |
| gtttagtcga ggttaaaaaa cgtctaggcc ccccgaacca cggggacgtg gttttccttt | 5460 |
| gaaaaacacg atctctaggc gccaccatga agctactgtc ttctatcgaa caagcatgcg | 5520 |
| atatttgccg acttaaaaag ctcaagtgct ccaaagaaaa accgaagtgc gccaagtgtc | 5580 |
| tgaagaacaa ctgggagtgt cgctactctc ccaaaaccaa aaggtctccg ctgactaggg | 5640 |
| cacatctgac agaagtggaa tcaaggctag aaagactgga acagctattt ctactgattt | 5700 |
| ttcctcgaga agaccttgac atgattttga aaatggattc tttacaggat ataaaagcat | 5760 |
| tgttaacagg attatttgta caagataatg tgaataaaga tgccgtcaca gatagattgg | 5820 |
| cttcagtgga gactgatatg cctctaacat tgagacagca tagaataagt gcgacatcat | 5880 |
| catcggaaga gagtagtaac aaaggtcaaa gacagttgac tgtatcgccg gaattcccgg | 5940 |
| ggatccggcc tgagtgcgta gtacccgaga ctcagtgcgc catgaagcgg aaagagaaga | 6000 |
| aagcacagaa ggagaaggac aaactgcctg tcagcacgac gacggtggac gaccacatgc | 6060 |
| cgcccattat gcagtgtgaa cctccacctc ctgaagcagc aaggattcac gaagtggtcc | 6120 |
| caaggtttct ctccgacaag ctgttggtga caaaccggca gaaaaacatc ccccagttga | 6180 |
| cagccaacca gcagttcctt atcgccaggc tcatctggta ccaggacggg tacgagcagc | 6240 |
| cttctgatga agatttgaag aggattacgc agacgtggca gcaagcggac gatgaaaacg | 6300 |
| aagagtcgga cactcccttc cgccagatca cagagatgac tatcctcacg gtccaactta | 6360 |
| tcgtggagtt cgcgaaggga ttgccagggt cgccaagat ctcgcagcct gatcaaatta | 6420 |
| cgctgcttaa ggcttgctca agtgaggtaa tgatgctccg agtcgcgcga cgatacgatg | 6480 |
| cggcctcaga cagtattctg ttcgcgaaca accaagcgta cactcgcgac aactaccgca | 6540 |
| aggctggcat ggccgaggtc atcgaggatc tactgcactt ctgccggtgc atgtactcta | 6600 |
| tggcgttgga caacatccat tacgcgctgc tcacggctgt cgtcatcttt tctgaccggc | 6660 |
| cagggttgga gcagccgcaa ctggtggaag agatccagcg gtactacctg aatacgctcc | 6720 |
| gcatctatat cctgaaccag ctgagcgggt cggcgcgttc gtccgtcata tacggcaaga | 6780 |
| tcctctcaat cctctctgag ctacgcacgc tcggcatgca aaactccaac atgtgcatct | 6840 |
| ccctcaagct caagaacaga aagctgccgc cttttcctcga ggagatctgg gatgtggcgg | 6900 |
| acatgtcgca cacccaaccg ccgcctatcc tcgagtcccc cacgaatctc taggcggcct | 6960 |
| ctagagcggc cgccaccgcg gggagatcca gacatgataa gatacattga tgagtttgga | 7020 |
| caaaccacaa ctagaatgca gtgaaaaaaa tgctttattt gtgaaatttg tgatgctatt | 7080 |
| gctttatttg taaccattat aagctgcaat aaacaagtta acaacaacaa ttgcattcat | 7140 |
| tttatgtttc aggttcaggg ggaggtgtgg gaggtttttt aaagcaagta aaacctctac | 7200 |
| aaatgtggta tggctgatta tgatccggct gcctcgcgcg tttcggtgat gacggtgaaa | 7260 |
| acctctgaca catgcagctc ccggagacgg tcacagcttg tctgtaagcg gatgccggga | 7320 |
| gcagacaagc ccgtcagggc gcgtcagcgg gtgttggcgg gtgtcggggc gcagccatga | 7380 |
| ggtcgactct agtccccgcg gtggcagatc tggaaggtgc tgaggtacga tgagacccgc | 7440 |
| accaggtgca gaccctgcga gtgtggcggt aaacatatta ggaaccagcc tgtgatgctg | 7500 |
| gatgtgaccg aggagctgag gcccgatcac ttggtgctgg cctgcacccg cgctgagttt | 7560 |
| ggctctagcg atgaagatac agattgaggt actgaaatgt gtgggcgtgg cttaagggtg | 7620 |
| ggaaagaata tataaggtgg gggtcttatg tagttttgta tctgttttgc agcagccgcc | 7680 |
| gccgccatga gcaccaactc gtttgatgga agcattgtga gctcatattt gacaacgcgc | 7740 |

```
atgcccccat gggccggggt gcgtcagaat gtgatgggct ccagcattga tggtcgcccc   7800
gtcctgcccg caaactctac taccttgacc tacgagaccg tgtctggaac gccgttggag   7860
actgcagcct ccgccgccgc ttcagccgct gcagccaccg cccgcgggat tgtgactgac   7920
tttgctttcc tgagcccgct tgcaagcagt gcagcttccc gttcatccgc ccgcgatgac   7980
aagttgacgg ctcttttggc acaattggat tctttgaccc gggaacttaa tgtcgtttct   8040
cagcagctgt tggatctgcg ccagcaggtt tctgccctga aggcttcctc ccctcccaat   8100
gcggtttaaa acataaataa aaaaccagac tctgtttgga tttggatcaa gcaagtgtct   8160
tgctgtcttt atttaggggt tttgcgcgcg cggtaggccc gggaccagcg gtctcggtcg   8220
ttgagggtcc tgtgtatttt ttccaggacg tggtaaaggt gactctggat gttcagatac   8280
atgggcataa gcccgtctct ggggtggagg tagcaccact gcagagcttc atgctgcggg   8340
gtggtgttgt agatgatcca gtcgtagcag gagcgctggg cgtggtgcct aaaaatgtct   8400
ttcagtagca agctgattgc caggggcagg cccttggtgt aagtgtttac aaagcggtta   8460
agctgggatg ggtgcatacg tggggatatg agatgcatct tggactgtat ttttaggttg   8520
gctatgttcc cagccatatc cctccgggga ttcatgttgt gcagaaccac cagcacagtg   8580
tatccggtgc acttgggaaa tttgtcatgt agcttagaag gaaatgcgtg gaagaacttg   8640
gagacgccct tgtgacctcc aagatttttcc atgcattcgt ccataatgat ggcaatgggc   8700
ccacgggcgg cggcctgggc gaagatattt ctgggatcac taacgtcata gttgtgttcc   8760
aggatgagat cgtcataggc catttttaca aagcgcgggc ggagggtgcc agactgcggt   8820
ataatggttc catccggccc aggggcgtag ttaccctcac agatttgcat ttcccacgct   8880
ttgagttcag atgggggat catgtctacc tgcgggcga tgaagaaaac ggtttccggg   8940
gtaggggaga tcagctggga agaaagcagg ttcctgagca gctgcgactt accgcagccg   9000
gtgggcccgt aaatcacacc tattaccggc tgcaactggt agttaagaga gctgcagctg   9060
ccgtcatccc tgagcagggg ggccacttcg ttaagcatgt ccctgactcg catgttttcc   9120
ctgaccaaat ccgccagaag gcgctcgccg cccagcgata gcagttcttg caaggaagca   9180 aagttttttca acggtttgag accgtccgcc gtaggcatgc ttttgagcgt ttgaccaagc   9240
agttccaggc ggtcccacag ctcggtcacc tgctctacgg catctcgatc cagcatatct   9300 cctcgttttcg cggttggggg cggctttcgc tgtacgcag tagtcggtgc tcgtccagac   9360
gggccagggt catgtctttc cacgggcgca gggtcctcgt cagcgtagtc tgggtcacgg   9420
tgaaggggtg cgctccgggc tgcgcgctgg ccagggtgcg cttgaggctg gtcctgctgg   9480
tgctgaagcg ctgccggtct tcgccctgcg cgtcggccag gtagcatttg accatggtgt   9540
catagtccag cccctccgcg gcgtggccct tggcgcgcag cttgcccttg gaggaggcgc   9600
cgcacgaggg gcagtgcaga cttttgaggg cgtagagctt gggcgcgaga ataccgatt   9660 ccggggagta ggcatccgcg ccgcaggccc cgcagacggt ctcgcattcc acgagccagg   9720
tgagctctgg ccgttcgggg tcaaaaacca ggtttccccc atgcttttttg atgcgtttct   9780 tacctctggt ttccatgagc cggtgtccac gctcggtgac gaaaaggctg tccgtgtccc   9840
cgtatacaga cttgagaggc ctgtcctcga gcggtgttcc gcggtcctcc tcgtatagaa   9900
actcggacca ctctgagaca aaggctcgcg tccaggccag cacgaaggag gctaagtggg   9960
aggggtagcg gtcgttgtcc actaggggggt ccactcgctc cagggtgtga agacacatgt   10020
cgccctcttc ggcatcaagg aaggtgattg gtttgtaggt gtaggccacg tgaccgggtg   10080
```

```
ttcctgaagg ggggctataa aagggggtgg gggcgcgttc gtcctcactc tcttccgcat   10140
cgctgtctgc gagggccagc tgttggggtg agtactccct ctgaaaagcg ggcatgactt   10200
ctgcgctaag attgtcagtt tccaaaaacg aggaggattt gatattcacc tggcccgcgg   10260
tgatgccttt gagggtggcc gcatccatct ggtcagaaaa gacaatcttt ttgttgtcaa   10320
gcttggtggc aaacgacccg tagagggcgt tggacagcaa cttggcgatg gagcgcaggg   10380
tttggttttt gtcgcgatcg gcgcgctcct tggccgcgat gtttagctgc acgtattcgc   10440
gcgcaacgca ccgccattcg ggaaagacgg tggtgcgctc gtcgggcacc aggtgcacgc   10500
gccaaccgcg gttgtgcagg gtgacaaggt caacgctggt ggctacctct ccgcgtaggc   10560
gctcgttggt ccagcagagg cggccgccct tgcgcgagca gaatggcggt aggggggtcta  10620 gctgcgtctc gtccgggggg tctgcgtcca cggtaaagac cccgggcagc aggcgcgcgt   10680
cgaagtagtc tatcttgcat ccttgcaagt ctagcgcctg ctgccatgcg cgggcggcaa   10740
gcgcgcgctc gtatgggttg agtggggggac cccatggcat ggggtggggtg agcgcggagg  10800 cgtacatgcc gcaaatgtcg taaacgtaga ggggctctct gagtattcca agatatgtag   10860
ggtagcatct tccaccgcgg atgctggcgc gcacgtaatc gtatagttcg tgcgagggag   10920
cgaggaggtc gggaccgagg ttgctacggg cgggctgctc tgctcggaag actatctgcc   10980
tgaagatggc atgtgagttg gatgatatgg ttggacgctg gaagacgttg aagctggcgt   11040
ctgtgagacc taccgcgtca cgcacgaagg aggcgtagga gtcgcgcagc ttgttgacca   11100
gctcggcggt gacctgcacg tctagggcgc agtagtccag ggtttccttg atgatgtcat   11160
acttatcctg tccctttttt ttccacagct cgcggttgag gacaaactct tcgcggtctt   11220
tccagtactc ttggatcgga aacccgtcgg cctccgaacg gtaagagcct agcatgtaga   11280
actggttgac ggcctggtag gcgcagcatc ccttttctac gggtagcgcg tatgcctgcg   11340
cggccttccg gagcgaggtg tgggtgagcg caaaggtgtc cctgaccatg actttgaggt   11400 actggtatt gaagtcagtg tcgtcgcatc cgccctgctc ccagagcaaa aagtccgtgc   11460
gctttttgga acgcggattt ggcagggcga aggtgacatc gttgaagagt atctttcccg   11520
cgcgaggcat aaagttgcgt gtgatgcgga agggtcccgg cacctcggaa cggttgttaa   11580
ttacctgggc ggcgagcacg atctcgtcaa agccgttgat gttgtggccc acaatgtaaa   11640
gttccaagaa gcgcgggatg cccttgatgg aaggcaattt tttaagttcc tcgtaggtga   11700
gctcttcagg ggagctgagc ccgtgctctg aaagggccca gtctgcaaga tgagggttgg   11760
aagcgacgaa tgagctccac aggtcacggg ccattagcat ttgcaggtgg tcgcgaaagg   11820
tcctaaactg gcgacctatg gccattttt ctggggtgat gcagtagaag gtaagcgggt    11880
cttgttccca gcggtcccat ccaaggttcg cggctaggtc tcgcgcggca gtcactagag   11940
gctcatctcc gccgaacttc atgaccagca tgaagggcac gagctgcttc ccaaaggccc   12000
ccatccaagt ataggtctct acatcgtagg tgacaaagag acgctcggtg cgaggatgcg   12060
agccgatcgg gaagaactgg atctccccgcc accaattgga ggagtggcta ttgatgtggt   12120
gaaagtagaa gtccctgcga cgggccgaac actcgtgctg gcttttgtaa aaacgtgcgc   12180
agtactggca gcggtgcacg ggctgtacat cctgcacgag gttgacctga cgaccgcgca   12240
caaggaagca gagtgggaat tgagcccct cgcctggcgg gtttggctgg tggtcttcta    12300
cttcggctgc ttgtccttga ccgtctggct gctcgagggg agttacggtg gatcggacca   12360
ccacgccgcg cgagcccaaa gtccagatgt ccgcgcgcgg cggtcggagc ttgatgacaa   12420
catcgcgcag atgggagctg tccatggtct ggagctcccg cggcgtcagg tcaggcggga   12480
```

```
gctcctgcag gtttacctcg catagacggg tcagggcgcg ggctagatcc aggtgatacc    12540
taatttccag gggctggttg gtggcggcgt cgatggcttg caagaggccg catccccgcg    12600
gcgcgactac ggtaccgcgc ggcgggcggt gggccgcggg ggtgtccttg gatgatgcat    12660
ctaaaagcgg tgacgcgggc gagccccegg aggtagggggg ggctccggac ccgccgggag   12720 aggggggcagg ggcacgtcgg cgccgcgcgc gggcaggagc tggtgctgcg cgcgtaggtt   12780
gctggcgaac gcgacgacgc ggcggttgat ctcctgaatc tggcgcctct gcgtgaagac    12840
gacgggcccg gtgagcttga acctgaaaga gagttcgaca gaatcaattt cggtgtcgtt    12900
gacggcggcc tggcgcaaaa tctcctgcac gtctcctgag ttgtcttgat aggcgatctc    12960
ggccatgaac tgctcgatct cttcctcctg gagatctccg cgtccggctc gctccacggt    13020
ggcggcgagg tcgttggaaa tgcgggccat gagctgcgag aaggcgttga ggcctccctc    13080
gttccagacg cggctgtaga ccacgccccc ttcggcatcg cgggcgcgca tgaccacctg    13140
cgcgagattg agctccacgt gccgggcgaa gacggcgtag tttcgcaggc gctgaaagag    13200
gtagttgagg gtggtggcgg tgtgttctgc cacgaagaag tacataaccc agcgtcgcaa    13260
cgtggattcc ttgatatccc ccaaggcctc aaggcgctcc atggcctcgt agaagtccac    13320
ggcgaagttg aaaaactggg agttgcgcgc cgacacggtt aactcctcct ccagaagacg    13380
gatgagctcg gcgacagtgt cgcgcacctc gcgctcaaag gctacagggg cctcttcttc    13440
ttcttcaatc tcctcttcca taagggcctc cccttcttct tcttctggcg gcggtggggg    13500
aggggggaca cggcggcgac gacggcgcac cgggaggcgg tcgacaaagc gctcgatcat    13560
ctccccgcgg cgacggcgca tggtctcggt gacgcgcgcg ccgttctcgc gggggcgcag    13620
ttggaagacg ccgcccgtca tgtcccggtt atgggttggc gggggggctgc catgcggcag   13680 ggatacggcg ctaacgatgc atctcaacaa ttgttgtgta ggtactccgc cgccgaggga    13740
cctgagcgag tccgcatcga ccggatcgga aaacctctcg agaaaggcgt ctaaccagtc    13800
acagtcgcaa ggtaggctga gcaccgtggc gggcggcagc gggcggcggt cggggttgtt    13860
tctggcggag gtgctgctga tgatgtaatt aaagtaggcg tcttgagac ggcggatggt     13920 cgacagaagc accatgtcct tgggtccggc ctgctgaatg cgcaggcggt cggccatgcc    13980
ccaggcttcg ttttgacatc ggcgcaggtc tttgtagtag tcttgcatga gccttctac    14040 cggcacttct tcttctcctt cctcttgtcc tgcatctctt gcatctatcg ctgcggcggc    14100
ggcggagttt ggccgtaggt ggcgccctct tcctcccatg cgtgtgaccc cgaagcccct    14160
catcggctga agcagggcta ggtcggcgac aacgcgctcg gctaatatgg cctgctgcac    14220
ctgcgtgagg gtagactgga agtcatccat gtccacaaag cggtggtatg cgcccgtgtt    14280
gatggtgtaa gtgcagttgg ccataacgga ccagttaacg gtctggtgac ccggctgcga    14340
gagctcggtg tacctgagac gcgagtaagc cctcgagtca aatacgtagt cgttgcaagt    14400
ccgcaccagg tactggtatc ccaccaaaaa gtgcggcggc ggctggcggt agaggggcca    14460
gcgtagggtg gccggggctc cggggggcgag atcttccaac ataaggcgat gatatccgta   14520
gatgtacctg gacatccagg tgatgccggc ggcggtggtg gaggcgcgcg gaaagtcgcg    14580
gacgcggttc cagatgttgc gcagcggcaa aaagtgctcc atggtcggga cgctctggcc    14640
ggtcaggcgc gcgcaatcgt tgacgctcta gcgtgcaaaa ggagagcctg taagcgggca    14700
ctcttccgtg gtctggtgga taaattcgca agggtatcat ggcggacgac cggggttcga    14760
gccccgtatc cggccgtccg ccgtgatcca tgcggttacc gcccgcgtgt cgaacccagg    14820
```

```
tgtgcgacgt cagacaacgg gggagtgctc cttttggctt ccttccaggc gcggcggctg   14880
ctgcgctagc ttttttggcc actggccgcg cgcagcgtaa gcggttaggc tggaaagcga   14940
aagcattaag tggctcgctc cctgtagccg gagggttatt ttccaagggt tgagtcgcgg   15000 gaccccggt tcgagtctcg gaccggccgg actgcggcga acgggggttt gcctccccgt    15060
catgcaagac cccgcttgca aattcctccg gaaacaggga cgagcccctt ttttgctttt   15120
cccagatgca tccggtgctg cggcagatgc gccccctcc tcagcagcgg caagagcaag    15180
agcagcggca gacatgcagg gcaccctccc ctcctcctac cgcgtcagga ggggcgacat   15240
ccgcggttga cgcggcagca gatggtgatt acgaacccccc gcggcgccgg gcccggcact  15300
acctggactt ggaggagggc gagggcctgg cgcggctagg agcgccctct cctgagcggc   15360
acccaagggt gcagctgaag cgtgatacgc gtgaggcgta cgtgccgcgg cagaacctgt   15420
ttcgcgaccg cgagggagag gagcccgagg agatgcggga tcgaaagttc cacgcagggc   15480
gcgagctgcg gcatggcctg aatcgcgagc ggttgctgcg cgaggaggac tttgagcccg   15540
acgcgcgaac cgggattagt cccgcgcgcg cacacgtggc ggccgccgac ctggtaaccg    15600
catacgagca gacggtgaac caggagatta actttcaaaa aagctttaac aaccacgtgc    15660
gtacgcttgt ggcgcgcgag gaggtggcta taggactgat gcatctgtgg gactttgtaa   15720
gcgcgctgga gcaaaaccca aatagcaagc cgctcatggc gcagctgttc cttatagtgc   15780
agcacagcag ggacaacgag gcattcaggg atgcgctgct aaacatagta gagcccgagg   15840
gccgctggct gctcgatttg ataaacatcc tgcagagcat agtggtgcag gagcgcagct   15900
tgagcctggc tgacaaggtg gccgccatca actattccat gcttagcctg ggcaagtttt    15960
acgcccgcaa gatataccat accccttacg ttcccataga caaggaggta agatcgagg    16020 ggttctacat gcgcatggcg ctgaaggtgc ttaccttgag cgacgacctg ggcgtttatc    16080
gcaacgagcg catccacaag gccgtgagcg tgagccggcg gcgcgagctc agcgaccgcg   16140
agctgatgca cagcctgcaa agggccctgg ctggcacggg cagcggcgat agagaggcc    16200 agtcctactt tgacgcgggc gctgacctgc gctgggcccc aagccgacgc gccctggagg   16260
cagctggggc cggacctggg ctggcggtgg caccgcgcg cgctggcaac gtcggcggcg    16320
tggaggaata tgacgaggac gatgagtacg agccagagga cggcgagtac taagcggtga   16380
tgtttctgat cagatgatgc aagacgcaac ggacccggcg gtgcgggcgg cgctgcagag   16440
ccagccgtcc ggccttaact ccacggacga ctggcgccag gtcatggacc gcatcatgtc    16500
gctgactgcg cgcaatcctg acgcgttccg gcagcagccg caggccaacc ggctctccgc    16560
aattctggaa gcggtggtcc cggcgcgcgc aaaccccacg cacgagaagg tgctggcgat   16620
cgtaaacgcg ctggccgaaa acagggccat ccggcccgac gaggccggcc tggtctacga   16680
cgcgctgctt cagcgcgtgg ctcgttacaa cagcggcaac gtgcagacca acctggaccg   16740
gctggtgggg gatgtgcgcg aggccgtggc gcagcgtgag cgcgcgcagc agcagggcaa   16800
cctgggctcc atggttgcac taaacgcctt cctgagtaca cagcccgcca acgtgccgcg   16860
gggacaggag gactacacca actttgtgag cgcactgcgg ctaatggtga ctgagacacc   16920
gcaaagtgag gtgtaccagt ctgggccaga ctattttttc cagaccagta gacaaggcct   16980
gcagaccgta aacctgagcc aggctttcaa aaacttgcag gggctgtggg gggtgcgggc   17040
tcccacaggc gaccgcgcga ccgtgtctag cttgctgacg cccaactcgc gcctgttgct    17100
gctgctaata gcgcccttca cggacagtgg cagcgtgtcc cggacacat acctaggtca    17160 cttgctgaca ctgtaccgcg aggccatagg tcaggcgcat gtggacgagc atactttcca    17220
```

```
ggagattaca agtgtcagcc gcgcgctggg gcaggaggac acgggcagcc tggaggcaac   17280
cctaaactac ctgctgacca accggcggca gaagatcccc tcgttgcaca gtttaaacag   17340
cgaggaggag cgcattttgc gctacgtgca gcagagcgtg agccttaacc tgatgcgcga   17400
cggggtaacg cccagcgtgg cgctggacat gaccgcgcgc aacatggaac cgggcatgta   17460
tgcctcaaac cggccgttta tcaaccgcct aatggactac ttgcatcgcg cggccgccgt   17520
gaaccccgag tatttcacca atgccatctt gaacccgcac tggctaccgc ccctggttt   17580 ctacaccggg ggattcgagg tgcccgaggg taacgatgga ttcctctggg acgacataga   17640
cgacagcgtg ttttccccgc aaccgcagac cctgctagag ttgcaacagc gcgagcaggc   17700
agaggcggcg ctgcgaaagg aaagcttccg caggccaagc agcttgtccg atctaggcgc   17760
tgcggccccg cggtcagatg ctagtagccc atttccaagc ttgatagggt ctcttaccag   17820
cactcgcacc acccgcccgc gcctgctggg cgaggaggag tacctaaaca actcgctgct   17880
gcagccgcag cgcgaaaaaa acctgcctcc ggcatttccc aacaacggga tagagagcct   17940
agtggacaag atgagtagat ggaagacgta cgcgcaggag cacagggacg tgccaggccc   18000
gcgcccgccc acccgtcgtc aaaggcacga ccgtcagcgg ggtctggtgt gggaggacga   18060
tgactcggca gacgacagca gcgtcctgga tttgggaggg agtggcaacc cgtttgcgca   18120
ccttcgcccc aggctgggga gaatgtttta aaaaaaaaaa aagcatgatg caaaataaaa   18180
aactcaccaa ggccatggca ccgagcgttg gttttcttgt attcccctta gtatgcggcg   18240
cgcggcgatg tatgaggaag gtcctcctcc ctcctacgag agtgtggtga gcgcggcgcc   18300
agtggcggcg gcgctgggtt ctcccttcga tgctcccctg gacccgccgt tgtgcctcc   18360 gcggtacctg cggcctaccg gggggagaaa cagcatccgt tactctgagt tggcacccct   18420
attcgacacc acccgtgtgt acctggtgga caacaagtca acggatgtgg catccctgaa   18480
ctaccagaac gaccacagca actttctgac cacggtcatt caaaacaatg actacagccc   18540
gggggaggca agcacacaga ccatcaatct tgacgaccgg tcgcactggg gcggcgacct   18600
gaaaaccatc ctgcatacca acatgccaaa tgtgaacgag ttcatgttta ccaataagtt   18660
taaggcgcgg gtgatggtgt cgcgcttgcc tactaaggac aatcaggtgg agctgaaata   18720
cgagtgggtg gagttcacgc tgcccgaggg caactactcc gagaccatga ccatagacct   18780
tatgaacaac gcgatcgtgg agcactactt gaaagtgggc agacagaacg gggttctgga   18840
aagcgacatc ggggtaaagt ttgacacccg caacttcaga ctgggggttg accccgtcac   18900
tggtcttgtc atgcctgggg tatatacaaa cgaagccttc catccagaca tcattttgct   18960
gccaggatgc ggggtggact tcacccacag ccgcctgagc aacttgttgg catccgcaa   19020 gcggcaaccc ttccaggagg gctttaggat cacctacgat gatctggagg gtggtaacat   19080
tcccgcactg ttggatgtgg acgcctacca ggcgagcttg aaagatgaca ccgaacaggg   19140 cggggggtggc gcaggcggca gcaacagcag tggcagcggc gcggaagaga actccaacgc   19200
ggcagccgcg gcaatgcagc cggtggagga catgaacgat catgccattc gcggcgacac   19260
ctttgccaca cgggctgagg agaagcgcgc tgaggccgaa gcagcggccg aagctgccgc   19320
ccccgctgcg caacccgagg tcgagaagcc tcagaagaaa ccggtgatca aacccctgac   19380
agaggacagc aagaaacgca gttacaacct aataagcaat gacagcacct tcacccagta   19440
ccgcagctgt tacccttgca tacaactacg cgaccctcag accggaatcc gctcatggac   19500
cctgctttgc actcctgacg taacctgcgg ctcggagcag gtctactggt cgttgccaga   19560
```

```
catgatgcaa gaccccgtga ccttccgctc cacgcgccag atcagcaact ttccggtggt    19620
gggcgccgag ctgttgcccg tgcactccaa gagcttctac aacgaccagg ccgtctactc    19680
ccaactcatc cgccagttta cctctctgac ccacgtgttc aatcgctttc ccgagaacca    19740
gattttggcg cgcccgccag cccccaccat caccaccgtc agtgaaaacg ttcctgctct    19800
cacagatcac gggacgctac cgctgcgcaa cagcatcgga ggagtccagc gagtgaccat    19860
tactgacgcc agacgccgca cctgccccta cgtttacaag gccctgggca tagtctcgcc    19920
gcgcgtccta tcgagccgca cttttgagc aagcatgtcc atccttatat cgcccagcaa    19980
taacacaggc tggggcctgc gcttcccaag caagatgttt ggcggggcca agaagcgctc    20040
cgaccaacac ccagtgcgcg tgcgcgggca ctaccgcgcg ccctgggcg cgcacaaacg    20100 cggccgcact gggcgcacca ccgtcgatga cgccatcgac gcggtggtgg aggaggcgcg    20160
caactacacg cccacgccgc caccagtgtc cacagtggac gcggccattc agaccgtggt    20220
gcgcggagcc cggcgctatg ctaaaatgaa gagacggcgg aggcgcgtag cacgtcgcca    20280
ccgccgccga cccggcactg ccgcccaacg cgcggcgggcg ccctgcttaa ccgcgcacg    20340 tcgcaccggc cgacgggcgg ccatgcgggc cgctcgaagg ctggccgcgg gtattgtcac    20400
tgtgcccccc aggtccaggc gacgagcggc cgccgcagca gccgcggcca ttagtgctat    20460
gactcagggt cgcaggggca acgtgtattg ggtgcgcgac tcggttagcg gcctgcgcgt    20520
gcccgtgcgc acccgccccc cgcgcaacta gattgcaaga aaaaactact tagactcgta    20580
ctgttgtatg tatccagcgg cggcggcgcg caacgaagct atgtccaagc gcaaaatcaa    20640
agaagagatg ctccaggtca tcgcgccgga gatctatggc cccccgaaga aggaagagca    20700
ggattacaag ccccgaaagc taaagcgggt caaaagaaa aagaaagatg atgatgatga    20760
acttgacgac gaggtggaac tgctgcacgc taccgcgccc aggcgacggg tacagtggaa    20820
aggtcgacgc gtaaaacgtg ttttgcgacc cggcaccacc gtagtcttta cgcccggtga    20880
gcgctccacc cgcacctaca agcgcgtgta tgatgaggtg tacggcgacg aggacctgct    20940
tgagcaggcc aacgagcgcc tcggggagtt tgcctacgga aagcggcata aggacatgct    21000
ggcgttgccg ctggacgagg gcaacccaac acctagccta aagcccgtaa cactgcagca    21060
ggtgctgccc gcgcttgcac cgtccgaaga aaagcgcggc ctaaagcgcg agtctggtga    21120
cttggcaccc accgtgcagc tgatggtacc caagcgccag cgactggaag atgtcttgga    21180
aaaaatgacc gtggaacctg gctggagcc cgaggtccgc gtgcggccaa tcaagcaggt    21240
ggcgccggga ctgggcgtgc agaccgtgga cgttcagata cccactacca gtagcaccag    21300
tattgccacc gccacagagg gcatggagac acaaacgtcc ccggttgcct cagcggtggc    21360
ggatgccgcg gtgcaggcgg tcgctgcggc gcgtccaag acctctacgg aggtgcaaac    21420
ggacccgtgg atgtttcgcg tttcagcccc ccggcgcccg cgccgttcga ggaagtacgg    21480
cgccgccagc gcgctactgc ccgaatatgc cctacatcct tccattgcgc ctaccccgg    21540 ctatcgtggc tacacctacc gccccagaag acgagcaact acccgacgcc gaaccaccac    21600
tggaacccgc cgccgccgtc gccgtcgcca gccgtgctg gccccgattt ccgtgcgcag    21660
ggtggctcgc gaaggaggca ggaccctggt gctgccaaca gcgcgctacc accccagcat    21720
cgtttaaaag ccggtctttg tggttcttgc agatatggcc ctcacctgcc gcctccgttt    21780
cccggtgccg ggattccgag gaagaatgca ccgtaggagg ggcatggccg ccacggcct    21840 gacgggcggc atgcgtcgtg cgcaccaccg gcggcggcgc gcgtcgcacc gtcgcatgcg    21900
cggcggtatc ctgcccctcc ttattccact gatcgccgcg gcgattggcg ccgtgcccgg    21960
```

```
aattgcatcc gtggccttgc aggcgcagag acactgatta aaaacaagtt gcatgtggaa    22020
aaatcaaaat aaaaagtctg gactctcacg ctcgcttggt cctgtaacta ttttgtagaa    22080
tggaagacat caactttgcg tctctggccc cgcgacacgg ctcgcgcccg ttcatgggaa    22140
actggcaaga tatcggcacc agcaatatga gcggtggcgc cttcagctgg ggctcgctgt    22200
ggagcggcat taaaaatttc ggttccaccg ttaagaacta tggcagcaag gcctggaaca    22260
gcagcacagg ccagatgctg agggataagt tgaaagagca aaatttccaa caaaggtgg     22320 tagatggcct ggcctctggc attagcgggg tggtggacct ggccaaccag gcagtgcaaa    22380
ataagattaa cagtaagctt gatccccgcc ctcccgtaga ggagcctcca ccggccgtgg    22440
agacagtgtc tccagagggg cgtggcgaaa gcgtccgcg  ccccgacagg gaagaaactc    22500
tggtgacgca aatagacgag cctccctcgt acgaggaggc actaaagcaa ggcctgccca    22560
ccacccgtcc catcgcgccc atggctaccg gagtgctggg ccagcacaca cccgtaacgc    22620
tggacctgcc tccccccgcc gacacccagc agaaacctgt gctgccaggc ccgaccgccg    22680
ttgttgtaac ccgtcctagc cgcgcgtccc tgcgccgcgc cgccagcggt ccgcgatcgt    22740
tgcggcccgt agccagtggc aactggcaaa gcacactgaa cagcatcgtg ggtctggggg    22800
tgcaatccct gaagcgccga cgatgcttct gatagctaac gtgtcgtatg tgtgtcatgt    22860
atgcgtccat gtcgccgcca gaggagctgc tgagccgccg cgcgcccgct ttccaagatg    22920
gctaccccct tcgatgatgcc gcagtggtct acatgcaca tctcgggcca ggacgcctcg    22980
gagtacctga gccccgggct ggtgcagttt gcccgcgcca ccgagacgta cttcagcctg    23040
aataacaagt ttagaaaccc cacggtggcg cctacgcacg acgtgaccac agaccggtcc    23100
cagcgtttga cgctgcggtt catccctgtg gaccgtgagg atactgcgta ctcgtacaag    23160
gcgcggttca ccctagctgt gggtgataac cgtgtgctgg acatggcttc cacgtacttt    23220
gacatccgcg gcgtgctgga caggggcccct acttttaagc cctactctgg cactgcctac    23280
aacgccctgg ctcccaaggg tgccccaaat ccttgcgaat gggatgaagc tgctactgct    23340
cttgaaataa acctagaaga agaggacgat gacaacgaag acgaagtaga cgagcaagct    23400
gagcagcaaa aaactcacgt atttgggcag gcgccttatt ctggtataaa tattacaaag    23460
gagggtattc aaataggtgt cgaaggtcaa acacctaaat atgccgataa aacatttcaa    23520
cctgaacctc aaataggaga atctcagtgg tacgaaacag aaattaatca tgcagctggg    23580
agagtcctaa aaaagactac cccaatgaaa ccatgttacg gttcatatgc aaaacccaca    23640
aatgaaaatg gagggcaagg cattcttgta aagcaacaaa atgaaagct  agaaagtcaa    23700 gtggaaatgc aattttctc  aactactgag gcagccgcag gcaatggtga acttgact     23760 cctaaagtgg tattgtacag tgaagatgta gatatagaaa ccccagacac tcatatttct    23820
tacatgccca ctattaagga aggtaactca cgagaactaa tgggccaaca atctatgccc    23880
aacaggccta attacattgc ttttagggac aattttattg gtctaatgta ttacaacagc    23940
acgggtaata tgggtgttct ggcgggccaa gcatcgcagt tgaatgctgt tgtagatttg    24000
caagacagaa acacagagct ttcataccag cttttgcttg attccattgg tgatagaacc    24060
aggtactttt ctatgtggaa tcaggctgtt gacagctatg atccagatgt tagaattatt    24120
gaaaatcatg gaactgaaga tgaacttcca aattactgct ttccactggg aggtgtgatt    24180
aatacagaga ctcttaccaa ggtaaaacct aaaacaggtc aggaaaatgg atgggaaaaa    24240
gatgctacag aattttcaga taaaaatgaa ataagagttg gaaataattt tgccatggaa    24300
```

-continued

```
atcaatctaa atgccaacct gtggagaaat ttcctgtact ccaacatagc gctgtatttg  24360
cccgacaagc taaagtacag tccttccaac gtaaaaattt ctgataaccc aaacacctac  24420
gactacatga acaagcgagt ggtggctccc gggctagtgg actgctacat taaccttgga  24480
gcacgctggt cccttgacta tatggacaac gtcaacccat ttaaccacca ccgcaatgct  24540
ggcctgcgct accgctcaat gttgctgggc aatggtcgct atgtgccctt ccacatccag  24600
gtgcctcaga agttctttgc cattaaaaac ctccttctcc tgccgggctc atacacctac  24660
gagtggaact tcaggaagga tgttaacatg gttctgcaga gctccctagg aaatgaccta  24720
agggttgacg gagccagcat taagtttgat agcatttgcc tttacgccac cttcttcccc  24780
atggcccaca acaccgcctc cacgcttgag gccatgctta gaaacgacac caacgaccag  24840
tcctttaacg actatctctc cgccgccaac atgctctacc ctatacccgc caacgctacc  24900
aacgtgccca tatccatccc ctcccgcaac tgggcggctt ccgcggctg ggccttcacg  24960
cgccttaaga ctaaggaaac cccatcactg ggctcgggct acgaccctta ttacacctac  25020
tctggctcta taccctacct agatggaacc ttttacctca accacacctt taagaaggtg  25080
gccattacct ttgactcttc tgtcagctgg cctggcaatg accgcctgct tacccccaac  25140
gagtttgaaa ttaagcgctc agttgacggg gagggttaca acgttgccca gtgtaacatg  25200
accaaagact ggttcctggt acaaatgcta gctaactata acattggcta ccagggcttc  25260
tatatcccag agagctacaa ggaccgcatg tactccttct ttagaaactt ccagcccatg  25320
agccgtcagg tggtggatga tactaaatac aaggactacc aacaggtggg catcctacac  25380
caacacaaca actctggatt tgttggctac cttgccccca ccatgcgcga aggacaggcc  25440
taccctgcta acttccccta tccgcttata ggcaagaccg cagttgacag cattacccag  25500
aaaaagtttc tttgcgatcg caccctttgg cgcatcccat tctccagtaa ctttatgtcc  25560
atgggcgcac tcacagacct gggccaaaac cttctctacg ccaactccgc ccacgcgcta  25620
gacatgactt tgaggtgga tcccatggac gagcccaccc ttctttatgt tttgtttgaa  25680
gtctttgacg tggtccgtgt gcaccagccg caccgcggcg tcatcgaaac cgtgtacctg  25740
cgcacgccct tctcggccgg caacgccaca acataaagaa gcaagcaaca tcaacaacag  25800
ctgccgccat gggctccagt gagcaggaac tgaaagccat tgtcaaagat cttggttgtg  25860
ggccatattt tttgggcacc tatgacaagc gctttccagg cttgtgttct ccacacaagc  25920
tcgcctgcgc catagtcaat acggccggtc gcgagactgg gggcgtacac tggatggcct  25980
ttgcctggaa cccgcactca aaaacatgct acctctttga gcccttttggc ttttctgacc  26040
agcgactcaa gcaggtttac cagtttgagt acgagtcact cctgcgccgt agcgccattg  26100
cttcttcccc cgaccgctgt ataacgctgg aaaagtccac ccaaagcgta caggggccca  26160
actcggccgc ctgtggacta ttctgctgca tgtttctcca cgccttttgcc aactggcccc  26220
aaactcccat ggatcacaac cccaccatga accttattac cggggtaccc aactccatgc  26280
tcaacagtcc ccaggtacag cccaccctgc gtcgcaacca ggaacagctc tacagcttcc  26340
tggagcgcca ctcgccctac ttccgcagcc acagtgcgca gattaggagc gccacttctt  26400
tttgtcactt gaaaaacatg taaaaataat gtactagaga cactttcaat aaaggcaaat  26460
gcttttattt gtacactctc gggtgattat ttacccccac ccttgccgtc tgcgccgttt  26520
aaaaatcaaa ggggttctgc cgcgcatcgc tatgcgccac tggcagggac acgttgcgat  26580
actggtgttt agtgctccac ttaaactcag gcacaaccat ccgcggcagc tcggtgaagt  26640
tttcactcca caggctgcgc accatcacca acgcgtttag caggtcgggc gccgatatct  26700
```

```
tgaagtcgca gttggggcct ccgccctgcg cgcgcgagtt gcgatacaca gggttgcagc   26760
actggaacac tatcagcgcc gggtggtgca cgctggccag cacgctcttg tcggagatca   26820
gatccgcgtc caggtcctcc gcgttgctca gggcgaacgg agtcaacttt ggtagctgcc   26880
ttcccaaaaa gggcgcgtgc ccaggctttg agttgcactc gcaccgtagt ggcatcaaaa   26940
ggtgaccgtg cccggtctgg gcgttaggat acagcgcctg cataaaagcc ttgatctgct   27000
taaaagccac ctgagccttt cgccttcag agaagaacat gccgcaagac ttgccggaaa    27060
actgattggc cggacaggcc gcgtcgtgca cgcagcacct tgcgtcggtg ttggagatct   27120
gcaccacatt tcgccccac cggttcttca cgatcttggc cttgctagac tgctccttca    27180
gcgcgcgctg cccgttttcg ctcgtcacat ccatttcaat cacgtgctcc ttatttatca    27240
taatgcttcc gtgtagacac ttaagctcgc cttcgatctc agcgcagcgg tgcagccaca   27300
acgcgcagcc cgtgggctcg tgatgcttgt aggtcacctc tgcaaacgac tgcaggtacg   27360
cctgcaggaa tcgccccatc atcgtcacaa aggtcttgtt gctggtgaag gtcagctgca   27420
acccgcggtg ctcctcgttc agccaggtct tgcatacggc cgccagagct tccacttggt   27480
caggcagtag tttgaagttc gcctttagat cgttatccac gtggtacttg tccatcagcg   27540
cgcgcgcagc ctccatgccc ttctcccacg cagacacgat cggcacactc agcgggttca   27600
tcaccgtaat ttcactttcc gcttcgctgg gctcttcctc ttcctcttgc gtccgcatac    27660
cacgcgccac tgggtcgtct tcattcagcc gccgcactgt gcgcttacct cctttgccat   27720
gcttgattag caccggtggg ttgctgaaac ccaccatttg tagcgccaca tcttctcttt    27780
cttcctcgct gtccacgatt acctctggtg atggcgggcg ctcgggcttg ggagaagggc   27840
gcttcttttt cttcttgggc gcaatggcca aatccgccgc cgaggtcgat ggccgcgggc   27900
tgggtgtgcg cggcaccagc gcgtcttgtg atgagtcttc ctcgtcctcg gactcgatac   27960
gccgcctcat ccgcttttt gggcgcccc ggggaggcgg cggcgacggg gacggggacg      28020
acacgtcctc catggttggg ggacgtcgcg ccgcaccgcg tccgcgctcg ggggtggttt   28080
cgcgctgctc ctcttcccga ctggccattt ccttctccta taggcagaaa aagatcatgg   28140
agtcagtcga gaagaaggac agcctaaccg ccccctctga gttcgccacc accgcctcca   28200
ccgatgccgc caacgcgcct accaccttcc ccgtcgaggc accccgcttg gaggaggagg   28260
aagtgattat cgagcaggac ccaggttttg taagcgaaga cgacgaggac cgctcagtac   28320
caacagagga taaaaagcaa gaccaggaca acgcagaggc aaacgaggaa caagtcgggc   28380 gggggacga aggcatggc gactacctag atgtgggaga cgacgtgctg ttgaagcatc      28440
tgcagcgcca gtgcgccatt atctgcgacg cgttgcaaga gcgcagcgat gtgcccctcg   28500
ccatagcgga tgtcagcctt gcctacgaac gccacctatt ctcaccgcgc gtacccccca   28560
aacgccaaga aaacggcaca tgcgagccca acccgcgcct caacttctac cccgtatttg   28620
ccgtgccaga ggtgcttgcc acctatcaca tcttttttcca aaactgcaag ataccccctat   28680 cctgccgtgc caaccgcagc cgagcggaca agcagctggc cttgcggcag ggcgctgtca    28740
tacctgatat cgcctcgctc aacgaagtgc caaaaatctt tgagggtctt ggacgcgacg    28800
agaagcgcgc ggcaaacgct ctgcaacagg aaaacagcga aaatgaaagt cactctggag     28860
tgttggtgga actcgagggt gacaacgcgc gcctagccgt actaaaacgc agcatcgagg   28920
tcacccactt tgcctacccg gcacttaacc taccccccaa ggtcatgagc acagtcatga    28980
gtgagctgat cgtgcgccgt gcgcagcccc tggagaggga tgcaaatttg caagaacaaa   29040
```

```
cagaggaggg cctacccgca gttggcgacg agcagctagc gcgctggctt caaacgcgcg   29100
agcctgccga cttggaggag cgacgcaaac taatgatggc cgcagtgctc gttaccgtgg   29160
agcttgagtg catgcagcgg ttctttgctg acccggagat gcagcgcaag ctagaggaaa   29220
cattgcacta cacctttcga cagggctacg tacgccaggc ctgcaagatc tccaacgtgg   29280
agctctgcaa cctggtctcc taccttggaa ttttgcacga aaaccgcctt gggcaaaacg   29340
tgcttcattc cacgctcaag ggcgaggcgc gccgcgacta cgtccgcgac tgcgtttact   29400
tatttctatg ctacacctgg cagacggcca tgggcgtttg gcagcagtgc ttggaggagt   29460
gcaacctcaa ggagctgcag aaactgctaa agcaaaactt gaaggaccta tggacggcct   29520
tcaacgagcg ctccgtggcc gcgcacctgg cggacatcat tttccccgaa cgcctgctta   29580
aaaccctgca cagggtctg ccagacttca ccagtcaaag catgttgcag aactttagga   29640
actttatcct agagcgctca ggaatcttgc ccgccacctg ctgtgcactt cctagcgact   29700
ttgtgcccat taagtaccgc gaatgccctc cgccgctttg gggccactgc taccttctgc   29760
agctagccaa ctaccttgcc taccactctg acataatgga agacgtgagc ggtgacggtc   29820
tactggagtg tcactgtcgc tgcaacctat gcaccccgca ccgctccctg gtttgcaatt   29880
cgcagctgct taacgaaagt caaattatcg gtaccttga gctgcagggt ccctcgcctg   29940
acgaaaagtc cgcggctccg gggttgaaac tcactccggg gctgtggacg tcggcttacc   30000
ttcgcaaatt tgtacctgag gactaccacg cccacgagat taggttctac gaagaccaat   30060
cccgcccgcc taatgcggag cttaccgcct gcgtcattac ccagggccac attcttggcc   30120
aattgcaagc catcaacaaa gcccgccaag agtttctgct acgaaaggga cgggggggttt   30180 acttggaccc ccagtccggc gaggagctca acccaatccc ccgccgcccg cagccctatc   30240
agcagcagcc gcgggccctt gcttcccagg atggcaccca aaaagaagct gcagctgccg   30300
ccgccaccca cggacgagga ggaatactgg gacagtcagg cagaggaggt tttggacgag   30360
gaggaggagg acatgatgga agactgggag agcctagacg aggaagcttc cgaggtcgaa   30420
gaggtgtcag acgaaacacc gtcaccctcg gtcgcattcc cctcgccggc gccccagaaa   30480
tcggcaaccg gttccagcat ggctacaacc tccgctcctc aggcgccgcc ggcactgccc   30540
gttcgccgac ccaaccgtag atgggacacc actggaacca gggccggtaa gtccaagcag   30600
ccgccgccgt tagcccaaga gcaacaacag cgccaaggct accgctcatg gcgcgggcac   30660
aagaacgcca tagttgcttg cttgcaagac tgtgggggca acatctcctt cgcccgccgc   30720
tttcttctct accatcacgg cgtggccttc ccccgtaaca tcctgcatta ctaccgtcat   30780
ctctacagcc catactgcac cggcggcagc ggcagcaaca gcagcggcca cacagaagca   30840
aaggcgaccg gatagcaaga ctctgacaaa gcccaagaaa tccacagcgg cggcagcagc   30900
aggaggagga gcgctgcgtc tggcgcccaa cgaacccgta tcgacccgcg agcttagaaa   30960
caggattttt cccactctgt atgctatatt tcaacagagc aggggccaag aacaagagct   31020
gaaaataaaa aacaggtctc tgcgatccct caccccgcagc tgcctgtatc acaaaagcga   31080
agatcagctt cggcgcacgc tggaagacgc ggaggctctc ttcagtaaat actgcgcgct   31140
gactcttaag gactagtttc gcgccctttc tcaaatttaa gcgcgaaaac tacgtcatct   31200
ccagcggcca caccggcgc agcacctgt tgtcagcgcc attatgagca aggaaattcc   31260
cacgccctac atgtggagtt accagccaca aatgggactt gcggctggag ctgcccaaga   31320
ctactcaacc cgaataaact acatgagcgc gggaccccac atgatatccc gggtcaacgg   31380
aatacgcgcc caccgaaacc gaattctcct ggaacaggcg gctattacca ccacacctcg   31440
```

```
taataacctt aatccccgta gttggcccgc tgccctggtg taccaggaaa gtcccgctcc    31500
caccactgtg gtacttccca gagacgccca ggccgaagtt cagatgacta actcaggggc    31560
gcagcttgcg ggcggctttc gtcacagggt gcggtcgccc gggcagggta taactcacct    31620
gacaatcaga gggcgaggta ttcagctcaa cgacgagtcg gtgagctcct cgcttggtct    31680
ccgtccggac gggacatttc agatcggcgg cgccggccgc tcttcattca cgcctcgtca    31740
ggcaatccta actctgcaga cctcgtcctc tgagccgcgc tctggaggca ttggaactct    31800
gcaatttatt gaggagtttg tgccatcggt ctactttaac cccttctcgg gacctcccgg    31860
ccactatccg gatcaattta ttcctaactt tgacgcggta aaggactcgg cggacggcta    31920
cgactgaatg ttaagtggag aggcagagca actgcgcctg aaacacctgg tccactgtcg    31980
ccgccacaag tgctttgccc gcgactccgg tgagttttgc tactttgaat gcccgagga    32040 tcatatcgag ggcccggcgc acggcgtccg gcttaccgcc cagggagagc ttgcccgtag    32100
cctgattcgg gagtttaccc agcgccccct gctagttgag cgggacaggg gaccctgtgt    32160
tctcactgtg atttgcaact gtcctaaccc tggattacat caagatctta ttcccttta    32220 ctaataaaaa aaaataataa agcatcactt acttaaaatc agttagcaaa tttctgtcca    32280
gtttattcag cagcacctcc ttgccctcct cccagctctg gtattgcagc ttcctcctgg    32340
ctgcaaactt tctccacaat ctaaatggaa tgtcagtttc ctcctgttcc tgtccatccg    32400
cacccactat cttcatgttg ttgcagatga agcgcgcaag accgtctgaa gataccttca    32460
accccgtgta tccatatgac acggaaaccg gtcctccaac tgtgcctttt cttactcctc    32520
cctttgtatc ccccaatggg tttcaagaga gtcccctgg ggtactctct ttgcgcctat    32580
ccgaacctct agttacctcc aatggcatgc ttgcgctcaa aatgggcaac ggcctctctc    32640
tggacgaggc cggcaacctt acctcccaaa atgtaaccac tgtgagccca cctctcaaaa    32700
aaaccaagtc aaacataaac ctggaaatat ctgcacccct cacagttacc tcagaagccc    32760
taactgtggc tgccgccgca cctctaatgg tcgcgggcaa cacactcacc atgcaatcac    32820 aggcccgct aaccgtgcac gactccaaac ttagcattgc cacccaagga cccctcacag    32880
tgtcagaagg aaagctagcc ctgcaaacat caggcccct caccaccacc gatagcagta    32940
cccttactat cactgcctca cccctctaa ctactgccac tggtagcttg ggcattgact    33000
tgaaagagcc catttataca caaaatggaa aactaggact aaagtacggg gctccttgc    33060 atgtaacaga cgacctaaac actttgaccg tagcaactgg tccaggtgtg actattaata    33120
atacttcctt gcaaactaaa gttactggag ccttgggttt tgattcacaa ggcaatatgc    33180
aacttaatgt agcaggagga ctaaggattg attctcaaaa cagacgcctt atacttgatg    33240
ttagttatcc gtttgatgct caaaaccaac taaatctaag actaggacag ggccctcttt    33300
ttataaactc agcccacaac ttggatatta actacaacaa aggcctttac ttgtttacag    33360
cttcaaacaa ttccaaaaag cttgaggtta acctaagcac tgccaagggg ttgatgtttg    33420
acgctacagc catagccatt aatgcaggag atgggcttga atttggttca cctaatgcac    33480
caaacacaaa tccctcaaa acaaaaattg gccatggcct agaatttgat tcaaacaagg    33540
ctatggttcc taaactagga actggcctta gttttgacag cacaggtgcc attacagtag    33600
gaaacaaaaa taatgataag ctaactttgt ggaccacacc agctccatct cctaactgta    33660
gactaaatgc agagaaagat gctaaactca ctttggtctt aacaaaatgt ggcagtcaaa    33720
tacttgctac agtttcagtt ttggctgtta aaggcagttt ggctccaata tctggaacag    33780
```

-continued

```
ttcaaagtgc tcatcttatt ataagatttg acgaaaatgg agtgctacta aacaattcct   33840
tcctggaccc agaatattgg aactttagaa atggagatct tactgaaggc acagcctata   33900
caaacgctgt tggatttatg cctaacctat cagcttatcc aaaatctcac ggtaaaactg   33960
ccaaaagtaa cattgtcagt caagtttact taaacggaga caaaactaaa cctgtaacac   34020
taaccattac actaaacggt acacaggaaa caggagacac aactccaagt gcatactcta   34080
tgtcattttc atgggactgg tctgccaca actacattaa tgaaatattt gccacatcct    34140 cttacactt ttcatacatt gcccaagaat aaagaatcgt tgtgttatg tttcaacgtg      34200 tttattttc aattgcagaa aatttcaagt cattttcat tcagtagtat agccccacca     34260
ccacatagct tatacagatc accgtacctt aatcaaactc acagaaccct agtattcaac   34320
ctgccacctc cctcccaaca cacagagtac acagtccttt ctccccggct ggccttaaaa   34380
agcatcatat catgggtaac agacatattc ttaggtgtta tattccacac ggtttcctgt   34440
cgagccaaac gctcatcagt gatattaata aactccccgg gcagctcact taagttcatg   34500
tcgctgtcca gctgctgagc cacaggctgc tgtccaactt gcggttgctt aacgggcggc   34560
gaaggagaag tccacgccta catggggta gagtcataat cgtgcatcag gatagggcgg    34620
tggtgctgca gcagcgcgcg aataaactgc tgccgccgcc gctccgtcct gcaggaatac   34680
aacatggcag tggtctcctc agcgatgatt cgcaccgccc gcagcataag gcgccttgtc   34740
ctccgggcac agcagcgcac cctgatctca cttaaatcag cacagtaact gcagcacagc   34800
accacaatat tgttcaaaat cccacagtgc aaggcgctgt atccaaagct catggcgggg   34860
accacagaac ccacgtggcc atcataccac aagcgcaggt agattaagtg gcgacccctc   34920
ataaacacgc tggacataaa cattacctct tttggcatgt tgtaattcac cacctcccgg   34980
taccatataa acctctgatt aaacatggcg ccatccacca ccatcctaaa ccagctggcc   35040
aaaacctgcc cgccggctat acactgcagg gaaccgggac tggaacaatg acagtggaga   35100
gcccaggact cgtaaccatg gatcatcatg ctcgtcatga tatcaatgtt ggcacaacac   35160
aggcacacgt gcatacactt cctcaggatt acaagctcct cccgcgttag aaccatatcc   35220
cagggaacaa cccattcctg aatcagcgta aatcccacac tgcagggaag acctcgcacg   35280
taactcacgt tgtgcattgt caaagtgtta cattcgggca gcagcggatg atcctccagt   35340
atggtagcgc gggtttctgt ctcaaaagga ggtagacgat ccctactgta cggagtgcgc   35400
cgagacaacc gagatcgtgt tggtcgtagt gtcatgccaa atggaacgcc ggacgtagtc   35460
atatttcctg aagcaaaacc aggtgcgggc gtgacaaaca gatctgcgtc tccggtctcg   35520
ccgcttagat cgctctgtgt agtagttgta gtatatccac tctctcaaag catccaggcg   35580
ccccctggct tcgggttcta tgtaaactcc ttcatgcgcc gctgccctga taacatccac   35640
caccgcagaa taagccacac ccagccaacc tacacattcg ttctgcgagt cacacacggg   35700
aggagcggga agagctggaa gaaccatgtt ttttttttta ttccaaaaga ttatccaaaa   35760
cctcaaaatg aagatctatt aagtgaacgc gctcccctcc ggtggcgtgg tcaaactcta   35820
cagccaaaga acagataatg gcatttgtaa gatgttgcac aatggcttcc aaaaggcaaa   35880
cggccctcac gtccaagtgg acgtaaaggc taaaccttc agggtgaatc tcctctataa     35940
acattccagc accttcaacc atgcccaaat aattctcatc tcgccacctt ctcaatatat   36000
ctctaagcaa atcccgaata ttaagtccgg ccattgtaaa atctgctcc agagcgccct     36060 ccaccttcag cctcaagcag cgaatcatga ttgcaaaaat tcaggttcct cacagacctg   36120
tataagattc aaaagcggaa cattaacaaa aataccgcga tcccgtaggt cccttcgcag   36180
```

```
ggccagctga acataatcgt gcaggtctgc acggaccagc gcggccactt ccccgccagg    36240
aaccatgaca aaagaaccca cactgattat gacacgcata ctcggagcta tgctaaccag    36300
cgtagccccg atgtaagctt gttgcatggg cggcgatata aaatgcaagg tgctgctcaa    36360
aaaatcaggc aaagcctcgc gcaaaaaaga agcacatcg tagtcatgct catgcagata    36420
aaggcaggta agctccggaa ccaccacaga aaaagacacc attttctct caaacatgtc    36480 tgcgggtttc tgcataaaca caaataaaa taacaaaaaa acatttaaac attagaagcc    36540
tgtcttacaa caggaaaaac aacccttata agcataagac ggactacggc catgccggcg    36600
tgaccgtaaa aaaactggtc accgtgatta aaaagcacca ccgacagctc ctcggtcatg    36660
tccggagtca taatgtaaga ctcggtaaac acatcaggtt gattcacatc ggtcagtgct    36720
aaaaagcgac cgaaatagcc cggggaata catacccgca ggcgtagaga caacattaca    36780
gcccccatag gaggtataac aaaattaata ggagagaaaa acacataaac acctgaaaaa    36840
ccctcctgcc taggcaaaat agcaccctcc cgctccagaa caacatacag cgcttccaca    36900
gcggcagcca taacagtcag ccttaccagt aaaaagaaa acctattaaa aaaacaccac    36960
tcgacacggc accagctcaa tcagtcacag tgtaaaaaag gccaagtgc agagcgagta    37020 tatataggac taaaaaatga cgtaacggtt aaagtccaca aaaaacaccc agaaaccgc    37080 acgcgaacct acgcccagaa acgaaagcca aaaaacccac aacttcctca aatcgtcact    37140
tccgttttcc cacgttacgt cacttcccat tttaagaaaa ctacaattcc caacacatac    37200
aagttactcc gccctaaaac ctacgtcacc cgccccgttc ccacgcccg cgccacgtca    37260 caaactccac cccctcatta tcatattggc ttcaatccaa aataaggtat attattgatg    37320
atg                                                                 37323
```

<210> SEQ ID NO 5
<211> LENGTH: 12166
<212> TYPE: DNA
<213> ORGANISM: Artificial Sequence
<220> FEATURE:
<223> OTHER INFORMATION: Ad-RTS-mIL-12 is VVN2539

<400> SEQUENCE: 5

```
taaacaaata ggggttccgc gcacatttcc ccgaaaagtg ccacctgacg tctaagaaac      60
cattattatc atgacattaa cctataaaaa taggcgtatc acgaggccct ttcgtcttca    120
agaaaattaa ttaagctagc atcatcaata atataccttta ttttggattg aagccaatat    180
gataatgagg gggtggagtt tgtgacgtgg cgcggggcgt gggaacgggg cggtgacgt    240 agtagtgtgg cggaagtgtg atgttgcaag tgtggcggaa cacatgtaag cgacggatgt    300
ggcaaaagtg acgttttttgg tgtgcgccgg tgtacacagg aagtgacaat ttcgcgcgg    360 ttttaggcgg atgttgtagt aaatttgggc gtaaccgagt aagatttggc cattttcgcg    420
ggaaaactga ataagaggaa gtgaaatctg aataattttg tgttactcat agcgcgtaat    480
atttgtctag ggagatccgg taccggcgcg cgcgccgttt ggccgcctcg agtctagaga    540
tccggtgagt gattaggcgc gcaccaggtg ccgcaataaa atatctttat tttcattaca    600
tctgtgtgtt ggttttttgt gtgaatcgat agtactaaca tacgctctcc atcaaaacaa    660
aacgaaacaa aacaaactag caaaataggc tgtccccagt gcaagtgcag gtgccagaac    720
atttctctat cgataatgca ggtcggagta ctgtcctccg agcggagtac tgtcctccga    780
gcggagtact gtcctccgag cggagtactg tcctccgagc ggagtactgt cctccgagcg    840
```

```
gagtactgtc ctccgagcgg agactcttcg aaggaagagg ggcggggtcg atcgaccccg    900
cccctcttcc ttcgaaggaa gaggggcggg gtcgaagacc tagagggtat ataatgggtg    960
ccttagctgg tgtgtgagct catcttcctg tagatcacgc gtgccaccat gtgtcctcag   1020
aagctaacca tctcctggtt tgccatcgtt ttgctggtgt ctccactcat ggccatgtgg   1080
gagctggaga agacgtttta tgttgtagag gtggactgga ctcccgatgc ccctggagaa   1140
acagtgaacc tcacctgtga cacgcctgaa gaagatgaca tcacctggac ctcagaccag   1200
agacatggag tcataggctc tggaaagacc ctgaccatca ctgtcaaaga gtttctagat   1260
gctggccagt acacctgcca aaaggaggc gagactctga ccactcaca tctgctgctc   1320
cacaagaagg aaaatggaat tggtccact gaaattttaa aaatttcaa aaacaagact   1380
ttcctgaagt gtgaagcacc aaattactcc ggacggttca cgtgctcatg gctggtgcaa   1440
agaaacatgg acttgaagtt caacatcaag agcagtagca gtccccccga ctctcgggca   1500
gtgacatgtg aatgcgtc tctgtctgca gagaaggtca cactggacca aagggactat   1560
gagaagtatt cagtgtcctg ccaggaggat gtcacctgcc caactgccga ggagaccctg   1620
cccattgaac tggcgttgga agcacggcag cagaataaat atgagaacta cagcaccagc   1680
ttcttcatca gggacatcat caaaccagac ccgcccaaga acttgcagat gaagcctttg   1740
aagaactcac aggtggaggt cagctgggag taccctgact cctggagcac tccccattcc   1800
tacttctccc tcaagttctt tgttcgaatc cagcgcaaga aagaaagat gaaggagaca   1860
gaggaggggt gtaaccagaa aggtgcgttc ctcgtagaga agacatctac cgaagtccaa   1920
tgcaaaggcg ggaatgtctg cgtgcaagct caggatcgct attacaattc ctcatgcagc   1980
aagtgggcat gtgttccctg cagggtccga tcctaggatg caacggatcc gaattccgcc   2040
cccctctccc tccccccccc ctaacgttac tggccgaagc cgcttggaat aaggccggtg   2100
tgcgtttgtc tatatgttat tttccaccat attgccgtct tttggcaatg tgagggcccg   2160
gaaacctggc cctgtcttct tgacgagcat tcctaggggt cttccctc tcgccaaagg   2220
aatgcaaggt ctgttgaatg tcgtgaagga agcagttcct ctggaagctt cttgaagaca   2280
aacaacgtct gtagcgaccc tttgcaggca gcggaacccc ccacctggcg acaggtgcct   2340
ctgcggccaa aagccacgtg tataagatac acctgcaaag gcggcacaac cccagtgcca   2400
cgttgtgagt tggatagttg tggaaagagt caaatggctc tcctcaagcg tattcaacaa   2460
ggggctgaag gatgcccaga aggtaccca ttgtatggga tctgatctgg ggcctcggtg   2520
cacatgcttt acatgtgttt agtcgaggtt aaaaaaacgt ctaggccccc cgaaccacgg   2580
ggacgtggtt ttcctttgaa aaacacgatg ataatatggc cacaaccatg ggtcaatcac   2640
gctacctcct ctttttggcc acccttgccc tcctaaacca cctcagtttg gccagggtca   2700
ttccagtctc tggacctgcc aggtgtctta gccagtcccg aaacctgctg aagaccacag   2760
atgcatggt gaagacggcc agagaaaagc tgaaacatta ttcctgcact gctgaagaca   2820
tcgatcatga agacatcaca cgggaccaaa ccagcacatt gaagacctgt ttaccactgg   2880
aactacacaa gaacgagagt tgcctggcta ctagagagac ttcttccaca acaagaggga   2940
gctgcctgcc cccacagaag acgtctttga tgatgaccct gtgccttggt agcatctatg   3000
aggacttgaa gatgtaccag acagagttcc aggccatcaa cgcagcactt cagaatcaca   3060
accatcagca gatcattcta gacaagggca tgctggtggc catcgatgag ctgatgcagt   3120
ctctgaatca taatggcgag actctgcgcc agaaacctcc tgtgggagaa gcagaccctt   3180
acagagtgaa aatgaagctc tgcatcctgc ttcacgcctt cagcacccgc gtcgtgacca   3240
```

```
tcaacagggt gatgggctat ctgagctccg cctgagtcga catcgagaac ttgtttattg    3300
cagcttataa tggttacaaa taaagcaata gcatcacaaa tttcacaaat aaagcatttt    3360
tttcactgca ttctagttgt ggtttgtcca aactcatcaa tgtatcttat catgtctggc    3420
gcgccggcct ccgcgccggg ttttggcgcc tcccgcgggc gcccccctcc tcacggcgag    3480
cgctgccacg tcagacgaag ggcgcaggag cgtcctgatc cttccgcccg gacgctcagg    3540
acagcggccc gctgctcata agactcggcc ttagaacccc agtatcagca gaaggacatt    3600
ttaggacggg acttgggtga ctctagggca ctggttttct ttccagagag cggaacaggc    3660
gaggaaaagt agtcccttct cggcgattct gcggagggat ctccgtgggg cggtgaacgc    3720
cgatgattat ataaggacgc gccgggtgtg gcacagctag ttccgtcgca gccgggattt    3780
gggtcgcggt tcttgtttgt ggatcgctgt gatcgtcact tggtgagtag cgggctgctg    3840
ggctgggtac gtgcgctcgg ggttggcgag tgtgttttgt gaagtttttt aggcaccttt    3900
tgaaatgtaa tcatttgggt caatatgtaa ttttcagtgt tagactagta aattgtccgc    3960
taaattctgg ccgttttggg cttttttgtt agacgagcta gcgccgccac catgggccct    4020
aaaaagaagc gtaaagtcgc cccccgacc gatgtcagcc tggggacga gctccactta    4080 gacggcgagg acgtggcgat ggcgcatgcc gacgcgctag acgatttcga tctggacatg    4140 ttggggacg gggattcccc ggggccggga tttacccccc acgactccgc ccctacggc    4200 gctctggata tggccgactt cgagtttgag cagatgttta ccgatgccct tggaattgac    4260
gagtacggtg gggaattcga gatgcctgtg gacaggatcc tggaggcaga gcttgctgtg    4320
gaacagaaga gtgaccaggg cgttgagggt cctgggggaa ccggggtag cggcagcagc    4380 ccaaatgacc ctgtgactaa catctgtcag gcagctgaca aacagctatt cacgcttgtt    4440
gagtgggcga agaggatccc cacttttcc tccttgcctc tggatgatca ggtcatattg    4500
ctgcgggcag gctggaatga actcctcatt gcctccttt cacaccgatc cattgatgtt    4560
cgagatggca tcctccttgc cacaggtctt cacgtgcacc gcaactcagc ccattcagca    4620
ggagtaggag ccatctttga tcgggtgctg acagagctag tgtccaaaat gcgtgacatg    4680
aggatggaca agacagagct tggctgcctg agggcaatca ttctgtttaa tccagaggtg    4740
aggggtttga aatccgccca ggaagttgaa cttctacgtg aaaaagtata tgccgctttg    4800
gaagaatata ctagaacaac acatcccgat gaaccaggaa gatttgcaaa acttttgctt    4860
cgtctgcctt ctttacgttc cataggcctt aagtgtttgg agcatttgtt tttctttcgc    4920
cttattggag atgttccaat tgatacgttc ctgatggaga tgcttgaatc accttctgat    4980
tcataatcta gcggccctag ccccctctc cctccccccc ccctaacgtt actggccgaa    5040
gccgcttgga ataaggccgg tgtgcgtttg tctatatgtt attttccacc atattgccgt    5100
cttttggcaa tgtgagggcc cggaaacctg gccctgtctt cttgacgagc attcctaggg    5160
gtctttcccc tctcgccaaa ggaatgcaag gtctgttgaa tgtcgtgaag gaagcagttc    5220
ctctggaagc ttcttgaaga caaacaacgt ctgtagcgac cctttgcagg cagcggaacc    5280
ccccacctgg cgacaggtgc ctctgcggcc aaaagccacg tgtataagat acacctgcaa    5340
aggcggcaca ccccagtgc cacgttgtga gttggatagt tgtggaaaga gtcaaatggc    5400
tctcctcaag cgtattcaac aaggggctga aggatgccca aaggtaccc cattgtatgg    5460 gatctgatct ggggcctcgg tgcacatgct ttacatgtgt ttagtcgagg ttaaaaaacg    5520
tctaggcccc ccgaaccacg gggacgtggt tttcctttga aaaacacgat ctctagggcc    5580
```

```
gcgccaccat gaagctactg tcttctatcg aacaagcatg cgatatttgc cgacttaaaa    5640
agctcaagtg ctccaaagaa aaaccgaagt gcgccaagtg tctgaagaac aactgggagt    5700
gtcgctactc tcccaaaacc aaaaggtctc cgctgactag ggcacatctg acagaagtgg    5760
aatcaaggct agaaagactg gaacagctat ttctactgat ttttcctcga gaagaccttg    5820
acatgatttt gaaatggat tctttacagg atataaaagc attgttaaca ggattatttg      5880
tacaagataa tgtgaataaa gatgccgtca cagatagatt ggcttcagtg gagactgata    5940
tgcctctaac attgagacag catagaataa gtgcgacatc atcatcggaa gagagtagta    6000
acaaaggtca aagacagttg actgtatcgc cggaattccc ggggatccgg cctgagtgcg    6060
tagtacccga gactcagtgc gccatgaagc ggaaagagaa gaaagcacag aaggagaagg    6120
acaaactgcc tgtcagcacg acgacggtgg acgaccacat gccgcccatt atgcagtgtg    6180
aacctccacc tcctgaagca gcaaggattc acgaagtggt cccaaggttt ctctccgaca    6240
agctgttgga gacaaaccgg cagaaaaaca tcccccagtt gacagccaac cagcagttcc    6300
ttatcgccag gctcatctgg taccaggacg ggtacgagca gccttctgat gaagatttga    6360
agaggattac gcagacgtgg cagcaagcgg acgatgaaaa cgaagagtcg gacactccct    6420
tccgccagat cacagagatg actatcctca cggtccaact tatcgtggag ttcgcgaagg    6480
gattgccagg gttcgccaag atctcgcagc ctgatcaaat tacgctgctt aaggcttgct    6540
caagtgaggt aatgatgctc cgagtcgcgc gacgatacga tgcggcctca gacagtattc    6600
tgttcgcgaa caaccaagcg tacactcgcg acaactaccg caaggctggc atggccgagg    6660
tcatcgagga tctactgcac ttctgccggt gcatgtactc tatggcgttg gacaacatcc    6720
attacgcgct gctcacggct gtcgtcatct tttctgaccg gccagggttg gagcagccgc    6780
aactggtgga agagatccag cggtactacc tgaatacgct ccgcatctat atcctgaacc    6840
agctgagcgg gtcggcgcgt tcgtccgtca tatacggcaa gatcctctca atcctctctg    6900
agctacgcac gctcggcatg caaaactcca acatgtgcat ctccctcaag ctcaagaaca    6960
gaaagctgcc gccttccctc gaggagatct gggatgtggc ggacatgtcg cacacccaac    7020
cgccgcctat cctcgagtcc cccacgaatc tctaggcggc tctagagcg gccgccaccg    7080 cggggagatc cagacatgat aagatacatt gatgagtttg gacaaaccac aactagaatg    7140
cagtgaaaaa aatgctttat ttgtgaaatt tgtgatgcta ttgctttatt tgtaaccatt    7200
ataagctgca ataaacaagt taacaacaac aattgcattc attttatgtt tcaggttcag    7260
ggggaggtgt gggaggtttt ttaaagcaag taaaacctct acaaatgtgg tatggctgat    7320
tatgatcccg gctgcctcgc gcgtttcggt gatgacggtg aaaacctctt gacacatgca    7380
gctcccggag acggtcacag cttgtctgta agcggatgcc gggagcagac aagcccgtca    7440
gggcgcgtca gcgggtgttg gcgggtgtcg gggcgcagcc atgaggtcga ctctagtccc    7500
cgcggtggca gatctggaag gtgctgaggt acgatgagac ccgcaccagg tgcagaccct    7560
gcgagtgtgg cggtaaacat attaggaacc agcctgtgat gctggatgtg accgaggagc    7620
tgaggcccga tcacttggtg ctggcctgca cccgcgctga gtttggctct agcgatgaag    7680
atacagattg aggtactgaa atgtgtgggc gtggcttaag ggtgggaaag aatatataag    7740
gtgggggtct tatgtagttt tgtatctgtt ttgcagcagc cgccgccgcc atgagcacca    7800
actcgtttga tggaagcatt gtgagctcat atttgacaac gcgcatgccc ccatgggccg    7860
gggtgcgtca aatgtgatg gctccagca ttgatggtcg ccccgtcctg cccgcaaact    7920
ctactacctt gacctacgag accgtgtctg gaacgccgtt ggagactgca gcctccgccg    7980
```

```
ccgcttcagc cgctgcagcc accgcccgcg ggattgtgac tgactttgct ttcctgagcc   8040
cgcttgcaag cagtgcagct tcccgttcat ccgcccgcga tgacaagttg acggctcttt   8100
tggcacaatt ggattctttg acccgggaac ttaatgtcgt ttctcagcag ctgttggatc   8160
tgcgccagca ggtttctgcc ctgaaggctt cctcccctcc caatgcggtt taaaacataa   8220
ataaaaaacc agactctgtt tggatttgga tcaagcaagt gtcttgctgt ctttatttag   8280
gggttttgcg cgcgcggtag gcccgggacc agcggtctcg gtcgttgagg gtcctgtgta   8340 tttttttccag gacgtggtaa aggtgactct ggatgttcag atacatgggc ataagcccgt   8400
ctctggggtg gaggtagcac cactgcagag cttcatgctg cggggtggtg ttgtagatga   8460
tccagtcgta gcaggagcgc tgggcgtggt gcctaaaaat gtctttcagt agcaagctga   8520
ttgccagggg caggcccttg gtgtaagtgt ttacaaagcg gttaagctgg gatgggtgca   8580
tacgtgggga tatgagatgc atcttggact gtatttttag gttggctatg ttcccagcca   8640
tatccctccg gggattcatg ttgtgcagaa ccaccagcac agtgtatccg gtgcacttgg   8700
gaaatttgtc atgtagctta aaggaaatg cgtggaagaa cttggagacg cccttgtgac   8760
ctccaagatt ttccatgcat tcgtccataa tgatggcaat gggcccacgg gcggcggcct   8820
gggcgaagat atttctggga tcactaacgt catagttgtg ttccaggatg agatcgtcat   8880
aggccatttt tacaaagcgc gggcggaggg tgccagactg cggtataatg gttccatccg   8940
gcccaggggc gtagttaccc tcacagattt gcatttccca cgctttgagt tcagatgggg   9000
ggatcatgtc tacctgcggg gcgatgaaga aaacggtttc cggggtaggg gagatcagct   9060
gggaagaaag caggttcctg agcagctgcg acttaccgca gccggtgggc ccgtaaatca   9120
cacctattac cgggtgcaac tggtagttaa gagagctgca gctgccgtca tccctgagca   9180
ggggggccac ttcgttaagc atgtccctga ctcgcatgtt ttccctgacc aaatccgcca   9240
gaaggcgctc gccgcccagc gatagcagtt cttgcaagga agcaaagttt ttcaacggtt   9300
tgagaccgtc cgccgtaggc atgctttga gcgtttgacc aagcagttcc aggcggtccc   9360
acagctcggt cacctgctct acggcatctc gatccagcat atctcctcgt ttcgcgggtt   9420
ggggcggctt tcgctgtacg gcagtagtcg gtgctcgtcc agacgggcca gggtcatgtc   9480
tttccacggg cgcagggtcc tcgtcagcgt agtctgggtc acggtgaagg ggtgcgctcc   9540
gggctgcgcg ctggccaggg tgcgcttgag gctggtcctg ctggtgctga agcgctgccg   9600
gtcttcgccc tgcgcgtcgg ccaggtagca tttgaccatg gtgtcatagt ccagcccctc   9660
cgcggcgtgg cccttggcgc gcagcttgcc cttggaggag gcgccgcacg aggggcagtg   9720
cagacttttg agggcgtaga gcttgggcgc gagaaatacc gattccgggg agtaggcatc   9780
cgcgccgcag gccccgcaga cggtctcgca ttccacgagc caggtgagct ctggccgttc   9840
ggggtcaaaa accaggtttc ccccatgctt tttgatgcgt ttcttacctc tggtttccat   9900
gagccggtgt ccacgctcgg tgacgaaaag gctgtccgtg tccccgtata cagacttgag   9960
aggcctgtcc tcgaccgatg cccttgagag ccttcaaccc agtcagctcc ttccggtggg  10020
cgcggggcat gactatcgtc gccgcactta tgactgtctt ctttatcatg caactcgtag  10080
gacaggtgcc ggcagcgctc tgggtcattt tcggcgagga ccgctttcgc tggagcgcga  10140
cgatgatcgg cctgtcgctt gcggtattcg gaatcttgca cgccctcgct caagccttcg  10200
tcactggtcc cgccaccaaa cgtttcggcg agaagcaggc cattatcgcc ggcatggcgg  10260
ccgacgcgct gggctacgtc ttgctggcgt tcgcgacgcg aggctggatg gccttcccca  10320
```

```
ttatgattct tctcgcttcc ggcggcatcg ggatgcccgc gttgcaggcc atgctgtcca    10380
ggcaggtaga tgacgaccat cagggacagc ttcaaggcca gcaaaaggcc aggaaccgta    10440
aaaaggccgc gttgctggcg ttttccata ggctccgccc ccctgacgag catcacaaaa     10500
atcgacgctc aagtcagagg tggcgaaacc cgacaggact ataaagatac caggcgtttc    10560
cccctggaag ctccctcgtg cgctctcctg ttccgaccct gccgcttacc ggatacctgt    10620
ccgcctttct cccttcggga agcgtggcgc tttctcatag ctcacgctgt aggtatctca    10680
gttcggtgta ggtcgttcgc tccaagctgg gctgtgtgca cgaacccccc gttcagcccg    10740
accgctgcgc cttatccggt aactatcgtc ttgagtccaa cccggtaaga cacgacttat    10800
cgccactggc agcagccact ggtaacagga ttagcagagc gaggtatgta ggcggtgcta    10860
cagagttctt gaagtggtgg cctaactacg gctacactag aaggacagta tttggtatct    10920
gcgctctgct gaagccagtt accttcggaa aaagagttgg tagctcttga tccggcaaac    10980
aaaccaccgc tggtagcggt ggtttttttg tttgcaagca gcagattacg cgcagaaaaa    11040
aaggatctca agaagatcct ttgatctttt ctacggggtc tgacgctcag tggaacgaaa    11100
actcacgtta agggattttg gtcatgagat tatcaaaaag gatcttcacc tagatccttt    11160
taaattaaaa atgaagtttt aaatcaatct aaagtatata tgagtaaact tggtctgaca    11220
gttaccaatg cttaatcagt gaggcaccta tctcagcgat ctgtctattt cgttcatcca    11280
tagttgcctg actccccgtc gtgtagataa ctacgatacg ggagggctta ccatctggcc    11340
ccagtgctgc aatgataccg cgagacccac gctcaccggc tccagattta tcagcaataa    11400
accagccagc cggaagggcc gagcgcagaa gtggtcctgc aactttatcc gcctccatcc    11460
agtctattaa ttgttgccgg gaagctagag taagtagttc gccagttaat agtttgcgca    11520
acgttgttgc cattgctgca ggcatcgtgg tgtcacgctc gtcgtttggt atggcttcat    11580
tcagctccgg ttcccaacga tcaaggcgag ttacatgatc ccccatgttg tgcaaaaaag    11640
cggttagctc cttcggtcct ccgatcgttg tcagaagtaa gttggccgca gtgttatcac    11700
tcatggttat ggcagcactg cataattctc ttactgtcat gccatccgta agatgctttt    11760
ctgtgactgg tgagtactca accaagtcat tctgagaata gtgtatgcgg cgaccgagtt    11820
gctcttgccc ggcgtcaaca cgggataata ccgcgccaca tagcagaact ttaaaagtgc    11880
tcatcattgg aaaacgttct tcggggcgaa aactctcaag gatcttaccg ctgttgagat    11940
ccagttcgat gtaacccact cgtgcaccca actgatcttc agcatctttt actttcacca    12000
gcgtttctgg gtgagcaaaa acaggaaggc aaaatgccgc aaaaaaggga ataagggcga    12060
cacggaaatg ttgaatactc atactcttcc tttttcaata ttattgaagc atttatcagg    12120
gttattgtct catgagcgga tacatatttg aatgtattta gaaaaa                   12166
```

<210> SEQ ID NO 6
<211> LENGTH: 193
<212> TYPE: PRT
<213> ORGANISM: Homo sapiens

<400> SEQUENCE: 6

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
                20                  25                  30

Ile Cys Asp Ser Arg Val Leu Glu Arg Tyr Leu Leu Glu Ala Lys Glu
            35                  40                  45

-continued

Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 7
<211> LENGTH: 240
<212> TYPE: PRT
<213> ORGANISM: Choristoneura fumiferana

<400> SEQUENCE: 7

Leu Thr Ala Asn Gln Gln Phe Leu Ile Ala Arg Leu Ile Trp Tyr Gln
 1               5                  10                  15

Asp Gly Tyr Glu Gln Pro Ser Asp Glu Asp Leu Lys Arg Ile Thr Gln
                 20                  25                  30

Thr Trp Gln Gln Ala Asp Asp Glu Asn Glu Glu Ser Asp Thr Pro Phe
             35                  40                  45

Arg Gln Ile Thr Glu Met Thr Ile Leu Thr Val Gln Leu Ile Val Glu
 50                  55                  60

Phe Ala Lys Gly Leu Pro Gly Phe Ala Lys Ile Ser Gln Pro Asp Gln
 65                  70                  75                  80

Ile Thr Leu Leu Lys Ala Cys Ser Ser Glu Val Met Met Leu Arg Val
                 85                  90                  95

Ala Arg Arg Tyr Asp Ala Ala Ser Asp Ser Val Leu Phe Ala Asn Asn
            100                 105                 110

Gln Ala Tyr Thr Arg Asp Asn Tyr Arg Lys Ala Gly Met Ala Tyr Val
            115                 120                 125

Ile Glu Asp Leu Leu His Phe Cys Arg Cys Met Tyr Ser Met Ala Leu
130                 135                 140

Asp Asn Ile His Tyr Ala Leu Leu Thr Ala Val Val Ile Phe Ser Asp
145                 150                 155                 160

Arg Pro Gly Leu Glu Gln Pro Gln Leu Val Glu Ile Gln Arg Tyr
                165                 170                 175

Tyr Leu Asn Thr Leu Arg Ile Tyr Ile Leu Asn Gln Leu Ser Gly Ser
            180                 185                 190

Ala Arg Ser Ser Val Ile Tyr Gly Lys Ile Leu Ser Ile Leu Ser Glu
            195                 200                 205

Leu Arg Thr Leu Gly Met Gln Asn Ser Asn Met Cys Ile Ser Leu Lys
210                 215                 220

Leu Lys Asn Arg Lys Leu Pro Pro Phe Leu Glu Glu Ile Trp Asp Val
225                 230                 235                 240

<210> SEQ ID NO 8
<211> LENGTH: 582
<212> TYPE: DNA
<213> ORGANISM: Homo sapiens
<220> FEATURE:
<221> NAME/KEY: misc_feature
<223> OTHER INFORMATION: human erythropoietn expression vector (contains
      signal peptide and stop codon)

<400> SEQUENCE: 8

```
atgggagtgc atgagtgtcc cgcttggctc tggctcctgc tgtccctcct gtccctgcct      60
ctgggactgc ctgtgctcgg agccccccca agactgatct gcgacagcag agtgctggag     120
agatacctgt tggaggccaa ggaagccgag aacatcacca ccggctgcgc cgagcactgc     180
tccctgaacg agaacatcac cgtgcccgac accaaggtga acttctacgc ctggaagcgc     240
atggaggtgg ccagcaggc cgtggaggtg tggcagggcc tggccctgct gtccgaggcc      300
gtgctgagag gccaggccct gctggtgaac agcagccagc cctgggagcc cctgcaactg     360
cacgttgaca aggccgtgag cggcctgaga gcctgaccac ccctgctgag agccctgggc     420
gctcagaagg aggccatcag ccccccgac gccgccagcg ccgcccccct gagaaccatc      480
accgccgaca ccttcagaaa gctgttcaga gtgtacagca acttcctgag aggcaagctg     540
aagctgtaca ccggcgaggc ttgcagaacc ggcgacagat ga                        582
```

<210> SEQ ID NO 9
<211> LENGTH: 2300
<212> TYPE: DNA
<213> ORGANISM: Homo sapiens
<220> FEATURE:
<221> NAME/KEY: misc_feature
<223> OTHER INFORMATION: human myelin basic protein

<400> SEQUENCE: 9

```
ggacaacacc ttcaaagaca ggccctctga gtccgacgag ctccagacca tccaagaaga      60
cagtgcagcc acctccgaga gcctggatgt gatggcgtca cagaagagac cctcccagag     120
gcacggatcc aagtacctgg ccacagcaag taccatggac catgccaggc atggcttcct     180
cccaaggcac agagacacgg gcatccttga ctccatcggg cgcttctttg gcggtgacag     240
gggtgcgccc aagcggggct ctggcaaggt accctggcta agccgggcc ggagccctct      300
gccctctcat gcccgcagcc agcctgggct gtgcaacatg tacaaggact cacaccaccc     360
ggcaagaact gctcactacg gctccctgcc ccagaagtca cacggccgga cccaagatga     420
aaacccgcta gtccacttct tcaagaacat tgtgacgcct cgcacaccac cccgtcgca      480
gggaaagggg agaggactgt ccctgagcag atttagctgg ggggccgaag ccagagacc      540
aggatttggc tacgaggca gagcgtccga ctataaatcg gctcacaagg gattcaaggg     600
agtcgatgcc cagggcacgc tttccaaaat ttttaagctg ggaggaagag atagtcgctc     660
tggatcaccc atggctagac gctgaaaacc cacctggttc cggaatcctg tcctcagctt     720
cttaatataa ctgccttaaa actttaatcc cacttgcccc tgttacctaa ttagagcaga     780
tgacccctcc cctaatgcct gcggagttgt gcacgtagta gggtcaggcc acggcagcct     840
accggcaatt tccggccaac agttaaatga gaacatgaaa acagaaaacg gttaaaactg     900
tccctttctg tgtgaagatc acgttccttc ccccgcaatg tgccccaga cgcacgtggg      960
tcttcagggg gccaggtgca cagacgtccc tccacgttca cccctccacc cttggacttt    1020
```

```
cttttcgccg tggctgcggc acccttgcgc ttttgctggt cactgccatg gaggcacaca    1080
gctgcagaga cagagaggac gtgggcggca gagaggactg ttgacatcca agcttccttt    1140 gtttttttt  cctgtccttc tctcacctcc taaagtagac ttcattttc  ctaacaggat    1200 tagacagtca aggagtggct tactacatgt gggagctttt ggtatgtgac atgcgggctg    1260
ggcagctgtt agagtccaac gtggggcagc acagagaggg ggccacctcc ccaggccgtg    1320
gctgcccaca caccccaatt agctgaattc gcgtgtggca gagggaggaa aaggaggcaa    1380
acgtgggctg gcaatggcc  tcacatagga aacagggtct tcctggagat tggtgatgg     1440 agatgtcaag caggtggcct ctggacgtca ccgttgccct gcatggtggc cccagagcag    1500
cctctatgaa caacctcgtt tccaaaccac agcccacagc cggagagtcc aggaagactt    1560
gcgcactcag agcagaaggg taggagtcct ctagacagcc tcgcagccgc gccagtcgcc    1620
catagacact ggctgtgacc gggcgtgctg gcagcggcag tgcacagtgg ccagcactaa    1680 ccctcctga  gaagataacc ggctcattca cttcctccca gaagacgcgt ggtagcgagt    1740
aggcacaggc gtgcacctgc tcccgaatta ctcaccgaga cacacgggct gagcagacgg    1800
ccccgtggat ggagacaaag agctcttctg accatatcct tcttaacacc cgctggcatc    1860
tcctttcgcg cctccctccc taacctactg acccaccttt tgattttagc gcacctgtga    1920
ttgataggcc ttccaaagag tcccacgctg gcatcaccct ccccgaggac ggagatgagg    1980
agtagtcagc gtgatgccaa aacgcgtctt cttaatccaa ttctaattct gaatgtttcg    2040
tgtgggctta ataccatgtc tattaatata tagcctcgat gatgagagag ttacaaagaa    2100
caaaactcca gacacaaacc tccaaatttt tcagcagaag cactctgcgt cgctgagctg    2160
aggtcggctc tgcgatccat acgtggccgc acccacacag cacgtgctgt gacgatggct    2220
gaacggaaag tgtacactgt tcctgaatat tgaaataaaa caataaactt ttaatggtaa    2280
aaaaaaaaaa aaaaaaaaa                                                 2300
```

<210> SEQ ID NO 10
<211> LENGTH: 500
<212> TYPE: PRT
<213> ORGANISM: Homo sapiens

<400> SEQUENCE: 10

```
Met Ala Ser Arg Leu Thr Leu Leu Thr Leu Leu Leu Leu Leu Leu Ala
1               5                   10                  15

Gly Asp Arg Ala Ser Ser Asn Pro Asn Ala Thr Ser Ser Ser Ser Gln
            20                  25                  30

Asp Pro Glu Ser Leu Gln Asp Arg Gly Glu Gly Lys Val Ala Thr Thr
        35                  40                  45

Val Ile Ser Lys Met Leu Phe Val Glu Pro Ile Glu Val Ser Ser
    50                  55                  60

Leu Pro Thr Thr Asn Ser Thr Thr Asn Ser Ala Thr Lys Ile Thr Ala
65                  70                  75                  80

Asn Thr Thr Asp Glu Pro Thr Thr Gln Pro Thr Thr Glu Pro Thr Thr
                85                  90                  95

Gln Pro Thr Ile Gln Pro Thr Gln Pro Thr Thr Gln Leu Pro Thr Asp
            100                 105                 110

Ser Pro Thr Gln Pro Thr Thr Gly Ser Phe Cys Pro Gly Pro Val Thr
        115                 120                 125

Leu Cys Ser Asp Leu Glu Ser His Ser Thr Glu Ala Val Leu Gly Asp
    130                 135                 140
```

-continued

```
Ala Leu Val Asp Phe Ser Leu Lys Leu Tyr His Ala Phe Ser Ala Met
145                 150                 155                 160

Lys Lys Val Glu Thr Asn Met Ala Phe Ser Pro Phe Ser Ile Ala Ser
                165                 170                 175

Leu Leu Thr Gln Val Leu Leu Gly Ala Gly Glu Asn Thr Lys Thr Asn
            180                 185                 190

Leu Glu Ser Ile Leu Ser Tyr Pro Lys Asp Phe Thr Cys Val His Gln
        195                 200                 205

Ala Leu Lys Gly Phe Thr Thr Lys Gly Val Thr Ser Val Ser Gln Ile
    210                 215                 220

Phe His Ser Pro Asp Leu Ala Ile Arg Asp Thr Phe Val Asn Ala Ser
225                 230                 235                 240

Arg Thr Leu Tyr Ser Ser Pro Arg Val Leu Ser Asn Asn Ser Asp
                245                 250                 255

Ala Asn Leu Glu Leu Ile Asn Thr Trp Val Ala Lys Asn Thr Asn Asn
            260                 265                 270

Lys Ile Ser Arg Leu Leu Asp Ser Leu Pro Ser Asp Thr Arg Leu Val
        275                 280                 285

Leu Leu Asn Ala Ile Tyr Leu Ser Ala Lys Trp Lys Thr Thr Phe Asp
    290                 295                 300

Pro Lys Lys Thr Arg Met Glu Pro Phe His Phe Lys Asn Ser Val Ile
305                 310                 315                 320

Lys Val Pro Met Met Asn Ser Lys Lys Tyr Pro Val Ala His Phe Ile
                325                 330                 335

Asp Gln Thr Leu Lys Ala Lys Val Gly Gln Leu Gln Leu Ser His Asn
            340                 345                 350

Leu Ser Leu Val Ile Leu Val Pro Gln Asn Leu Lys His Arg Leu Glu
        355                 360                 365

Asp Met Glu Gln Ala Leu Ser Pro Ser Val Phe Lys Ala Ile Met Glu
    370                 375                 380

Lys Leu Glu Met Ser Lys Phe Gln Pro Thr Leu Leu Thr Leu Pro Arg
385                 390                 395                 400

Ile Lys Val Thr Thr Ser Gln Asp Met Leu Ser Ile Met Glu Lys Leu
                405                 410                 415

Glu Phe Phe Asp Phe Ser Tyr Asp Leu Asn Leu Cys Gly Leu Thr Glu
            420                 425                 430

Asp Pro Asp Leu Gln Val Ser Ala Met Gln His Gln Thr Val Leu Glu
        435                 440                 445

Leu Thr Glu Thr Gly Val Glu Ala Ala Ala Ala Ser Ala Ile Ser Val
    450                 455                 460

Ala Arg Thr Leu Leu Val Phe Glu Val Gln Gln Pro Phe Leu Phe Val
465                 470                 475                 480

Leu Trp Asp Gln Gln His Lys Phe Pro Val Phe Met Gly Arg Val Tyr
                485                 490                 495

Asp Pro Arg Ala
            500
```

```
<210> SEQ ID NO 11
<211> LENGTH: 60
<212> TYPE: PRT
<213> ORGANISM: Artificial sequence
<220> FEATURE:
<223> OTHER INFORMATION: Ecallantide inhibitor sequence

<400> SEQUENCE: 11
```

-continued

Glu Ala Met His Ser Phe Cys Ala Phe Lys Ala Asp Asp Gly Pro Cys
1               5                   10                  15

Arg Ala Ala His Pro Arg Trp Phe Phe Asn Ile Phe Thr Arg Gln Cys
                20                  25                  30

Glu Glu Phe Ile Tyr Gly Gly Cys Glu Gly Asn Gln Asn Arg Phe Glu
            35                  40                  45

Ser Leu Glu Glu Cys Lys Lys Met Cys Thr Arg Asp
    50                  55                  60

<210> SEQ ID NO 12
<211> LENGTH: 604
<212> TYPE: PRT
<213> ORGANISM: Homo sapiens
<220> FEATURE:
<221> NAME/KEY: MISC_FEATURE
<222> LOCATION: (1)..(601)
<223> OTHER INFORMATION: Prostoglandin synthetase 2 protein

<400> SEQUENCE: 12

Met Leu Ala Arg Ala Leu Leu Cys Ala Val Leu Ala Leu Ser His
1               5                   10                  15

Thr Ala Asn Pro Cys Cys Ser His Pro Cys Gln Asn Arg Gly Val Cys
                20                  25                  30

Met Ser Val Gly Phe Asp Gln Tyr Lys Cys Asp Cys Thr Arg Thr Gly
            35                  40                  45

Phe Tyr Gly Glu Asn Cys Ser Thr Pro Glu Phe Leu Thr Arg Ile Lys
    50                  55                  60

Leu Phe Leu Lys Pro Thr Pro Asn Thr Val His Tyr Ile Leu Thr His
65                  70                  75                  80

Phe Lys Gly Phe Trp Asn Val Val Asn Asn Ile Pro Phe Leu Arg Asn
                85                  90                  95

Ala Ile Met Ser Tyr Val Leu Thr Ser Arg Ser His Leu Ile Asp Ser
            100                 105                 110

Pro Pro Thr Tyr Asn Ala Asp Tyr Gly Tyr Lys Ser Trp Glu Ala Phe
        115                 120                 125

Ser Asn Leu Ser Tyr Tyr Thr Arg Ala Leu Pro Pro Val Pro Asp Asp
    130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Arg Arg Lys Phe Ile Pro Asp
                165                 170                 175

Pro Gln Gly Ser Asn Met Met Phe Ala Phe Phe Ala Gln His Phe Thr
            180                 185                 190

His Gln Phe Phe Lys Thr Asp His Lys Arg Gly Pro Ala Phe Thr Asn
        195                 200                 205

Gly Leu Gly His Gly Val Asp Leu Asn His Ile Tyr Gly Glu Thr Leu
    210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala
            260                 265                 270

Val Gly Gln Glu Val Phe Gly Leu Val Pro Gly Leu Met Met Tyr Ala
        275                 280                 285

```
Thr Ile Trp Leu Arg Glu His Asn Arg Val Cys Asp Val Leu Lys Gln
    290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
            340                 345                 350

Phe Asn Lys Gln Phe Gln Tyr Gln Asn Arg Ile Ala Ala Glu Phe Asn
        355                 360                 365

Thr Leu Tyr His Trp His Pro Leu Leu Pro Asp Thr Phe Gln Ile His
370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Pro Ala Val Gln Lys
            420                 425                 430

Val Ser Gln Ala Ser Ile Asp Gln Ser Arg Gln Met Lys Tyr Gln Ser
        435                 440                 445

Phe Asn Glu Tyr Arg Lys Arg Phe Met Leu Lys Pro Tyr Glu Ser Phe
450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
            500                 505                 510

Ala Pro Phe Ser Leu Lys Gly Leu Met Gly Asn Val Ile Cys Ser Pro
        515                 520                 525

Ala Tyr Trp Lys Pro Ser Thr Phe Gly Gly Glu Val Gly Phe Gln Ile
530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
            580                 585                 590

Pro Thr Val Leu Leu Lys Glu Arg Ser Thr Glu Leu
        595                 600

<210> SEQ ID NO 13
<211> LENGTH: 599
<212> TYPE: PRT
<213> ORGANISM: Homo sapiens
<220> FEATURE:
<221> NAME/KEY: MISC_FEATURE
<222> LOCATION: (1)..(599)
<223> OTHER INFORMATION: Prostoglandin synthetase 1 protein

<400> SEQUENCE: 13

Met Ser Arg Ser Leu Leu Leu Trp Phe Leu Leu Phe Leu Leu Leu Leu
1               5                   10                  15

Pro Pro Leu Pro Val Leu Leu Ala Asp Pro Gly Ala Pro Thr Pro Val
            20                  25                  30

Asn Pro Cys Cys Tyr Tyr Pro Cys Gln His Gln Gly Ile Cys Val Arg
```

```
                35                  40                  45
Phe Gly Leu Asp Arg Tyr Gln Cys Asp Cys Thr Arg Thr Gly Tyr Ser
 50                  55                  60
Gly Pro Asn Cys Thr Ile Pro Gly Leu Trp Thr Trp Leu Arg Asn Ser
 65                  70                  75                  80
Leu Arg Pro Ser Pro Ser Phe Thr His Phe Leu Thr His Gly Arg
                 85                  90                  95
Trp Phe Trp Glu Phe Val Asn Ala Thr Phe Ile Arg Glu Met Leu Met
                100                 105                 110
Arg Leu Val Leu Thr Val Arg Ser Asn Leu Ile Pro Ser Pro Pro Thr
            115                 120                 125
Tyr Asn Ser Ala His Asp Tyr Ile Ser Trp Glu Ser Phe Ser Asn Val
            130                 135                 140
Ser Tyr Tyr Thr Arg Ile Leu Pro Ser Val Pro Lys Asp Cys Pro Thr
145                 150                 155                 160
Pro Met Gly Thr Lys Gly Lys Lys Gln Leu Pro Asp Ala Gln Leu Leu
                165                 170                 175
Ala Arg Arg Phe Leu Leu Arg Arg Lys Phe Ile Pro Asp Pro Gln Gly
            180                 185                 190
Thr Asn Leu Met Phe Ala Phe Phe Ala Gln His Phe Thr His Gln Phe
            195                 200                 205
Phe Lys Thr Ser Gly Lys Met Gly Pro Gly Phe Thr Lys Ala Leu Gly
210                 215                 220
His Gly Val Asp Leu Gly His Ile Tyr Gly Asp Asn Leu Glu Arg Gln
225                 230                 235                 240
Tyr Gln Leu Arg Leu Phe Lys Asp Gly Lys Leu Lys Tyr Gln Val Leu
                245                 250                 255
Asp Gly Glu Met Tyr Pro Pro Ser Val Glu Ala Pro Val Leu Met
            260                 265                 270
His Tyr Pro Arg Gly Ile Pro Pro Gln Ser Gln Met Ala Val Gly Gln
            275                 280                 285
Glu Val Phe Gly Leu Leu Pro Gly Leu Met Leu Tyr Ala Thr Leu Trp
290                 295                 300
Leu Arg Glu His Asn Arg Val Cys Asp Leu Leu Lys Ala Glu His Pro
305                 310                 315                 320
Thr Trp Gly Asp Glu Gln Leu Phe Gln Thr Thr Arg Leu Ile Leu Ile
                325                 330                 335
Gly Glu Thr Ile Lys Ile Val Ile Glu Glu Tyr Val Gln Gln Leu Ser
            340                 345                 350
Gly Tyr Phe Leu Gln Leu Lys Phe Asp Pro Glu Leu Leu Phe Gly Val
            355                 360                 365
Gln Phe Gln Tyr Arg Asn Arg Ile Ala Met Glu Phe Asn His Leu Tyr
            370                 375                 380
His Trp His Pro Leu Met Pro Asp Ser Phe Lys Val Gly Ser Gln Glu
385                 390                 395                 400
Tyr Ser Tyr Glu Gln Phe Leu Phe Asn Thr Ser Met Leu Val Asp Tyr
                405                 410                 415
Gly Val Glu Ala Leu Val Asp Ala Phe Ser Arg Gln Ile Ala Gly Arg
            420                 425                 430
Ile Gly Gly Gly Arg Asn Met Asp His His Ile Leu His Val Ala Val
            435                 440                 445
Asp Val Ile Arg Glu Ser Arg Glu Met Arg Leu Gln Pro Phe Asn Glu
450                 455                 460
```

```
Tyr Arg Lys Arg Phe Gly Met Lys Pro Tyr Thr Ser Phe Gln Glu Leu
465                 470                 475                 480

Val Gly Glu Lys Glu Met Ala Ala Glu Leu Glu Leu Tyr Gly Asp
            485                 490                 495

Ile Asp Ala Leu Glu Phe Tyr Pro Gly Leu Leu Leu Lys Cys His
            500                 505                 510

Pro Asn Ser Ile Phe Gly Glu Ser Met Ile Glu Ile Gly Ala Pro Phe
        515                 520                 525

Ser Leu Lys Gly Leu Leu Gly Asn Pro Ile Cys Ser Pro Glu Tyr Trp
530                 535                 540

Lys Pro Ser Thr Phe Gly Gly Glu Val Gly Phe Asn Ile Val Lys Thr
545                 550                 555                 560

Ala Thr Leu Lys Lys Leu Val Cys Leu Asn Thr Lys Thr Cys Pro Tyr
                565                 570                 575

Val Ser Phe Arg Val Pro Asp Ala Ser Gln Asp Asp Gly Pro Ala Val
            580                 585                 590

Glu Arg Pro Ser Thr Glu Leu
        595

<210> SEQ ID NO 14
<211> LENGTH: 24753
<212> TYPE: DNA
<213> ORGANISM: Homo sapiens
<220> FEATURE:
<221> NAME/KEY: misc_feature
<222> LOCATION: (1)..(24753)
<223> OTHER INFORMATION: Prostoglandin synthetase 2 nucleotide

<400> SEQUENCE: 14
aggtgacagc tggagggagg agcggggtg gagccggggg aagggtgggg aggggatggg        60
ctggagctcc gggcagtgtg cgaggcgcac gcacaggagc ctgcactctg cgtcccgcac      120
cccagcagcc gcgccatgag ccgtgagtgc gaccccggtg cccggtgggg aattttcttg      180
gcctcctggt ggagccttga atgccaggct cagcccctca tctctctcct ctgcagggag      240
tctcttgctc tggttcttgc tgttcctgct cctgctcccg ccgctccccg tcctgctcgc      300
ggacccaggg gcgcccacgc caggtaggcg gccccatccc tccccaaggg aatccccggt      360
cttgcgcccc tggcctggtt tcaaccccct cctttcccct ccagcgggcc cagcttcccc      420
tttctgctcg cggtgctgag aaagactgag gctgagtctt ttggtgggat ggggctccc      480 tgaagccccc ccggcggtgt ggccttggct aatgggctat ctagttcttt caggggaaac     540
agcagactgg gatctggtgc caacttgggg agaagggaca gtccctatcc atcccctca      600 cctgttctgg gccccagatg tctaagcagc ctctgcaccc aacaacccg ctgtttccta      660 taggggcctc tttgggagga agccgcaggc accaagggaa atgagttccc tttctccagc     720
ctctaaccgt ctgggaaccc atcctgattc ccattgccag tggagaaggt ctcccctggt     780
gaagacttcg ggagaacatg ggagatggaa atacatttag gagccgggat gcttcatctg     840
gggtttaaga gatccccatt gagcaaatga ggaaaccgag gctcagtagg tgccatgatt     900
ccccaagctc acaaaataca tggtgggccc aggatctgaa ctcaggtctg tctgcgtcca     960
cacacttcgc aaggtctttc cacagaaagc tgcttctacc cacaatggac ccggagccac    1020
tctgggtttc atgggggagg ttgatgggga aattccgccc ttccctcccc catgcatgtg    1080
ccaggttcca ggtgaaggaa ttcagctcct cgctcagcca accttcctcc cccagctcgc    1140
tgcttgtgtg tgtgcgtgtg tgtgagcatg tgtcccagtt ggatatagtt tcctccacca    1200
```

```
cctagctgtg taaaatctct aaaatgaggc ccagagaggg caggagggag cagagggagt   1260
ccgcactttc tgctgtgatg ctctaaggat ctggtgcgtg ggggaaagag gaaagatatg   1320
tacatggatt ttggatcaga ccaagtttcc tgaaacgggc tttgggtggg tggcatttag   1380
gggacccaaa gagaggacgg agggtgctct aggaaaggga ttgcgttgaa taaaagtctg   1440
gtttatggga agaggaggag gaagactcat gtggccagca ctttaaagtt tacaaaggtt   1500
ggttgtggac atccacctct ttggtgctct caacagccct gccagagaga tgcgttagac   1560
ccagtctaca gaaggggact ctgaggccca gagggagtga agccacttgt ctgaatcctc   1620
acagtgagct ggtggtgggg agtagaaggg gctcttcagg ttgcctcgct gacccatctt   1680
gtcagtccct ggatcagccc agcacttcct ctgaggcccc atctggcctc atccaggcac   1740
tcttggtata caggtcccac ccgtctgtat tcttttttag tccattcact aatgcacaat   1800
gagccatggt ctgtgctatt ttgttttttg ccttttctgt ttccttttgt ataataaatg   1860
tttacacgga attgtttttt tttatcccca agggttattt atgccagtct ttggctgggg   1920
cctggagaca cggagctggg aggagctgac aggctgatgg tggagccaga aatgccaaca   1980
gactgtcatc aaggggacc agggctgtgc ggagctcatg gaggaagca ggggtatagg   2040 gagcccaggg aagggagcag gggtgtgcgg agctcagggg agggagcagc tgcctctcag   2100
tgcgaagaat tgagggaggc ttcttggatc tgatgacttt tggactggac ctcgaaggag   2160
gtggcgggtg ggggaaacac taagagactc gaccaggaaa caccgtaagg gtaatgtgga   2220
gcaggaggct gaggttggat gcgtaatgtg gggatgagac tggaggccag aaaactggta   2280
ccgaggctcc tgcaaggatc taggaaagaa cgaatgactg gtggagtgca ggggcagaag   2340
gtctgggttg ccctcatatt tccaagtctg cgagtaaact gagggccaag ctacttgggc   2400
atctgcccca ggaagccaaa gcctgtcttt tacctctaga ggcaaaggag atgaagagat   2460
gagggctgca ctcacctaag agggcaggcg gagggagaga atgctgcttt tgcctctctg   2520
gtgggtgagg agatggaggc cagcctggag gcaaggctgt gccgggggcg ccctgaatgc   2580
tcaagtactt cccctctagt ctctggactt gactcagtgc ccatcttcta gatgggggata   2640 gggcatgacc tggcaaccag agctgcatgc caggcagagg agcccaggc cagctgaccc   2700 gggcacatgg ggcaagatgc cagctgtgcc aaggctgccc gggtgcctgc acctgctctc   2760
gccagcacca gttgggtctg tgggccggga gagggcttcc ccaccagcag gctcttccag   2820
ctgctgggcc cagttgtctg gatctggtgt ggtggtgctt aggtgtgggg actggggccc   2880
aggccaaacc agtcagggtt ccccaccttt tttttttttc tctctggctg ccaggtcccc   2940
agagactctc taaatattac tctttagggg atttgggtcc tgcctcttca ctgggcaatc   3000
ttgcagcctg acacctctgc atcctggagg acttggtgtt ccctggctgt gcctgtcccc   3060
tagtcacgct cagtcctgga cctggagccc tgacttttgg gctaggggt gttccttgcc   3120 caaacccttg gaaaggtcct ggaaccaggc agttctggac agtcctcatc tgtggggatg   3180
gggactagca gcttggcctt tgggctgcgt gtgtctggca tgcagcgtgg tgtgctgatc   3240
atctctgcct ccgcgtgtct tggggactca gtgagagcaa atgggaaggt tctctgctga   3300
tggggcagtt gtgggagggt tgtattgata caaataatgg agagggacag attggctcta   3360
cccagagtag agggcctgga cgtcgaaagg aaggcctcct ttagcccgcc tgctaaaccc   3420
ccttcatggg atatacagaa aaatgaggct ccagaggtgg gagggactca cccaagaatg   3480
cacagccagt aagagcagcc actctctaat acagctctcc caagcaacta cttggtgcct   3540
```

```
ggccctgtgc tgagtatggg ggactcaaag tgaattagac ttggtacctg catctccttg    3600
gttttctttc ttgatgaaca ggggtgtcct ccactgagca tagaactgag ttggcatgaa    3660
aacatgcagg attgaagtta gaccgaagga aggccttcct gtacgaatac ttcctaaaga    3720
tctggttgtg gcaggagatg gtgatccccc tggggtcctg gtttcattcg ttctggattt    3780
tcaaggttca ctttgaagga atgtgacaaa tccaactcaa ctgggtcatc ctcagtctgc    3840
atcaaagcga ctctcccttt ccatcccttc cccaaatcca gtcctgggta cctccaggag    3900
taggaggagg agggagatta agtcttggct ccgcaacttc aaagcagtgg ggtctgggca    3960
agcctcctgc tttctctggg ccctacattc ctcattatgc aatggggagt ctcacctacc    4020
tctcttaggg agtgctgggg agataaatga gcgtgggtgt ggaaggttgt ggacttggtc    4080
ggctggagcc ctggctttct ggctgggctg tgatggtcag gctgtagtct agtggcaccc    4140
agtctcctct ccgcccaccc tgacaccttg gggcaccagc ggcaggccca ctgttgtcct    4200
tcctgggaga acttttcctg ccccagagca gtggtgttta tggaaagaac gtggcggggg    4260
aggcgggagg ggggaagctg gatgggccgg actgggaggg aggagcctca gctcccgcac    4320
agcctctctt ggcagggagg gtgtgggcag ccgttccagc ttcagcgtct ggagcttgtg    4380
gctcttctgc ctgccgaggc agagctctag gccatggcg ggaggcctcc cggctccacc    4440
tcagacagct gttgagggcc tggaagatga gggactcctt ttggtcaggc tggaggtgac    4500
caatctcctc acttcatttt atttattcca caaacattcg ttaagctctg ctaccacat    4560
ctggatccca gacctggtta agccccaact gtgtgcatag cctgtgctgg gggaagagaa    4620
agccttaagg gaagcggggg tcccttctcc tggaagctta tggtggagaa gagcaggttg    4680
aattggaacc cggagccagg gcaagggaga gtgggaggag ggagtgtgga catttgggga    4740
agacttcttg gggaggcaag gcgtgggctc agctgatttg gaggaaatgt attaaggagg    4800
ctaacagcct ggatgaagga tggagatgct gagggtttgg ggctaaggga ggggctggcg    4860
cagaatgttg gagctgcacg gacctctgga gttcattttg agatccctgc tgtggcaggg    4920
atggggaaat tgagcctagg ggaggcctaa cccctgtgcc cttagagtgg tagaactaga    4980
ccgtgagtcc tagcggacct tgtgtgccag ggttgggagc tgggcagtgg gtgctacagg    5040
ggctcctggg caggtgagag agccaggcca gcaggagggg caagaagaag agttctagca    5100
gggtgacaag tccttttcttg ggggaaccag acctctgagc cagcacgggg gctgctccag    5160
aggcttcttg gccttctgg gcctgtggct gggggaggcg ggggctgggg tactgccagg    5220
ccctttccct ggatcctgcc tgccaggttt gcctgtggct gcctgataaa gccttttgt    5280
ccagccttct tcccctgacc cctccctcct acacccctgc tggggccatt gtgggctgt    5340
ggggagttgc cagggcttaa gcaaaactat ttgcatgatt cttgtggtcc ttgcttgtgt    5400
gtgtgtgtgt gtgtgtgtgt gtgtgtgtgt gtgtgtgtgt atttgaggtg gtgttgccgt    5460
cttcgaagtg gggaccaaga ggactctgct gcccaggtca gccctgtgc tgtgaagtga    5520
ggagtgagga gactgagacc agggcagggg ataggggca ggtcttgccc agggtcatgc    5580
tctctgatcc tagcaccctg agatgacagc atttcaccct cagctgctct ggcctttcac    5640
tacccttttg acctgcaata accagttgca caaagaatcc atattccctg taacgttggc    5700
tctgagccca gataaggaag tatgtttgca gaaaggagcc cggcgttttc tgtgtaaggt    5760
cagagatgga gcctcctgcc aggcgctagg agttttttggt ctgcccagct ctgttctgtt    5820
tccttggcca agttatcacc tgtccctgaa cctcagtttc cttcactgaa cagggtggtg    5880
ggggtgatgg tggatcctac tgaacctgag gagtctgtaa cttgtgctgct aaagaatcac    5940
```

```
tgaggcagat ttagcaaggg ggtggtggtc tgagggatct gggttagatg ccaagaggga    6000
tttccttata gagtttctcc aggaggcagc agggcggatg ccagagctcc atgcaccctc    6060
ccaggagatt ttctagccct atctctccta ttcccttggt ctgtgacctt cttctggatc    6120
ctagagccca gaccccaccc tgatgtgggc caagtctgat tccatcagga atgggggctg    6180
aggcagctga gaccttggag tcccctcct cctgcacacc caccctctgt ccccagggtt     6240
ctggaaaact tctttcctta gacttggctg ctgaggctgt gggggtggag tggaagtgaa    6300
gggatgggca tttggtctgg tgagacttgt ggggtgatag gtctggcttt cccttttttct   6360 ggcttcaatt tccccatctg caatgtggac attatgatac ctgctcttct ctaccttctg    6420
cagaaatgga ggaatggtga gggatctcgt tttcctagtg ttcatggggt ggtggtctgg    6480
gagaagtccc cgtcctcgtc ctcgtccctt ttctgaccgc cccccaccc cccgcccgg      6540 cctgctcttg ctactgaact ctgactaggc aggaagtgaa cgctctagaa gcccgtggct    6600
gaggagtttt atcagctctt tcttaacttt cagtgtcaca gccggggaat cttctcctgc    6660
cgccgtttgg tggcaatagg gagggagggg gcgcttcccc tggggcctg atgtgggcta     6720 ggctggagtt ccagagcagg gcctggaaat gtcaggatgg gtggtttatg ttcacagagg    6780
tgggaacagg ggtcccctg ggggaaccct gaagccctgg cacccagtga ttcaggacgg     6840
agctgcgact taagtccatg cctctggccc ctcattcccc catcagggc tagatggggg      6900 tcaggaggcc accctagcat ggtctctgac ctccatttct cacccacagt gaatccctgt    6960
tgttactatc catgccagca ccagggcatc tgtgtccgct tcggccttga ccgctaccag    7020
tgtgactgca cccgcacggg ctattccggc cccaactgca ccatccgtga gctgggcctt    7080
cagccctcac tccttccgtc ttgagcccctt ctgctcccg ggcccttct cctagaccct     7140 aacttcctac cctcctctct gaccatggcc ctgttctcct tccttgcctg gttctgcccc    7200
tctccctgac ctggcttcag catgagctct cgctcttggt ccaccctcac tccctgcttc    7260
tgagttccat ggtgagtctt caccacatgc cctggcccct gtcctcacgc ccggttctgt    7320
ctctgtcatg tgtcattgct cccaaggttc catccttacc cacttcccca taggtgctac    7380
tctgttccac cctggccctt gtcctcagtg ccccatcttc caccctggct acttctggtt    7440
ctggtaggag ggaccaactg agtgactgcc attgcccctg cagctggcct gtggacctgg    7500
ctccggaatt cactgcggcc cagccctct ttcacccact tcctgctcac tcacgggcgc     7560
tggttctggg agtttgtcaa tgccaccttc atccgagaga tgctcatgcg cctggtactc    7620
acaggtgggt gtgggggcagg gcccctgac ctggggagc aagcaagcct gctagtcctt     7680
ttggattctt ggcatctgat aagggtagtg ggtgggagga gtctatgatg cctgataaaa    7740
taagccccaa cccaggagga ggcaagaact gggatggagc tgggggtgga aacacccttg    7800
tcaccgttat ttttgctctc tgcagtgcgc tccaaccttc tccccagtcc cccaccctac    7860
aactcagcac atgactacat cagctgggag tctttctcca acgtgagcta ttacactcgt    7920
attctgccct ctgtgcctaa agattgcccc acacccatgg gaaccaaagg taaaatgggg    7980
tgaggagctg ggcctgggga ttacaggagg tgctcagttc ttctctttgg gaaaaatcag    8040
gcgaagaaca attattgacc caattctgca gatggctaga ccaaggcaag acatatgaca    8100
tgtccagagc ctgggctgag aacaggcaag ggcagcagag ggtcttgcct gaggtcacct    8160
agagtcagac caatgtttcc atagttccag ggtgcctctt tgcttgatcc tttttctaatg   8220 atcagttggg tcctgccggg gtggaagtga cttagaagtt gagatgtagg aaagaatagt    8280
```

```
gagctattta ttgggtgctg tctctgtgtt tgggtctttta cagatgtaaa tagttttaca   8340
tgcttcacca gtgtaaggta caaataagcc acatttttt ctttcgttac tcaagacttc    8400
acttagccac actggcaggg gtcttccttg taagaccttc ccatgccacc tgtaattatc   8460
caaaaacctg ggatattatt catttcagac ccatcagttc agcatcaagt acagagagga   8520
caagagaggc tcatcagtcc actgctgcta tactccagtt cctgccacat ggtggcactg   8580
ttgaatgcca gtcctgtgca gcctcatggt tatgtgcttt tttgggttca aaaccttgca   8640
ccatgtccct gcttgggtct caagagcact actgtgacgg ttttccatca tatggttagc   8700
tgcttttccc aaagcatgac tattctacca ggatagctga gtcttgccaa ctttgctgaa   8760
atcatgcttg cccagtgtca gtgagtgatg attccaaatt acggttgaca gatcactccc   8820
tctaacttcc cttttggtgg attttcttta ggggtacttg atatttttc ctgccagagg    8880
aacccagtca gccatcttaa tccaagtaat ttccattgat cttgaacctt caacatcagg   8940
gctcacatct tgatgcattg tgaagagatg cctttaccag aactcaaaaa attctattcc   9000
tttctgtgag ggcaattggg tgacaactca tttgacactg acataattaa ggaaggcctc   9060
tcaatactta ttctaaggat gacttgtctt tatgccagac atagaaagat tggcatcatt   9120
taaaataggt tgacacacct attttaaggg gagcaagcaa gcctgctagt ccttttggac   9180
tcttggcatc tgataagggt agtgggtggg gagagtctat gatgcctgat aggtggtggt   9240
gtggtggcac acgtctgtaa tcccagcact ttggagggtt ggggtgggtg gattgcttga   9300
gctcaggagt tcaagtccaa cctggatgac atggtgagac accttgtcta caaagaata    9360
caaaagttag ctgggtgaag ttgtgtgtgc ctgtagtccc agctactcag gaggctaagg   9420
tgggtggatc aattgagccc aggaggtcga ggctgtagtg agccataatt gcggcactgc   9480
actctggcct gggcaataga gtgagaccct gtctcaaaaa taaataaata aataaataaa   9540
taaataaata aataaataaa taggttggca aactacagcc tgcaggccaa attcggccca   9600
cctctccatt tttgtaaata aagttttatt ggaacacagc cacacacatt tgtttatgtg   9660
tcatctgtga ctgctttccc gctacaatag caaaaactga atagatgtga catgtctgta   9720
tggtctgcaa agcctaaaat gtttactatc tggcttttc cagaaaaagc ttgctgacct    9780
atgatttaaa aaattctacc cactggttct ctgccatgct tacattatct ctcgcagtcc   9840
tcagattcac tgtatcaaat gggtatcatt tgccccttt taaagatgga gaaattgaca    9900
cccagagaga tgagatgatt tatctgtatt cacacagcta gcaaatagca tagtcagttg   9960
caaacacagg ctaccttgac tcagggcaag ggagttcatg tttgtttttt tctgtttctt   10020
tatttctttt tggtgaaatg tttcattatg gaaaaattgc aaagatacac aaaagttgag   10080
agaaaagcag aatgaactat gtacccatct ttcagtttca acatttaccc acagtttctt   10140
catcttattt catttctccc ctctcatatt tttataaagt attttaaatc aaattctaaa   10200
aatcatgcca cttaaaattc taaaaatcat gccacttcac ccataaatac ttctagggtc   10260
ttttggtaga gagtgggtta cttggtggtg gtggggaggt ggtcctgagg aggccactct   10320
gggcttcctg cttgggccag tttgcctggt gagcccagat gtccccaggg cagcaagatc   10380
cagataggag aagctactgc tgtttcctac cccccaacca gggaagaagc agttgccaga   10440
tgcccagctc ctggcccgcc gcttcctgct caggaggaag ttcatacctg acccccaagg   10500
caccaacctc atgtttgcct tctttgcaca acacttcacc caccagttct tcaaaacttc   10560
tggcaagatg ggtcctggct tcaccaaggc cttgggccat ggggtgagta cctaggaggg   10620
gctcaggact gctctggacc taatttggca cgcgtatgtc atcgacagtg ggccggcacc   10680
```

```
ctggtgacct gagggaaccc ctctctgtcc acaggtagac ctcggccaca tttatggaga    10740
caatctggag cgtcagtatc aactgcggct ctttaaggat gggaaactca agtaccaggt    10800
agtgctgggc caggggggtag ggcagaggga ggggtctccc atggtcttcc ctggcaaaga   10860
ctgcttgggg cgggggtctg ggtcatgtcc tgagagggcc aaccacggga gtgggaagct    10920
tgtgccagga gcgacagtat acgctgggag gaggcagcag gtatgagaag ccagggagga    10980
gcagacgtgg cctcccatgt cagccaggga ggtggatttt ggagctcaac aggagatgaa    11040
catttgtagt ctgcatttat ttatttaatt attccacaat attaattgga cacgagaata    11100
tacctggcac aggtgattga gtagtgacca ttatagttaa tgggccctgc cctcaaaaaa    11160
ccacaggcaa actctaggat gttcattcta tgagggcttt tgtttaaatc agaacggtcc    11220
aacagaaata taatgtgaac cacatacata gttaaaattt tctaatgtcc atattaaaag    11280
agggaaaaag aaacaggtga aatgatttta ataatacatt ttacttaatg caatatgtcc    11340
aggtaattag cattttagca tgtaatcaat acattattaa taaatatgt cacattcttt     11400
tttcatgctg aagcttcaaa atctggtgta tatttcacac tcacagggca tctcaatttg    11460
gatgctctat tttcactgga gtgatctaat ctgtattaag atttcataaa atgtacagct    11520
gaataagtag agtgacatgt ccgacttgtt ccacgcatac ttaaaggttt tccaatagct    11580
gaagtatcag ttttaaaatt caaatagaaa ttaagataaa cctaaataaa ataaattaag    11640
taacattcag ttcttcattc acactagcca aatttctagt gctcagtagc tacacgtggc    11700
tagtggctac catattggat cgtacaaatc ttaggcaagc accaaaacaa agtttgatgc    11760
tgaatcttta gggctaagaa cagtacttgg catgtagtag tctcttggca tgtatttact    11820
gaatgaatga agaagctgcc atataattag gtacacttgt agctgccacc aaggagaagc    11880
tgtgagtgcc actagagtgt ttggatgatg ggtaaaactt ccctaggaag ttacaaataa    11940
acccagagtt gcataaagga tgaggaggag ttagggatgc taagaatggg agagggcttt    12000
ccaggtagag ggtttagcaa gtacaaaagc ttagaggtgg agaacagctt ggtgacttgg    12060
agggagtgta aaaatgggag cgtttgctga gcctagtgat ggagcgtaag aatgacttta    12120
caggaaggtg gagatgtctg tggggaccgt gttaaggaat tctactttct gccaagagca    12180
gagagagtat ttggaaaggt tttaagtcag ctcatgatgc aagatttgtt gttttttttt    12240
ttttaagttt ttttttttctt ttttttttttt ttcttttttg cttgggtgca gtgcagagac   12300
tggcctgtct ggggatagga gtggaaatag ggagcccact tagggaaagg agtcagagtg    12360
gaagatgagc gggggttgct tgaggtagtg gtggtagaga tggagagcag gggactgatt    12420
ttaagagaca ttttggaggt ggaatcaaca gccttggctg aggggaactg gcagctggag    12480
gcaggagtgg gagggagttg gttgtgggca gctgtgggtg accccaaccc ccaggttgcc    12540
aggtggcccc atcccacagg tgctggatgg agaaatgtac ccgccctcgg tagaagaggc    12600
gcctgtgttg atgcactacc cccgaggcat cccgccccag agccagatgg ctgtgggcca    12660
ggaggtgttt gggctgcttc ctgggctcat gctgtatgcc acgctctggc tacgtgagca    12720
caaccgtgtg tgtgacctgc tgaaggctga gcaccccacc tggggcgatg agcagctttt    12780
ccagacgacc cgcctcatcc tcataggtga ggactccaga cctgccctgc cctggaaggt    12840
cattccctcc atcctgagaa gttgggggcg ggggggtact tagaggtgga ggctgggatt    12900
agaatcctca cccttctgct tagtggctag aagaccttga gcaggcccct caacctctgt    12960
gagcctcggt ctccaaatct gtacgttggg gtgaacgatg attgtaagga tttattgaga    13020
```

```
tcatgaatgg gaaggcaact agcacatagc aggccttcag aaaatagatg actgtgatgg   13080
ttgattatta gctgggtgac tcagcacatt tgattagcca ccctgagtct cggtttcccc   13140
tgtgtgctgc gcccggatgc atacttgtgg tccccagcac gtgcagggtc aaactgtaac   13200
ttgcccggcc ttcaggaatc ttcatgttcc cttccctgca tgtatctacc ttcctgcagt   13260
ttggtagctt ctaggtgact cagggacagg atattttgt gttccctatg ggcgagtc     13320 tgcaacctaa aatgtcagat ggtttcctgc ctgggagctt ggcccctgac atccctgtcc   13380
agaccatgtt cgctctgagt caccagtaac tcccttcccc cacctctggc accactgggc   13440
atggctggtc ccaattatag agcctaattc actggagcca tgaagagcca ggcattggga   13500
ataggaacag tcattagagg gaagaggggc tggttctgaa gtttcagcgt tgcaaagacc   13560
ttgacctgag agagctggag gctgtccagc acactggctg gagatgaagc tgtgaccaaa   13620
ggcaggaccc tagggcacca tttaactccc ctacaacctc atgagccggg tatgattacc   13680
ctgtgaaaat caagattcag agaggtgaag tgaactctcc agggacactc agcagatgga   13740
gacttgaggt ctggttgcca ccaaaatcta tgctacttcc actccatcac aaaggggct    13800 cttcttgaat gggaaggggt tgcaaacctg agtctgatct gtgacatgtg agtattggaa   13860
agggattccc cctcgcgtct acacttagta ttcctacttt tggctgacat atatggacac   13920
cccgtcttat gccaggcact gtgccagcag ttttgctgta ttcattgtct acttctctca   13980
acaaccctaa tatagtattg cattgatgtt attattatta ttatttgaga tggagtcttg   14040
ttctgttgcc cacacagtag tgcaatggcg tgatcttggc tcactgcaac ctctgcctcc   14100
cgggttcgag caattctcgt gtctcagcct cccgagtagc tgggattaca ggtgcccgcc   14160
accatgcctg gctaattttt gtattttag tagagacagg ttttgccat gttggccagg    14220 atgatcttga actgctgacc tcaggtgatc cacccgcctt ggcatcccaa agttctgggt   14280
ttataggcat gagccacagc gcctggccgc actgatatta ttataacaca cattttacag   14340
ttaaggaaag tgagattctg agagattaag taactcagcc caagctcagg tggctggaaa   14400
tggtaaagcc aagatttgaa tccaggtctg ctgatcccac agtctgtagc tccaggtcga   14460
tttccaaaag ccaatttgtc taatggctaa ttggcctgca tatcagtttc tttcaatatc   14520
tagttgccca gttttaattt tgttacagaa tgttcaattt gcattttccc tggcttttg    14580 ctttctagct ggttatagct acaaatgggg cagaggaaaa acttatttat aagaatcctg   14640
ttatataaga acatatagga aatatgtttt tgaaatata tttagggcta ggctcccctt     14700
ctgtcctcag tattctcttt tgccactgca gcagctctga gtggtctcct tgaagtcccc   14760
ctctatcacc gagggtgtca gcatgatgac agctctcacc agtaaatcct ccactttcc    14820 atctttgta gtctctccac cttctttaa tgggcttcag gagggaggtc ataagaccaa     14880
ttcttggaca cctcctttgc atgtcctgct tagctgggcc tagaacctcc ctctgaaatg   14940
tgggagtagc tggtgctctt gtcttgagac ctcagtcaaa atagaccaaa agttctattt   15000
tcacatcctg ttacaaagag acaaaatgga agaggccaaa caaaattaaa catcaacagc   15060
aaggccaggt gtggtggctc acacttgcaa ttccagggct tttgggaggc tgaggtgaga   15120
gaagtgcttg agacttgcag ttcaagacca gcctggataa catagtgaga ccccatctct   15180
taaaaaaaaa aaaaagaaa gaaagaaagc tgggtgtggt ggtacacctg tggtcccagc   15240
tacttgggag gctgaggtgg gaggattgct tgagcccggg aaagttcagg ctgaagtgag   15300
ctgtaattat accattgcgc tccagcttgg gtgacagacc aagaccttgt ctgtaaaaat   15360
aaaaataaac atcaacagca acaacaacaa taaagagacc aaaagcaagc acctctcatg   15420
```

```
aactggcctg ctttccaagc tgggcatcta aatcactgtg cttggctgac cctatttcca   15480
atcctgccct gcccagggga gaccatcaag attgtcatcg aggagtacgt gcagcagctg   15540
agtggctatt tcctgcagct gaaatttgac ccagagctgc tgttcggtgt ccagttccaa   15600
taccgcaacc gcattgccat ggagttcaac catctctacc actggcaccc cctcatgcct   15660
gactccttca aggtgggctc ccaggagtac agctacgagc agttcttgtt caacacctcc   15720
atgttggtgg actatggggt tgaggccctg gtggatgcct tctctcgcca gattgctggc   15780
cgggtaagcc ccagaggagt gctggtgagg gcaggtgggc tgagggatcc agcagacctg   15840
ggtccaaatt ccaggttctt cttctgtaaa atggggctga tgtcacttct acagggcagt   15900
tgtaagcatt cctgtgtgag ttcattggtt catttgtcca ttccacaata ccagacatta   15960
ctccaggtac tggagatgta gtgggaacaa gacttttgtg gttcttggct catcttttag   16020
tgctcccacc ctagaaagtg atggcagtca tacgacagct gacagcatta gggcccttac   16080
tgcgtgtcag gcactgttct aagagcttct cctatgttat cagaattcta agagtatgtt   16140
ataaaccata gtagaaaagc ccaccatgct ctgggagtca ggaagggaca tctgacccag   16200
agttgcgggt tatgggaaaa gaagggatgt ccaagcagaa attggaagga gggatagaga   16260
tttcccaggg taagaggtgg tgttagtggc aggggatggc tgtgttccag atagagagga   16320
cggcatgggt gaaaggcatg gaagtcgaga gacatggcag tttgaggaac agaaggacat   16380
tcagggcatg gtaatgtatg taacagtgcc cgcctatggt gtttattaaa tcataagcct   16440
ccgctctggg ctgaattgtg gctctttaa agttcgtatg ttgaaatcct aaccgccaga   16500
accttagtat gtgactgcat ttggagacaa ggtctttaaa gaggtaatta agtttaattg   16560
aggtcattag gctgggccct aatccagtgt gacttataag aagaagagat taggtcacac   16620
acacagaggg aaggccacat gaagatgtag ggagaagaaa gccatctaca agccaaggaa   16680
agaggcctca ggagatacca accctgctga caccttgatc ttgaacctct ggtctccaga   16740
cagaggaaat aatttctatt gtttgagcca ctcattctgt ggtacattgt catggcagcc   16800
ctagcaaaca aacacattct cttttccctgg aattcccagc caacgccttc ctcaatctcc   16860
ccttctccac attcggaagc tcccatctgc ttcatcgcag tctctggctc ccctgttgcc   16920
tcacagtcct ctgcttctct ctaatccttg tccctaaacc ctgtcatgaa gctgtggcac   16980
acatggattt ccatttcctt ctggtaattt gactgaaatt agcatttgct gccccggtgg   17040
gcagctgctg gctgctttat ggcctctttg tcggtttctt tatggttctt tgtggggaca   17100
caagacatga acagagacaa tagcctttgt gtgaggctgg atggttttca gaacgttttc   17160
aaggaatgac catgatgatg tacgtgaaaa gccccggcgt cgtacctggc acaaggcaga   17220
aaggccgcag agatgtatgg actgtcaaga tttttttttct tttttctttt tttttaaata   17280
gagatggggt tttgccatat tgcccaggct ggtcttgaac tcctgggctc aagcgatctg   17340
cccgcctagg cctctcaagg tgctgggatt ataggcgact ctcaggatat taagaagagt   17400
gagtgatgat aagacagggc ttcccctgat aaccattgtc catggctacc ctctcagggg   17460
ttcccatgtg accaatactg agataacagc tttgcatagt ttatcccatt taaattgacc   17520
acagccatat caggtagatg ctcttccctt ccccattttt acatatgcgg gaactcaaac   17580
ttagcttgaa tagctgccca aggtccctat attagtttcc tcaggctgct gcaacaaagt   17640
accacaaact gggaagctca gagcaacaga tggaggctag aagtctgaat tcaaggtgtc   17700
agcagtgcca tgttctctct caaggctcta tgcctccttg gcatctggtg gtggccgaca   17760
```

```
gtccctggca ttcctcagct tgcagaggca tcgctctagt ctctgccttt atcatcctgt    17820
ggtgctctcc ctgaacttgt ctttcctcat tttataaaga caccagttat tggattggag    17880
cccaccctaa tccagtagga tctcatctta acttgattac ttttgcaaag acttcatttc    17940
caaataagga tgcattcacg gatgcagaga gttagggctt caacacatat ttaatatttt    18000
agggaacaca attcaaccct caacagcccc acagcttgta aagctgtaat tggcaccatc    18060
ctctgcttgc tttgctcata ttatttcatc caaccatgcc tttctttttt gcccaattat    18120
agttgttgat caaaatgact atctcttaag catgaacgtt attatttcat cctaagcacc    18180
agagctttct tttctttcct tttttttttt ttttttttg agatacaatc ttgctctctt    18240
gcctgggctg gagtgcagtg gtgtgatttt ggctcactgt aacctctatc tcctgggttc    18300
aagtgattca cctgcctcag tctcccaaat agctgggatt actggcacct gccaccacgc    18360
ccagctaatt tttgtatttt tagtagagac gagtctttgc catgttggcc aggctggtct    18420
tgaactcctg gcctcaagtg atccaccgc ctcggcctcc taaggtgctg ggattacagg     18480
cacaagccac tgtgcctggt cagcaccaga gctttcttta gactaatgcg ccttaactgt    18540
tagtaatcag aatcttttc tgcagctttt ttatcttgcc aggttacctg ggctttgagt    18600 tctatttttcc ctcccttcac aggggggttac actacctctt ggtgtaattc aacggtctgg   18660
ggagcagtgt gagccacaaa agaggtcctc ttggcccatt ccacacttca aagatgagga    18720
agctgccgga tgtggtggtt catgcctgta atcccggcag tttgggaggc tgtggtggga    18780
ggatcatttg agaccaggag tttgagacca gcctgggcaa tatagtgaga cctcacctct    18840
acaaaaataa aataaaacaa aattagccag gcatggtggc acgtgtctgt agtcctagct    18900
acttgagaag ctgaggtggg aggattgctt gagcctgagg aagttgaggc tacactgagt    18960
caagatcatg ccactgcact ccagccaggg caacagagtg agacagtgtc taaaaaaaaa    19020
cccacaaaaa aaaatgagg aagctgagac tcagaggggc ttcctgagag agcatgacag    19080
cagcaggccc ggggcaggtc tgcagcatca caactgctag gctgcccaac actctccatc    19140
ctagctcaga agggactccc actggaagct cttgtcccag gaacttaccc aggctccagg    19200
acagcctggc ctggctccca gaccactgct gtgcttctct ctcggcagat cggtggggc    19260 aggaacatgg accaccacat cctgcatgtg gctgtggatg tcatcaggga gtctcgggag    19320
atgcggctgc agcccttcaa tgagtaccgc aagaggtttg gcatgaaacc ctacacctcc    19380
ttccaggagc tcgtaggtga gcagctgttt cctggatgca gtccctgccc ttgagggact    19440
ggcagcaaag tcagggagac atcaaggaaa tagaacggga caatacatgc ggcaatgtgt    19500
aacaaccaga cttataatgg gcgtggaagt gctgtgccag ggtggtaaat aagcctgctt    19560
ggggagagaa ggtgactttt cagctgggtt tggagaacaa atggcatttt cagtgggaga    19620
agagagggag gagtgtttta ggcagagcaa tagaaagtac aaaggctgcc gggcaaggtg    19680
gctcgcgcct gtaatcctag cactttggga ggctcaggcg ggtggatcac gaggtcagga    19740
aatcgagacc atcctggcta acacgatgaa accccgtctc tactaaaaat acaaaaaatt    19800
agccgggcat ggaggcaggc gcctgtagtc ccagctactc gggaggctga ggcaggagaa    19860
tggtgtgaac ctgggaggca gagcttgcag tgagctgaga ttgcgccact gcactccagc    19920
ctgggcgaca gagcgagaca ccatctcaaa aaaagaaag tacaaaggca tagaggtcag    19980
acagcaggta tctagggaaa cagtcataga tgtggctggg gcaaggagct tatgttgtgg    20040
gaatgattag tgatgggagg ttggggccaa accgtgtaga atcttggttt tcatactaaa    20100
tattttgagt tttatttggt ctagtgcttt ctaagtaccc acttacgggc cagctgcata    20160
```

```
aaaatcattt agaaagctga ttaagatacc aaatctcaga tgcctctcct acggattctg   20220
attcaaccag cctgggtggt gcccaagaat ctgcgtattc atatgaataa agtatatata   20280
catatatatg aatatatata tgaatagagt atatatacat atatatcaat atatacatat   20340
acatatcaat acatatatac atatacacac acatatatat gtgtgtgtat atatatacta   20400
tatatataca tatatatata tacatatata tatatacata tatatataca tatatatata   20460
catatatata tatatataca tatatatata tatatatttc ccccaatatc tcagatgtt    20520
gggcagccaa gtttccagcc cttgtcacat acaatgggga gccactgaag caggtgtgac   20580
atggcccatg agagttccca gtggaggatg gatttgagga actgggcagg gaagcaggga   20640
agctccatat ttgtctcccc ttggccacat gaacatgtgg atattgcaga gtggagcaga   20700
ttctgtgcat gagctccttg tgatcctgga acagcatctt attctttact ctcccatgac   20760
aaatggtccc cggggcaga aggaacactg ccactgaatt tctgtgtgag ctcggacatg   20820
ttacatcttt gagctctagt agtaaaaggg cttggcccag gctaaggtct tgaaatctgt   20880
ctgtgaagga agccagatgg ggagcattct cccttctgtg atgatcaggt aattagggcc   20940
cagagttgct caaggttata ggctgtttgg tggcagatct aggcccctga ctttctcttt   21000
agtagcattt tccttcccta gacccagtcc ctgaggaggg gcaatttgtg cttttcctct   21060
tgaccctttt ccccagtgcc aaccatgcca aattctaggg cacatgctca gttgctcaag   21120
ttagtctcct ggagtcccta ttatccccag aaaaaggtgg acctggaagg gtcccgcccc   21180
aggttgacct taatggcatc atggatctga tgctagcatt tcccctttatc tccttgtagg   21240
agagaaggag atggcagcag agttggagga attgtatgga gacattgatg cgttggagtt   21300
ctaccctgga ctgcttcttg aaaagtgcca tccaaactct atctttgggg agagtatgat   21360
agagattggg gctcccttt ccctcaaggg tctcctaggg aatcccatct gttctccgga    21420
gtactggaag ccgagcacat ttggcggcga ggtgggcttt aacattgtca agacggccac   21480
actgaagaag ctggtctgcc tcaacaccaa gacctgtccc tacgtttcct tccgtgtgcc   21540
ggatgccagt caggatgatg ggcctgctgt ggagcgacca tccacagagc tctgagggc    21600
aggaaagcag cattctggag gggagagctt tgtgcttgtc attccagagt gctgaggcca   21660
gggctgatgg tcttaaatgc tcattttctg gtttggcatg gtgagtgttg gggttgacat   21720
ttagaacttt aagtctcacc cattatctgg aatattgtga ttctgtttat tcttccagaa   21780
tgctgaactc cttgttagcc cttcagattg ttaggagtgg ttctcatttg gtctgccaga   21840
atactgggtt cttagttgac aacctagaat gtcagatttc tggttgattt gtaacacagt   21900
cattctagga tgtggagcta ctgatgaaat ctgctagaaa gttaggggt tcttattttg     21960
cattccagaa tcttgacttt ctgattggtg attcaaagtg ttgtgttcct ggctgatgat   22020
ccagaacagt ggctcgtatc ccaaatctgt cagcatctgg ctgtctagaa tgtggatttg   22080
attcattttc ctgttcagtg agatatcata gagacggaga tcctaaggtc aacaagaat    22140
gcattccctg aatctgtgcc tgcactgaga gggcaaggaa gtgggtgtt cttcttggga    22200
cccccactaa gaccctggtc tgaggatgta gagagaacag gtgggctgta ttcacgccat   22260
tggttggaag ctaccagagc tctatcccca tccaggtctt gactcatggc agctgtttct   22320
catgaagcta ataaaattcg ctttctaaag ttacctgtta tatatctctt ttggtcccat   22380
cctctaaagc agaggcaaca ctggaacatg gctagccttt cttgtagcca tggctgggcg   22440
tgctagaggt tgcagcatga gactttctgc tgggatcctt gggcccatca ctgtatagac   22500
```

```
atgctaccac tggtacttcc tttctccctg cgggccaggc actgcccttt tcaggaagct    22560
ctcttaaaat acccattgcc ccagacctgg aagatataac attcagttcc caccatctga    22620
ttaaaacaac ttcctcccct acagagcata caacagaggg ggcacccggg gaggagagca    22680
catactgtgt tccaatttca cgcttttaat tctcatttgt tctcacacca acagtgtgaa    22740
gtgcgtggta taatctccat ttcaaaacca aggaagcagc ctcagagtgg tcgagtgaca    22800
cacctcacgc aggctgagtc cagagcttgt gctcctcttg attcctggtt tgactcagtt    22860
ccaggcctga tcttgcctgt ctggctcagg gtcaaagaca gaatggtgga gtgtagcctc    22920
cacctgatat tcaggctact cattcagtcc caaatatgta ttttcctaag tgtttactat    22980
gtgccagttc ctgtaacagg tgtggggaca cagcagtgag taatcaatac agacaaggtt    23040
ctgcccttat ggagctcaca ctccagtggc agacaaacag accataaata aggaaacgat    23100
gaaataagat atatacaagg tgagtgtgac ttcccttcta accccctctg ctctgtcctc    23160
ccctattgcg ctctcaagac cagagaccca acagcagtga tctcagggca gacagccctc    23220
cactccagct ctgagaccct tttctcagga cctctgtagg cagcagagag agaggacaga    23280
ggggtaagat gaggggttga gggaaggttc ttcatgatcc acactttggg cttagtattt    23340
ctcaggaaga gctatggccc agaaacaaca ggggaaacta gagttcggtc tgacagtcct    23400
tggggttaag tctcctgtct tatggtccag aaactcctgt ttctccttag ttggctggaa    23460
actgctccca tcattccttc tggcctctgc tgaatgcagg gaatgcaatc cttccctgct    23520
cttgcagttg ctctgacgta gaaagatcct tcgggtgctg gaagtctcca tgaagagctt    23580
gtgtcctgtc ctttcttgca gattctattt cccctcttct gctaataacct cttactttgc    23640 ttgagaatcc tctccttcct tattaatttc agtcttggtg gttctatcag gggtgcattc    23700
tggccaaggg gtgggcctgt gaatcaatcc tgggcaatca gacaccctct ccttaaaaac    23760
tggcccgtgg agactgagat cactgactct gactcatccc cacagctggc tctgacaaga    23820
tggtccattt gttcctgctt ccgagatccc cagggcagcc tggatccctg cccttctcaa    23880
gactttagct tttccttcca tccggtggcc tattccagga attcctcttt tgcttaaatc    23940
agttggagtt tgtgtctgtt gcttgtaatc aagcctttat ggctgctggg ctgagtgaca    24000
caagcacttt aatggcctgg agggactttt aatcagtgaa gatgcaatca gacaagtgtt    24060
ttggaaagag caccctcgag aagggtggat gacagggcag agcaggaagg acaggaagct    24120
ggcagaacgg aggaggctgc agccgtggtc caaccaggag ctgatggcag ctggggctag    24180
gggaagggct ttgagggtgg aaggatggga tgggttccag aggtattcct ctcttaaatg    24240
caagtgccta gattaggtag actttgctta gtattgacaa ctgcacatga aagttttgca    24300
aagggaaaca ggctaaatgc accaagaaag cttcttcaga gtgaagaatc ttaatgcttg    24360
taatttaaac atttgttcct ggagttttga tttggtggat gtgatggttg gttttatttg    24420
tcagtttggt tgggctatag cacacagtta tttaatcaaa cagtaatcta ggtgtggctg    24480
tgaaggtatt ttgtagatgt gattaacatc tacaatcagt tgactttaag tgaaagagat    24540
tacttaaata atttgggtga gctgcacctg attagttgaa aggcctcaag aacaaacact    24600
gcagtttcct ggaaaagaag aaactttgcc tcaagactat agccatcgac tcctgcctga    24660
gtttccagcc tgctagtctg ccctatggat ttgaagtttg ccaaccccaa caattgtgtg    24720
aattaatttc taaaaataaa gctatataca gcc                                 24753

<210> SEQ ID NO 15
<211> LENGTH: 8616
```

```
<212> TYPE: DNA
<213> ORGANISM: Homo sapiens
<220> FEATURE:
<221> NAME/KEY: misc_feature
<222> LOCATION: (1)..(8616)
<223> OTHER INFORMATION: Prostoglandin synthetase 1 nucleotide

<400> SEQUENCE: 15
```

| | | | | | |
|---|---|---|---|---|---|
| gaccaattgt | catacgactt | gcagtgagcg | tcaggagcac | gtccaggaac | tcctcagcag | 60 |
| cgcctccttc | agctccacag | ccagacgccc | tcagacagca | agcctaccc  | ccgcgccgcg | 120 |
| ccctgcccgc | cgctgcgatg | ctcgcccgcg | ccctgctgct | gtgcgcggtc | ctggcgctca | 180 |
| gccatacagg | tgagtacctg | cgccgcgca  | ccggggactc | cggttccacg | cacccgggca | 240 |
| gagtttccgc | tctgacctcc | tgggtctatc | ccagtactcc | gacttctctc | cgaatagaga | 300 |
| agctacgtga | cttgggaaag | agcttggacc | gctagagttc | gaaagaactc | cgtggatatt | 360 |
| ccagctttcc | cacaagcact | gatcattatg | agccagttac | ttaaccgatc | tgagacactc | 420 |
| tcacctccta | aatagggata | gatgatacta | atttgcaggt | tgtcattatg | ataagacagg | 480 |
| atctgatcaa | tatatgtgaa | ttgtttatat | ttggaacctt | tttattgagt | ggaagaagtt | 540 |
| gttttaaata | ttctagtcag | ttcttttcctg | ctcccaggaa | agcccggatt | atgttttaag | 600 |
| ataagcaaaa | tgtcttaaaa | gtaagctgtt | ttactttgaa | ttttcccta | aatgttgatt | 660 |
| agtgtactag | atccatttta | atttggaaag | tgaagtgcta | cttatttgaa | cttcttaaaa | 720 |
| atgctaattt | taacatctaa | agagttaact | aagaaaagct | tagtaacatg | atgtaccaag | 780 |
| ttgaatatgc | tgttatcctt | atttagaata | gaaaattggt | atttctacgt | tttatccatt | 840 |
| ctaaggcagg | ttaaaaaatt | gtatttccat | gactacctat | atatttcttg | aatttattat | 900 |
| tgtaaagttg | attcatagtc | aaacaattaa | atgtttaaat | taagattaag | acactagaga | 960 |
| atgatttatt | tgctgtcctt | taattgcagc | aaatccttgc | tgttcccacc | catgtcaaaa | 1020 |
| ccgaggtgta | tgtatgagtg | tgggatttga | ccagtataag | tgcgattgta | cccggacagg | 1080 |
| attctatgga | gaaaactgct | caacacgtaa | gtttgtcctt | tggttgcctc | attaggagtg | 1140 |
| gggctggata | cagttatcat | tgtatagatt | tgtgtcttat | aatgagtccc | attaatttct | 1200 |
| ccctcccttt | cttcgtcttc | ttgcagcgga | attttttgaca | agaataaaat | tatttctgaa | 1260 |
| acccactcca | aacacagtgc | actacatact | tacccacttc | aagggatttt | ggaacgttgt | 1320 |
| gaataacatt | cccttccttc | gaaatgcaat | tatgagttat | gtgttgacat | gtaagtacaa | 1380 |
| gtgtctttct | aaggtttta  | gccttctcaa | agaaaatat  | gctttataat | actgtaagcc | 1440 |
| taatctaaaa | acatatttcc | aagcttatca | aaaagacttt | aagatagctt | ttaagtttgc | 1500 |
| cttccatctt | aatcgccaaa | aatattgaca | tttagtccca | tccagtttat | acagtctgct | 1560 |
| cacaactctg | tatacctctt | ctaacctta  | ctgtttggtc | agtttgtgga | ggtagcatgg | 1620 |
| tccagctgtt | tattgaatgc | ccatgggcca | cagaattgtt | ctgaacatgt | agcacccatt | 1680 |
| aaaataaatt | tggatttgga | tcagcaagaa | aataactttc | catgattcta | aagtgggtgc | 1740 |
| catactcagc | cattcctttc | ataggcctct | tggatagtga | gcagatggct | acctgaaaaa | 1800 |
| tcaatattgc | cagattataa | tgtgcagagt | atatgtattt | tattaaagat | gtatttcaag | 1860 |
| tggccattag | actataaagt | gtagttgttt | aaaaatagat | ttttttttatt | ttggagttac | 1920 |
| attcaacctc | aggtgccact | ttccacattt | tacaataaaa | ataatggttg | atttacttaa | 1980 |
| caaatgagaa | taaataaaac | atttttttct | ttgaaaattt | cagccagatc | acatttgatt | 2040 |
| gacagtccac | caacttacaa | tgctgactat | ggctacaaaa | gctgggaagc | cttctctaac | 2100 |

```
ctctcctatt atactagagc ccttcctcct gtgcctgatg attgcccgac tcccttgggt    2160
gtcaaaggtg agtaagaaga atccattaga gatgtattaa ctataagacg ggctgcattg    2220
ctgccaaaaa aaaaaattga ccttagacta ccatttattt attaacaaaa gcagttttta    2280
cttttagcat ggttatctat gggtatttt taaagtatga gtctatataa actattatgt     2340
aaaagcaaat gagcgtcttg gtataatgtc ttaatatttt caaattattt ctttagaaat    2400
gaaataattc taattaaaat agataaaatc attcagtaag aagttgttcc accatatctt    2460
agaactgttg tttatattat gatcctattc acaattgtaa ttctcatata aatgaagaat    2520
tcttggtaga ttgacagtca ccatctcctt tcttgaatac atagatggat tcttaccta    2580 gctttctcat ttttcaggta aaaagcagct tcctgattca aatgagattg tggaaaaatt    2640
gcttctaaga agaaagttca tccctgatcc ccagggctca aacatgatgt ttgcattctt    2700
tgcccagcac ttcacgcatc agttttcaa gacagatcat aagcgagggc cagctttcac     2760
caacgggctg ggccatgggg taagatagag ttaatatctt agagttagta aaattatacc    2820
aaatcatagt caagggctaa cattaaagga gatatacaga tagatagatc caaataactt    2880
atccactttt tttaaaaaga agtcttatct ataaaaacct taaaggaatt ttccatttac    2940
ttcactggtc tagtaaaatt atacacacac acagacatgc acacacatat ataaacattc    3000
acacacatac atatgtacag gtattgttat ttgtaatttg acccttgtat tttttagttt    3060
aaaatgttag tactgcaaaa tgttatgtcc tcaaaaacac attgtaccat gattatgccg    3120
ctttcaatat tgtaaagtga ggttttgcc gcattattat tttttggatt tcaatagcat      3180
agcttcaagt tattcgtaag aatttttat aaataataca ttttatact ttttataat        3240 taccatatca tcatagtgaa gtatataata tatgatat aagctcaata tagtatatta       3300
attccgttaa acacaaagac atatcagttt gtagctttgg tggataaaca aattaattta    3360
gcaattcatg gctatgaaaa atgtatattt tatttaaaaa ttttaaagaa agctaaatga    3420
tcaaattatt taatgatgaa ttatatgata gacactttat ataagaaaaa cttcaacagc    3480
aacaaattaa aattttttca tcattttcta ggtggactta aatcatattt acggtgaaac    3540
tctggctaga cagcgtaaac tgcgcctttt caaggatgga aaaatgaaat atcaggtatg    3600
cttcctttga ctattaagac ttagttatta ccgcttatac ccatatttta aaatccctaa    3660
aaatgtgttc cttaactttt taactgatgt ttatttattt atttattttt ttagataatt    3720
gatggagaga tgtatcctcc cacagtcaaa gatactcagg cagagatgat ctaccctcct    3780
caagtccctg agcatctacg gtttgctgtg gggcaggagg tctttggtct ggtgcctggt    3840
ctgatgatgt atgccacaat ctggctgcgg gaacacaaca gagtatgcga tgtgcttaaa    3900
caggagcatc ctgaatgggg tgatgagcag ttgttccaga caagcaggct aatactgata    3960
ggtaaacaag aaaatgattt atataaaacc ctcttcccca gggaaaatta gtgtgctatc    4020
tttgttatgt tttgagtaaa tgacaagatg tggtaaatga aaactcacac attctatata    4080
cattaaatat gtaagcatga ctgataaaat agctatcttt tgatactgac aaggaagaaa    4140
acagaaatga aggaatagca aattttaaaa attgcattcc agttgcttga aagcttgtga    4200
tcagatgcaa taaatgtttt tattatttat tttgtgcaaa taggagagac tattaagatt    4260
gtgattgaag attatgtgca acacttgagt ggctatcact tcaaactgaa atttgaccca    4320
gaactacttt tcaacaaaca attccagtac caaaatcgta ttgctgctga atttaacacc    4380
ctctatcact ggcatcccct tctgcctgac acctttcaaa ttcatgacca gaaatacaac    4440
tatcaacagt ttatctacaa caactctata ttgctggaac atggaattac ccagtttgtt    4500
```

```
gaatcattca ccaggcaaat tgctggcagg gtaagcatta ttattgaaaa ccaaaacaaa    4560
agactagtca gtaactttag aatttctgcc acgaaaatta ttttcttaa acttactaaa    4620 agagtagtta gttatattgc tagtaaaatt attttattga tataagaagc ctaactttgt    4680
ttgaaaagtc taaactttta gtctagtcta cagttgtcag acaaatagca aattgtaccc    4740
ctaccttaaa aatattttca aaaagtatct ataatcttat aggaataaat attttaggct    4800
tgaatactag tgttattttt gaaatgtaaa aaggcaaatt agttctaggc tggtgtccca    4860 ttgaattta  agcagagctc ctgttgaaat gtaggtaagc atctttccag caaataaaaa    4920
ttgtctccgc tgggagtttc agttttacct gatttgtacc taaggcaagc tgaatacaaa    4980
cagtaaatat gcctaaaatt cttgttttac aactaatttt actttccaca ggttgctggt    5040
ggtaggaatg ttccacccgc agtacagaaa gtatcacagg cttccattga ccagagcagg    5100
cagatgaaat accagtcttt taatgagtac cgcaaacgct ttatgctgaa gccctatgaa    5160
tcatttgaag aacttacagg taagaaacag tttctaaact tcttcgtttt ttgtttgttt    5220
gtttgttttt gttgttttg gttttctttt cgagatggag ccgccctctg tcacccaggc    5280
tggagtgcag tggcgccatc tcggctcact gcaacctccg cctcctgggt tcaagcaatt    5340
ctcctgcctc aacttcctga gtagctggga ctacaggctc acgtcgcacg catggataat    5400
tttttgtatt ttcagtatag acggggtttc accgtgttag ccaggctggt ctcaaactcc    5460
tgacctagtg atccgccggc ttcggcctcc cgaagtgctg ggattacagg cgtgagccac    5520
cgcgcctggc ccctaaactt cttaaaagaa tcagggtca  aatggaaaca gagaagttgg    5580
cagcaaattg agcaaaagaa tcaaactgtt ttttattttg tgaagtttga cattggttgt    5640
atctctgtct tcatcgcctt cacaggagaa aaggaaatgt ctgcagagtt ggaagcactc    5700
tatggtgaca tcgatgctgt ggagctgtat cctgcccttc tggtagaaaa gcctcggcca    5760
gatgccatct ttggtgaaac catggtagaa gttggagcac cattctcctt gaaaggactt    5820
atgggtaatg ttatatgttc tcctgcctac tggaagccaa gcacttttgg tggagaagtg    5880
ggttttcaaa tcatcaacac tgcctcaatt cagtctctca tctgcaataa cgtgaagggc    5940 tgtccctta  cttcattcag tgttccagat ccagagctca ttaaaacagt caccatcaat    6000
gcaagttctt cccgctccgg actagatgat atcaatccca cagtactact aaaagaacgt    6060
tcgactgaac tgtagaagtc taatgatcat attatttat  ttatatgaac catgtctatt    6120
aatttaatta tttaataata tttatattaa actccttatg ttacttaaca tcttctgtaa    6180
cagaagtcag tactcctgtt gcggagaaag gagtcatact tgtgaagact tttatgtcac    6240
tactctaaag attttgctgt tgctgttaag tttggaaaac agttttatt ctgttttata    6300 aaccagagag aaatgagttt tgacgtcttt ttacttgaat ttcaacttat attataagaa    6360
cgaaagtaaa gatgtttgaa tacttaaaca ctgtcacaag atggcaaaat gctgaaagtt    6420
tttacactgt cgatgtttcc aatgcatctt ccatgatgca ttagaagtaa ctaatgtttg    6480
aaattttaaa gtacttttgg ttatttttct gtcatcaaac aaaaacaggt atcagtgcat    6540
tattaaatga atatttaaat tagacattac cagtaatttc atgtctactt tttaaaatca    6600
gcaatgaaac aataatttga aatttctaaa ttcatagggt agaatcacct gtaaaagctt    6660
gtttgatttc ttaaagttat taaacttgta catataccaa aaagaagctg tcttggattt    6720
aaatctgtaa aatcagtaga aattttacta caattgcttg ttaaaatatt ttataagtga    6780 tgttccttt  tcaccaagag tataaaacctt tttagtgtga ctgttaaaac ttccttttaa    6840
```

```
atcaaaatgc caaatttatt aaggtggtgg agccactgca gtgttatctt aaaataagaa    6900
tattttgttg agatattcca gaatttgttt atatggctgg taacatgtaa aatctatatc    6960
agcaaaaggg tctacccttta aaataagcaa taacaaagaa gaaaaccaaa ttattgttca    7020
aatttaggtt taaacttttg aagcaaactt tttttttatcc ttgtgcactg caggcctggt    7080
actcagattt tgctatgagg ttaatgaagt accaagctgt gcttgaataa tgatatgttt    7140
tctcagattt tctgttgtac agttaatttt agcagtccat atcacattgc aaaagtagca    7200
atgacctcat aaaatacctc ttcaaaatgc ttaaattcat ttcacacatt aattttatct    7260
cagtcttgaa gccaattcag taggtgcatt ggaatcaagc ctggctacct gcatgctgtt    7320 cctttttcttt tcttctttta gccattttgc taagagacac agtcttctca tcacttcgtt    7380
tctcctattt tgttttacta gttttaagat cagagttcac tttctttgga ctctgcctat    7440
attttcttac ctgaactttt gcaagttttc aggtaaacct cagctcagga ctgctattta    7500
gctcctctta agaagattaa aagagaaaaa aaaaggcct tttaaaaata gtatacactt    7560
attttaagtg aaaagcagag aattttattt atagctaatt ttagctatct gtaaccaaga    7620
tggatgcaaa gaggctagtg cctcagagag aactgtacgg ggtttgtgac tggaaaaagt    7680
tacgttccca ttctaattaa tgcccttttct tatttaaaaa caaaaccaaa tgatatctaa    7740
gtagttctca gcaataataa taatgacgat aatacttctt ttccacatct cattgtcact    7800
gacatttaat ggtactgtat attacttaat ttattgaaga ttattattta tgtcttatta    7860
ggacactatg gttataaact gtgtttaagc ctacaatcat tgattttttt ttgttatgtc    7920
acaatcagta tatcttctttt gggggttacct ctctgaatat tatgtaaaca atccaaagaa    7980
atgattgtat taagatttgt gaataaattt ttagaaatct gattggcata ttgagatatt    8040
taaggttgaa tgtttgtcct taggataggc ctatgtgcta gcccacaaag aatattgtct    8100
cattagcctg aatgtgccat aagactgacc tttttaaaatg ttttgaggga tctgtggatg    8160
cttcgttaat ttgttcagcc acaatttatt gagaaaatat tctgtgtcaa gcactgtggg    8220
ttttaatatt tttaaatcaa acgctgatta cagataatag tatttatata aataattgaa    8280
aaaaattttc ttttgggaag agggagaaaa tgaaataaat atcattaaag ataactcagg    8340
agaatcttct ttacaatttt acgtttagaa tgtttaaggt taagaagaa atagtcaata    8400 tgcttgtata aaacactgtt cactgttttt tttaaaaaaa aaacttgatt tgttattaac    8460
attgatctgc tgacaaaacc tgggaatttg ggttgtgtat gcgaatgttt cagtgcctca    8520
gacaaatgtg tatttaactt atgtaaaaga taagtctgga aataaatgtc tgtttatttt    8580
tgtactattt aaaaattgac agatcttttc tgaaga                              8616
```

<210> SEQ ID NO 16
<211> LENGTH: 187
<212> TYPE: PRT
<213> ORGANISM: Homo sapiens

<400> SEQUENCE: 16

Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

```
Ile Lys Gln Leu Gln Gln Phe Gln Lys Glu Asp Ala Ala Leu Thr Ile
 65                  70                  75                  80

Tyr Glu Met Leu Gln Asn Ile Phe Ala Ile Phe Arg Gln Asp Ser Ser
                 85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185

<210> SEQ ID NO 17
<211> LENGTH: 31
<212> TYPE: PRT
<213> ORGANISM: Homo sapiens

<400> SEQUENCE: 17

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
             20                  25                  30

<210> SEQ ID NO 18
<211> LENGTH: 33
<212> TYPE: PRT
<213> ORGANISM: Homo sapiens

<400> SEQUENCE: 18

His Ala Asp Gly Ser Phe Ser Asp Glu Met Asn Thr Ile Leu Asp Asn
 1               5                  10                  15

Leu Ala Ala Arg Asp Phe Ile Asn Trp Leu Ile Gln Thr Lys Ile Thr
             20                  25                  30

Asp

<210> SEQ ID NO 19
<211> LENGTH: 244
<212> TYPE: PRT
<213> ORGANISM: Homo sapiens

<400> SEQUENCE: 19

Met Leu Leu Leu Gly Ala Val Leu Leu Leu Ala Leu Pro Gly His
 1               5                  10                  15

Asp Gln Glu Thr Thr Thr Gln Gly Pro Gly Val Leu Leu Pro Leu Pro
             20                  25                  30

Lys Gly Ala Cys Thr Gly Trp Met Ala Gly Ile Pro Gly His Pro Gly
         35                  40                  45

His Asn Gly Ala Pro Gly Arg Asp Gly Arg Asp Gly Thr Pro Gly Glu
     50                  55                  60

Lys Gly Glu Lys Gly Asp Pro Gly Leu Ile Gly Pro Lys Gly Asp Ile
 65                  70                  75                  80

Gly Glu Thr Gly Val Pro Gly Ala Glu Gly Pro Arg Gly Phe Pro Gly
```

```
            85                  90                  95
Ile Gln Gly Arg Lys Gly Glu Pro Gly Glu Gly Ala Tyr Val Tyr Arg
            100                 105                 110

Ser Ala Phe Ser Val Gly Leu Glu Thr Tyr Val Thr Ile Pro Asn Met
            115                 120                 125

Pro Ile Arg Phe Thr Lys Ile Phe Tyr Asn Gln Gln Asn His Tyr Asp
            130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Met Leu Phe Thr Tyr Asp Gln Tyr Gln Glu Asn
            180                 185                 190

Asn Val Asp Gln Ala Ser Gly Ser Val Leu Leu His Leu Glu Val Gly
            195                 200                 205

Asp Gln Val Trp Leu Gln Val Tyr Gly Glu Gly Glu Arg Asn Gly Leu
            210                 215                 220

Tyr Ala Asp Asn Asp Asn Asp Ser Thr Phe Thr Gly Phe Leu Leu Tyr
225                 230                 235                 240

His Asp Thr Asn

<210> SEQ ID NO 20
<211> LENGTH: 167
<212> TYPE: PRT
<213> ORGANISM: Homo sapiens

<400> SEQUENCE: 20

Met His Trp Gly Thr Leu Cys Gly Phe Leu Trp Leu Trp Pro Tyr Leu
1               5                   10                  15

Phe Tyr Ala Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
            35                  40                  45

Gln Ser Val Ser Ser Lys Gln Lys Val Thr Gly Leu Asp Phe Ile Pro
        50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
            115                 120                 125

Asp Ser Leu Gly Gly Val Leu Glu Ala Ser Gly Tyr Ser Thr Glu Val
            130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 21
<211> LENGTH: 1480
<212> TYPE: PRT
<213> ORGANISM: Homo sapiens

<400> SEQUENCE: 21
```

```
Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
                100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
                180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
                260                 265                 270

Lys Ala Tyr Cys Trp Glu Glu Ala Met Glu Lys Met Ile Glu Asn Leu
                275                 280                 285

Arg Gln Thr Glu Leu Lys Leu Thr Arg Lys Ala Ala Tyr Val Arg Tyr
                290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
                355                 360                 365

Asn Lys Ile Gln Asp Phe Leu Gln Lys Gln Glu Tyr Lys Thr Leu Glu
                370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415
```

```
Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
```

-continued

```
            835                 840                 845
Tyr Leu Arg Tyr Ile Thr Val His Lys Ser Leu Ile Phe Val Leu Ile
        850                 855                 860
Trp Cys Leu Val Ile Phe Leu Ala Glu Val Ala Ala Ser Leu Val Val
865                 870                 875                 880
Leu Trp Leu Leu Gly Asn Thr Pro Leu Gln Asp Lys Gly Asn Ser Thr
                885                 890                 895
His Ser Arg Asn Asn Ser Tyr Ala Val Ile Ile Thr Ser Thr Ser Ser
                900                 905                 910
Tyr Tyr Val Phe Tyr Ile Tyr Val Gly Val Ala Asp Thr Leu Leu Ala
                915                 920                 925
Met Gly Phe Phe Arg Gly Leu Pro Leu Val His Thr Leu Ile Thr Val
        930                 935                 940
Ser Lys Ile Leu His His Lys Met Leu His Ser Val Leu Gln Ala Pro
945                 950                 955                 960
Met Ser Thr Leu Asn Thr Leu Lys Ala Gly Gly Ile Leu Asn Arg Phe
                965                 970                 975
Ser Lys Asp Ile Ala Ile Leu Asp Asp Leu Leu Pro Leu Thr Ile Phe
                980                 985                 990
Asp Phe Ile Gln Leu Leu Leu Ile  Val Ile Gly Ala Ile  Ala Val Val
            995                 1000                1005
Ala Val Leu Gln Pro Tyr Ile  Phe Val Ala Thr Val  Pro Val Ile
        1010                1015                1020
Val Ala Phe Ile Met Leu Arg  Ala Tyr Phe Leu Gln  Thr Ser Gln
        1025                1030                1035
Gln Leu Lys Gln Leu Glu Ser  Glu Gly Arg Ser Pro  Ile Phe Thr
        1040                1045                1050
His Leu Val Thr Ser Leu Lys  Gly Leu Trp Thr Leu  Arg Ala Phe
        1055                1060                1065
Gly Arg Gln Pro Tyr Phe Glu  Thr Leu Phe His Lys  Ala Leu Asn
        1070                1075                1080
Leu His Thr Ala Asn Trp Phe  Leu Tyr Leu Ser Thr  Leu Arg Trp
        1085                1090                1095
Phe Gln Met Arg Ile Glu Met  Ile Phe Val Ile Phe  Phe Ile Ala
        1100                1105                1110
Val Thr Phe Ile Ser Ile Leu  Thr Thr Gly Glu Gly  Glu Gly Arg
        1115                1120                1125
Val Gly Ile Ile Leu Thr Leu  Ala Met Asn Ile Met  Ser Thr Leu
        1130                1135                1140
Gln Trp Ala Val Asn Ser Ser  Ile Asp Val Asp Ser  Leu Met Arg
        1145                1150                1155
Ser Val Ser Arg Val Phe Lys  Phe Ile Asp Met Pro  Thr Glu Gly
        1160                1165                1170
Lys Pro Thr Lys Ser Thr Lys  Pro Tyr Lys Asn Gly  Gln Leu Ser
        1175                1180                1185
Lys Val Met Ile Ile Glu Asn  Ser His Val Lys Lys  Asp Asp Ile
        1190                1195                1200
Trp Pro Ser Gly Gly Gln Met  Thr Val Lys Asp Leu  Thr Ala Lys
        1205                1210                1215
Tyr Thr Glu Gly Gly Asn Ala  Ile Leu Glu Asn Ile  Ser Phe Ser
        1220                1225                1230
Ile Ser Pro Gly Gln Arg Val  Gly Leu Leu Gly Arg  Thr Gly Ser
        1235                1240                1245
```

-continued

```
Gly Lys Ser Thr Leu Leu Ser Ala Phe Leu Arg Leu Leu Asn Thr
    1250                1255                1260

Glu Gly Glu Ile Gln Ile Asp Gly Val Ser Trp Asp Ser Ile Thr
    1265                1270                1275

Leu Gln Gln Trp Arg Lys Ala Phe Gly Val Ile Pro Gln Lys Val
    1280                1285                1290

Phe Ile Phe Ser Gly Thr Phe Arg Lys Asn Leu Asp Pro Tyr Glu
    1295                1300                1305

Gln Trp Ser Asp Gln Glu Ile Trp Lys Val Ala Asp Glu Val Gly
    1310                1315                1320

Leu Arg Ser Val Ile Glu Gln Phe Pro Gly Lys Leu Asp Phe Val
    1325                1330                1335

Leu Val Asp Gly Gly Cys Val Leu Ser His Gly His Lys Gln Leu
    1340                1345                1350

Met Cys Leu Ala Arg Ser Val Leu Ser Lys Ala Lys Ile Leu Leu
    1355                1360                1365

Leu Asp Glu Pro Ser Ala His Leu Asp Pro Val Thr Tyr Gln Ile
    1370                1375                1380

Ile Arg Arg Thr Leu Lys Gln Ala Phe Ala Asp Cys Thr Val Ile
    1385                1390                1395

Leu Cys Glu His Arg Ile Glu Ala Met Leu Glu Cys Gln Gln Phe
    1400                1405                1410

Leu Val Ile Glu Glu Asn Lys Val Arg Gln Tyr Asp Ser Ile Gln
    1415                1420                1425

Lys Leu Leu Asn Glu Arg Ser Leu Phe Arg Gln Ala Ile Ser Pro
    1430                1435                1440

Ser Asp Arg Val Lys Leu Phe Pro His Trp Asn Ser Ser Lys Cys
    1445                1450                1455

Lys Ser Lys Pro Gln Ile Ala Ala Leu Lys Glu Glu Thr Glu Glu
    1460                1465                1470

Glu Val Gln Asp Thr Arg Leu
    1475                1480

<210> SEQ ID NO 22
<211> LENGTH: 178
<212> TYPE: PRT
<213> ORGANISM: Homo sapiens

<400> SEQUENCE: 22

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
                20                  25                  30

Phe Pro Gly Asn Leu Pro Asn Met Leu Arg Asp Leu Arg Asp Ala Phe
            35                  40                  45

Ser Arg Val Lys Thr Phe Phe Gln Met Lys Asp Gln Leu Asp Asn Leu
        50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
```

-continued

```
            115                 120                 125
Phe Leu Pro Cys Glu Asn Lys Ser Lys Ala Val Glu Gln Val Lys Asn
        130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```